(12) United States Patent
Shen et al.

(10) Patent No.: US 7,105,491 B2
(45) Date of Patent: Sep. 12, 2006

(54) BIOSYNTHESIS OF ENEDIYNE COMPOUNDS BY MANIPULATION OF C-1027 GENE PATHWAY

(75) Inventors: Ben Shen, Verona, WI (US); Wen Liu, Madison, WI (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 476 days.

(21) Appl. No.: 10/292,198

(22) Filed: Nov. 12, 2002

(65) Prior Publication Data

US 2003/0157654 A1    Aug. 21, 2003

Related U.S. Application Data

(63) Continuation-in-part of application No. 10/159,257, filed on May 31, 2002, which is a continuation-in-part of application No. 09/478,188, filed on Jan. 5, 2000, now abandoned.

(60) Provisional application No. 60/115,434, filed on Jan. 6, 1999.

(51) Int. Cl.
*A61K 31/70* (2006.01)
*C07H 15/00* (2006.01)
*C07H 17/00* (2006.01)

(52) U.S. Cl. ............... 514/25; 514/8; 536/17.2; 536/17.9; 536/18.1; 530/387.2

(58) Field of Classification Search ............... 514/8, 514/25; 536/17.2, 17.9, 18.1; 530/387.2
See application file for complete search history.

(56) References Cited

U.S. PATENT DOCUMENTS 5,527,805 A    6/1996    Smith et al.
6,297,284 B1   10/2001   Kerwin et al.

OTHER PUBLICATIONS

Xie, Y., et al. (1997) Anti-Cancer Drug Design 12, 169-179.
Liu, W., et al. (2002) Science 297, 1170-1173.
Thorson, J.S., et al. (1999) Bioorganic Chemistry 27, 172-188.
Liu, W. et al. (2000) Antimicrobial Agents and Chemotherapy 44, 382-392.
Görth, F.C., et al. (2000) Eur. J. Org. Chem., 2605-2611.
Thorson, J.S., et al. (2000) Current Pharmaceutical Design 6, 1841-1879.

(Continued)

*Primary Examiner*—Elli Peselev
(74) *Attorney, Agent, or Firm*—Godfrey & Kahn, S.C.; Sonali S. Srivastava

(57) ABSTRACT

This invention provides nucleic acid sequences and characterization of the gene cluster responsible for the biosynthesis of the enediyne C-1027 (produced by *Streptomyces globisporus*). Methods are provided for the biosynthesis of enediynes, enediyne analogs and other biological molecules. This invention also provides enediyne and enediyne analogs biosynthesized by manipulation of the C-1027 gene pathway.

13 Claims, 28 Drawing Sheets

C-1027 chromophore

Benzenoid diradical

OTHER PUBLICATIONS

Tanaka, T., et al. (2001) J Mol Biol 309, 267-283.
Kuo, H.M., et al. (2002) Biochemistry 41, 897-905.
Lopez-Larraza, D.M., et al. (2001) Chem Res Toxicol 14, 528-535.
Jones, G.B., et al. (2000) Org Lett 2, 811-813.
Tuntiwechapikul, W., et al. (2002) Biochemistry 41, 5283-5290.
Jiang, B., Li, D.D., et al. (1995) Biochem Biophys Res Commun 208, 238-244.
Xu, Y.J., et al. (1994) Biochemistry 33, 5947-5954.
Okuno, Y., et al. (1994) J. Med Chem 37, 2266-2273.
Xu, Y.J., et al. (1997) Biochemistry 36, 14975-14984.
Cane, D.E., et al. (1998) Science 282, 63.
Du, L., et al. (2001) Curr. Opin. Drug Discov. Dev. 4, 215.
Staunton, J., et al. (2001) Nat. Prod. Rep. 18, 380.
Shen, B. (2000) Top. Curr. Chem. 209, 1.
Smith, A.L., et al. (1996) J. Med. Chem. 39, 2103-2117.
Sievers, E.L. et al. (2001) Curr. Opin. Oncol. 13, 522-527.
Chen, Y., et al. (2002) Acta Crystallogr D. Biol Crystallogr 58, 173-175.
Mitchell et al, Future of Monoclonal Antibodies in the Treatment of Hematologic Malignancies, Cancer Control, Mar./Apr. 2002, pp. 152-166, vol. 9, No. 2.
Katrin et al, Targeted Therapy of Experimental Renal Cell Carcinoma with a Novel Conjugate of Monoclonal Antibody 138H11 and Calicheamicin I11, Cancer Research 60, 6089-6095, Nov. 1, 2000.
Reff et al, Future Approaches for Treating Hematologic Disease, Current Pharmaceutical Biotechnology, vol. 2, No. 4, Dec. 2001, pp. 369-382(14).
Liang et al, Antitumor activity of anti-type IV collagenase monoclonal antibody and its lidamycin conjugate against colon carcinoma, World J Gastroenterol Aug. 7, 2005;11.
Marshall et al, Calicheamicin Derivatives Conjugated toMonoclonal Antibodies: Determination of LoadingValues and Distributions by Infrared and UVMatrix-Assisted Laser Desor, Analytical Chemistry, vol. 69, No. 14, Jul. 1997.
http://users.rcn.com/jkimball.ma.ultranet/BiologyPages/M/Monoclonals. html.
Nicolaou et al, Chemistry and biology of natural and designed enediynes, Proc Natl Acad Sci U S A. Jul. 1, 1993;90(13):5881-8.
Henry, Celia M., Drug Delivery, CN&E, vol. 8, No. 34 pp. 39-47, Aug. 26, 2002.
Hinman, Lois M. et al.; "Preparation and Characterization of Monoclonal Antibody Conjugates of the Calicheamicins: A Novel and Potent Family of Antitumor Antibiotics" Jul. 15, 1993; Cancer Res. 53, 3336-3342.
Zhen, Li J. et al.; "Biodistribution of monoclonal antibody and Fab fragment and antitumor effect of their conjugates on hepatoma xenografts", Oct. 16, 1994; Inst. Of Med. Bio., Beijing;16(5):328-33.
Zhou, CS et al., "A monoclonal antibody directed against an enediyne antitumor antibiotic and its preliminary application," 1997; Inst. Of Med. Bio., Chinese Acad. Of Med Sc; 32(1):28-32.
Liu, XY et al., "Antitumor effect of lidamycin-containing monocional antibody immunoconjugate with downsized-molecule" 2001: Inst. Of Med. Bio., CAMS, Beijing: 23(6):563-7; Dec. 23, 2001.
Borders, Donald B. et al., eds. "Enediyne Antibiotics as Antitumor Agents." (NY, Basel, Hong Kong:Marcel Dekker, Inc.); 1995, no mth available.
H. Maeda et al., eds. "Neocarzinostatin—The Past, Present, and Future of an Anticancer Drug." (Springer-Verlag Tokyo); 1997.
E.L. Sievers et al., "Selective Ablation of Acute Myeloid Leukemia Using Antibody-Targeted Chemotherapy: A Phase I Study of an Anti-CD33 Calicheamicin Immunoconjugate;" Blood 93: Jun. 11, 1999, pp. 3678-3684.
Brukner (2000) "Curr. Opinion Oncologic, Endocrine & Met. Invest. Drugs" 2:344, no mth available.

Fig. 6

```
         BamHI       EcoRI
   1  GGATCCGGGAAGACCGGAATTCCGCCCCCAGCCGGTCGAACTCGTATCGCTCCTGTAGAACTGACGAAGGTCATCGCCGAGGAGGCGGACCG       100
                                                                              sgcA >
 101  ATGAGGATGCTGGTCACAAGCTGACGTACTCCGGCGGGGAGGCGTTTCATCGGCGGTTCGTGCGGAGCACGCTGCACGGCGAGCCCGGGTGA       200
        M  R  M  L  V  T  G  G  G  A  G  F  I  G  S  Q  F  V  R  A  T  L  H  G  E  L  P  G  S  E  D  A  R  V  T
                                                                     SacII
 201  CGGTCCTGACAAGCTGACGTACTCCGGCAATCCGGCGGCCAATCTCACCTTCGTCCAGGGCGACACCGTCGACCC                      300
        V  L  D  K  L  T  Y  S  G  N  P  A  N  L  T  S  V  A  A  H  P  R  Y  T  F  V  Q  G  D  T  V  D  P
 301  GCGCGTCGTCGACGAGGTGGTCGCCCACGACGTCATCGTCCACTTCGCGGCGGAGTCGCACGTGGACCGCTCGATCGACACCGCCACCCGGTTCGTC       400
        R  V  V  D  E  V  V  A  H  D  V  I  V  H  F  A  A  E  S  H  V  D  R  S  I  D  T  A  T  R  F  V
 401  ACGAACAAGTGCTGGGACACCAGAGCTCGGAGACGTCGTCGAAGGGGGCGTCGAAGGCGGGTTCGTGCACGTGTCGACCGACGAGGTCTACGGGTCGA      500
        T  N  V  L  G  T  Q  T  L  L  E  A  A  L  R  H  G  V  G  R  F  V  H  V  S  T  D  E  V  Y  G  S  I
 501  TCGCCTCGGGCTCATGGACCGAGGACACCCCGCTGGCGCCCAACGTCCCCTACGGCGTCGAAGGCGTCGATGCGGTCGACCTGATGGCGCTGGCCACCG      600
        A  S  G  S  W  T  E  D  T  P  L  A  P  N  V  P  Y  A  A  S  K  A  G  S  D  L  M  A  L  A  W  H  R
 601  CACCCGGGGCCTGACGTCGTGCGACCGGTGCAACGCCGGTGCAACCAACTACGGCTGCCCTACCAGTACCCCGAGAAGGTGATCCCGCTCTTCGTCACCAACATCCTC      700
        T  R  G  L  D  V  V  V  T  R  C  T  N  N  Y  G  P  Y  Q  Y  P  E  K  V  I  P  L  F  V  T  N  I  L
 701  GACGGCTTGCGGGTGCCCCTGTACGGGGACGACGGCGCGCACCGGCGGGACTGGCTGCACGTGTCCGACCATTGCCGGGCCATCCAGATGGTCATGAACTCCG       800
        D  G  L  R  V  P  L  Y  G  D  D  G  A  H  R  R  D  W  L  H  V  S  D  H  C  R  A  I  Q  M  V  M  N  S  G
 801  GCGCGGGCCGGGGAGGTCTACCACATCGGCGGCGGCACGGAGGCACGGAACTCCAAGGAACTCACGGGGCTGTTGCTCACGGCGTGCGGCACCGACTGGTCCTG       900
        A  G  E  V  Y  H  I  G  G  G  T  E  L  S  N  E  L  T  G  L  L  L  T  A  C  G  T  D  W  S  C
 901  CGTGGACCGGGTGGCCGACCGGCAGGGCCATGACCGGCGGCGCGACCTCGGGGCTACGGGGAACTCGGCTACGAGCCCCTGGTCGCCTTC                    1000
        V  D  R  V  A  D  R  Q  G  H  D  R  R  Y  S  L  D  I  T  K  I  R  Q  E  L  G  Y  E  P  L  V  A  F
1001  GAGGACGGCCTGGCCGCGACGGTGAAGTGGTACCACGAGAACCGTTCGTGGCAGCCGGTCGAAGGAGCGCGGCTGCTCCTCGGACGCGTCGGCTGAC         1100
        E  D  G  L  A  A  T  V  K  W  Y  H  E  N  R  S  W  Q  P  L  K  E  A  A  G  L  L  D  A  V  G  *
                                                               sgcB >  M  T  A  V  K  E  P  T  S  R  A  G  R  R  E  W  I  A  L  V
1101  GGCAGCCACCGCTAGGAACACCCCGTGAGGAGCCACCTCCGTGACAGCCGCAGTGAAGGAGCCGACGTCCCGCGGAGGAGCGCGGGAGTGGATCGCTCTCG       1200
                        KpnI
1201  TCGTCCTCCTCTTGCCCACGATGCTGTTGATGCTGGACATCAACGTCCTCATGCTGGCGGACCATCAACGTCCTCATGCTGGCGCTGCCGCAGCTCGAGGATCTCGGCGCGCAGCAGGCCACGCA       1300
        V  L  S  L  L  P  T  M  L  L  M  L  D  I  N  V  L  M  L  A  L  P  Q  L  S  E  D  L  G  A  S  S  T  Q
1301  ACTGTGGATCACCGACATCTACGGATTCGCGATCGCCGGCTTCCTGGTGACCATGGGCACCCTGGGCGATCGGATCGGCGCGCGGCTCCTGCTC       1400
        Q  L  W  I  T  D  I  Y  G  F  A  I  A  G  F  L  V  T  M  G  T  L  G  D  R  I  G  R  R  L  L
1401  GGGGGGCGCGGCCGTCTTCGCGGTCGTGAGCGTCGTGGCCGCGTTCAGCGACTCGGCCATGCTGGTCGTCTCGCGCGCCGTCTCGGGCGTCGGCGGG         1500
        G  G  A  A  V  F  A  V  V  S  V  V  A  A  F  S  D  S  A  A  M  L  V  V  S  R  A  V  L  G  V  A  G  A
1501  CCAGCGGTGATGCCGTCGCGACCCTCGCGCTCATCAGCAACATGTTCGAGGACCCCAAGGAGCGGGGCACGGCCATCGCGATGTGGGCGAGCGCCATGATGGCC        1600
        T  V  M  P  S  T  L  A  L  I  S  N  M  F  E  D  P  K  E  R  G  T  A  I  A  M  W  A  S  A  M  M  A
1601  CGGAGTGCAGGCGGATCGGCCCGCCGTTCGTGCTGATGCTGTGCTGGTGCTGTG         1700
        G  V  A  L  G  P  A  V  G  G  L  V  L  A  A  F  W  G  S  V  F  L  I  A  V  P  V  M  L  L  V  V
```

Fig. 6 cont'd.

```
1701 GTCACCGGCCCGGTGCTGCTCACCGAGTCCCGCGACCCGGACGCCGGGCGCCTCGACCTGCTCAGCGCCGGGCTCTCCCTCGACGCGGCTGCCGGTGA  1800
      V  T  G  P  V  L  L  T  E  S  R  D  P  D  A  G  R  L  D  L  L  S  A  G  L  S  L  A  T  V  L  P  V  I
1801 TCTACGGACTGAAGGAGCTGGCCCGGACCGGTGGGACCTGGGACCCGCTCGCCGCGGGCGCTGTCGTCCTCGGCGTGATCTTCGGCGCCCTGTTCGTCCAGCGCCA  1900
      Y  G  L  K  E  L  A  R  T  G  W  D  P  L  A  A  G  A  V  V  L  G  V  I  F  G  A  L  F  V  Q  R  Q
1901 GCGGCGTCTGGCCGACCCCATGCTGGACCTCGGGCCCTCTTCGCCGACGAGCACCCTGCGCGCCGGTCTCACGGTCAGTCTGGTCAACGCCGTCATCATGGGC  2000
      R  R  L  A  D  P  M  L  D  L  G  L  F  A  D  R  T  L  R  A  G  L  T  V  S  L  V  N  A  V  I  M  G
                                                                                                    SphI
2001 GGGACCGGACTGATGGTCGCCCTGTACCTCCAGACGATCGCCGGCCACTCCCCGTTGGCCGCCGGCTGTGCCTGCATGCTCGTCG  2100
      G  I  G  L  M  V  A  L  Y  L  Q  T  I  A  G  H  S  P  L  A  A  G  L  W  L  L  I  P  A  C  M  L  V
2101 TGGGCGTACAGTGTCGAACCTGCTGGCCCAGCGGATGCCGCCCTTCCCGGGTGCTGCTGATCGGGCTGCTGATCGCCGTCGGACAGCTCCTGATCAC  2200
      G  V  Q  L  S  N  L  L  A  Q  R  M  P  P  S  R  V  L  L  G  L  L  I  A  A  V  G  Q  L  L  I  T
2201 CCAGGTGGACACCGAGGACACCGCCCTCCTCATCGCGGCCACCACCCTGATCTACTTCGGGGCCGATCACCACGGCGCCGATCATG  2300
      Q  V  D  T  E  D  T  A  L  L  I  A  A  T  T  L  I  Y  F  G  A  S  P  V  G  P  I  T  G  A  I  M
2301 GGACCGGCCCCCCGGAGAAGGGCGCGGCCGCCAGCAGCCTGTCGGCGACGGGCGAGTTCGGAGTGGCCCTCGGCATCGCGGGCTCCTGGGGAGTCTGG  2400
      G  A  P  P  E  K  A  G  A  A  S  S  L  S  A  T  G  E  F  G  V  A  L  G  I  A  G  L  G  S  L  G
2401 GCACCGGTCGTGTACAGCGGGGTCGAGGTCCCGGACGCGGCCGGCCCGGCCGACGCCGACGCAGCCCAGGAGTCCATCGCCGGCGCTCTCCACACG  2500
      T  V  V  Y  S  A  G  V  E  V  P  D  A  A  G  P  A  D  A  D  A  A  Q  E  S  I  A  G  A  L  H  T  A
2501 CGGTCAGCTGGCCAGGGCTCGGCCGATGCGCTCCTGGACTCCGCGACTCCGACTCGGCGCCGTCCAGTCCGGTGCAGTCGCGGAGAACGACGCTCAACCGG  2600
      G  Q  L  A  P  G  S  A  D  A  L  L  D  S  A  R  A  A  F  T  S  G  V  Q  S  V  A  V  C  A  V  F
2601 TCCCTGGCGCTCGCGGTCCTCATCGGGACTCCGTCTCCGGACGCATTTCCGGACATGGATCACGGGCATGGCGAGCCAGCGGAAAACGACGCTCAACCGG  2700
      S  L  A  L  A  V  L  I  G  T  R  L  R  D  I  S  A  M  D  H  G  H  G  E  E  P  A  E  N  D  A  Q  P  A
2701 CCACATGAGCCGGAACGGCCACTTCCGGAGATGCAACGGCCCGCCAGGAACTGCACGGCCATGATGACCGGCCAGGAAGTCCTTCGCCCTT  2800
      T  *
2801 GGAACAGCCACGGGCGAGAGACCATGCCCCGAGAACATCACCTCCATGGCGGACTACGGCGGCGGGTGCCTCTCCGCCAAGGCCCAGAAGGCTTTCGCCCTT  2900
2901 CTGGGCGGGAACGACTCCCGGACACTGGCCCTGGCCTGCTGGATCC  3000
                          BamHI
3001 TCTCCCCTTACGGCACCTGGCCTGGCCTGGATCC  3035
```

```
Gdh       1:~~~MRVLVTGGAGFIGSHYVRQLLGGAYPAFAGADVVVLDKLTYAGNEENLRPVADDPRF: 57
TylA2     1:~~~MRVLVTGGAGFIGSHETGQLLTGAYPDLGATRTVVLDKLTYAGNPANLEHVAGHPDL: 57
SgcA      1:~~~MRMLVTGGAGFIGSQFVRATLHGELPGSEDARVTVLDKLTYSGNPANLTSVAAHPRY: 57
MtmE      1:MTTTSILVTGGAGFIGSHYVRTLLGPR..GVPDVTVTVLDKLTYAGTLTNLAEVSDSDRF: 58
consensus 1:    mrvLVTGGAGFIGShyvr lL g  pa      v VLDKLTYaGn  NL  Va   prf: 60

Gdh       58:RFVRGDICEWDVVSEVMREVDVVVHFAAETHVDRSILGASDFVVTNVVGTNLLQGALAA:117
TylA2     58:EFVRGDIADHGWWRRLMEGVGLVVHFAAESHVDRSIESSEAFVRTNVEGTRVLLQAAVDA:117
SgcA      58:TFVQGDTVDPRVVDEVVAGHDVIVHFAAESHVDRSIDTATRFVTTNVLGTQTLLEAALRH:117
MtmE      59:RFVRGDICDAPLVDDLLAVHDQVVHFAAESHVDRSILGAADFVRTNVTGTQTLLDAALRQ:118
consensus 61:  FVrGDi  d       vv evm   dvvVHFAAEsHVDRSI a   FV TNV GTntLL  aAl    :120

Gdh       118:NVSKFVHVSTDEVYGTIEHGSWPEDHLLEPNSPYSAAKAGSDLIARAYHRTHGLPVCITR:177
TylA2     118:GVGRFVHISTDEVYGSIAEGSWPEDHPVAPNSPYAATKAASDLLALAYHRTYGLDVRVTR:177
SgcA      118:GVGRFVHVSTDEVYGSIASGSWTEDTPLAPNVPYAASKAGSDLMALAWHRTRGLDVVVTR:177
MtmE      119:GIETFVHISTDEVYGSIDAGSWPETAPVSPNSLYSAAKASSDLVALAYHRTHGLDVRVTR:178
consensus 121:gv kFVHvSTDEVYGsI  GSWpEd pl PNspY A KAgSDLiAlAyHRThGLdV vTR:180

Gdh       178:CSNNYGPYQFPEKVLPLFITNLMDGRRVPLYGDGLNVRDWLHVTDHCRGIQLVAESGRAG:237
TylA2     178:CSNNYGPRQYPEKAVPLFTTNLLDGLPVPLYGDGGNTREWLHVDDHCRGVALVGAGGRPG:237
SgcA      178:CTNNYGPYQYPEKVIPLFVTNILDGLRVPLYGDGAHRRDWLHVSDHCRAIQMVMNSGRAG:237
MtmE      179:CSNNYGSHQFPEKVIPLFVTSLLDGREVPLYGDGTNVRDWLHVDDHVRAIELVRTGGRAG:238
consensus 181:CsNNYGp  QfPEKvlPLFiTnllDG  VPLYGDG n RdWLHV DHcRgi lV   GRaG:240

Gdh       238:EIYNIGGGTELTNKELTERVLELMGQDWSMVQPVTDRKGHDRRYSVDHTKISEELGYEPV:297
TylA2     238:VIYNIGGGTELTNAELTDRILELCGADRSALRRVADRPGHDRRYSVDTTKIREELGYAPR:297
SgcA      238:EVYHIGGGTELSNEELTGLLLTACGTDWSCVDRVADRQGHDRRYSLDITKIRQELGYEPL:297
MtmE      239:EVYNIGGGTELSNKELTQLLLDACGAGWDRVRYVTDRKGHDRRYSVDCTKIRRELGYRPA:298
consensus 241:eiYnIGGGTELtN ELT  vLe cG dws v   V DR GHDRRYSvD TKIr ELGY P :300

Gdh       298:VPFERGLAETIEWYRDNRAWWEPLKSAPDGGK~~~~:329
TylA2     298:TGITEGLAGTVAWYRDNRAWWEPLKRSPGGRELERA:333
SgcA      298:VAEDGLAATVKWYHENRSWWQPLKEAAGLLDAVG~:332
MtmE      299:REFGDALAETVAWYRHHRAWWEPLTRAYGAVAA~~~:331
consensus 301:    f egLA Tv WYrdnRaWWePLk a  gg          :336
```

Fig. 7

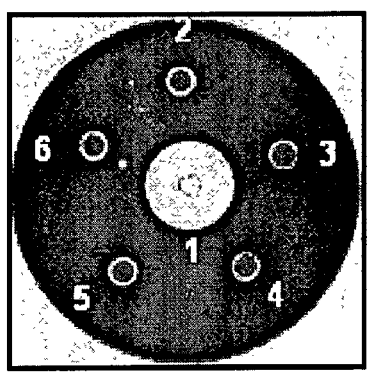 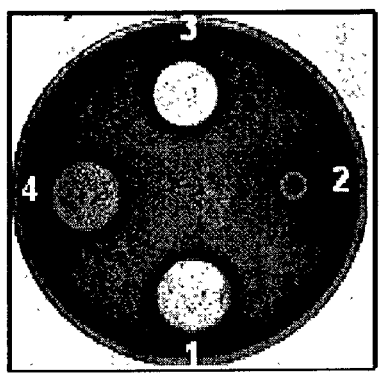 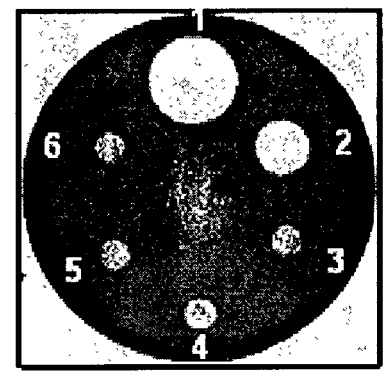
*Fig. 9A*   *Fig. 9B*   *Fig. 9C*
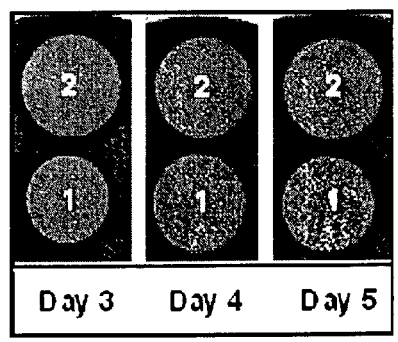
*Fig. 9D*

Fig. 17
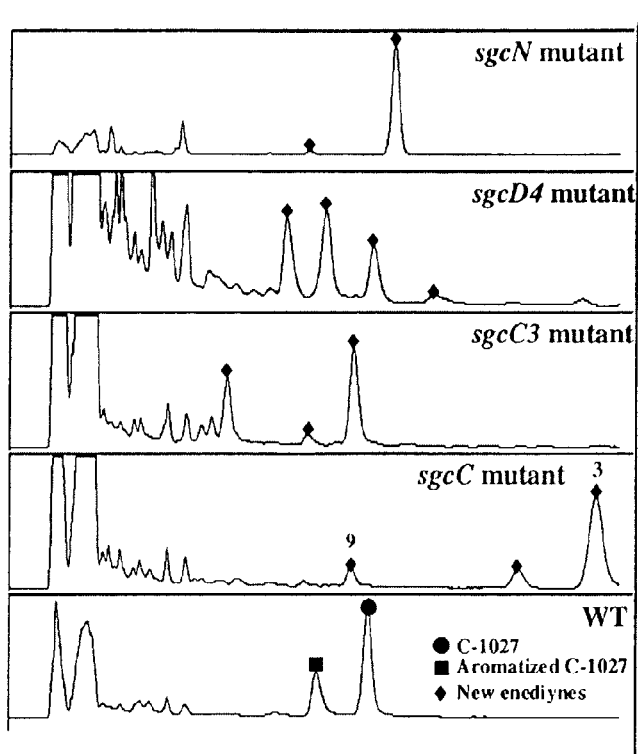
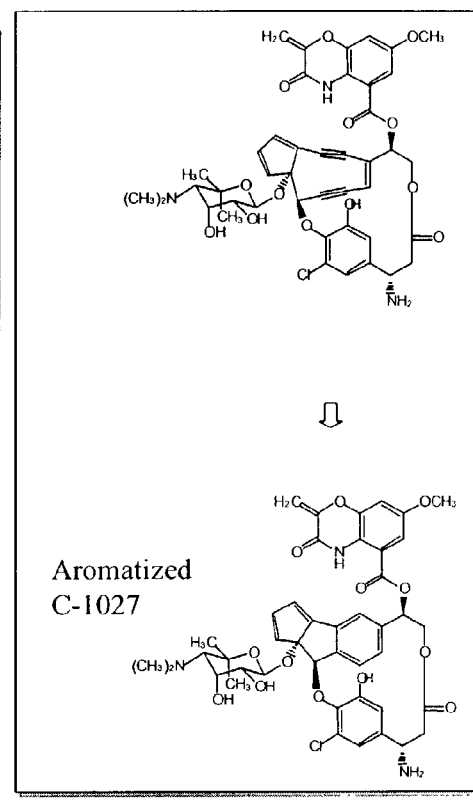
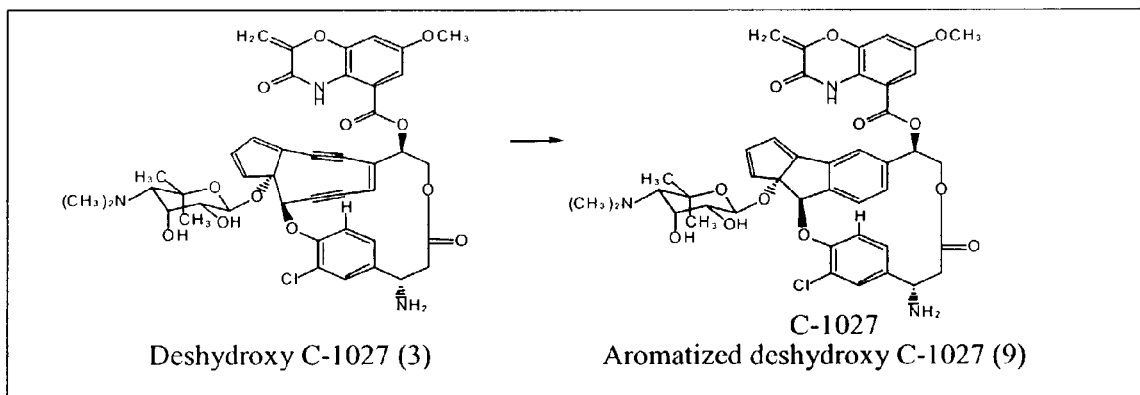

C-1027: $R_1$ = OH, $R_2$ = Cl, $R_3$ = $OCH_3$
Deshydroxy-C-1027: $R_1$ = H, $R_2$ = Cl, $R_3$ = $OCH_3$
Deschloro-C-1027: $R_1$ = OH, $R_2$ = H, $R_3$ = $OCH_3$
Desmethoxy-C-1027: $R_1$ = OH, $R_2$ = Cl, $R_3$ = H Deshydroxy-C-1027

C-1027

Deschloro-C-1027

C-1027

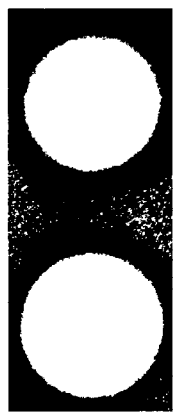 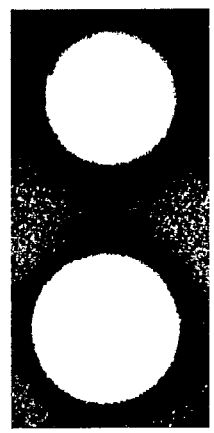
Fig. 22 A                    Fig. 22 B

Comparison of Degradation Rate of Enediyne Compounds

C-1027 chromophore

Deshydroxy-C-1027 chromophore 90 min
60 min
30 min
0 min

Enediyne compound;

Aromatized compound;

*Room temperature: 25°C.*

SEQUENCE LISTING

<160> NUMBER OF SEQ ID NOS: 146

<210> SEQ ID NO 1
<211> LENGTH: 63158
<212> TYPE: DNA
<213> ORGANISM: Streptomyces globisporus

<400> SEQUENCE: 1

| | | | | | | |
|---|---|---|---|---|---|---|
| gtcgactcta | gaggatcccg | ggtgcggagt | aggggttacg | gacgaaggag | gggtgcccgg | 60 |
| cgacgcctgc | ggcgaagggc | ggttccttga | gttcgaggcc | ggtggcgagg | acgacgtggt | 120 |
| ccgcgtcgag | gatctgcgtg | tcggggagcg | gcccagggcg | cagcccctcg | gtcaggtacg | 180 |
| gggtgaggcc | cctgacggtc | acctcgaagc | agcggtcgtg | ggaccgggcg | tcgagcgcct | 240 |
| ccccgtccgc | ttccacaagg | acgacgccgg | gacaggactc | ccgtgcggcc | tcgaccagtc | 300 |
| gggcgtcgag | gtagtcctgg | aagatgcggc | ggggggcggg | gccctgttcg | gtgaacttcc | 360 |
| acgaagccca | gcgccggggc | cagtcgcgcc | ggtcggcctc | ctggttggcc | cagttgatga | 420 |
| agtcgagcac | gtcctcgcgg | aacaccgaca | tcctgccggc | ctggatattg | aagacgtggt | 480 |
| cccagggggtt | gccgtcacgg | tgataggcga | cgccggccga | gcggtaggcg | gcgcgccgct | 540 |
| ccaggaggac | gacttccagc | ggtcttctcg | cgaaatgaag | caggcgtatc | gcggtcgccg | 600 |
| tgcctgccag | gcccgcccct | acgaccagca | ccctggggcg | cgcacccgtc | atgcccatga | 660 |
| agcctccccc | gctgactcag | ggcggcgcgt | cgcgcgctcc | cgtcggtgtc | ctcgctgact | 720 |
| ggaagttccc | tgacctggcg | tcaactccac | tgatccgtaa | ggggatcgcg | ggagtggata | 780 |
| cgggtcaggt | cgtgcacgat | cgtggcacca | gacagatcac | cacgtcgata | ggcactcgtg | 840 |
| agccgcgccc | ggggctcgac | ggggcgggggc | accggcaggg | gcggccgcgt | gatcagccgg | 900 |
| agcctgtccg | ggggcgtgcg | tgcggggcgt | cagctgtcga | tgtcgggaac | gccagggacg | 960 |
| tcgatctcgg | tgcgggcgta | gtggttgaag | tagttggtgt | agaggttcac | ggccacgtgg | 1020 |
| acgaagacct | cggcgagctc | ggtgtccgtc | catccctgtg | ccacggccgc | gttccacgag | 1080 |
| gcgtcagacg | cctcgcccac | ttcgccggcg | atctccctgg | ccacctggac | cagtgcttcg | 1140 |
| agcttcacgt | cgtcgccggg | cgtccccccgg | cgaatcgcca | cggtctcctc | cagcgtgaaa | 1200 |
| cccgcgacct | tcgccgacac | cgtgtgcgcc | gcctggcagt | acgcgcacgc | gtcgaccgcg | 1260 |
| cccacggcga | gggcgatcgc | ctcgcgtgtg | cgggcgtcga | acgttccatg | ttcggcgacg | 1320 |
| gctccggtga | tcgcggcgta | ggtttccagg | accacggggg | aatgggccat | tccccgtgg | 1380 |
| atgttgagca | ctcgcccgaa | ccgcttctcc | agtcggcgca | ggatgtctcc | gccggctgcg | 1440 |
| ggtgcggtgt | cgatggtgtg | gacgggaatc | gcggcatgg | gaatgcctct | cctcgtagtg | 1500 |
| atgggagttc | ctcgtccctc | cagtctgccc | aagcacctcc | cccggtgagc | tgtcccggcc | 1560 |
| gccctccggc | cccttctagg | caggtcgccc | ggtggtgcgg | ccccaggacg | tcacctcgcc | 1620 |
| gcaccaccgg | gagccccgag | gggcgaggtc | agaggccgag | cacctcctcg | gccagggcgg | 1680 |
| tgccccgaac | acgggcctcg | atcttggcga | aggccaggtc | gcgtgtggtg | gaggtgtcgt | 1740 |
| cggcgaacgg | ggagaagccg | cagtcgtcgc | aggttcccag | ttgctcgacg | gggatgtagc | 1800 |
| gggcggcgag | caggatgcgg | tcgcgtacct | gctcgggggt | ctcgaccact | gggtcgatcg | 1860 |
| ggtcggtcac | cccgaggaag | acgggcgcgg | cagggggcag | gtggtcacgg | acgatgctca | 1920 |
| ggacccgctc | ggggtccgct | tcgccggcca | gttcgagata | gaagttgccc | gccttgagct | 1980 |
| ggaagagctt | gggcagcagt | tcggcgtagt | cgatgtcgag | gctgtgcgtg | gagtcctggt | 2040 |

-continued

```
cgccgccggg gcaggtgtgt acgccgatgc gggcggtttc ctcggcgctg aagcgcccca      2100
ggacttcgtt gttgagggcg atgaagtcgt cgaggacgcc gccgctgggg tcgagcttga      2160
gggacagccg cccctcggtg aagtcgagct ggaccacgtg tgccccgcg tccaggcagc       2220
ctcggatgtc ggcttcggcc tcgtcggcga gtcgcgcag gaactgctcg cggggtagc        2280
cctcgatggg agtggcgggg tagggaggc tgagggcgga gggtgcgatg accgcctgct       2340
tcagggggcg gtccgtgagc tgccgtgcgg cgcgcagata ggtttcggcc cgcacctggt      2400
agcggaaggg cccttgggtg atgctgggga gctgccgggt gtgcccgtct gcgaaggggga     2460
tgacagcgcc gtcgggcgag agggtgtcga ggccggtcac ggggtaggtg gcgaagctcg      2520
gcttggactg ttcaccgtcc acgaggacgg ggctgccgac tcgttccagt cgtgtcaggg      2580
tgtccgcgac ggcctgttcc tgctgtttgg ccaggtccgt ggcgtccagg gttccctggg      2640
catgcgcggc aagggcgtgc aggagtgtcg cggagcgcgg aaggctgccg atcggctcag      2700
tggcgatggt catggccgaa gagtagggaa gaggctgggt ttcgaaccac cgcaaagctt      2760
tgattgccgc ttttttcaggg gaagttgatg cgaagtcgcc gagcggcgga acgtgctgat     2820
gtatgggggg cgggaggagc ctgcggggtt ctaggagccg gtcgcggcca cggtggagga      2880
ggtgcccagc tgggagcggg gggtcttttc gccgacgcgg ttgggctcga tggtgcgggg     2940
gtcgacggcc tctccggggg caccttgccg gtagacgcct tcggggtcgg agtcccggtc     3000
atggggggagc aggaagaaga cccggcgccg gtacagaccg ctgtccgggt ccgcttcggc    3060
gtcggccccg agttcgatgt agccgatcat gcggccgtcg cgggcgtagc gcggcttgtt     3120
cttgcgccgg ggggtcttgt ccagggcctg gcggacgtag tcgagtccct cgggatcttc     3180
gagccacacg accttcgcct cgtgaacgag atcgctgtcg gtcagtagcg agctcatggc     3240
ggcgacctct ccttcgtcgg cgtgcaccgg gtggggaagc ggtgcctgcg tgatgtgtgt     3300
tcgtctgcgg cggtgggccg cagtggtgcg gaccgcccgt ggtgccggtt ctcggccaaa     3360
gcacgggcag gtacgtcctg gggcactcac atcgtagatg gggtccgctt ccgcagggca     3420
gtgcctccgg tcgaggacg ttcattcgtc ggctgccaga gcgaggttgg ggtagaactt      3480
ccggccgttg gatttgatca tgtcggcagg tgaggcgagg cccacttcct ggcggacccg     3540
ggtggcgaag gcacgggcgg tcccggggcg gatgccttca ctgtgtgcgc accaggtgct     3600
gtaggacgtg tagagaaggc cctgttcgac gcgtagctcg ctgttctcgg ggtcgtggag    3660
gcagcactcg gcgaggaagc ggccgatgtg gtcctcggtg ttcgcgtatg cgctggtggc    3720
gatgcggacc cggtcggggc cggcgagtgt gtcgcgggtg gcgaggtagc ggcgggcccc    3780
ttcggtgagc cagtgcagga tcccggggcc ctcgtcctgg acgagttcga cagccaggtt    3840
gtcgatcttg cgttcgtcgg ggacgatccg ttcgaagggc aggaggcgga tgcggcgcca    3900
gaaggcgaag ccgccggtgg agacctcggg gcggtggttg cccagcagcc acagcttgtg    3960
cgtgggtgtg aaggagaaat agtcctgccg catgcggcgg gccttgatct tgtcaccgcc    4020
ggtcagcagg cggacgcgcg cctcgtcgaa gcggtcgttg ggcttgagct cgctgcacac    4080
gatgaggcgg cggccgtgga gttcggtgag ctcggtggag tgttcggagt atgcgccacg    4140
gtccatgagg aaacccggcg gggctgcgtc ggcgtagtcg ccgagaatct ggatcatcac    4200
gtcgaggaga acgatttgc cgttctttcc ctggccgtga agaaagggca gcacctgcgc     4260
cccgacgtca ccggtgatgg agtagccgag aaggaggtgg aggaagtcga tcatctcccg    4320
ccccttcggcg tcactgccga aggtgtcttc gaggaaacgg tgccagcggg gggtggggat   4380
```

-continued

| | | | | | |
|---|---|---|---|---|---|
| gtcctgggggg | gaggcgctgg | tggcgcggga | gtggaagtcc | cgggtgtggggt | cgggcttgcg | 4440 |
| catacggccg | ttgcggaggt | cgaccactcc | gtcagggtg | cacagggcgt | agggtctcc | 4500 |
| gtcgagggtg | tcgggatcga | gggagaggtc | gggagaggcc | tttgcctggg | tgaggagcgc | 4560 |
| cttcataccg | gtcgtcgaca | gggtgcggcg | tttgtggtgg | tgcagttccc | ggtcggtgaa | 4620 |
| cagcccgcgg | ggatcgctgc | cgggcatctc | ctccgccatc | tctccggcag | cccacagggc | 4680 |
| agctttctcg | cctccggccc | gcttccaccg | gtagccgtcc | caggagtacc | agcccaggcc | 4740 |
| ctccacgtgc | cggaactggt | cacggtagag | acggacgaag | agcttggcgt | tgccgcggtc | 4800 |
| ggtcaggctg | gcgggaatct | cgcccgcctc | caggcggtc | gcggcgacgg | gggcctcggg | 4860 |
| agcggcctgg | acaggagga | gcggcgctgg | ggccggggtg | gtttcgaggg | ccagcatctg | 4920 |
| ctgagcggcg | gcagttgcgt | caaagcgagg | gccctcggcg | ctgctgctca | tggacgtcct | 4980 |
| tcgagatgga | gcggtcgggc | ggtccccgct | gcgggaacgg | catgaatgat | cttcccggtg | 5040 |
| cggacagagt | gccaggggca | gcgcatgtgc | gggggggacaa | cggcccgttt | cggacgaggg | 5100 |
| ccggccgacg | gggggaagca | ggggccggca | accgggtggc | ggggcggcgt | gagcgagggc | 5160 |
| acgagcggcc | cggtacgggg | ggaagggctc | gtctctccgt | ggggcggcac | gttgtggtcc | 5220 |
| tcgtccgtca | gcttgcgtct | ggcttcagcc | tcctgacccc | caataaggcg | aaagctgctg | 5280 |
| gtcaagcatc | tttcgtgaca | ctcggcgagg | gactgaaggg | actgtctttc | ggaatgagtg | 5340 |
| taggggggttg | tcgggtgggg | accgcgcctc | gactccccgg | cggacgggat | ctgttcggtc | 5400 |
| ggtcccttgg | gtccctcccc | ggatcgcggc | agggacccaa | gggggcggtg | cggcgggcgg | 5460 |
| tcggtgaggg | gccccggtgg | agggactgag | ggtctgtatg | gagcgataag | agggtctgaa | 5520 |
| ggggcggaga | gagtttcggt | ccctgcgttg | agtccctggt | catcaccgca | ggtcagaggg | 5580 |
| gttttgaggg | gtgaaaaagg | gactgaaggg | actcaacttc | cccattatga | gctgagtaga | 5640 |
| agaaagcagt | atgacgatat | cggcgcctac | atacgcgcgc | gtacatagtg | agcttataat | 5700 |
| gcggaagttg | agtcccttca | gtcccttttc | gtgggggtcgt | atccctctg | actgcgttga | 5760 |
| ccgtcgccgc | tccgcgcagg | gaccgaagag | ggaccaagtc | cctgcgcggg | gcgggcgacg | 5820 |
| gtaatcgtgc | agtgcccccct | cccccgtttc | ccacagcgag | tcgtcgctcc | cctgtgaggc | 5880 |
| cggagagggt | cctagaaccc | ctcagggcc | gttctgtggc | cctctgggcc | tcctcctggc | 5940 |
| catttacccc | atgggggcgc | ttgggggcgt | caggagggct | tgtgagggct | ctgccgggaa | 6000 |
| gtggcggatt | gcgcatggca | ggagatgccc | cgacagcggc | cgggaatcga | cgatgtcccc | 6060 |
| cgaccctat | ccagcgtccg | ctgatcctca | ggaggcagac | cttgcaggct | ccagaagcga | 6120 |
| agaacggccg | gtccccggag | cagccgcagg | aagagcggat | cgtcctggac | gtatggctgg | 6180 |
| cgaactaccc | gttccccacc | tatgacgggc | gtgacttcct | cgctccgctg | cgcgagcggg | 6240 |
| cggcggagtt | cgagcgcgcc | cacccccgat | accgggtcga | catcaacggc | cacgacttct | 6300 |
| ggaccatccc | cgagaaggtg | gcgcgcgcca | ccgcggaggg | caggcctccg | cacatagcgg | 6360 |
| gctactacgc | caccgacagc | cagttggcgc | gggacgcgcg | caggcccgac | gggaagccgg | 6420 |
| tcttcacctc | ggtggaggcc | gcgttggccg | gccggacgga | gatactggga | cacccggtgg | 6480 |
| tggtggagga | cctcgacccc | gtggtgcgcg | actcctactc | gttcggggc | gagttggtgt | 6540 |
| cgctgccgct | cacggtcacc | accatgtctct | gctacgccaa | ctcctcctc | ctcgcgcgcg | 6600 |
| ccggtgttcc | ggagttgccc | cgtacctggg | atgaggtcga | agcagcctgc | caggcggtgg | 6660 |
| ccagcgtcga | cggggggccc | ggtcacggaa | tcacctgggc | caacgacggc | tgggttttcc | 6720 |
| agcaggccgt | cgcccttcag | aacgggggtgc | tgaccgatca | ggacaacggc | cgctccggct | 6780 |

-continued

```
ccgccacgac ggtggacgtc acatcggacg agatgctgga ctgggtccgc tggtggacgc   6840
acctccatga gcgcggccat tacctctaca cgggcgggcc ctcggactgg ggcggggcgt   6900
tcgaggcttt cgtccagcag aaggtcgcat tcaccttcga ctcgtccaag gccgcccggg   6960
aactcatcca ggccggtgca caggccggtt tcgaggtcgc ggtgttcccg ttgcccagga   7020
acgcgaaggc cccggtagcg ggccagcccg tctcgggaga ctccctgtgg ctggccgcgg   7080
gactcgacga gaccacgcag gacgggctgc tcgctctcac ccagtacctg atcagcccgg   7140
ccaacgccgc ggactggcac cgcaccaacg gtttcgtacc ggtgaccggc gcggccgggg   7200
aactgctgga agcgacaggc tggttcgacc gccggccgca gcaacgggtg gccggggagc   7260
agttgaaggc gtccgaccgg tcaccggcgg cgctcggcgc gctgctcggc gacttcgcgg   7320
ccgtcaacga ggtcatcacc gcagcgatgg acgatgtcct gcgcagtgga gcggaccccg   7380
cgaaggcctt cgccgaagcc ggcgtggccg cccagcaact gctcgatgcc tacaacgccc   7440
ggaaccgctc cggatccggg acccctccg ccgtctgaga tccggtaccg gggcacaggg   7500
gcgccgccgc ccgctttccc ggcggggcac tggccggggg acatgctctc cgcccccgg   7560 caggacgtag ggtcaacccg cctgcgcctt caggtggcgg cgcagatact caccggtcag   7620
ggaggaatcc gcggcgagca ggtccttcgg tgtgccggtg aagacgatct cgccgccctc   7680
ccgtcccccg tcgggaccca ggtcgatgat ccagtcggcc tgctgcacca catcgaggtt   7740
gtgctcgatg accacgacgg tgttcccggc ctcgacgagc ccgtccagga gcttcagcag   7800
ggtgtcaacg tccgacatgt gcagcccggt ggtgggctcg tccaggacat agaccgtgcc   7860
cgtgcggtgc agctggtcgg caagtttgat ccgctgcagt tcaccgccgg agaggctgga   7920
aagcggctgg cccaggctga ggtacccaag accgacgtcg acgagagcgc gcagtttcgg   7980
cagcagggcc ttctcggtga gaactcgac ggcctcgtcg gcgggcagct ccaggacgtc   8040
cgcgatcgac ttcccgcgaa gctggtgctc caggacctcg ggcttgaagc ggcgcccctc   8100
acagacaccg cagtgcgtgg tcaccggatc catgaaggcc agctcggtga tgatgacccc   8160
gcggccctgg cactcctcgc acgacccctt ggagttgaag ctgaacagcg aggcgttcgc   8220
gccggtctcc ttcgcgaaca gcttgcgcag cgggtccatc aggccgaggt aggagaccgg   8280
tgtggagcgc gacgaggcgg cgatcgcgga ctggtcgaca aagaccgcgt cggggtgcgc   8340
ctccatgaat gccccggaga tcaggctgct cttgccggaa cccgccaccc cggtcaccgc   8400
ggtcagcaca ccggtgggca cggccacgga gacctgcttc aggttgtgga gatccgcgtt   8460
ctccacggtc agctccccg tgggcgggcg gacctcctcc ttcacgcggg cccccgccg   8520 cagagcctcc ccggtccggg tcttcgcctt ccgcagcttc gcgaaggacc cctcgaacac   8580
gatctcgccc ccgtgcactc ccgccccggg accgacatcg acgatgtggt cggcgatctc   8640
gatcacatcg gggtcgtgct cgacgaccag cacggtgttc cccttgtcgc gcagcgcgcg   8700
cagcaggtcg ttgagccgcc ccacgtcgcg cgggtgcagg ccgatgctgg gctcgtcgaa   8760
gatgtacgtg agcccggcca gaccactgcc gaggtggcgc accatcttca gccgctgccc   8820
ctcgcccccc gagaggtcgg ccgtgggcct gtccagggtc aggtagccga gcccgatgga   8880
cacgatccgc tccagggccg tgcgcgcgg tttcgcgaga ggggcagcgg ccggctccgt   8940
gacgccggcg agcacctccg tgaggtcgcg gacctccatg ctcgagtagt cggcgatgtt   9000
cttgccgtcg atccggacgt cgagcgcggc ggcgttgagc cgcgcgcccc ggcaggaggg   9060
acagactccg tcggtgacga aacgttcgat gacctcgcgc ttgcggtcgc tcagcgcgct   9120
```

```
gaggtcgcgc ttgaggttga gccgctcgaa ccggtcggcc aacccctcgt agttcgtctg    9180
gaactcggtg ctcttggtct tcagcgtcac cttcccgccg gtgccgcgca gcagcgtgtc    9240
cagctcctcg gcgctgtact cggcgatcgg cttggccgga tccagacggc cggacttcgc    9300
ccagatctgc cagtccgggc tacccacctt gtactcgggg aaaaggaccg ccccgtcgtc    9360
cagggacttc gagcggtcca gcatcttgtc caggtcgagg gcgatgctct ggccgagacc    9420
gtcgcagtcc gggcacatgc cctggggtc gttgaacgag aacgcggaga cgccgagcga    9480
ggacggcccg tcgtccttcg tcgtgccgaa ccgtgcgaac agggcccgga tcatcggctg    9540
tacgtccgtc atggtcccca ccgtggaccg gcgttgccc cccacgggct tctggtcgac    9600
gatcaccggg gtggtgaggt tctcgatcgc ctcggcctga ggacgttcgt acttcggaag    9660
ctggttgcgg atgtaccagc tgaaggtgga gttcagctgt cgctgggcct ccacggccac    9720
cgtgtcgaag acgatcgacg acttgcccga acccgagacc cccgtgaaga ccgtgatctg    9780
gttgcgggga atcgtcaggg agacatcttt gaggttgtgg atccgcgcgc ccgcgatgcg    9840
gatgccgtct cccgggccgg atgttttttcc cgcgccggcg gtggggtcgg tgacgctcac    9900
agagttttcc tcctggcttc cgtacatgat ttaccgtgtc agccgggcaa accggcggaa    9960
cggtaaccac ctagcttgta ctcaggaggt gtccggggtc ttctcctccc gtgctgactt   10020
gggggccggc ccgccggaca gggccggctc cgtgttccac cccgccagcc gatcccccg    10080
ctccgtctcg tcctcctcga aacgatccg gctgctcgcc cagcgcagga tcggcggcgc    10140
cgtcaccgag gtgatgaggg cgaccagcac gatgatcgtg aaggtcacgg tgtccagtac   10200
gccgatacgc aggccgacca gggcgatcac cacctcgatc attccacgcg agttcatccc   10260
cgctccgagc gccagcccct cgtagcggct catcccgcca ctacgggcgg cgacgtacgc   10320
accggcgaac ttgccgaaag tggccaccaa cagcacccg aggcccgtga gcagcaccga    10380
cggctccgcg agtgcggtca ggtccatgcg aagcccaca ctgcccagga acaccggtgc    10440
gaacacggcc atgaccagcg tgcgcagcgg ggcgagccgt accggggcga tgtgcctcag   10500
cagggtcgca ccggccacga acgccccgaa caacgcctcc atcccggccg ccgcggtcag   10560
cgccccgtac aggacgacca cggccacgcc gacggtgacg gccgatacgg ggacccggct   10620
gtcacccgta cgggacagcc gcctgccgat cgggccgccc accgcacacg ccgcggcgac   10680
gaagacggtc gtccaggcca tcgtggtcag gaccacgggc ccccggccg ccccactcgc    10740
cagcgccgtc accagagcga gcagcagcca gcccaccgcg tcgtcgaaca ccgctgccgc   10800
gatgagcagc tggccgacgt tgcggtgcgt cagattcagg tcggcgagcg tcttggcgat   10860
caccgggagg gccgtgacac acatcgcgac cccgaggaac agcgcgaaga cgccccgctc   10920
tccggagtcc gcgagcagcg aggcgggcac caggtagccg gtggcgatgc ccagcccag    10980
aggaatcaga agacccgcca ggctgacccg ggcggccaga ccccgcgct tgcgcaggat    11040
ccggggtcg aactgggcac ctgcgatggc caccagcaga aggacgccga actggcagaa    11100
cgcgtcgagc aggtgcgcct gcgagatgtc ctcgggaaac agcctgccgg aaagtcccgg   11160
cgagatctgc cccagcaggg tcggcccgag cagtaccccc gcggtcagct cccccaccag   11220
cggcggcaga ccgatccggg tccccagccg tcccagaccg taggcacagg cgagcaggag   11280
gccgacctgg agcaggaaga ccgtcagcgg ctccccgccc agcggcgacg tggctgcgag   11340
cacagccacg tcaggaccgc gcaccgggaa cccagcccag cccgtccgtc gacgcggcca   11400
gaccccctg cctcaccggt cgctcggccc ccgcctcatc cccagaaga gcccgtgcct    11460
gcagtgcggc gctctgctcc atgaggcggc ccaccacctt tcccggcacg cgccgtgcg    11520
```

```
gcccgtcggc gtcgcccgca gcggtgtgcg tcatgccggc catctcgtcg gacgcctcgg   11580
agaaccgctg cctggcccgg gccgtgtcgg cgaactcgtc ggaggagacc ccgccgatca   11640
gttcgacgaa ggactgcagg tcggagtccg cggtgttgga gatcttccgg gcctgccaga   11700
aataggagtc ctccgaatgg tgcatgtcgt agaagccgac caggaactcg tagaagcggc   11760
cgtactccag ccggtagcgg gcctcgaact cctcgaacgc gctggtctcg tcgaccgacc   11820
cgtccaggca ggagttgagc gagcgcgctg ccagcagtcc gctgtaggtg gcgaggtgca   11880
ccccggagga gaacaccggg tcgacgaagc acgcggcatc cccgaccagg gccatgcccg   11940
gcgcccagaa cttcgtgttg ctgtacgacc agtccttgcg gacccggagc tcgccgtagg   12000
ggccctcggt cacccgggtg gcctcggaga gcttctccgc gatcagcggg caggccgcga   12060
tgaacgactc catcgccttc tcggggtcgc cctgcaccag gctcgccgag tcccggttca   12120
ccactgcgcc gacactcgtc agctcggag acagggtat gtaccagaac cacccgtgct    12180
cgaaggtgca ggtgaagatg ttcccggagt tcggcttcgg aagccgcttg ccgccgttga   12240
agtagccgaa cagggccagg ttgcggaaga agggcgagta ctcgcgcttg gcgcccgact   12300
tcttgtacag cccaccggtg ttgccggagg cgtccacgac gaaacgggag cccacctcgt   12360
gctcgcgccc ctcggagtcc cggtagcgca cgccccgcac ccggccgtcc tcggccttga   12420
gcacgtcgag gacatcgctg ttctcccgca cctcgacacc gtgcctgcga gcgttgtcga   12480
gcaggatctg gtcgaacttc atgcgctcga cctggtacgc gtaccccgtc gcccccggca   12540
tccggcgcga gacggcgaag tcgaacgtcc acggttcggg gttggcaccc cacttgaacg   12600
tcccgccgtg cttgatcgtg aaggctgcct tcttcagctc gtcggagaca ccgaggaggt   12660
gtgcgatgcc gtggacggtg gaggggagga gcgactcacc gatctggtag cgcgggaagg   12720
tctccttctc cagctggagt acgcgatggc cccgcttgcg gaccagcgtg gagacggtcg   12780
agcccgccgg acctccgccg accacgatga cgtcgtactg cgctgacacg tccacggact   12840
ctccttctcg cacatcgggc gtctcatatt cccaggaatc ctctggcccg cccaggtgct   12900
gccgcatctt cggtattgcg aagtcgtggg cattctgcga aagcatgaa ccgcgtggcc     12960
cggtctacag tggcgtggaa tttcagtgat tgcgctgaag ggcggcacac gatgaaggca   13020
cttgtactgt cgggtggttc ggggacccgc ctgcgcccga tcagttacgc catgccgaag   13080
cagctcgttc cgatcgccgg gaagccagtc cttgaatatg ttctggataa tatccggaac   13140
ctcgatatca aagaggtcgc cattgtcgtc ggtgactggg ctcaggaaat tattgaggca   13200
atgggtgacg gcagccgttt cggtctgcgc ctcacctaca tacgccagga gcaacctctg   13260
ggcatcgcgc actgcgtgaa actggcccga gacttcctcg acgaggacga cttcgtcctc   13320
tacctaggcg acatcatgct ggacggagac ctgtccgcgc aggcggggca cttcctccac   13380
acccgccccg ccgcgcggat cgtcgtgcgc caggtgcccg accccgggc cttcggggtg    13440
atcgagctgg acggcgaagg gcgtgtgctg cgcctggtcg agaaacccg tgaaccgcgc    13500
agcgacctcg cggcggtcgg cgtgtacttc ttcaccgcgg acgtgcaccg cgccgtcgac   13560
gcgattagcc cgagccgacg gggcgagctg gaaatcaccg acgccatcca gtggctgctg   13620
gagcagggcc tgccggtcga ggccggccgc tacacggact actggaagga caccggccgg   13680
gtcgaggacg tcgtggagtg caaccggcgg atgctcggcc gtctggcgct ccaggtgtcg   13740
ggcgaggtgg acccgagag cgaactggtg gtgcgtgtg tcgtcgagga gggcgcccgg    13800
gtgacgcgtt cgcgggtcgt gggaccagcg gtgatcggcg cgggcacggt cgtcgaggac   13860
```

```
agccagatcg gaccgtacgc ctccatcggc cggcgctgca ccgtgcgggc gtcccggctc    13920
tccgactcca tcgtccttga cgacgcctcg atcctcgcgg tgagcggact gcacggctcg    13980
ctgatcggaa ggggcgcgcg gatcgcgccc ggggcccggg gcgaggcccg gcaccggctg    14040
gtcgtcggcg accacgtgca gatcgagatc gcggcctgac gcacccaccg gagcaccggg    14100
gggaggctcg gcaggggcgt caggccgtaa gaagggctgc cggggcggga cggacccgcc    14160
ccggcagccc acaggtcccc ggtccgcgga tatggggac tcgaggttcg atcagccgaa    14220
ggtcagagcc acgtggccga ggtcgagccc ggagttgccg gcgccgaggt tacaggcggc    14280
cgtggcgcag tcgacgctgc cgaccggcgt gccttcgggc gtggagcccg tgtacgactt    14340
gcgcacgacg aagctgaacg acgccgctcc ggacgcgtcc gtggtgaagg acgtcgcggt    14400
cgccgggttg cacgcgtcct ggccaccgac cggagcgcac tggcgatgt agtaggtctc    14460 gccggcggcg gcaccgctga ccgacaccga cacgctctgt ccgtcactca gacccgaggc    14520
gggactgacg gagaaggcgg gcgcggcgaa ggcgacggac tgtgcggcgg cggccaggcc    14580
gatggatgcg acggccacga cgccgaacct ggaagcacgg cgggacatgt gacgtaacga    14640
catgcgtagg ctccgattcg aggaggggt tgatcactcc atgaaaggat cacctcgccg    14700
gacggccgcc tgcatctccc tctgtgctct cgtggatttc cggcacggca ctcccgtcga    14760
cggccgcccg cagaatgcgg cagaccccc gcacctcctc cggccccacc gccgtaccgg    14820
tgggcagcga cagcacccgc tcggtgagcg cctccacctt cgggagcgga tcgggcgcgt    14880
ggcgcgcgag gtcggaccgg tagggctcgc agctgtggca gccggggctg aagtaggcgc    14940
gggccaggac gttgtgccgt tggagcaccg cctggagttc gtcgcggtgc agcccggcgc    15000
ggacggcgtc cacctcgatg acgacgtact ggcagttcga cagctcgttc ggatcctgcg    15060
ggcggacccg gacgccgggc agtccgtcga ggtactgctc gtacagacgg tagttgcgcc    15120
ggttgatcgc ggtgaagtga tcggcggact ccagggaggt gaggcccatg gccgcgctga    15180
tctcgtgcat ccgcgcgacc gttccgctcc cggtgatctc atgcgcggcg ttgagcccct    15240
ggtggcgcat ggcccggagc cggtcggcca gggcgtcgtc gtcggtgacg atcgccccgc    15300
cctcgaagct gttcacgaac ttcgtcgcct ggaagctgaa gatctccgcc gtgccgaagc    15360
cgccgatcgg cttcgaccgg taggtgcagc cgaaggcgtg ggcggcatcg aagagcaggt    15420
gcagcccgtg ctcggcggcc agcttggtca gctcgtcgat ccgggccggt ctgccgaaga    15480
cgtgcacgtc caggatggcg cgggtacgcg ggccgatgag ccgctccacg tgtgccacgt    15540
ccgcggttcc ggtctcctcg tccagttcgc agaagacagg caccgcaccg atccagtcca    15600
gtgcgtgggc ggtggcgacc caggtgaagg agggcacgat cacctcgtcc ccaggaccga    15660
tgcccagggc cttcgcggcg acctggatgc cggtggtggc gttcgatacg cgacgcagt    15720 gcctgacctg ggtcagctcg gccacacggg cctcgaactc ccggaccagg gggccgtcat    15780
tggtgaacca caggcgctcc agcgcccgt cgatccgttc catcaaacgg tcgcgggagc    15840
ccacgttcgg gcgtcccacg tgcagcggtt cgctgaagta gggcgtgggt agggagtcca    15900
gacgcaccgg gccgccgctc atgccgtgcg cacgccgacg aagaggccgg ggctgttggg    15960
ccggccgtcg gccagccgga agccgggcac gaaccgcacc gagagcccca ccgattcgaa    16020
ggcgtcggtg tactgctcgc gggtgaagag gctggaggtc aggacctcgg agaactctct    16080
gaagccggag gcgtccgcga cccggaaccg gacctccaga cgtgacttgt cgccctggcg    16140
cacggagtgc gtcatccgcg tgatgacacg gccctcctcc tggtgcagat ggccgccgac    16200
atgcccgtcg aggaagttct cggggaaata ccagggttcg gcgacgagga ctcccccggg    16260
```

```
gttcaggtgg tgggccatgg ccgacaccgc ggccttgagc tcggtgacgg accccatctc   16320
gccgagcgcg ttgcccatgc aggtgatcgc gtcgaaggtg cggcccaggt cgaacgaacg   16380
catgtcaccg gcgtgcagcg ggacgccggg aagccggccc gccgcctgct ccagcatcgc   16440
gggcgcgtac tcgaggccct ccacatggcc gaagagcgtg gcgagcgtct ccagatgggc   16500
tccggtgccg caggcgacgt ccaggagcga cacggcgtcg gggcgggcgg cgaggatcag   16560
ctcggtgagc ccgcgggcct ccaggtcgaa gtccttgccg cggctgcgga acacgaggtc   16620
gtagaacttc gcgtgctcgg ggccgtactc catcagacga gctccttcgc agactgggcg   16680
gagatgattc tgggctccgg gatgggaacg atgaacttcc ctcccgcctc caggaagcgg   16740
cgctccttgc ggacgacctc gtcggtgtag ttccaggcga ggaggaggta gtagtccggc   16800
tcggtggcag cgacctcctc cggaggaagg accgggatgc ggttcccggg cagcagtttg   16860
ccgtgcttga ggctggtggt gtcgccgcag acggtgatgt cctgatccgt cagaccgcag   16920
gccatcagca actgggtccc cttggacggt gctccgtagc cggccacgcg gtggccgtcc   16980
gcggccagac cgcgaacgag cgtacggatc gcttcggtca cgcgcgtcac ccgctcggcg   17040
aacgcccggt aggggcatc cgtcagcagt ccgcgctcct cctccaggcc gagcagcgcc   17100
gcgaccgagg gctccgggac ccgtgcggcc gactcgcgcg cggcgacgac cgcgatcgaa   17160
ccgccgtgca cggcgacccg ctccacgtcg atgatccgca ggccgtgcgc gccgaagagg   17220
tggcgcagtg tgtgcaggga gaagtacgac aggtgctcgt ggtagatcgt gtcgaactgg   17280
ttctcgtcga gcaggttcag caggtacggc acctcgatga ccaggacgcc gtcgtcgtcg   17340
agcactgcgt cgacgccgtc caggatgcgg tgcacgtcgt cgatgtgcgc gaagcactgg   17400
cggccgatga cggccttggc cctgccctgc tcaaggcga tgcggcccgc gggctccggg   17460
ccgaagaagt ccgggtccgt ggggatcccc cgggcgttgg cgatctcggc gaggttggcc   17520
gccgggtcga ccccggccac ccgcatgccc gccgccgga acatcgcgag ctgggtgccg   17580
acgttgctgc ccagctccac gaccaggtcg ccggaggcga ggcttgcccg gcgggtcgcc   17640
agcccgacga tgtgcgccat gtgctcgcgg atctggtcgg agtcggagga gacgtagacg   17700
tagtgcttga acagtgtccc ggggtcgacg acatggcgaa gcgtcatcag ccggcacgac   17760
cggcacacga tgacgtcgag cgggaagacg tcctgcgcct catcggcgtc ggccggatcg   17820
acgaacccgt tggccagcgg cagcgagccg aaggagatca cctcggtcca gtcgtccgca   17880
ccgcatacac ggcacgtctc gtcccgcctg catttctcca gcatgaagtc tcctgacggc   17940
gaatgccgac gcatcgggcc cgtcggtccg gggacggtca atctagggtt ccggccgacg   18000
ggcgctccac ttcgtatgtg ccctactggt tcagcggagc ggacgggtga acgcccgtac   18060
gtcctcgatg aggagctgcg gctgctccat ggccgcgaag tgcccgccgc ggtcgaactc   18120
ggtccaccgc gtcagggtcg gcaggatgcc ctcggcgaac gaccggatcg gccgggtggc   18180
gtcgtccggg aacaccgcga cgccgacggg ggccgtcagc ggccagggcc cgccccaggt   18240
gcgggcgaag tccgccatgc cgcgagccga ctcgtagtac aactgagcgc tggaaccggc   18300
cgtcgcggtc agccagtaga tcatcacgtg ggtgagcagc cggtcccggg agatggcctc   18360
ctccacgttc ttgccgccgc tccactcctg gaacttgtcg agaatccagg cgagctggcc   18420
gaccggggag tcggtgaggc cgtaggccag ggtctgcggg cgggtggcct ggatgcgctg   18480
ccagccgatg ccggtgtcgg cgaactcccc gctgtgcgcc agcttgccca ggtcgctctc   18540
gtccaggcgc ccgatggcct ccggggcgtc ctggggcggg aaggtcacca gcatgttcag   18600
```

-continued

```
gtggacgccg gccacgtgct cggggtcggc cagccccagc tccagcgaga cgacctttcc   18660
ccagtcgccg ccctgggcga cgtaacgctc gtagccgagg cggttcatca gctccgccca   18720
ggcgcgtgcg atccgccgca cgtcccagcc cggctcggca gtcgggccgg agaagccgta   18780
gcccggcatg gaggggacga cgacgtggaa ggcgtccgcc gggtcgccgc cgtgcgcgcg   18840
cgggtcgctc agcggcccga tgacgtcgag gaactcggcg accgagcccg gccagccgtg   18900
ggtgaggatc agcgggatcg cgtccggctc gggcgaacgc acgtgaagga agtgcacgtc   18960
ggcgccgtcg atcgtggtga cgaactgggg gaacgcgttc agctcggcct ccgcggcacg   19020
ccagtcgtag ccgtggcgcc agtggtcggt gagctccttg aggtaggaca gcggcactcc   19080
gcggtcccat ccggatccgg gtatctccga cggccaccgg gtcgcgtcga tccggcggtt   19140
caggtcgtcg atgtcggact ggtcgatctc gatacgaag  ggacgcacag tgaatccacc   19200
ctcgtgattg tgggagcggg gcggcgcgag gcggccgccc cgatgtgatc ggggaccgtg   19260
ctcaggccgc ttcggccggc gcggccgcgc cttcccgtgc ggagaaggac cgcacggagg   19320
acaggaagtt gcggatcatc ggcatgccgt gttcggtccg gaagctctcc ggatggaact   19380
ggacggactc caccggcagc gaacggtggc gcaggcccat cacgtagccg tcgtccgtgg   19440
agcgcgcggt gacctcgagg gacggcggga ccgtgccctc cggcacgatc agtgagtggt   19500
agcgggtcgc gaagaacccc gcgggcagcc cggtgaacac tccgcgcccg tcgtgcgtga   19560
tccggctcgt cttcccgtgc atgagatgcc gggcggggac ggtggcggcg ccgtaggcgc   19620
gggcgacggc ctgatgcccc agacagaccc gagcagcgg gacccggccg gcgaaggcct   19680
ggacgatctc gacgtgcccg gaggtgtcgg ggtggccggg gcccggcccc agcaggaccg   19740
cgtccggccg catcagcccc atctcgtccg gggtcatgag atgcgaccgc accatgacgg   19800
gctccgcgcc ggcggacatc agatactggc gcaggatgtc gacgaagctg tcgaacgcgt   19860
cgaccaccag gacccgcggg gcctcggtgc ctgcgccgga tccgtcggga gaccacaagc   19920
tcacagcaac tcctctccgg tgaccgccca gtgagtggcg ctcatcttgg ccagcgtctc   19980
ggtccactcc gcccccggtt cggaatcggc gacgattccg gccgaggccc gggtgcggta   20040
gacgccctcg tggtggaaaa gggtccggat gcacagcgcg aggttggtgt accgcccac   20100
gtcgaggagg ccgagcgccc cggcgtacag gccgcggcgg ctgcgttcga cggactcgat   20160
gatctccatg gcgcggatct tcggcgcgcc cgtcatggtg ccggcgggga cagggcggc   20220
gatggtgtcg aaggcatcgg tgtccacccg cgcccggccg acgaccgtgg agaccaggtg   20280
cagcacgtgg gagtagccct ccacgtccag ctggtcgggt acgtcgagcg tgttcggccg   20340
ggcgatccgt ccgatgtcgt tgcggcagag gtccaccagc atggtgtgct cggcgatctc   20400
cttgggatcc gacctcagcc ggactcccgc ggcgatgccg ccgtccgcgc cggaccgcgg   20460
caccgtgccc gcgatcggcc gcatcgtgac ctcgccgtcc tcgatgcgta cgaacagctc   20520
ggggctggcg ccgatcagac ggtgcccgtc gatgcccgcc agatacatgt acggggaggc   20580
gttccgcccg cgcaggcgct ggtagacgtc cgcggggtcg gccgtcgagc ggatggagag   20640
ctcgtgacca atctgcacct ggtagatgtc gccgacggca atgtgcttca gacaccgctc   20700
gacgtcgttc gcgaacactt cggggcgct gtcgtcggtg accgcggagg cggggaagcc   20760
gtctgcggac ggatcgggcc aggcctgctc cacgtcggcg aggagccgg tgacggtctc   20820
cggcgcgagg ccgggccagt acggggactc gtggagcagc agttcgcatc ggccggtggc   20880
gagatcggtg accacgctgc cccggtgcag gaccatgcgt acgtccggca ggccaggcc   20940
gttctcgatg aggtggggca ggtcctcgat gtagcgggcc gtgtcgtacc cgaagaaccc   21000
```

```
gaggaacccg aagcggaagc cggacgcgga cccctcggcg tcgaacatgt cccgcatggc   21060
ccgcagcagc ggccacaacc cgcccgcggt acgcagccgc agccctgggg ggccgtcctc   21120
caggagcgcc ccgccccgct ccaggagcag gccccgcagg gcgggtacgc cctcgacgcg   21180
caccacccgg tcggtgaccg agagcgagag cagcgcgccg aagccgacga actggtgcct   21240
gcggtcgcgg gccgggccgg ccgcggactc caggaggtag acctcgtcgg ggccgaagtg   21300
ctcggccagc gcgcggtagg cgggcagggc gcccgtctcc ttcacatcga ggcgtcgtgt   21360
ccgcacccgc accggggccg agaccacgca ctggtcggtc atcctgggtc tcccggatc    21420 acgtggtgat ggcgtagcgg tgtgccacct gacgggcggt cagcaccgcc cggtcggggc   21480
cggagcggtt gtcgacgacg cgcgcggcct tccagctgac gaaggagccg gtgtgggtca   21540
cggggtcgag gtcggtgtcc acgacgatgc cggcgtgcgc gccggtccgc tccctgagcc   21600
gggcggcgac ggcctcgccg atgccctgcc gttcccccte ggcgccggcc agcaggtcca   21660
tgcgcacggt gacggcgtcg ctgccgtcgt cctgccggtc gatgacgacc tggtagccga   21720
ggcagccgcc gaccccgtcg aggatcgcgc cctccagctc ggcgggctgg agggtcacgt   21780
cgcccagggg gatgcggtcc gcgacccggc cgatgacctg gatccgcggt cccggcagcg   21840
gctccccggg gcccgccggg aggatgcgga ccaggtcccc ggtgcggtag cggatcagtg   21900
gtttgatgcc gtccaccagc atggtgagga cgagttcgcc ctctcccgtg tcgccgacca   21960
cggcgccggt gtccggttcg acgagttcgg tcaagtagtt gggctgggcg aggtggagcg   22020
ctccggtgtc cgctccggtg gcgatgcaca gggcttcctg ggagccgtag agcgtgggcc   22080
gcacgacggc ttgcggccag agggtcgcca cgttgtcggc gaactgcggg gtgcagatct   22140
cacccagcgt gaggaagagc ttcacgggaa gccgggccag gtcgtagccg tagtgcaggg   22200
ccgccttggc aaggctcagg cacagcgccg gagcacagac gacgacctcg acctccagct   22260
cctcgatcag ccgcagcgcc ttacggaatc ccaccctggg ggactcgggc cagatcttga   22320
cgtgacaggc ccccagctcc gctgccaccg cggtgaacac gtccccgaac gcgtacagct   22380
ccgacggccc catcaggccc acgacgggca tccgccccccc gaacctcgct tccagcatgc   22440
ggcgccagga ctcccggacg gcgatgttgc tggtcgcgat gtccttctcg ccgcgtgggc   22500
acggggtggc cgccccggtg gtcccggtgg tctcgtagta gatgcgtgct tcgtgcagcg   22560
ggcccgacag gacgtcgtgc atctcccgcc gcaggtcgtc cttggtggtg aagggcaggt   22620
ccgccaggtt cgcgggggtg acggcctcga cgtccacgcc tgccagatgg cggcggtaga   22680
acggcgagcg gcgggtgacg tggcgcagta cggccgtcag ccgttcgccc tcccagcgct   22740
cgcggtcggc ggcggtgagt tcgccgcggt agaacgcgtc gctcacctgc cgtaggcgg    22800 accagaactc gctgtccgcg tcggggtcca gcggcccggt cccgccggga ccgggccgcc   22860
ggccgtctct cacggctgtg cctggagttc gttgagcgcg aggccgaccc gctcgttgac   22920
ctcgttggag gccagcacgt ccgaacggcc ggtgagccga cggtgttcgt cgagcagttc   22980
gatcatgtcc gtcatcctct cgaccaggcg cgagacgttg tgaggccct cctcgtcctt    23040 gagcgcgtcg ccccggtgca gcgcgtgcac cgtcgccggg aagccgctgc ccaccaggat   23100
catccggttg agcagggcat tgacggtcag ctgagcccat acctcgccgg cgctgtagcg   23160
gcgggcgacc gagatgatcc ccgcgacctt gttgctcagc ggccggtcga agcgcagata   23220
accgactccg gcacgctcga tgaaggtctg catgaggctg gccgtgccga atccgtgcac   23280
gggcgccgcg aagatgatcc cgtccgccgc gaccatcttc gccacgacct cgggcacccc   23340
```

```
gtcggccagg gtgcaggcca ccggcctgtc gttgcagtcc ccgcagggcc cgcaccgctc    23400
catcctgatc gagcgcaggt cgacggcctc gaagtcgacg ccgcggttct ctgctacgcg    23460
tgccgcgtgc cgcagtacgt cggcggtgtt gccgtcacgt tccgaaccgt tgatcgcgag    23520
gatcttgagt tgtgcgctca cgaggggcct ccttggtgag tcaggtgcgc tcggcggtcg    23580
gctcggggga actgtctggc cgccgctggt ccgggagccg cagggccggc tcggcggggg    23640
cgggaggaag accgccccgc ggcgggccgc cacgctcgcc gaaccggatg aggggcttct    23700
cgacgagata gaagctgatg gtcgccagca cgacgctgat cgagatcgtg aagaggaaca    23760
gttcccagaa ccccatgtca ccccggaatt ccggcgttgg cacgggagac ttgccgaaga    23820
tgctgccgtt cctgagccag aggttgatca cgatctcgtg ccagaggtag acgccgaggg    23880
agatctggcc gaggaagagg atcggcttgc tggtgaagag cgcgtccgag aaccgggact    23940
cggcgccggg gaccgtcatc ggtgccagga gcagcagggt gaaggaggtc aggatgaagt    24000
ggtcgacgag ctcctgggcc agggccgcgt tgtcgcccat gcccgggatg ccgatgggct    24060
tggtggcgta gaggaggtac agcgggatga gcgggaccca gcagatcagc gggcgccgga    24120
tcacgaaacg gtagaagccc ggggtccctg cgtcgcctc ggcgtacgcg gagtagatgg    24180
ccagtgccat gcccgcggcg aagcagccgg cgtagtaggg cggccagtac cactgcatcg    24240
tcgcgccggt ggaggggagg ttggtgtacg tgacccagcc gatggccatg acttccagcg    24300
cggccagcgg cagcaggagg cggcgtgcct tctgcccggg agtgctgccg ccccgcgcga    24360
gccggtggcc gatccaggcg atcagcggca gggcgaggta gaacgtgaac tcggcgggga    24420
ccgtccaggt gggctcgatg ccgtgcatcg gctggccctc gggcagatag aagtgcatga    24480
gcagcacggg ccgcaggacg tcgctgacgc tgtcgatctc gaaccagttg tagccggggga    24540 ttgcgaagac gagcaacagg tagtaggcgg gcaggatgcg cagggcccgg cgtttgagga    24600
accgtccggt ggcgggccgc ttcgtcccac tgatggtgac gcgggcgtag ggcttgtaca    24660
gcatcattcc ggacagagcg aagaagggg aaggcatacc cccagaccgt ccgcgaggac    24720
gccccagaac ggtttgcccg gctcaccgac gaagctgccc actccggcct ggaaggcgac    24780
gtggtagacg accacaccca gcgcgaggac acctcgcagt ccctcgaact tcggtattcg    24840 cttgctttt gcgccacctg cgtcgcgaag gacgtccccc atggaacagt ccccttccc    24900 ttggcacttg ctcgttgact tcccgaaata gtcgggtctg cggagtgtga gccgcatctc    24960
caatcgtgct gttccggtgc tcaggacgac ttgtttcggc ctgagtggga aggcagccac    25020
ccccgccgcc ccgcctcggc cagaccgggg gccgaggagt cccgttccga gaggatcgga    25080
gtgatctccg gcggccaggc gatgcccacc tccggatcca gcggattcaa gccatgttcg    25140
agccgggggt cgtaggccgc cgagcacagg tagacgatca ccgcctcgtc gctcagcgtg    25200
aggaatccga agcccagccc cgcggagacg tacagcgccc gtccgttctc ctcgccgagc    25260
tccacggtcc gccagccgcc gaaggtgggc gaccccaccc ggatgtcgac cacggcgccg    25320
aacacgctgc cgcgcaggca gctgaagtac ttggcctggc cgggtacgcc cccggcgaag    25380
tggatgcccc gcagcacccc gtgggaggag atcgcgcagt tcgcctgccg caggtcgaag    25440
gagtggccta cggtgcggcg gaagggctcg ccctggaacc actcgcgaaa cgagcccgt    25500 tcgtcacgga agacctgctt ctcctccgtc cacgctcccg agatcccgat cggcttcatc    25560
gctggcccct tctctcgact tctctcgacg actcgcggga ggcggccgag gggtccgccg    25620
ggcccgtggg aacgccgcag tctagatgcg gcggcaccgg gggcaggggg gtgcggacga    25680
cgtccgcccc acctcagcac accgggagat gcaggtcggt gacgggcgac gtgacgatgc    25740
```

-continued

```
aacggtccga ggcccggttg cccggacgac ggcccacaga gccatcggag caacggaggc    25800
ggaccgcaga tgaccaagca cgcccgtgac cgcgcggtag tcctcggcgc agggatggcg    25860
gggctgctcg ccgcgcgcgt cctgtccgag acgtacaagg aagtgctggt gatcgaccgg    25920
gaccggttgg gcggcacgga gcagcgccgc ggtgtcccgc acggacgcca cgcccatgcg    25980
ctgctggcca agggacagca gatcctcaac gaactcttcc ccggactcga caccgaactc    26040
acctcggccg gaatccccgc cggggacatc gccgggaacc tgcggtggta cttcaacggc    26100
cgccggctcc agcccttcga caccgggctg atcagcgtct cggcgacgag gcccgagctg    26160
gagtcccacg tgcgcgcacg ggtcgccgcg ctgccacagg tgaagatcat ggacgggtgc    26220
gtgatccggg gcctgaccgc ctcggccgac cgcagccgcg tcaccggtgt cgaggtggtc    26280
gacgagtcgg gtacggacac cccgacgcgc ctggaggccg acctcgtcgt cgacgtcacg    26340
gggcgcggct cgcggactcc cgcctggctg gaggagttcg gatacgagcg gcccgcggag    26400
gaccgcttca agatcgatct ggcgtacacc acgcgccact tcaagctcaa ggaagacccc    26460
tacggcacgg acctgtcgat caacccggtg gcatcgccga gcaacccgcg cggcgcgttc    26520
ttcccccggc tcgcggacgg cagctcccag ctctccctca ccggaatcct cggcgaccac    26580
ccgcccaccg acgacgaggg cttcctggcg ttcgccaagt cgcttgccgc gccggagatc    26640
taccgggccg tccgcgatgc cgaacctctc gacgaaccgg tcaccttccg cttcccggcg    26700
agcgtccgcc gccgttacga gaggctgcgc cgtttccccg gcgggttcct cgtcatgggc    26760
gacggcgtgt gcagcttcaa ccccgtctac ggccagggca tgacggtcgc cgccctggag    26820
gccgtggcgc tgcgggacca cttgcgcgac gccccggacc ccgacgccct gcgcttcttc    26880
cggcgtatct ccacggtcat cgacgttccg tgggacatcg ccgccggagc ggatctgaac    26940
ttccccgggg tggagggccc ccgcaccatg aaggtgaaga tggccaacgc ctacatggcc    27000
cgcctgcacg cagcggcagc cgtcgacggc gcggtgaccg gggcgttctt ccgggtggcc    27060
gggctggtgg accccccgca ggccctgatg cgcccctccc tcgccctgcg ggtcatgcgc    27120
aactcctcgg cgaagccgtc ggtcccttcg ggcgccgccg tatgaccgcg cggcccgtcc    27180
ggggcggctg ccggggccag gagccgacat gcgggtgatg atcacggtgt tcccggcgcg    27240
ggcgcacttc ctgccgctgg tgccctatgc ctgggccctg cagagcgcgg ccacgaggt     27300 atgtgtcgtg gcgccccggg gctatcccac cggggtggcc gaccccgact ccacgaggc     27360 cgtcaccgcg gccggcctga agtcggtgac ctgcgggcag ccgcagccgc tggcggtcca    27420
cgaccgcgac gaccccggct acgcggcgat gctgccgacc gcggcggagt cggagcgcta    27480
cgtggcggcc ctcgggatca gcgagaagga gcgccccacc tgggacgtct tctaccactt    27540
caccttgctg gcgatccgcg actaccatcc gccgcggccg cggcaggacg tggaccaggt    27600
gatcgagttc gcccggatct ggcagcccga tctggtgctg tgggacgcct ggttcccctc    27660
gggcgcgatc gcggcgcggg tcagcggcgc gcgcacgcg cgggtgctcg tagcccccga    27720
ctacaccggc tgggtcaccg agcggttcgc cgccgcgggc cccgcggcgg gggccgacct    27780
cctggccgag acgatgcggc cgctggccga cggtacggc gtggaggtcg acgacgatct    27840
tctgctcgga cagtggacgg tcaatccgtt cccggcgccg atgaacccgc cgacccggct    27900
cacgaacgtt ccggtgcgct acgtgcccta caccggtgcc agcgtcatgc ccgcgtggct    27960
gtacgcgcgg ccgtcgcggc cgcgggtggc gctgtcgctc ggagtgtccg cgcgggcgtt    28020
cctcaagggt gactgggggc gtaccgccaa actgctggaa gcggtcgcgg agctggacat    28080
```

```
cgaggtgatc gccacgctca acgacaacca actggcggag agcgggccgc tgccggacaa   28140
cgtccacacc ctcgactacg taccgctcga ccagttgctg cccacctgct cggccgtcat   28200
ccaccacgga tcgacgggca ccttcgccgc ggcgagcgcg gccgggctgc ccaggtggt    28260 ctgcgacacc gacgagcccc tcctgctctt cggcgaggac accccgacg gcatcgcgtg    28320 ggacttcacc tgccagaagc agctcaccgc gacgctcacc tcccgcgtgg tcaccgacta   28380
cggggcgggg gtgcgcgtcg accaccagaa gcagtccgcc ggacagatcc gtgagcaact   28440
acgcagggtg ctcaccgaac cttccttccg cgagggcgct cgacggatcc gggaagaccg   28500
gaattccgcc cccagcccgg tcgaactcgt atcgctcctg gtagaactga cgaagcgtca   28560
tcgccgtgac aaggaggcgg accgatgagg atgctggtga cgggcggagc gggtttcatc   28620
ggctcgcagt tcgtgcgggc cacactgcac ggcgagctgc cgggttccga ggacgcccgg   28680
gtgacggtcc tggacaagct gacgtactcc ggcaatccgg ccaacctcac ctccgtcgcg   28740
gcccatccgc ggtacacctt cgtccagggc gacaccgtcg acccgcgcgt cgtcgacgag   28800
gtggtcgccg gccacgacgt catcgtccac ttcgcggcgg agtcgcacgt ggaccgctcg   28860
atcgacaccg ccacccggtt cgtcacgacc aacgtgctcg ggaccagac gctgctggaa    28920 gcggctctcc ggcacggggt cggccggttc gtgcacgtgt cgaccgacga ggtctacggg   28980
tcgatcgcct ccggctcatg gaccgaggac accccgctcg cccccaacgt ccctacgcg    29040 gcgtcgaagg cgggttcgga cctgatggcg ctcgcctggc accgcacccg gggcctggac   29100
gtcgtcgtca cccggtgcac caacaactac ggtccctacc agtaccccga gaaggtgatc   29160
ccgctcttcg tcaccaacat cctcgacggc ttgcgggtgc ccctgtacgg ggacggcgcc   29220
caccgccggg actggctgca cgtgtccgac cactgccggg ccatccagat ggtcatgaac   29280
tccggccggg ccggggaggt ctaccacatc ggcggcggca ccgaactctc caacgaggaa   29340
ctcaccggcc tgttgctcac ggcgtgcggc accgactggt cctgcgtgga ccgggtggcc   29400
gaccggcagg ggcacgaccg ccgctactcg ctcgacatca cgaagatccg gcaggaactg   29460
ggctacgagc ccctggtcgc cttcgaggac ggcctggccg cgacggtgaa gtggtaccac   29520
gagaaccgtt cgtggtggca gccgctgaag gaagcggccg gcctcctgga cgccgtcggc   29580
tgacggcagc caccgctagg aacaccccag gaaaggagcc acctccgtga cagcagtcaa   29640
ggagccgacg tcccgcgcag gacggcggga gtggatcgct ctcgtcgtcc tctccttgcc   29700
cacgatgctg ttgatgctgg acatcaacgt cctcatgctg gccttgccgc agttgagcga   29760
ggatctcggc gcgagcagca cgcaacagct gtggatcacc gacatctacg gattcgcgat   29820
cgccggcttc ctggtgacca tgggcaccct cggcgaccgg atcggccgcc gcaggctcct   29880
gctcgggggc gcggccgtct tcgcggtcgt gtccgtcgtc gccgcgttct ccgacagcgc   29940
ggcgatgctc gtcgtcagcc gcgccgtgct cggcgtcgcc ggggccacgg tgatgccctc   30000
gacgctcgcg ctcatcagca acatgttcga ggacccaaag gagcggggca ccgccatcgc   30060
catgtgggcg agcgccatga tggccggagt cgccctcggg cccgccgtcg gcggcctggt   30120
cctcgccgcg ttctgtgtgg gatcggtgtt cctcatcgcc gttccggtga tgctgctggt   30180
ggtggtcacc ggccccgtgc tgctcaccga gtcccgcgac ccggacgccg gacggctgga   30240
cctgctgagc gcggggctct cctcgcgac cgtgctgccg gtgatctacg gactgaagga    30300
gctggcccgg accgggtggg accgctcgc cgccggcgcg gtggtcctcg gcgtgatctt    30360
cggcgcgctg ttcgtccagc gccagcggcg gttggccgac cccatgctgg acctcggcct   30420
cttcgccgac cgcaccctgc gggcgggtct gacggtcagt ctggtcaacg ccgtcatcat   30480
```

-continued

```
gggcgggacc ggactgatgg tcgccctgta cctccagacg atcgccggtc actcccgtt    30540 ggccgccggg ctgtggctgc tgatcccggc ctgcatgctc gtcgtgggcg tacagctgtc    30600
gaacctgctg gcccagcgga tgccccctc ccgggtgctg ctgggggac tgctgatcgc     30660 ggccgtcgga cagctcctga tcacccaggt ggacaccgag acaccgccc tcctcatcgc    30720 ggccaccacc ctgatctact tcggcgcctc accggtgggg ccgatcacca cgggcgcgat   30780
catgggagcc gcgccccgg agaaggcggg tgccgcctcg tcgctgtccg ccaccggcgg    30840
cgagttcgga gtggcgctcg gcatcgcggg cctggggagt ctgggcaccg tcgtgtacag   30900
cgccggggtc gaggtgccgg acgcggccgg gcccgccgac gccgacgccg cgcaggagag   30960
catcgccggc gccctgcaca cggccggtca gctggcaccg ggcagcgccg acgccctgct   31020
ggactccgcg cgcgcggcct tcaccagcgg cgtgcagtcc gtcgccgccg tctgcgccgt   31080
gttctccctg gcgctcgccg tcctcatcgg caccgcggctg cgggacattt ccgcgatgga   31140
ccacgggcac ggcgaggaac cggccgagaa cgacgctcaa ccggccacat gagcgcactt   31200
ccggagatgc aacggccgcc gtcgaggtat gaggatcacc ttccggggtg cacctgcacg   31260
gcaacggagg cgtagtggag tactggaaca gcacggcgga gaccatgccc cgccaggaac   31320
tcgaacagtg gaagtggcgc aggctccagg ccgccatgga ccacgccaga aggctttcgc   31380
ccttctggcg ggaacgactc cccgagaaca tcacctccat ggcggactac gcggcgcggg   31440
tgcctctcct gcgcaaggcc gacctcctcg ccgcggaagc cgcgtctccc ccttacggca   31500
cctggccctc gctggatccg gcgctcggag tgcgccatca ccagaccagc ggcaccagcg   31560
gtaacccccc catccggacg ttcgacaccg aacgcgactg ggcctggtgc gtggacacgt   31620
tctgcacggc gctccacagc atgggcgtgc gcccgcacca caagggtctg gtggcgttcg   31680
gctacgggct gttcgccggt ttctggggca tgcactacgg cctcgagcgc atgggcgcca   31740
cggtcatccc ggccggcggc ctcgactccc gctcccgggt acggctgctg gtcgactacc   31800
agatcgaggt gctcggcctc acaccgagct atgcgatgcg gctgatcgag acggcccgcg   31860
agatgggcat cgacctcgcc cgcgaggcta acgtccagat catcctggcc ggggcggagc   31920
cgcgctccgc gttcaccacc cgcaccatcg aggaggcctt cggcgcccgg gtcttcaacg   31980
ccgcgggcac cactgagttc ggggggggtgt tcatgttcga gtgcaccgcc cggcgcgagg   32040
cctgccacat catcgaaccc tcgtgcatcg aggaggtgct cgaccggggtg acggaacagc   32100 ccgtcggcta cggcgaggag ggcgtccgag tcaccaccgg gctgaaccgt gagggggatgc   32160 agctcttccg gcactggacc gaggacgtcg tggtcaagcg gccccacacc gagtgcggct   32220
gcggccggac gtgggacttc tacgacgcg gcatccttcg cgcgcgtggac gacatgcgca   32280 agatacgcgg ggtctcgatc accccggtga tgatcgagga tgtgctgcgc ggcttcgacg   32340
aggtgaacga gttccactcg tccatccgga ccgtccgcgg actcgatacg atccacgtca   32400
aggtcgaggc gggagacatc tcgggtgagg cggccgagag cctgtgcggc cgcatcaccg   32460
aggagttcaa gcgtgagata ggcatacggc cccaggtgga gctgacccccc gcggcagcc   32520 tcccccgatc gaagtggaag gcggcacgac ttcatgacga gcgcgaactc gccctcagg    32580 cctgagcagg tggagcagct cctggtgagc taccggagcc tgggcctgct ggagcagagc   32640
tgcgcggtcc cggccgtgct cgccgcggtc agggccgccc gtgcggaact ccgtatcgcc   32700
ctggacggcc agggcgtgga gttcgagtac taccgggggc acgacgacag cctcgtggcc   32760
tgaacccacc cccggtccgc cgggtcagac gaaagggaga ccggtgcccc acggtgcaga   32820
```

```
gcgcgaagcg agcccggccg aggagagcgc cggcacccgg ccgctgaccg gcgaggagta   32880
tctggagagc ctgcgggacg cgcgggaggt gtacctcgac ggcagccgcg tcaaggacgt   32940
caccgcgcat cccgcgttcc acaacccggc ccggatgacg gcccggctgt acgacagcct   33000
gcacgacccc gcccagaaag cggtcctgac ggcgcccacc gatgccggtg acggtttcac   33060
ccaccgcttc ttcaccgcac cgcgcagcgt cgacgacctg gtcaaggacc aggccgccat   33120
cgcatcctgg gcgcgcaaga gctacggctg gatgggcgc agccccgact acaaggcgtc   33180
gttcctcggc acgctggggg ccaacgccga cttctacgag cccttcgcgg acaacgcccg   33240
gcgctggtac cgggagtcgc aggagaaggt gctgtactgg aaccatgcct tccttcaccc   33300
gccggtcgac cgctcgctgc ccgccgacga ggtgggcgac gtcttcatcc acgtcgagcg   33360
ggagaccgac gcgggcctgg tggtgagcgg ggccaaggtc gtcgcgaccg gatcggccct   33420
cacccacgcg gcgttcatct cgcactgggg acttcccatc aaggaccgga agttcgccct   33480
ggtgccacc gtgccgatgg acgcggacgg cctcaaggtg atctgccgtc cctcctactc   33540
cgcaaacgcg gcgaccacgg gcagcccgtt cgacaacccg ctgtcctcac ggctggacga   33600
gaacgacgcc atcctcgtac tcgaccaggt gctgatcccc tgggagaacg tgttcgtcta   33660
cggcaacctg ggcaaggtac atctcctcgc cggacagtcc gggatgatcg aacgcgccac   33720
cttccacggg tgcacccggc tcgccgtgaa gctggagttc atcgccgggc tgctggccaa   33780
ggcgctggac atcaccgggg cgaaggactt ccgcggtgtg cagacccggc tcggagaagt   33840
cctggcctgg cgcaacctct ctggtcact gtcggacgcg gcggcccgca acccgtccc   33900
ctggaagaac ggcacgctcc tgcccaaccc tcaggcgggt atggcctacc gctggttcat   33960
gcagatcggc tacccgcggg tcctggagat cgtccaacag gacgtggcca gcggcctcat   34020
gtacgtcaac tcctccacgg aggacttccg caaccccgag accgcccct acttggagaa   34080
gtacctccgg ggcagcgacg gcgcaggcgc cgtcgagcgt gtcaaggtga tgaagctgct   34140
gtgggacgcg gtgggatccg acttcggcgg ccggcacgaa ctctacgagc ggaactactc   34200
cgggaaccac gagaacaccc ggatcgagtt gctgctgtcg cagacggcga gcggcaaact   34260
ggactcgtac atggacttcg cccaggcatg catggacgag tacgacctgg acggctggac   34320
cgctcccgac ctggagtcgt ttcacgcgat gcgttccgcc tcccgcgacc ttctcggagg   34380
gctgtagttc cccgacggtg tactgcggcc cccgatccgg gggccgcagt acaccgtcgg   34440
ggcggctggt gctcagccgc gcaggaatcc gatgagctcg ggggcgagct tcttgggcgc   34500
catgcgacg gcaccgtggt tgagcccgtt cagggtgcgg tggctcgcgt cggggaggac   34560
tccggtgagt tccttcgcgg cacgctggaa accgtcgggg ctcttggaac cggtcagcac   34620
cagggtcggg gccgacgccg ccgaccacgg ctcggcgggg agcggcttgc cctgctgggt   34680
gtcgcccatc accgcgatgt cgtagggaag cgtgttggcc agacccttga ggttggacca   34740
gacaccgggc atcaggcgca tggcgccgac catgaaggag ggcatgccct gtgccttgac   34800
catgaaggcc ttgaccgcgt cgctgcgtcg gtcctccgcc agaaggctgt cgatctgacc   34860
gccgaagccg gcgggcgggc cgaagccgtc cgaggtgacg gagaacggcg gctcgtagac   34920
cgcgagcttg ttcaccttca ggccggcggc ggcggctcgc agggcgagca ccgcgccgga   34980
agagctgccg aacagggagg ccgaaccgcc gacctggtcg atcagcgccg cgatgtcctc   35040
gatctcgcgc tcgaccgcgt acgccggacc gtcggcgctg gcgccgcggc cccgacggtc   35100
gtagttgacg accgtgaagt gctcggcgag gagaccggcg agcttcttgg cgtcggagcg   35160
gtcggccaag gcggaggcca ccaggatcac cgccggcccc tcgcccgact gtcgaaggc   35220
```

```
gatcgtggtg ccgtcggccg ataccgtcgt tgattccacc ttggctgctt tctcacgggt    35280
tgaagacata gcttccctca gatcacattg tggggcgtgc tgccgacagt ggagaccggc    35340
gtccggagga aaagtaatcg gtcctgccag aattgggggt tccggagggc acgccgaccg    35400
ctgcacgacg gcgcgccccg accttccgga cattgtcgtg ccctcagatg tgtttcgcat    35460
cttcaggagt gctcagtgat ccgtgaggtg agaaagggac ggtggtccgg tcagtcgttg    35520
ccgcgcgggc tgttctggta agcggccaga cgccactgcc cgtcctgttc gacggccagc    35580
caggaggccc ggacgcgcc gtcgccgctc gcctcggtct cccccggggc gaggatgccg     35640
ccctcggtga tgagcagggc gatgccgtcg ccgagcaggc gcgcgtcgat ggggctgccg    35700
atgacacggg tgcccttgta cgggcccgcg aaggcggccg ccatgtgggt gcggatgttc    35760
tcgcggccct tgcggaagag gccggggagg atcatcgtcc cgtcctcggc gaagacgtcg    35820
gcgaaccggt cggcgtcgtg gtcggcccag gcggccacga tgcgcgccgg cagagcggct    35880
accgctgcca gggcggcgtc gggagcggag gtggtcgagt cggtgctggt catatcgcgg    35940
ttcccgtccg ttggttggcg gtttcggcac ggcccgcagc cctgcccgag cccgacgctg    36000
gcaggcggcc ccgtcatcag gcatctcctg cgttgcgccc cacgccagtc acttcacggc    36060
cagaacaagt cgcgcattct ggaagaagct gaggcccgcg accggtgcg acgatctgcg     36120 gtgtcacgga gttcgcacac gtttacgcac ggaggctcga tgcccgctgt caatggatcg    36180
gtgcagtcag gccagtcgca ccgacgctcc gtcgtggcga cggtggtggg caacttcgtg    36240
gagtcgttcg actggctcgc ctacgggctc ttcgctcctc tcttcgcggc tcagttcttc    36300
ccctcgtcca accagttcac ctccctgctc ggcgcgttcg cggtcttcgg cacgggcatg    36360
ctcttccggc cgatcggcgg ggtcctgctg ggccgcctcg ccgaccggcg cggccggcgc    36420
cccgccctga tgctggcgat cggactgatg accggcggct cgaccctgat cgccgtcgtc    36480
cccacctacg agcacatcgg gatcctcgcc ccgctgcttc tgctgctcgc ccggctcgcc    36540
cagggagtct cctcgggcgg ggaatggaca gcggcggcca cctacctgat ggagatcgcg    36600
ccgaagaacc gccggtgcct ctacagcagc ctcttctccg tgacgaccat ggcgggcccc    36660
ttcgtcgcat cgctgctggg cgcgggcctc ggcgtgtggc tgggaaccgc gacgatggag    36720
gcctggggct ggcgggtgcc gttcctcctc ggcggcgtct tcggcgtgat cctgctgttc    36780
ctgcgccgtc ggctcaccga gaccgaggtc ttccgccggg aggtgcggcc ccgggcccgg    36840
cgcggctcac tggccagct gatcggagcc caccgccccc aggtgctgct ggccgtgatg    36900
ctggtggccg gactgggcgt catcggcgga acgtggtcga ccgcggtccc ggcgatgggc    36960
caccgtctga tcggctcgca gacgatgttc tgggtggtgg tctgtgtgac cggctcggtc    37020
atcctgctgc aggtacccat agggctgctc gccgaccggg tggaaccggg caggttcctg    37080
atcgtctcca gcgtcgtctt cgccgctgtg ggctcgtacg cctacctcac cgtccaggac    37140
tccttcgcga gcctggcgtt cacgtacagc accggagtga tcttcctcgg ctgcgtcacc    37200
atggtgctgc cgaagatgct ctccagaatc ttccctccgc agatacgcgg cctgggcatc    37260
gggctgccgc acgcctcgac caccgcactc ctcggcgggg cggggccact gctggccgcc    37320
tactccgacg agcgaggcgc ctcggctgg ttcatcgccg ccgtgatggc cgcggtcctg      37380
ctcgcctggc cggccaccct gtgggagcga cggctgttcc gcgcccggac ggccccggga    37440
agcgagccgg ttcccgaatc cgccgtcgcc cgccccgtcg ggtgaccgtc cgcacttctg    37500
catcccgtcc ggcaccgagc gccggcgacc ttcccgactg agaggttgac atcatgacga    37560
```

```
cgtccgacac caccgaccgg tcccaggacg gcgtgccgcc gctctccttc caccaggagt   37620
tcctgtgcat gttcgacagc gggaacgacg gcgccgacgt ggggccgttc ggccccatgt   37680
accacatcgt cggagcctgg cggctgaccg gcgggatcga cgaggagacc ctgcgcgagg   37740
cgctgggtga cgtcgtcgtg cgccacgagg ccctgcgcac atcgctggtc cgcgaaggtg   37800
gcacgcaccg gccggagatc ctgcctgcgg ggcccgccgc gctggaggtc cgtgatctcg   37860
gcgacgtcga cgagtcggag cgggtgcggc gcggtgagga actgctcaac gaggtggagt   37920
cgaccggtct gagcgtgcgg gagctgcccc tgctgcgggc cgtgctcgga cgcttcgacc   37980
agaaggacgc ggtgctggtc ctcatcgccc accacaccgc cgcggacgcc tgggccatgc   38040
acgtcatcgc ccgcgacctg ctcaacctgt acgccgccag gcgcgggaac ccggttcccc   38100
cgctccccga gccggcccag catgccgagt tcgcccgctg ggagcgcgag gcggccgagg   38160
caccgcgggt cgcggtctcg aaggaattct ggcgcaagcg cctccagggc gcgcggatca   38220
tcgggctgga gacggacata ccgcgctcgg cggggctgcc caagggcacc gcgtggcagc   38280
gcttcgccgt acgcggggaa ctggccgacg ccgtggtgga gttctcacgg gccgccaagt   38340
gctccccgtt catgaccatg ttcgccgcct accaggtgct gctgcaccgc aggacgggcg   38400
agctggacat caccgtgccg accttctccg gggggcgcaa caactcgcgg ttcgaggaca   38460
ccgtcggttc cttcatcaac ttcctgccgc tgcgtaccga cctctccgga tgcgcatcct   38520
tccgcgaggt cgtgctgcgc acccgcacca cctgcggaga ggcgttcacc cacgagctgc   38580
ccttctcccg gctgatcccg gaggtgccgg agctgatggc gtcggcggcc tccgacaacc   38640
accagatctc cgtcttccag gccgtgcacg cgcccgcgtc cgaggggccc gagcaggccg   38700
gggacctgac gtactcgaag atctgggagc ggcagctgtc gcaggcggag ggctccgaca   38760
tccccgacgg ggtgctgtgg tcgatccaca tcgacccctc gggctccatg gccggcagcc   38820
tcgggtacaa caccaaccgc ttcaaggacg agacgatggc ggccttcctg gccgactacc   38880
tcgacgtgct cgagaacgcg gtggcccggc cggacgcccc cttcacctcc tgagacagtt   38940
ccggcggcgg cgaacccgcc cgaagaaagg aaagccagtg tccaccgttt ccgacacagc   39000
ggccggctcc tccctggagg agaaggtcac ccggatctgg acgggtgttc tcggcacgtc   39060
cggtgaggaa ggcgcgacgt tcatcgagct cggagggcag tcggtctcgg ccgtgcgcat   39120
cgccacgcgt atccaggagg agctcgacat ctgggtcgac atcggcgtcc tcttcgacga   39180
cccggatctg cctaccttca tcgcggcggt cgtccggacg gccgacgccg cggcggcga   39240 gggctccgga acgcagtgag actcgccggg cgccgtctcc ccgcggcgcc cggtttcaca   39300
tggctgaggc ggttcacccg gtaccgggtg aaccgcctca gccatgtgaa accgggcctg   39360
gtcagcgcag ctggatgtcc gtctcccggg cgatcgcccg gaggaactcg ccgcgggaca   39420
gcgcgtcggc gaccagctcg atgtcgtcgg ccatgtaccg gtcgacgccc agcgtcggaa   39480
ccagccggcg caccgcttcg tacgtggcct tcgccgccgg gctcaagccg tcgaaccggc   39540
cggagatgtc gaccgcctgg gcggcggcca ggtactccac cgcgaggatc ttgttgttgt   39600
tcgacaggac ccggcgggcg ttgcgggccg agatcaggcc catgctcacc acgtcctggt   39660
tgtcgccgtt ggacgggacg ctctgggtgc tggccgggcc gatcgtccgg ttctcggcca   39720
ccagtgcggt ggccgggtac tgggcgccgg cgaatccgct gtgcagcccc gggtccccgg   39780
agacgaggaa ctccgggagg ccgtagctga ggtgccggtt caggaccgg ttgatctgcc   39840 gctcggccag gacgccgagc tggtgagcgc gatggtcac gaagtccatc gcgaacgcga   39900
tcggctgacc gtggaagttc gccccgtgga agatctcctt gccctcgaag aagagcgggt   39960
```

-continued

```
tgtcgttggc cgagttgagc tcgatgcgca gcttgtgccg cgcgtggtac aaggtgtcgc    40020
gcaccgcccc gacgacctgg gggatggccc gcagcgagta ggccttctgc aggtagatct    40080
ccgagcgctg gacgtccttg ccggcctcct tgtccttctg gagttctcgg cgcaggtcgg    40140
cgtgctcgac cgtcagtccg ctgccccgca tcagggcccg catgttggcg gcggtgtcga    40200
tctggccctc gtgcgggcgg gctatgtcgt gccctccgc gaggaagggg ctggtcgatc     40260
cgcgtaccgc ctcgatgagc agagccgtca cgatctcggc ctgctgggcc tgctccaggg    40320
cccgtccgac gaccagggag cccagaccgg tcatcccgga cgtgccgttg atcagtgcga    40380
ggccctcctt gaagcgcagt tcgagcggct cgatgccccg ctcggccagc acctgggcgg    40440
tctccaccgg ccgtccgtcg cgcaggacgt agccctctcc gatgagggtg ctcgcgacgt    40500
gggagagggg agccaggtcg ccgctcgccc cgagtgaccc gatctcgggt atggccgggg    40560
tgatgccctc gttcaggtac tgcgcgaggc gttcgaggat gatggggcgc accgcggagt    40620
ggcccttggc gagggtgttc agccgggcgg cgacgatcgc ccgcgcctcg tcctcggcga    40680
acagcggacc gactcccgcg ctgtggctac ggacgagatt ggtctgcagt tcgacttcct    40740
tcgacttgtc gacctgcatg tagatcatct cgccgtaccc ggtggtcacc ccgtagatgg    40800
ggatgttctg ttcggcgatc ccttcgaaga tctcccggct cttctgggcc ttcgcgatgg    40860
attcggccgg tacgtcgacc gtcgcgcgtt cctccgcgac gcggcgtacg gcttcgacgg    40920
tcagggtctc gccgtcgacg gaaaccggga cgatctcggt ctcgacttga gtcaatgcca    40980
tcactccatg ggtagcggcc gaggccggtg tacgacaggt caggggtgg gttcgtgagg     41040 cgcggctcag cgggtgagcc gggagcggtc caccttcccc gcggcgttgc gcggcaggcg    41100
tgaagtcagg cgggtgaaga cggcgggcag tgcgagggg ccgaactggc cgcgcagatg     41160
ggaacgccag gcccggatgt ccgcgcgcac gtcctcccgg ccctctcctt gtggcaccac    41220
gtacacggcg aggcgggtca ccaggccctg gccgttgacg tgggggagga ccgcgcactc    41280
caggaccgag gggtcacggt tcagcgcggc ctcgatctcg gtgagttcca gcggttccc     41340 gaacagcttg acctggaagt ccttgcggcc ccggaattcc agggctccgt cgaaccgtac    41400
ccgcgccaga tccccggtcc ggtaccaccg gtcaccgtcc ggggcgaggc cggcgagggg    41460
cgcgaacagc gcgctgtggt ccgggccgcc ctcgacggcg agataacccg gcgtcacgta    41520
cggggagcgg atcaccagtt cgccggtgac gccggcgggg ctcggccggt cgtccgcgtc    41580
cacgacgagt acctggcggc cggggagcgg gtacccgatc ggggccgggc ccgtgaccgg    41640
cccggtgatc tcgtgccagg tcgcggcgat cgtctcggtg ggcccgtaga ggttgatcag    41700
gcgggtccgg ggcagggccg cgcgcagtcc gtccacgagt tcgccgggca gcgcctcgcc    41760
catcaggagc aggtggccca gggtgccggg ccgatcgccc gggtcggagg cggtgatcac    41820
tcccaggagg tccgggcga agctgggcac ggtctggaga tgagtgatcc gctcctggac     41880
gagccacggc accagcttgt cggggttcac cctgacgcgc tccggcaccg gacacagcgt    41940
cccgccggcc acgagcgtcg cgaagacctc ggccagcgcc gggtcgtgct ccggggagac    42000
ccactgcgcc accgcgcgc ccggccccat cgcgaaccgt tcgcccatcc agcccgcgaa     42060
ctggcccagc gcggcatgcg actgggcgat ccccttgggc cgcccggtcg aacccgaggt    42120
gaacgccacg taggccaggt ctgccaggcc cggccccgcc gcggtcgtcg cgtccgggcc    42180
ggcggcgggt cgaggccga gcacagagga ggcgtccagc agggtggcgc ccggttcacc     42240
ggcgtaccag agcgccagcg gatcctcctg cggatcgccg tcgaggacca ggcacgccgg    42300
```

-continued

```
gcgcagatcg ctgagcatcg accggtgtcg ttcgcccgcg ccgtccggag cgaaccacgc    42360
caggtgggcg cccgcctcca ggactcccag cagcaccgcg atccggcggg cgcccggctg    42420
catccgcacc gccaccggcg agccgtgccc cgcgccggcc gcggtgaggg ccgaggcgac    42480
gcgggccgcg tccgcggtca gttcsgcggt cagttcggcg tagcttgtgc gcgtgccgcc    42540
gaacgagacg gcgacaccgt cgtgttccgc gtggcggcgg accgaggcgt gcaccggccg    42600
cgtcatgtcc ccgccggacg cccggcggtc cgaagcgcgc agggcgtggt cccggtggcg    42660
gtcgtcgtcc agcggcagag cgcccacggg tgtgtccgga tccgtggtcg cggcggtcag    42720
gaggacggcc agctgatcca gcatccgccg ggccgaagcg ggctcgaaca gagcttcgcg    42780
gtactccagg tagccggtga ccgagggcgc ggtgtcctgc agcaccaggg tcaggtcggc    42840
ggcggcagtg ccgttgtgca cggacagccg cctcacctcg gcgcctggta tccgcaggcc    42900
cggccgctcc tcgtggacga acacggcgtc ggcccctcg atccggcacg gcccgggggc    42960
cggggccggc gtcgtgtgca gcagctcccg gaaggcggtg gccggcgtgc cgtcgtcctg    43020
tccggcgtag cgctggacca gggctcggaa tccggccagc accacggccg cggcggtgac    43080
cccttccgct tcggcgagcc gggccgtacg gaagccgagg tccggactcc agccgaaggc    43140
gacggtgctc cccgcgtgcg agggcaggtg cgggcggttc cggtcggcgg gcaggacctg    43200
tccggaggcg gtcgccgaag actcctcgct cccgggcgcc cggggcgttt gcggcgcggg    43260
cgcagtggga ggccggccgc cggtggtgac ggcgaggtac gcgttcgaca acgcggccgg    43320
cagggccccg gacggcccgt cccaggctcc ggagtgcgag gccaccagga gaagcaggtg    43380
cgcgcgtggg cctctgcggg cgatgtggag ccgtgcgggc gcgtcaccct cggcgaaggg    43440
acgggccgcc cagcgagcgc agagttcctc ctccccgcac tcctcgtcgg cactcggccc    43500
gtccacggcg gccccgtctc cggcggcggc ccgccaggcc gtccgcaggg cctccaggtc    43560
gagtccgccg ctcacgtggt aggccgcgta cgggtgcaac accgcagatc cggaggccgg    43620
cgaaggcccc cggtccggct cggtcacagt cacgtcattc gccacgacgc ccatcttggg    43680
gcggcggcgc acaggacgct tctccttgag tgcggagctc cgcgtacggc gccgaagcgt    43740
tcggtcaaac cttgttcgac caactgcgca atctggaagt tgacgtcttc caggtggagt    43800
tgggaacgat ggaggccccc gccggccgcg tcggaacggc cgtgcagtgc ggccctctcc    43860
aacactcccg gccatcgcgg aatccgagac gtgcccgaag gagcccccct tgcaagcctg    43920
gttcaagcgc accagtggtg tgcccggtga cagacgtgga aagtggctgg tcctggccgc    43980
ctggctcatc atcgcgatgg cgctgggccc gctggcgggg aagctcgccg acgtccagga    44040
ctccagcgcc aacgccttcc ttccgcgcag ctcggagtcc gcgaagctga caaggaact     44100
ggagaagttc cgcgccgacg agctgatgcc ggccgtggtg gtctacagcg ccgacggctc    44160
gctgcccgcc gaggggcggg ccaaggccga gaaggacata ccgccttcc aggagctggc     44220
cgccgagggc gagaaggtcg aagcgcccct ggagtcggag gacggccagg cgctcatggt    44280
cgtcgttccg ctgatcagcg acgccgacat cgtcgccacg acgaagaagg tccgcgatgt    44340
cgcggacgcc aacgccccc cgggcgtcgc catcgaggtg ggcgggcccg ccgggtcgac     44400
gaccgacgcc gccggcgctt tcgagtccct cgactccatg ctgatgatgg tcaccggcct    44460
tgtggtcgca atcctgctgc tgatcaccta ccgctccccc atcctgtggc tgctgccct     44520
gctctccgtc ggcttcgcct ccgtgctgac ccaggtcggc acctacatgc tcgccaagta    44580
cgccgggctg ccggtcgacc cgcagagctc cggcgtcctg atggtcctcg tgttcggtgt    44640
cggcaccgac tacgccctgc tgctcatcgc ccgctaccgt gaggaactgc gccgcgagca    44700
```

```
ggaccggcac gtggccatga agaccgcgtt gcgacggtcg ggcccggcca tcctggcctc   44760
ggccggcacc atcgccatcg gcctcgtctg cctggtcctc gcggacgtca actcctcccg   44820
ctccatgggc ctggtcggcg cgatcggcgt ggtctgcgcc ctcctcgcca tggtcacgat   44880
cctgcccgcg ctgctggtca tcctgggccg ctgggtgttc tggcccttcg ttccccgctg   44940
gacgccggag tcggccgcgg cccccgaggc accggcgtcc cacagccgct gggagcgcat   45000
cggctccgtc acggccgccc ggccgcgccg cgcctgggtg ctgtccttgg ccgcgacggg   45060
gcttctcgcc ctcagttccc tcggcctcga catgggactc acccagagcg aactgctcca   45120
gacgaagccc gagtccgtcg tcgcccagga gcggatctcc gcccactacc cgtccggctc   45180
ctccgacccc gccaccgtcg tcgcacccag cgcggacgtg gccgaggtcc gccgggccgc   45240 cgagggggacc gacggagtgg tctccgtcca ggacggcccc accactcccg acggagagct   45300
gaccatgctg tccgtggtgc tgaaggacgt tcccgacagc agcggggcca aggacaccat   45360
cgatgcactg cgggacaaca cggatgctct cgtgggggt acgacggccc agagcctgga   45420
cacccagcgc gcctcggtcc gtgacctctg ggtcaccgtc cccgcggtcc tgctggtggt   45480
cctgctcgtc ctgatctggc tgctgcgctc ggtcaccgga ccgctgatca tgctcggcac   45540
cgtggtcgtg tcgttcttcg cggccctggg ggcgtccaac ctgctcttcg agtacgtgat   45600
ggggcacgcc ggcgtcgact ggtcggtgcc gcttctcggg ttcgtgtacc tggtcgccct   45660
cggaatcgac tacaacatct tcctcatgca ccgggtgaag gaggaggtcg ctctgcacgg   45720
ccatgccaag ggcgtgctca ccggcctgac caccaccggg ggcgtcatca ccagtgccgg   45780
cgtggtcctg gccgcgacgt tcgccgtcat cgccacactg ccgctggtcc cgatggccca   45840
gatgggtgtc gtggtcggcc tgggcattct gctggacacc ttcctcgtcc ggacgattct   45900
tctgccggcc ctggcgctcg atctggggcc ccggttctgg tggccgggcg cgctgtcgaa   45960
gacgtccggg ggaccggccc ccgtccgcga ggaccgcacg tcccagcccg tgggctgaga   46020
cccgtcccga cgagacccgt acggcgggcg gccggttccc ccgggccgta cgactgagca   46080
acccagaaga tgggccgccc gcgaccaggc gtcacgatgg tggcccaccg gccgcaggcc   46140
gatctcccgg aaggaagcgc cgtgttgggc gatgaggacg gcaaggccgc cgagctgtgg   46200
tcgatggcga acctgggtac accgatggcc gtgcgcgtcg cggcgaccct gcgcatcgcc   46260
gaccacatca cggccggagc gcacaccgcc ggcgaaatcg ccgaagcggc cgccgtgcac   46320
gaggaatccc tcgaccggct gctgcgctac ctcaccgtcc ggggcctgct ggaccgtgac   46380
gggctcggcc ggtacacgct gaccccctg gccggccgc tgtgcgagga ccaccccgcc   46440
ggcgtccggg cctggttcga catggaggga gcggggcggg gcgagctgtc gttcgtcgac   46500
ctgctgcaca gcgtacggac cgggaaggcc gccttccccc tgcgctacgg ccgcccttc   46560 tgggaggacc tggcggagga cccccgccgc gcggagtcct tcaaccggct gctcggccag   46620
gacgtcgcca ctcgcgcccc ggccgtggtg gccggcttcg actgggcgag caccggtcat   46680
gtcatcgacc tcgaggcgg cgacggctcc ctgctgaccg cactgctgac cgcctgtccg   46740
tcactgcgcg gcacggtcct ggacctgccc gaagcggtgc agcgtgccaa ggagtcgttc   46800
gccgtgtccg gactggacga ccgggcgaac gcggtcgcgg gcagcttctt cgacgccctc   46860
cccgccggcg cgggcgccta cgtcctgtcc ctggtcctgc acgactggga cgacgaggcg   46920
tccgtcgcga tcctgcggcg ctgcgccgag gcggcgggc agacgggatc ggtgttcgtc   46980
atcgagtcga ccggctcggc gggggacgcc ccgcacacag gtatggacct gcgcatgctg   47040
```

```
tgcatctacg gagccaagga gcgccgcgtg gaggagttcg aggaactcgc cggccgggcc      47100
gggctccggg tcgtcgccgt ccaccccgcg ggcccttccg cgatcatcca gatgtccgcg      47160
gtctgaccgc ccggagcccc ggcccatcgc ggcgcgggcc acggcagaca aggagagagc      47220
gtatggccgg cctggtcatg tcgccggtgg aggcgctcga cgcgctgggc acggtgcagg      47280
ggcgtcagga cccctatccc ttctacgagg cgatccgcgc gcacgggcag gcggtcccca      47340
cgaagcccgg ccgcttcgtg gtggtcggcc acgacgcgtg cgaccgggcg ctgcgggaac      47400
cggccctgcg cgtccaggac gccaggagct acgacgtcgt cttcccctcg tggcggtcgc      47460
actcctcggt ccgggggttc accagctcca tgctctacag caacccgccc gatcacggcc      47520
ggttgcgcca ggtggtgagc ttcgcgttca ccccgcccaa ggtgcgccgg atgcacgggg      47580
tgatcgagga catgaccgac cggctcctcg accggatggc ccggctcggc tccgcggct      47640 ccccggtcga cctcatagcc gagttcgccg cccggctgcc cgtcgcggtg atcagcgaga      47700
tgatcggctt tccggcgaag gaccaggtgt ggttccgcga catggcctcc cggggtcgccg      47760 tggcgacgga cggtttcacc gaccccggcg cgctcacggg ggccgacgcc gccatggacg      47820
agatgagcgc ctacttcgac gacctcctgg accgtcgccg ccgcacccg gccgacgacc      47880 tggtcaccct gctcgccgag gcccacgacg gctcccccgg gcgcctggac cacgacgaac      47940
tgatgggcac catgatggtg ctgctcacag ccggggttcga gaccacgagc tttctgatcg      48000
gccacggggc gatgatcgcc ctcgaacaac gggcgcacgc ggcccggctg cgggccgaac      48060
ccgacttcgc cgacggctac gtcgaggaga tcctcaggtt cgagccgccg gtccacgtca      48120
ccagccggtg ggctgccgag gacctcgacc tgctgggcct gtccgtaccg gcgggctcca      48180
agctggtcct gatcctggcc gccgcgaatc gcgatcccgg ccgctacccc gagcccggcc      48240
gcttcgaccc cgaccgctac gcgccccggc cgggcgggcc ggaggccacc agaccgctga      48300
gcttcggcgc gggcggccac ttctgcctcg gcgctccgct ggcgcggctg gaagcccgga      48360
tcgcgctgcc gcgtctgctg cgccgcttcc cggacctggc cgtgtccgag cccccgtct      48420 accgcgaccg ctgggtcgtc cgcggcctcg aaacctttcc cgtgaccctc gggtcctgag      48480
cccccgccgg ccggaacacg tgaccgtccc ggccggcggg tgcgcgccct ctcagacgta      48540
cagggtgttg ggcccctgac cacacagcac ccggccgtac agctccaggt tggtgctcgg      48600
gttcatgcag gtgcagcgtg atgctctggg catcgctgca cgcgctggat cgggacgtcg      48660
ttgtagatcg aggacccgcc gctcgcctgg gcgaggatgt ccaccgactc cttgcccagt      48720
cggcacgccc gccccagcag gccgcggcac agcaccgct cctccagcgt ccaggcctcg      48780
cccgaagccc ccttggagtc gacgaggtcg ccagccgat gggcgtggaa ccgtgcctcg      48840
tcggccagca gggtcgcctc gccgagctgc aggtgggtga tcgcgccga gccctgctcc      48900 tcgtactcgg tgtaggtgat cttgcggccg gcagcctcc cgcggaagac gtcctgagcg      48960
gccgcggcca gtcggtcat ggtgccgacc gacgaggccg aggccacggc cagcatcggc      49020 gccggaaca tcggtgatcc ggcgttgagt tcggaggcgt actgctgctg gagcaccgcg      49080
cccagcggaa ggacgcgctc ctggggaacg aagacgtccg cggcgatggt gctgacgctt      49140
cccgagcccc ggagccccga ggtgtgccag tcgtcgacga tctgcagctg gtcggtcggc      49200
accagggcca tcacgggctg catgccgccg tcggggtcg gtgagacggc gatcagaacc      49260
tgccagtgac tgtgccaggc accgctgatg aagccccact tgccgttcac tacgacaccg      49320
ccgtcgaccg gggccgccat gccgccggga ctgagggtgc cggagacccg gacatccggc      49380
cgggagaaca cctcgtcctg cacgtggtcg gggaagaggc ccgccatcca ggtgggtatc      49440
```

-continued

```
caccacaccg aggccgtcca ggcggccgat ccgtcgccgc gcgccagctc ggcggccacg    49500
tccaccaggg tgcgggcgtc ggactcgaag ccgccgtaac gggccggcac gcgcatgcgg    49560
aagatcccgg cttcggccat cgcctcgacc gactcctcgt gcagccgccg gttctcctcg    49620
gtccaggccg cgtgggactg gagcagcggc ctcagcttcg aggcccgttc caccagttcg    49680
gtacgggcgg gcgtagacgt ctggtccact cgatcctcca ggaatcatga gacgccctgt    49740
ccgcggtatg cggaagcagg cgtctgcgcg catcggtcag gacggcgtcg ccctgctccc    49800
gcatggttca ccgagttccg cggacgtcgc atctccttga ttgccggtca cctaccccga    49860
tgccgatcgg gctggtgcga cagcgcatcc cacgagaagt ccacgaacgg tccgggaagc    49920
cagaatgtgc ttctcggccg gagtcacggc cggcgccggc gcccgtcgcc ggtcacgccg    49980
gaccacgccc ggaccggtca tggaggcagc ccatgagtga caacgacagt ccgtcccggg    50040
tgccggccgc ggtggcaccc gccaccgcga aaccgtcggc cggcacggtc ctcggcgccg    50100
cggtggcttc gcccgccgcc tacaccgcgg cgaccgccca ggaagcggcg accgcgctgg    50160
tccgcatgct gatggaacag atggtgctcg gtcccggcgc ggtcggtccc gagacccgcg    50220
cggacggccc ggcgcggcgg accggctccg gccacgcccc ggcgccgcag accggaccgg    50280
acgcgccggg cgaaccccg cccacgtggg cgccgaacct cgacgacggg aaggtaggag    50340
gacgatgagg ccgctcgttc gggcagtgct gcggggttcc ctgcggcagg tgaggtacgt    50400
ggacgtggtc tccccgcgcc gggcgcgctc cctggtggcg cgggtgtacc gggagaccga    50460
ggagcagttc ggcgtgctcg cgcccccct ggccctccac tcgcccgccg cggcgtcgct    50520
ggccgcgacg tggctcatgc tgcgggagac actgctggtc gacggcgggg tgagccgggc    50580
ggtgaaggag acgtcgcca ccgaggtctc ccgtgccaac gactgtccgt actgcgtcca    50640
ggtccatcag gcggtactcg ggacactgcc tccggacggc ggccaggccg ggctcctgcg    50700
gtgggtccgg gaggcaggcc gacggcccgg cggcggtgcg gtgggcggcg ggcggccgct    50760
tccgttcagc ggtgaacagg caccggaact gtgcggcgtc gtggtcacgt tccactacat    50820
caaccgcatg gtctccctct tcctcgacga ctcccccatg ccgacccgga cgccgacacc    50880
gttgcgcggg cccatcatga ggaccaccgc actggccatg cgtcccgtcg gcccggggct    50940
gctgacaccg ggcgcatcgc tcggcctgct gcctccggct cccctgccgc ccggactgga    51000
gtgggccgag ggcaacccct tcgtggccca ggcgctgggg cgtgccgtcg ccgctgtgga    51060
ccagggagcg cactgggtgc ccgaaccggt ccgggagcgg ctgcgcacac gtctggacac    51120
ctgggacgga tcggcgccgg gcctcggccg gggatggctc gacgaggccg tgtccggcct    51180
gccgccccag gacgtgcccg cggcacggct ggcgctgctg acggccttcg cccctacca    51240
ggtgctcccg gacgacgtcg aggagttcag acggcgtcgg cccaccgacc gcgaactcgt    51300
cgagctcacg tcctacgccg cgctgaccac ggccgtccgt gtcggtcgca cgctcgtcgt    51360
gcccgacgcc gccgggccgg gatgaacggc cccgcaacgg ctcgggaagg ctgtctcacg    51420
gccggaggcg tacgccggtg aggtgctcgg actcctccca gaggcggcgc cgggccctgg    51480
ggtcgacggc tgctccgccg gggcgcacga gcccgggtgc gccccgggtc tcggtcacgc    51540
cgaggggccc gtagaactcg ccccgcgcg cgccgggatc ggtggccgcc cgcagaccag    51600
gcagcatccc cgccgcggcg ggctgcagga acaacggggc gagcggggag ccgagcctgc    51660
gcacgggcgc gggaaagtcc cggcccagac cggtcgcgt cagcccggga tgagcggcga    51720
gcgaggccag ttccgcgccg gactccgcca gtctgtgatg gagttccagc gcgaacatga    51780
```

```
ggttggccag cttggactgg ttgtaggccc ggtaccggct gtagcggcgt tcgccgtgaa    51840
ggtcgctgaa gtcgatgcgc cccagccggt gcagatagct gctgatcgtc acgacccgcg    51900
cgcccggcgc ggcccgcagg ctgtccagga gcaggccggt gagggcgaag tgccccaggt    51960
ggttcgtggc gaactggagt tcgtgaccgt ccggggtgcg ggcccggtcg gtccacatca    52020
cgcccgcgtt gttgaccagc aggtggatgc gcgggaagcg gtcgcgcagt tcctcggcgc    52080
cggcacgcac cgacgcgaga cgggaaagat ccagccgtct gaccgtcagt tgcgccgacg    52140
gcacccggct ttggatgcgg gccgccgcgg cgaccccgcg gtccggatcg cgcacggcca    52200
gcaccacgtg ggcgccgtgc cgggcgagct cctgcgccag gtgcagtccg atgccggagc    52260
tggcaccggt gaccaccgcg gtggttccgg tacggtccgg gacatcggcg gcgctccagc    52320
gtcgccgcgt tctcatcggt cgtccctccc ggggatgcg tcagccggcc tgggccatcg    52380
cggcccggta gccgttggcg acgatctgcc gggcggagtg ctcgtagtac tcgtcgtcct    52440
tcggcagctc cgtggcgaga ccgctgacgt accggttgaa catgcagaac gcggcggcga    52500
tcagaacggt gtcgtgcaga gcggtgtcgt ccgctccctc ggcccgcgcc gaggcgatca    52560
cccctgcgga gaccgggcgc gccgcgctct ggacctcggc ggcgacggcc agcagcgcgc    52620
gcgtcctgcc gtcgatgggc gcggtggcgg ggtcggcgag gacggcctcg acgagctgcc    52680
ggcctcccgg cagctgcgcg gcggcgaagg ccccgtggga ggcggcgcag aactcggtgg    52740
agttgagatg cgagacgtac gccgcgatga gctcgcgttg ccccggttcc agcgaggacg    52800
gcgcccgcag cagggcgttc gcgagatcgc ccagcggtgc tgcggtgccg gggtggtgag    52860
ccatcagacc actgatgccg gggaggtcgt tgtcgagtgc tatgtggggc acggctcttc    52920
cttccgggtg gacgaggggc ggacggcggc ggatcagggc cattcgactt cgtcgtcggc    52980
ggccgcgcag atgcgggtga agggccattc cacgtcttcc cctcccgttg cggagtgggc    53040
ggaggccgtg gtgaagaggg tgacgagtcc gaacgtgccg aagaggaggg acagtcgggc    53100
aacgtgaagt gcggtaccca tgcgagctcc tagcgagggc ggcgtgaccg cgggacggtg    53160
agacctcgtg atgccaggaa gctagcgaat cggactgagg gtggcaacga tatgccagac    53220
tttggcaact tgcctgtgta tcagccggac tgtcggccgc tggtaaagac ggaacggcga    53280
gatcccgcga ccgcgtcgca gagcagcagg gtctgctcac ccagcgtcgg ggcggccagc    53340
atgtcgcgta ccgggagcgt gacgcccagc tcgcggttga tcctgcggac cagccgggtg    53400
atgagcaggg agtcgccgcc gtgggcgaag aaatcagcac cttcggaggg gtccgggaag    53460
ccgagcaggt caccccagcc gcgcaccagt acctggcgga tgtcgccggt ggtgacgacc    53520
gtgcgccggg agccccgacg tgccgagcgc agccgcgagg catgcaccag cgccacctgg    53580
tcgccgaggt tgcgccgcga cagctcgcgc agcgacaccg tgacgccgaa cctctcggtg    53640
atcctgcgga ccagccgcgt gatcagcagc gtgtccccgc cgcgcgcgaa gaaatccgaa    53700
tgctcggtga ggtcggagcg gccgaggagc tcgctccacg cgccgaccat gaactccccc    53760
acgtcaccga gccggtgctc gtcgccgtcg ggcccttcg gcgcgccgga tcccgcggaa    53820
cggttccggc cggagacggc agagcggtca ctggtcactt tcgccacctc caggggcatg    53880
tgtcggctgc atcggcttcc cgccacggta cgggagcaca tgttgcatgg caatacccttt   53940
ccaagtcggt ggcaaccctc cttgccatcc acccactgca gttgggcgag atgtgtaggc    54000
attcgaggtc cgcaggtttg ccaagccgcg cgcgaccggc atactctctg gcacaactgg    54060
aatgagtagc gtggcaggcc acggggaccg ggccgggcca ggaaccttcg tcctccatct    54120
attcgctggg gcgtgcacgt gttggagcag ccatctttcg gccgtcgcct gaggcagctg    54180
```

```
aggaccgagc ggggtctttc ccaggccgcg ctcgcggggg acggcatgtc tacgggctat   54240
ctctcgcgcc tggagtcggg cgcccggcag ccctccgatc gcgccgtcgc ccacctggcc   54300
ggacaactcg gcatcagccc gtcggagttc gaagggtccc gggccacctc gctcgcccag   54360
atcctctccc tctccacttc cctggagtcc gacgagacca gtgagcttct cgccgaggcg   54420
gtacgttccg cgcatggcca ggatccgatg ctccgctggc aggccctgtg gctgctggga   54480
cagtggaagc gccggcacgg cgactcggcc ggcgagcacg gctacctcca gcgtctggtg   54540
acgctgagtg aggagatcgg cctggccgag ttgcgcgcac gggccctgac ccagttcgcc   54600
cggtcgctgc gggtactggg cgagatcgtt ccggcggtgg aggctgccgc cgccgcccac   54660
cggctcgcgg tggaccatgc gctgtccagc caggacaggg ccgcttcgct gctggttctg   54720
gtgtcggtgg aggccgaggc gggacggatg cccgacgccc ggcgccacgc cgacgaactg   54780
accgtcctgg tgaggggacg gtccgacact ctgtgggccg aggcgttgtg gacggcgggt   54840
gcgttgaagg tgcggcaggg cgagttcgcc gcggccgagg tccttttcca ggaggctctg   54900
gacgggttcg acagccggga gaacctgacg atctggctgc ggctgcgcat cgcgatggcc   54960
gaactccacc tgcagaaact tcctcccgag cccgacgccg cgcagctctg catcgaggcg   55020
gcggaggcgg cccttccctt tgcccgcaca tccgctctgg aacagtccct cgccgctctg   55080
cgggcgcgcc tcgccttcca tgagggcagg ttcgccgatg cccgcgcgtt gttggagagg   55140
ctcggcagga ccgagctccg gctgcccta t cagagccgga tccgcctgga ggtcctcggt   55200
catcagctgc gcatcctgag cggggaggag gaggaaggcc tggccggcct ccagctcctg   55260
gccgaggagg cgcaggagaa ctccaacatc aacctcgccg cggagatctg gcggctcgcg   55320
gcggaatgcc tgatgcgggc gcgcgggaag gtccgcggcg ccaccggcgg ctgacgccgc   55380
gccggttcgc gaggtccacc gcgccgccgt ggccaccgcc gtcggcgtga ggcgccggcg   55440
tgtgccgccc ccacggttg ctcgcccttg gtggtgcatc tgttggcaca tgtgtacctc   55500
ctacacagtc aattgttgcc aaaattgtcg aaccgaatgg caattgcttg cctttgctga   55560
agaggcgtgc tgatatgcaa gtcaagtagc ctcctccgat ctcgggcggc catatgggaa   55620
acatcgagtt gagcggcgat ggcgttcgtc agtgctgccg ttctggccag gcaactgatg   55680
tcgatgggga tggcaagatt ttgccgaaaa ccgatacatc tctgtccgtc ccggacagcc   55740
ttcgcccccc gggtgacact gctccggcat ggctccggtt tctcgtcgcc ggccgacgg   55800 accgcaccgt ccggaacgag gcgccggtgt cgtccgctg atgggcacag cggcctcggc   55860
cgcagcaggt tcccaccgag aagaatgccg aggcccagcc gtgaaccacg acatgtccca   55920
gcgtgccttg ctggaggcgg cggccgaggg gctgcggcgg ctggccggcg acgcgcggtg   55980
ccggagcgcg tcggccgcgc cctcctcggc attgagggac atgttctccc ccgccgcccg   56040
ccggtacgtg ctcgcctcgg accgcgcggg gttcttcgag caggctgtcc ggctgcgctc   56100
ccgggggtac cgggtgagcg cggagttcgt cggccccgat cagggagcca ccgacgccct   56160
ccacgcggag cacgtggtcg aagagcacct gaggctgctc gatcaggagc cggcccctga   56220
ccggatcggt gtggacgtct cccggatcgg cctcgcccac tcggcgcaga ctgccctgcg   56280
caacaccggg cggctggctg ccgctgcggc gctccgcggg agcgaggtcg tcctgctcat   56340 ggagggtgtcc gaggacatcg acaccgtgct ggccgtccat gacgccctgg tgaaccgtta   56400
cgacaacgtg gggatcaccc ttcaggcgca cctgcaccgc accgtggacg acgccatggc   56460
ggtcgcgggt cctggccgca ccgtgcggct ggtcatgggc tcctcggccg agcctgccgg   56520
```

```
caccgctctg tcccggggcc ccgctctgga ggaccggtac cttgacctcg cggagcttct   56580
cgtggaccgt ggcgtccggc tgagtctggc cactccggac gccgaggtcc tggccggggc   56640
gcaggagcgt ggtctgctcg aacgcgtcca ggacatcgag atgctctacg gtgtgcggcc   56700
cgagctgctg cgccgccacc gggcggcggg ccgcccctgt cgcatccacg cggcctacgg   56760
gatgaactgg tggcttcccc tgctgcggag gctggccgac aacccgccga tggtgctcaa   56820
cgccctggcc gacatcggcc gggaccggga gcccgtcgcc caccaggcgt actgacccgc   56880
cccgggccgc gatccgcggg gcaccggccc cggggcgccg gtcagctccc ggtcgccgcg   56940
aactgcccgg gcctgcgccc ctcgcccgcc ggccccggt aggcctgggc gatgtccagc   57000
cacttctccg cctcctgacc agacgcggtc agggcgaggt cgtcgcggtg gcggcgccgg   57060
gtgaccagca ggcagaagtc gtgcgcggga ccgctgaccg tctcggtggc gtcctcgggg   57120
ccgaccgtcc agacctcgcc cgaggggcg gtgagctcga agcggaacgg cgcggccggc   57180
ggggtcagac cgtgggactc gtagccgaag tcgcgtgtca gccaggcgaa gtcgacgatg   57240
ttgcgaagcc gctcggtggg cgtgcgccgg acacccaggg cgtcggcgac gtcctggccg   57300
tgggcgaaca cctccatgat cccggcgcag cccagaacga ccggcggcag cgggttgacc   57360
agccacggaa ccacctggcc ggcggggacc gcggcgagcg cctcgaccga ggcccgcccc   57420
atgcccggga gcgggtgag cagttcctgc ggcgggaagc ccttgaactg ctgcagagcc   57480
gcgttgaccg ctccgtcgaa gttgcctgcc gcggcggccg tgacggcctt gaactcctcc   57540
ggcgccgccg ccgcggtcct ggccaggttg aagacgaagg tgaggtgggc gatctggtcg   57600
gtgacggtcc agccgggcgc cggcgtcgga gtgttccagg cttcgtcgtc gatcttctcg   57660
accagctgcg ccagctcctc gatgtcggtg gccaggtgct tgaggacgtc gtcgagcgaa   57720
ttcatctcgt acttccttca ctgggggtgt tccgggctgg gacggatgtc ccgccgggtg   57780
ggccggcggc cggcggaagc gccgtcgcgg agcgtcggcg acagtcgcta ggcggcgcgt   57840
cccgcgtagg agccggcccg gtcggaatag ggcgcgagcg cctcggccag ggcttcgggt   57900
atcagggtcg gcacggtcgc cgtgttgggc ccgcgcatgc aggcgatgcg ctggcgtccc   57960
cgcgccacca gggtctcgcc gccgtcgtcg cccagcttga tgtagtcgaa ggtgaactcc   58020
agctgggtct gccgcagctc cgagagcctc atccggatcg acagttcgtc gaaggcggtg   58080
atctccgcga agaactcgca gtccaccttg agggtgaaga gcttgaggtc ctcctggacc   58140
tcggcgagca ccgaaggcgc cctctccttg agaaagagtt cccggcaacg cccctgccaa   58200
cgaaggtagt tgacgtagta gacgttgccg acgaggttcg tctcctcgaa gccgacggtg   58260
tggcggagct cgaagtagtc aggattcgtc gcggtcatag gtctgtgccc ttcgtcgtcg   58320
gggccggtcg tcgcaccgag ttgcgtgaag caactcactg gtcgcgatgg cctgcggggt   58380
cggtggcccg cgctccgggc ggagagtgcg ggcggggtgc cggccggcgc gggtcagcc   58440 gcgcgccgac ggcagcaggg gaagaaccct ctcgcgcccg ctcgtggagc cgtcggggc   58500 cggtgcgccg taggtgacgg agataccccg gctctgcgcg gcgcgcacga tccccggcat   58560
cgcgcgttcg gcgagcgccg cgatggtcat cgcgggattg accgtcagcg cgccgggaac   58620
cgacgatccg tcggtgacga agatccccgg gtggtcgcgg agctcgttgc tgtcgtccag   58680
ggcggatgtg tgggggtcgt cgcccatccg gcaggaggag agcgggtgga cggtgtaggc   58740
gccgacgagg tcgttggtcc agggcatgac cttggccagg ccgtccttct ccaggatctc   58800
cttgacctcg gcgtcggatg cggcccaggc gcccaggggtg ttcttcgtcg ggtcgtagcg   58860
caggttgccc cggccgagca tctgctggga gatgcggtgg gcgttaccgg tggcgggagg   58920
```

-continued

```
ggggccgaag acgccttcgt tgtcgtcctc gatcatcgtg aagatcgtga gccaggaggt    58980
ccactgcttc aggatctcct tcttctcctt gccgaaccag gaggggcccg tggcgccggg    59040
cacctgggcg aggatcgtgc cgaggccggg cgggaagtag agctgttcca gggagtagcg    59100
ggagtactcg ggcaacgagc cgtccagcct gtcccagctc gccacggtgg gccccttgcc    59160
gatctggttg gccgcgtagg cgagcccgtc gccccggtcc aggccgaaca gctcggccgc    59220
cttggcctcg tcgatgatgg cggtgttgag ccgctcgccg ttgccggaga agtagcgtcc    59280
gaccgctcgt ggcatggtgc ccaggtgggc ctcgctgcgc tggaggatca ccggggtcgc    59340
gcccgcgccg gccgccatca ccacgatctt cgcctcgatg acgccgctgc ccgcctggag    59400
gcggtagtcg tcgtcgtgca cgacgttgta gtgcacccgg taggagccgt cggggtgcg    59460
cgagaggtgc tggacctcgt gcagcgggcg gatgcgcgcc ccatgggcga tggcggcggg    59520
caggtagttg accagcaagg actgcttggc ctcgaagcgg cagccggcca tcatccagtt    59580
gcagttcacg cacttggtgt tgtcgatggc gacggcgagg gggttggcgg tgcggccggc    59640
gtggttgcac gccgcggccc acagtccgcc ggcgtagctc acgtcgttcc agtcctgccg    59700
ggtcacggag agggactcct cgacacggtc gtaccagggg tccagggttt cgcggctcac    59760
cgcctgcggc cacatccggc gtcctatgga cccctgccgg tcgaagacga agcgcggggc    59820
gcggggcatc gcggcgaagt agacgacgct gccgccgccc acacagttcc cgccgaggat    59880
gctcatgccg tccccgaccg tgaagtcgaa cgccctcgtg tacgaggagc cgagtttgta    59940
gtcgtgctcg aactccttgc tctccagcca cggcccgcgt tccaggacgg tgacgtcggc    60000
gcccccgcc gccaggtggt aggcggcgat ggcaccgccg aatccgctgc cgatgacgag    60060
gacgtccgtg cgctcggccg tggtgctcat gcggggctcc cggtggacgt ggtgtcgggg    60120
tggaggcggg cgaactcacg cccgtagctg taatccttga agcgccacag gccgtcggcg    60180
tccggcatgc tcaggcccat ggcctccagt cccggatggc cgtcctccat cgcctgtgcc    60240
gtgttgaggt gcgcggccga atcgaaggcc atgttgcaga agagggacag cagcacccag    60300
aactccttct cggggtggcc tggtgtcgtc agccgctgga tcagcgcggc ccggtccggg    60360
tagtcgagcg ccacgaaggg cgggaccgtc gggtcgggag ccaggcggcg ctccgccgcg    60420
taggccagcg cgtgctcgtt caccaggcgc accaggtcgt ccagaccctc gtggatgccg    60480
gtcgcatccc attgcaggag ctccagggct cccgcctgga cggcgccacc gccggtggac    60540
acccccgcga tggcccggtc gtccgcgaag cgcttctggc ccggcacgat cgtgtccgcg    60600
taggcctcca gggtcatggt ccggatatcg ccggccggcg cccctcgctc attgtcgtcg    60660
cgcaactcgc tctccattct cgcagtccgg agtgggatgc cttgtggcga ggagaaagct    60720
aggttcgttc gaccggttca agcaactagc caaagtcgag gcgaccttga aaccgactcc    60780
acggagttgg cgcgaagcgg cggatggatt acacgcgcgg gcgagcggct cactagtctg    60840
gccgcacgga tgtcttcatc acctgcacgt ggaaaagctt ctgcacgggc accgcatgtg    60900
gaagtgagcc ctggtctcat gtcttggggg aaacgtgaaa agtgactctg cccaacgcgc    60960
cgtggagcga tcacgccgtg tcgtacggat cgatgaactc attcccgccg attccccgcg    61020
cctgaacgga atcgatcgtt cccatgtgca gcgcctcgcg accgtgtacg cgtccctgcc    61080
gccggtcctg gtgcaccgcc cgaccatgcg ggtcgtcgac ggcatgcacc gcatcggcgc    61140
ggcccgcctg aagggctgg acacggtcga ggtcaccttc ttcgagggcg ccgaggagca    61200
ggtgttcctg cgttccgtcg cggcgaacat caccaacggc ctgccgttgt cggtggccga    61260
```

-continued

| | |
|---|---|
| ccgcaagacc gccgcggccc gcattctggc ctcccacccg accctgtccg accgcgcggt | 61320 |
| cgccgcacac gtcggcctcg acgccaagac cgtggcgggg gtacgacgt gttcagccgc | 61380 |
| gggttctccg ctgctgaaca tgcgcaccgg ggcggacggc cgcgtccacc cgttggaccg | 61440 |
| caccgccgaa cgcctgcacg cggccgcgct gctgacccag gacccgggac tcccgttgcg | 61500 |
| ctccgtcgtc gagcagacgg ggctgtcgct gggcacggcc cacgacgtcc gccgtcggct | 61560 |
| gctgcgggc gaggacccgg tcccgcagaa ccggcagagc gcgatgctgg agccgggact | 61620 |
| cgccccgcag aagaaggcga cggccaagcc gcccgtcggc ccggccgccc gtccggtccc | 61680 |
| gaaggtgccg cccgccgtcg ccggcaggcc gccggtgtca ccgcggtccc gggccccgct | 61740 |
| ggaggcgctg cgcaagctct ccaacgaccc ctccctgcgc cactccgacc aggggcgcga | 61800 |
| actcatgcgc tggctgcaca accggttcgt cgtcgacgag gcgtggcgcc ggcgcgcgga | 61860 |
| cgcggtcccg gcccactgcg tcgactcgat ggcggagctg gcgcagcact gctcggacgc | 61920 |
| ctggcaccgg ttcgccgagg agatggttcg gcgccggcac agcgccgcgg ccgacggctc | 61980 |
| cggactccgc acgactcagc caactcgccg ttgacggcct acttcgacag ggagttacgg | 62040 |
| tgaccacgaa caccatcgag gacgcggtcc gccgggtcgt cgagtacatg cacgtcaacc | 62100 |
| tgggtcagaa cctcacgatc gatgacatgg cgcgcacggc gatgttcagc aagttccatt | 62160 |
| tcacccgcat cttccgcgaa gtcaccggta ccctctcccg gcgtttcctg tccgccttac | 62220 |
| ggattcagga ggccaagaga cttctcgtgc acactgcact cagtgtggcc gatatcagca | 62280 |
| gtcaggtcgg ctacagcagt gtcggtactt tcagttctcg cttcaaggcc tgtgtggggc | 62340 |
| tttccccgag cgcctatcgc gacttcggcg gggtgcagcc gggttttccc tccgccgcgg | 62400 |
| cccgtctcac tcccaccgcg cacaatccct ccgtgcgcgg ccgcattcac tccgccccgg | 62460 |
| gtgacaggcc cggaaggatc ttcgtgggcc tgttccccgg caggatgcgc cagggccgcc | 62520 |
| cggcgcgctg gaccgtcatg gagagtcccg gggccttcga gctccgggac gtgcccgtgg | 62580 |
| gcacctggca catcctggtc cactccttcc ccgccggaca ccgccgcac cagctcgact | 62640 |
| ccgaaccgct gttgctcggg cacagcggac cgctcgtggt gcaccccggt gccctgctcc | 62700 |
| ggccggcgga catcctcctg cgcgcggtgg acgccctcga tccaccggtc ctgctggccc | 62760 |
| acttcgcgct ggagagccgc ctcacctcgc cgtactcacc gtcatcggta gccctccgcg | 62820 |
| catccgcagg gagagcatgg gttcggcaac cgcccggtgt ccggcgacgg tacgcagatc | 62880 |
| gagatcgcgg gtgaccaggg ccgtgacgaa caccgcctcc atcatcccga ggttgctgcc | 62940 |
| gacgcagaac cggggcccccg cgccgaacgg gatgtacgcg taccgcggcc ggtcggcggt | 63000 |
| ctgccggggt tcgaaccgct cggggtcgaa gcgctcgggg tcctcccaca gccccggatg | 63060 |
| gcggtgcatg atgtacgggc agaccagcac atccgatccg gcggacaccg tgtagccgcc | 63120 |
| gaccacatcg cgttgctggg ccaccctggg caggatcc | 63158 |

<210> SEQ ID NO 2
<211> LENGTH: 22005
<212> TYPE: DNA
<213> ORGANISM: Streptomyces globisporus

<400> SEQUENCE: 2

| | |
|---|---|
| acacgggagg gaacagccgc atcgcctcct gcaccaccat cgtggtgtac gtcagccgat | 60 |
| gcaggtcctc cggtccgggg acgccgtcgc cgagggcggc acgggcctcc gcgcggaccc | 120 |
| ggtcacgtac ctcggggtga cgttccagca gatgcagggt ccagccgagc gtactggcag | 180 |
| tggtctcgtg gcccgccagg agcagggtga ccagttcctc gcgcagcctg ttgcgagccc | 240 |

-continued

```
gggcggggtc gtcccggcgc ctgtccgcgg cgacgatgat ccgggacagc gcgtcgtcgc    300
ccggcccgcc gtcggccatc ctggagcgcc ggtcggccac cagcaggtcg gccacccggt    360
acagctccct gcgggcgcgc cggaagcgtg cttgcgcagg cagcggcagc caggccggca    420
ccgtgccctg gctcaccatt ccagcatggg cctggtcctg gacctcctcg aaggagtggg    480
cgagcgactc gtgcgcggtg aggttcgagt cgagcagggt ccggcccagt acgcctaggg    540
tgagaccggt gacctcctgg agaacgtcca cgggaccgcc cccctcgtga ccgcgcagca    600
gggcgaccag cttggccgcc tcctcggcga cggcggccgc ctgctggttg atgcggcccg    660
gtttgaacgc cggctgcacg atcctgcgct gttcgcgcca cgtctcaccg tcactggtga    720
gcagcccgtc gcccagcacc cggcgggact gcaccagacc gatgcccttg tggtagttgt    780
cgctgttgtc cgccaggacg tgcttggcgt agtcggggcg gttgaagatg tacagcttct    840
tgggccccat ggagacgcgg acggcgtccc cgagcccggc cgcgtccctc atcatcccga    900
ggcggtccac cgccagcttt ctcagcagtc ccggaagcgc ccggaggggc gggccgggcg    960
ggtcgatcct catgccgccc ttccttcgtc cgcatccgga gcgaagcggc ggaagcggcc    1020
gccggagaac agcatcccct cgcgggccgg ccagcgcgtc gccgtgatga cctcgccgag    1080
gaagatggtg tggtcgccgc cttcgtagag ccggtgtatc gcacattcca ggtgggccac    1140
cgcacccgcg atcagcggtg cgccggattc ctctccgagc acccagtcca cggtgtcgaa    1200
ctggtccacg cccgggggc gcgagtggtc cgcgaagtgc ctgcggcct tctcctgccc    1260
ggcctccagc accgatacgg cgaacgtcgg cagcgcggtg aggcgttggt gcatgacggc    1320
gtccttgccg acgcagatca gcaccagggg gggtgagagc gagacggatg tgaacgagtt    1380
ggcggtcatt ccccggggct cgctcccgcc gacggtcacc acggtgacgc cggtcgggaa    1440
gtccccgaac accctcctga gctgtacgcg gtctttcggg tcgaccagtt ctgcgggcgg    1500
agcgatgatc ggactcattt ctgcctcctg ccggctgccg gagcccggct cgatggtgtg    1560
ccggtggatc gggggatcga tgggaaggg gtacctgctc acgcgcgggc gctcccgggg    1620
gccgcatcgt ccgtgccggc ggtgaggaac gcgagcacca cgggctcttc gacgtgccgc    1680
agcgtggtgg cgaaggtcgc gatgcgcagc ccgcccgccg tcaggacgat ccacccgctt    1740
ctgacctgag gctccagggt gagaggcgcc ccggccggaa ggccggcctt cttcaggcac    1800
tcgacggccg tccacacgcg ggtcgccgcg tggtccggcg tctccccggt ctccttggcg    1860
accagggccg ccaggttccc gtgctcgccg agcagtccct cccactcctg cgcaccgcga    1920
gcggtgaccg cctcgatgtc gcaggccacc gtggtggtgc cgacgacgcc cagcgtcacc    1980
cccgggccgt gtgctgccga caggcggcgc acgccgtcga gttcgggccg ccgtcgggc    2040
cggtagcgca cctttacact ctcaccgagc gcccgctgga cggcccgtgc ggtggccttg    2100
cggcgatcgg ccacggagcc cccggagtct gctgggaccg gctccacggc gacgtcgaca    2160
tgggtgccga gcacttcctc cagggttctt tcgagatagg agccgagcag cggtgcgacc    2220
catgggccga agccgtccga cttgcgcacg gcatgaaggg tgagcccgtc ccaccgctcg    2280
acgacggagc cgtcggagt ccgcacggcg atgtcgtaca cataggtgtc gccgtcccgg    2340
tggcgctcgg tcgcgcagta gcggaccagc tccgggagat cctcgccggc cgccatcgga    2400
tacagccgct cgatgccgga cggcagcagg gtcgcgtcgg ggacgcacac ctggtttccg    2460
tgcatcaggg cgtcgcgcat ccccgggtcc gagagcagca gcgtgcccgg caggaagccg    2520
gcgaaccagc cggacgccgt gtcgagcgcc acctcggcgt cgacgtgccg ggcggcggcc    2580
```

-continued

```
cggtggaagc gccgcagccg ctggaaacgc tcgccctgga agagcacccc gccgtacagg    2640
tcggtcgcgg ggtccagcgg agccgtcggc accttcggcc ccacctggtc gggggcgccg    2700
tccgggatcg ccgcgccgcc gtagaccagc cgcgcccgga agtgctccgc cgcgaaaccg    2760
gtgtcctgcg cgtggacggc cacgtccaca cggtcggtgc cggtgacggt ggccgcgatc    2820
cggatgcggg tcgtgccgcc gggtggcacc acgatcggcc gcaggaaccg ggcgtcctcg    2880
atgaccggca cgtcccgccg gccggtgacg gctgagccga cctggaccat ggcctccatt    2940
ccgatcaccg cgggcagcag caggttgccg tccagcatgt ggtcggtgag gtagaggtcc    3000
gtgccggcgt tcagttctgc ctcggtgacg agttccacgc cgtggtagcg caccaggggc    3060
tccccggtga aacgcagcag cggcagcggg ggctgctcgc gccggacggt tccgatgcct    3120
tccgtccggc cgctgatcac cgtcaccacc ggggcgtcgg ggtcggagat cagacgcagc    3180
aggatctcga tgccctggtc gggcgagacc ggcacgatgc cctcgcggga gagggactcg    3240
acgacggaca gcttctcgcc catgccgacg ccggaccaga cggaccattc catgcacagc    3300
gcccggcagt ccgggttccg gcgggccacg tcctcggtga gtccggccag ccactcgttg    3360
gccgtggcgt agtgggcctc ccctcgaagc ccgcccggc cgatgatgct gccgaaggtg    3420
accaggagtc tgaggttctg ctcgccgacc acgtccagca cgtgccgcag cccgtcgacc    3480
ttgggggcga gcgtgctgcg gacggcggcc atgtccagcc cgccgagcgc agtcggctcg    3540
ttgcgtcccg caccgtgcag gacagcggtc acggatccga gtgccccggt cagttcggcg    3600
acggccccgg cgacgcgcac cggatcggtg acgtcggcgg ccgcgtaggc gacgcgtatc    3660
ccgctctccc tcatccgtcc caggttcgcg gcgaggtcct ggtcgctgcc cgggtccgag    3720
cggcccagca cggccagcgc cgcgccggtc cgctcggcga cggccagcgc gcactcggcg    3780
gtgatgccct tgccgccgcc cgtgacgagc aggacgtcgt ccgggcccag cacctggtcg    3840
gtacggtccg gggcgaaggg cagggcccgc agcacgggca cccgccgggt gccgtcccgg    3900
tcgaggtgca cctcgctgaa gtgcgtggtc gccgcgacct cggctgccac ccggtccgcg    3960
gctccgtcgg ccaccggagt gtggacgacg gtggttcgca ggtggggcgc ctccaggtgc    4020
agggtcttgg ccagaccggc cgcgcccgg tcgtgctgca ccaggacgaa gcgtccctcc    4080
tggctgcccg cgagggccga tctcgcccc tccaggggcga gttcgagctg atcaggggag    4140
cagccggccg gcaggcacac cagaactccg gaacccaccg cggcgtcctg gagagcgcgc    4200
cggacttcct cggcgaacgg gtggtcggcg gaggtgaaca gctcccacgt gccgtccttc    4260
tcatccgcca ccgccgagg gagggcagt tcgtcgaggt cgacggagaa gggccgggcc    4320
caggccgcgg acccggtcac gacgggcgcc gccgtcgggt ccgcacccgt ctcgaccagg    4380
gtcgtgaggg ccgacgccag ttccgccagg gtcgccgtgg cgaagttcgt cggaatgctg    4440
gacggggcga gtccgagccg gacagccgtc tggttgacga tctggccgac ggtgatcgag    4500
ctcatgtgca gatcgtcgag gagactgctg ttctcgtcga tcaactcgct cggaagctcc    4560
gcccgctcgg ccaccagtgc gcgcagcacg tccagcgccg actcctccgc cgtgtcgccg    4620 gcgcccgcg tcgtcgggc gtcgtgctcc tggacgagcg gttcacgagc ggcggcggga    4680
agcgtgaact cggggggcctg ctcgcagggg ctggacagga agaggaactc cttgcccacc    4740
tccaacggcc gggtcagccg gtcgttgaag agccgctcgt gaatgatcgg ggccccgatc    4800
acgaaggcgg cgccgaccac ttgcagcagc ccgcgcagcg actcgtcgtc ggtgttcagc    4860 gcgacgcgg gtttccggc ggtctccgcg ccaggacgac tcagcacccg gccgggcccg    4920
acctcgacga acaggtcgac ctcggccgcc gccgcccgga ccgcctgggt gaacagcacc    4980
```

```
gggtcggtga tctgctgccg cagcagcttg gcgagatcgg tgtcgcgctc cagctccgca    5040
ccggtgacgg tggagacgac ccggcgtccc agcccaccca gcggagcctt tgccagccag    5100
tcgccgaagg actcggcggc cggggcgacg agaggggagt ggaaagcgtg cgacacggcc    5160
agacgggtga aggcgatctc cgcggccgcc gcccgctccc cgacactctc cacggcctcg    5220
acggtcccgg cgaccaccgt ctgccggggg ccgttgtacc cggagatcac gaccggcagc    5280
ccctcgacga gcctgaccgc ctcctccggg gtggccgtca gggaggccat cgtgcccgaa    5340
gcgctgtgtg cggccatggc cgcaccgcgg gtgcgcgcgg cctccagcag cgtggtctcg    5400
tccagcgcac ccgcccagtg cagggcggag agctcgccga gactgtggcc gagtgcgatg    5460
tcggcctcga ttcccagagc ttccagcacc cggagtccgg ccgtggaacc ggtcacgatc    5520
cgcggctggg ccacatgggt ggcgaccatg tctccagcgg tgggaaggcc tgcgcgcgcg    5580
tagacctcgg cggcctcggt gaacctgcgg gcgagcgcgc cccggccgt cgaagtgccg     5640 gaaccctgtc ccgggaagag gaagccgacg cgggctccct cggcggcggt gccgaggaag    5700
gcgcggccgt cctgggagaa gaccgggccg tcgtcgggcg cccgccccc ggcggttttcg    5760 gccagtccgc gcagcctgag ctcggcgtcc tccggcgagg tggccacgac ggcggcccgg    5820
tggggcaggt cgcgcagttc ccgctggagg gtcgcggcca gatcgccgag ctgggcatag    5880
gagacctgcg cggcgaagtc ggcgacctgg gtcagccgcc gtgccagcgc cgcgggcgat    5940
tccccgtcca ggagcagcag ttcggagtcc tggagggagt tggccagcag cgtggtccgg    6000
cggttgacgg cagggcggcg cccggaggcg tccgacctgt cgaggacgac atgggtgttg    6060
atcccgccga agcccatggc ggtgatgccg ccccgcagcg gcgcgttctc gggccaggac    6120
tccgccttgc gcaggacgcg caggttggcg gactcgtcgg tgagcaggtc gtgggggtcc    6180
acgcagccga tggcgggggg cagcacccg gagtccaggg ccatcaccgc cttgatcagt     6240
ccggcgatcc ccgctgccgc cttggtgtgg ccgatcatgc ccttgatgga ggtgatgacg    6300
gcgctcgggg cgtgggggtc ggctgcggcg cgcgcactca tgatcgcccg gagttcggtg    6360
gcgtcaccga cggcggtgcc ggtgccgtgg ccctcgaaga gcggcacggt ctcgatgccg    6420
aagcccgccc ggtcgtaggc gcgcgacagc gcgagctgat acccgctcac ctcgggccgg    6480
gtgatgcctc cctggccgtc ggacgagatg ccccagccgg cgatgacgc gtagatgcgg     6540 tgcccggagg cgaccgcgtc ctcctcgcgc atgaggacca ccatgccgca gccctcgccc    6600
ggccagaagc cgttggatcc gcggtcgtag agccgcatct ccttgcgggc gagcgccccg    6660
gtcttggcga aaccgatgat ctcgaacggg tcgatggaca gatcgacgcc accggcgacg    6720
gccacgtcga ggtcgccgct ctgcagcgag gtggccgcgg tggtgatgga caacagcgag    6780
gacgagcagg cgccgtcgac ggtgtagccg ccgccgttca ggtcgaagtg gttgcagatc    6840
cgcccggcga tggtgttgga caggcccccc gcgagggtgt cctcgtccac ggcggggaag    6900
ggcttcttgt acgcctcctc cacgcctcgg aggaatgcgc cgaggcggtc gtcgtcccac    6960
tcctgctcct ggagggcgtc ggcgaggatc cggcgtacgt agggccatcg cagtcgcagg    7020
ccgttggcgc gggagaactc tccggtcagc gtgttgccga cgacgactcc ggtgcgctcg    7080
gtgggcagcc cctcaccggc cgggaagccg cgtccgccga cgctcgggt cgccgtgtcc     7140 agggcgagcc agtgggtgag gtcggtggag cggaaggtgc tgccggcgat ccggtgggcg    7200
acgcggtcga actcccagcc ctccagcacc gccgcattgc gggcgtagaa ggtgtcgggg    7260
accgtggggt ccggggttcca gtagtcgtcc aaccgcatcc ggacgtcggg cagtctgcgg    7320
```

-continued

```
aaggcccgcc gtccggcgac ggcgttctcc cagagctccc gggggtggt ggcgtcgggg    7380
tacgtgcacg cgactccgac gatggctatg cggctcatac aggcaccgtc gccttttct    7440
tcgacgctcg ttcggctgcg cacttgccgt ggaagcaggt gccgtccta cagggttgc     7500
ccgagaggac gaccgtcgcc ggctcgggcg atccgtccgc cggtccggaa gcggcggcgg   7560
gcgccgggc ggccgtcatc tgctcgaccg cggtgtcggg gcggtggccc tggaccccga    7620
gggcgggagg cgcctgagcc tcacgctgct ggcgaggaa gtgcagcccc cacaggtagc    7680
ccccgcggat caggcagacc aaggcggtcg cgaagaagat gccgtacgcg attccgagag   7740
cggtcagcac gccgtacatc gccgcgactc cggctccgaa gaagatctgg gaggatcgct   7800
tggagggtga ggtgccgggg tcggtgacca tgtagttggt gaagagcacg aaggcgacgc   7860
cggtcatcat gccgagtgcc gcggggatgg atgtgcccgt gaccagccct cggacgacgg   7920
cctgcaccac gaagccgccg agccaggcca tgatcagcca catgcgtccg gtcagcttgg   7980
cgttgagcat ggtgcccagg accaggatga tcgcggggag cacccagtcc gccgggccgt   8040
acaggtactc ggtgaagtgg tagggcggcg cgatgctcgc ccacgggaag aggaccagga   8100
tcattgcgat cccgaagttc gacggggtca tgtagtgccg catgcggccc ttgagcggag   8160
cccgcagcac ccacttggtg ccgacggcca cgatgacgcc gaagaccatg acccacacgc   8220
ggtcgttgac gtaggtcagc atgttcacgg cgaggcccgt gatgtgggcg gggaagagga   8280
attcgaccat ccccttgaac ccccgccgg cgaagcgggg cgcccgcttc tcgccgcggg    8340
cgctgacggc ctccaggacg atctccaccg cataggcggt gaggaccgcg atgaagggcc   8400
acagccatgg ctgttcgaag ccgaggaagg tgtacccggc gatgttgagg atcgagatcg   8460
agatcgcgaa ccggcggagg gcggtggtga ccttcacatc gtgccggggg gcgggcgtga   8520
gcgtctttga accgggcacg gtcacttctc cttcacgtcg gcgccgagtt ccagcgcgtg   8580
cctgccggga gtcagctgga ggtccttgtt gcgcacctga ccggtgcggt cgcgccaggt   8640
cagacgggtc tccatcgggc cgtcggcctc ctggccgagt ccgatgtgca cgtcctggct   8700
gcgcttgccg gagtggccgc tgccgccgtc gacgcggccc aggcgggtgc tgccgtcgga   8760
cagggtcacg gtgacctgcg cgccgatcac gggcgatccg gcctcgtcga cgaggctgag   8820
gttgaggtat tccccggtgt ccttgctcat gttgcagtag aagaccgggt cctcccactg   8880
gcgggcgacc accatgtcca ggcggccgtc cccgtcggcg tcgccggtgg cgatgccccg   8940
gctgggcacg gtacagcca gaccgagctg cttggacagg tcgctgtagg cctcgccgtc    9000
cttgtcctgt acgaagaagc gcaggtgctg atcgccggca aggtcgtcgc cctcctccac   9060
ccggggccag aagcgggggt gcttgaccag cgcgtcgttg gcggtggcga gctcctggag   9120
ctgggcccag cggttgcgct tgcccttgac gaagccgacc gctgggtga tctcctggat    9180
tccgttgttg tcgaagtccc ccatcttcac gtcccagccc caaccggacc aggcgaggtt   9240
gagaggtgcg ctctcgtcct tgtagggggc gacgccgtca cggaacttcg cccgcagatc   9300
cgccttgtcg cgagcggtcg cgacgaaggc gaagttcgac tcctggatgc gaaggaggt    9360
ggtgatgttg gagacgaagg cgtcgtacag gccgtcgttg tccagatcac cgaagtcgac   9420
gcccatgccc ttgaaggagc tgcggccgat ctccttggac ttcggagtgg tcgcggtgtg   9480
tacgccttc acctcgctga acttgaacgt tccggggtc gacctgttgt acagcagcgc     9540
cgaggttccg aagtcgtgcg ccaggtacat ctcggggcgc tggtcgccgt ccaggtcggt   9600
ggcggagacg gcaagtgtcc agcccggggtc gatgcccttc ggcaggacgt tcttgacctc  9660
ctcgaagccg gagggggtcc agcggaagaa gtgaccgccg ccgccgttct gggcgtggga   9720
```

-continued

```
gagcgagtcg ttcatcgtca cgccgccgtg cacgctgtcg tccaggacgg ggctgtcggg    9780
gaagtagttc ccgatgtaga tgtcattgtg accgtcgccg tcgaagtcgg cgaccgtcgc    9840
ggcgttggag ttccacaggg ggcccttgta ggtgctgccg ttgctgccgg gaaccagttc    9900
gacgggcttg aaggacttcg ggtccatcgc cgtggtgtcc tcgcccggct tcctctccgc    9960
ctggaagatc accggggtgc ggccccagta gtagacgagc aggtccatcg cgccgtcctc   10020
gttgaagtcc ccggggacgc agccgatcgg cgccatgatg tcgctcttgg gcagcggagc   10080
cgggtcgagc acgaaggggg cgtacgtggg actctcgcga ccgggcgccg gggccggggt   10140
gacgacggtc tggtcgatct gcggatcggt gatgcagagg tcgttgggca ggccgtcgcc   10200
gtcgatgtcg ttcatggcga cgccggcgcc gacggaggag atccacgcct cgatgtgctt   10260
gtaggccttg ttgaccttgc ggacgctctg tttcttgtaa ccgccaggca tggatatcgc   10320
catcggctcg aaagtgaaac tctccgccat ttccttttc tcggcggcgc tcgactccga   10380
cggcttcacc gcgtagaaag tgccgaccat gacagcgagt gcgacgaccc ccggagcctg   10440
cttccgcagc cacgaaattg gatgtgtcat gcgacggcgc ccttctgcgt gggaggaatg   10500
gaactgatgg tggcggcgat ctgctgccgc caggtctcga aggccgggt ctccccgccg   10560 gcacaggtgg cgggccgtgc gtccgtgcac acctgtgcgg cttccgccgg ggtccggccg   10620
ccgcacagga tctgggcggc caggtgcgtg tgggcggttg tcgtccccgc ccgctcccgc   10680
gcctcgcagg cgaaagcgga gccctgtacg aggctgggca gatggtcgcc cgcgtgcttg   10740
gcgaagcgcc gcagttcgtc cccgtccacg cttcccgcgt aggtgcaggc cagcccggcg   10800
cccgcgtaga ggtcggcgtg gcggtgctcg gggaacgtgc cgatgaggtc ggccacgacg   10860
tcggggtcgg tgccccgac gaaccacatg gcccggccga tgccctggtc gatggcgcgc   10920
gcgctgtagg cgtccgggcc gcccttccag gtgaagggt gctcggcggc gggattgcga   10980
acgtaggagt ccgtcttgaa gtacgcctgg tggaagccgt acccgtccag gatcagccag   11040
cgcagcaccg ggtcggtcgc ggtcacgtcg ggccacagga acttggggag ccgggccatt   11100
gcccacccga tgccgacgta gatcatgtag ttgtgacgcc ggccctcgcc ctccaggatc   11160
cccgtcagcc gccgactgct cccggtgagg gagccgagca tgaccgcacc catgcccgcg   11220
ccctcgtagg cgaacccgcg aaaggcccgg ggcacggtct ccagccagtc gacggcctgg   11280
ctcgccgaac gggcctcgac cgcgtacgcg taccctgca ggaagctcgt cccgaccgtc   11340
tccaactggt gcttggcctc cgcgtccttg atgtggaaac cccgtgtttc cagctgtgtt   11400
tctcgaacac tgggagtgag aattcggcgc ctcagcgctc gcaacatgga cacctgaaag   11460
accgcccctc gatactcttg cctgacatcc tcattggctc agccgaactt attcaattga   11520
ggtgaccgaa tgtctactcc ggaaatgctc aggggtatgt gagcggaagc ttctcgcgta   11580
ctgatctgcg ccagatctcg tagctgggaa caccgtcgcc gacgcccgcg ggggcgcgg   11640 cgtcatcggc gagttcggca gcggactcga cggtgaggcc ggtcagcgcg tgcagcgctg   11700
tccgggtgtg ctcgggaacc gtcagcgaga agtggcgggc cttggcgcg aagaccgagc   11760 cctgggcgac atgcccggcc agctcacccg accggacgcg aagcgtgtcc agctccgccg   11820
cggtggagca gccggcgaac gtggccgcga gcccgacacc ggcccacagg tccggcctgc   11880
gatcggaggc gaaccggttg accgcggcgc acacggcatc caccgcggcg ccgtggatga   11940
accacagggc tcgcccgatg ccctggtcca cccgcccgct ggaagtagcc gggccggtcc   12000
tcccagccgt acggggtgtc cagccgctgc tcgtccaccc atcgctccgg ggcgaagtag   12060
```

```
gcgcggtcga agccgtagcc gtcgaccgcg agccagctca tcgacgggta gaggtcgtcg    12120
ccgtcgagcg cgggcacggc cttcttccac agcggcctgg gcagcttggc catcgcgaaa    12180
ccgatgccga tgtagttgag gaagatgtgg cggcgtccgg ctccctggag cagttccgcg    12240
gtgcggcctc cccgtccggg catcgagtcc cggatcaccg aagccatggt cgcgccctcg    12300
taggcgaagc cccgcagctc ctcgtcgacc agggagagcc gccgctcggt ctcccacagg    12360
ctcttcgact cgatgcccca ctcgaatccg gtgaccaccg tctgggggat ggtctccagc    12420
tggcgggtcg cggcggtctc gaccaccggg aaaccccggc ccgcgaagct cacgtcggcc    12480
agggacggag ccatgagaag tctgcgcagg gatcccggta ccgatgccac gcgtgtgcct    12540
ccctcgaccg gccaccaggg ggtggcgaag ggcctcatgg tcggctcggc gcgaagatca    12600
gagcatcttc gcaaatgcgc aacacctctg tgctgcaagg gggtttgagg atgaatgaac    12660
gcgctggcaa ctcgtgccgt gcgcaatgcc gtccggctct cacggagccc ggaatcagcg    12720
cgtccggcgt accgccacct cgtcctcgtg gacgtcccgc ccgcaggacg cgcagcccag    12780
ccgcacccgt acaccgccgt cgcatccggt gtgctgcgcc tgccgggacg gtcccagctc    12840
cgcgggcagg ttccggtcgc cccactgcat gagggcgacc acggcgacgg tgagttcacg    12900
gcccatgggc gtgagcgggt actcgtggcg taccggcttc tcctggtaca cgacccgccg    12960
catgacaccc aggtcgacga gacggccgag acggtcggcc agcacgttcc gggagatcgg    13020
catctggcgc aggaactcgt cgtaccggca ggcgcccagc agggcggagc ggacgatcag    13080
caggttccag cgctctccga tcacttccag ggaccgggcc agcgagcagt cctgtccttc    13140
gtacgtccgt ggcagcatgc ctgaccgtac cgttcgagtt gtttcacagg acccacggaa    13200
ggcccggctc acggagaaga gagcactccg gaagaagccc gcgcgcgcga agtgctggtg    13260
tgatgaccca ctgcccctcc caaaccgacc gtggaggccc agggatggcc atcagcaccg    13320
gagcatcacc tttcaccgtt cgcggcggga tcgaagccgt caacacccgc caccaccaac    13380
tcggcctgcg tgtgttcatg ttcatcgtcg tcgcgcactg ggctgagcac ctggtccagg    13440
cctaccagat ctacgtcatg ggctggccca ttccggaggc gcgcggcgtc tcgggatgc    13500 cgttcccctg gctggtcacc tcggagtgga tgcactacgg ctacgccctg gtgatgatgg    13560
tcggcctgtt cctcctgcgg ccgggggttca ccgggcgctc ggccacctgg tggaagatct    13620
ccctcggcat ccaggtctgg caccacatgg aacatctgct gctcctggtg caggcactgg    13680
ccggggccaa cctgctgggg aggccggcgg caaccagtct gatccagctg atagcgcccc    13740
gcgtggagct gcacctcttc tacaacaccc tggtgacggt tcccatggtg gtcgcgatgt    13800
acctgcacac ccggcccggc cgaccggaca cgccgacgc acggtgcacc tgcgccccga    13860
aggcctgacc ccgtgacgac gagcggcaga aggccttcgg ggttcgtgtc cttgctgctc    13920
ctgcttctcg gagtcctgct gttctggctg acggtgccga acctgggtga cgcggcccgg    13980
accgccacgg cggacgggcc cctgggcacc ttcaccgcta cccgcctggt gtgcgccggg    14040
cacgccggac acaccacctg cgagtggctg gggacgttcc gctccaccga cggcaccgtg    14100
gatctcggga gcgtcaagct gtacggaagc gaccgcgacg ccttcgaagc cggccggacc    14160
gctccggccg tggacgtggg caaccccggg cgggtctacg atccggccgg ttcgtacacc    14220
tggatcgtca cggtcgggct ggccgttctc tcctacgccc tgctcatcac ggtcgcccgc    14280
cgccacctcg ggcctccccc gcgggcggcg ggcgtcctgc cggcggcgag ctgagcgccc    14340
gggaagggga gaagcgcgcg ggtgggtccg ggaaccggga accgccgt atccccctcg    14400 gccgtccacg agggacgcgt cgctcagctc ccctcctggg agccgggccg gcggccggac    14460
```

```
agctccagca ggttgtacgc cgaagccgcc gacacgagag tcatgtggtg atgccagccg  14520
ggaaaggacc gtccctcgaa gtcgagcaga ccgaagtcgt cctccagcga ctgcaccgcg  14580
gtgcccgccc ggtgctggag cccggccagc gccagcagtt cgtcggtccg ccgctgcgtc  14640
atgttggtca gccagatccg cgcggagcgg ggccccgagt aggacggcat accgaagatc  14700
cggtacgtgg cgtgcggcgt gtgacgtgcc agccgcacct gcggcagccg caccagcgtg  14760
gtcatcgtgg cggtgcgatc ggcgccgccg tgcccatcat gggcgccggg tctgagatgc  14820
ccggcgtgct tgaggccgaa gaggcgctgt gcctccacgg gggcgggcag gttcgcggag  14880
tacgcgccgc gcgccgtcgt tctccccacc gggaccaccg gggtccggcc cggcagtgac  14940
acgacgaact cgcgtcccct ggcggtgagt ccgcgcacca gcgagatgac cccggaatga  15000
tgactcagat cggccaccac cggccgggga ctcagttgcg tgctcccgca cagcgcgtcg  15060
acgaggtcca gcgcatgctg ctcgacgctg cgctggccga ccgattcggg gatgcgggcc  15120
cgtgcgcggc gcgcatggtc ctcgacccag gccccgggca gcaggagccc ccagtggacg  15180
ggcacggccg tcgcgccggt ggagaggaac gcacccaccg cgagctggca gttgacggag  15240
cgtccggtgg cggggacgaa gcgccggtgc accccgcagg agtgatctcc ccgcttgcgt  15300
aacaccgcca ccgacaggac ccaggcgcgc ggatcgagct gctgctcgac ccatctcatc  15360
agctcggcac gtgccggggc ccagtcccag gggctggcat tgaggaactg gtgcatcgac  15420
tgcgacgcgg tgggcgaacg ggagacggtg gcggccatcc gtctgatcga cttcttgccg  15480
tcggtggtca gcagccccgt caggtaggcc tgggcccacg ccctctgatc ggccctcggc  15540
aggtgcccga agatctgatc ggcaagtacg gagaccggca ggtgcgcgtg cctcacgtcg  15600
tgtgccgcca tggctcgttt cccttctcct gggcaaccga tcgagcgccg cgatatcgca  15660
gcgagcgata tggtgttcta cggggagggc gcttccgtcg gccggagacc tggcagggaa  15720
cgtcggcccc atgggctcg aagatcgccg acatccctcc ccctcccccg cttgaccaag  15780 cctttacct gcttgatcga ttcgtggttg tcacctggtc gccattgcgc cgaaacttga  15840
gtgccgtcgg cctgccccc cgggcaaggc tccgaacccc ttcggcataa aactccgcac  15900
gctgcttcgc catgccgatc atcgtcggag aggacatcgt aaatcaggat cggccggtac  15960
gtacacggag catggtcccg cgatccggta ccgcacggtt cgggcgccac ggctgaaaag  16020
ggaccatccg ggaaacctgg cgccggcgga ggaaccagct gaaacgccac cggtgaatcg  16080
ctccgacggt cctacggcag ccgggcatcg gccatcacgg attccgttga gcggaccgtg  16140
ccgggcctgc actccgccgc cctggcgcg caagaggacc gggccgcacg gcgggaccgc  16200
cgacggtggg cggatgggcg ctcccccgtc cgcacatcgt tccgtctgcc gcgacccacc  16260
cgtcatcgcg cccacgcgaa cctcccctac gtccccgtc ggcggcacgg gctcgaaccc  16320
ggtcgccgat tcgcaggggc acgacccttag cgggagttgg gtgaatggcc gaagtcttct  16380
ggcagaaaat catcaaaagc ccgggccggc tgcccccgcc tccgcctccc ccgcggactc  16440
ccgacgtgcc gagggcggcc tgaacccgc gtgcacactt ctacagaaca cacccttgt  16500 cggggtgaat cggccaaaaa ttttagtctc ccatggacaa aaaagaatc gttcctatga  16560 tgcatcgaag acgttttccg ggggtgcctc ggcgcgttca gtcacgcgaa catgaccagt  16620
tccgatgatt caggaagcgc acacgtgatg agttcagccg aaggcaacgc ttcgacccgt  16680
ccaccggatc cgcgcctcac ggcggccggc cctccggccc ccggggctgc tcccgcacca  16740
ccgcgacatg ccactccggc acccgatgcc ccgggcgccg ggcgacaggc cgagcggttc  16800
```

```
tgagaagcgg gaccgatccg ttcgccaccc gccgctcacg cgcgcggggc ggacacgcac   16860
ggctcagccc ttttcgtatc caccgacggt caggagcgcc cgtggacgag gccggctctg   16920
caggtcattt tcgctcgaac gctgtgcccg ccacaccggt cggccccgc ggaacctcct    16980 cggaactgtc acccgccgcc cgcccctcg gccttcccga gcgccggcgc acctactcgg    17040
ccccggcgcg ccgcagacgc ctgcggaccg tgcgcagcac ccctcggtg ttgggggtgg    17100 ggttgttacc ggattcgttg acggatcggg ggaacgcgaa gctgttcgtg cggttgtacg   17160
cgcaggacta ccggcatgtg acggggctgg ggtggtaccg gtgggacggc acgcggtggc   17220
agagcgatga ggacgacacg gtgctgtggg tcgctggtga gatggcggag agtatcgcgg   17280
cgaccgatcc gcgggggggtg tattccgatg cggcgctgcg caagcaccgg cggcgtgcgt  17340
tgagcacgtc ggggatcaac gcgttgttga gccaggcgag atcggcgccg gggatggtgc   17400
tcagtgcggg ggcgctggac gcggatccgt acatgctgtg cacgccggcg ggggtggtgg   17460
acctgcggtc ggggaagctg cgggccgcg acccggaccg ggacttccat tcgcgctcga    17520
cctcgatcgg ccccccggcag atgccgacgc cgcgctggga tctcttcctg accgatacct   17580
tcggggacga cgcgcggggc cgggagatga tccgtttcct gcatctcctg ctcggttact   17640
ccctcaccgg tgacgtcgga gcgcaggtca tgccgttcct gttcggatcg ggcaagaacg   17700
gaaagtccgt actgctcgac gtcctgatca agctgctggg cgactacgcg gacgccgcgc   17760
cgcccggttt cctgatggcc cgtcccttcg aggggcaccc caccgacctc gccgaactcc   17820
acggacgccg cgtgatcgtg tgttccgagg tcaagcccgg tgaccggttc gacgagtccc   17880
gggtgaaact cctgaccggc ggcgaccgca tcaaagcacg ccggatgcgc caggacttct   17940
tctccttcgc ccccacccac aaactctggc tcctgggcaa ccaccgcccc gaagtcggca   18000
ccggcggcta cgccttctgg cgccggatgc gcctgatccc cttcgaccgc gtcgtctccg   18060
accagcagaa aatcgacaac ctcgccgaca tcctcgtcac cgaggaaggc cccggcatcc   18120
tcaactggct catcaccgga gcccaccact acctcaacag ccccgcgac ctcaccggac    18180 cggaaaccgt ccgcatcgcc accacggcct acgccgaaac cgaagaccac accggccgct   18240
tcctcaccga acacgggacg acctcccggt cagggcggac acgtcaccgc ggaacggaat   18300
cgtccggggg aacgacatcc gggtgagggg gggtggagag ggggcctcct tcggatcgtt   18360
cggtcttctg gcctttggtg cgggggggtga gggtggcggg gtcgacggct tcggccggtg   18420
cgccggtggc gtagaggccc tgggggggcgg tgtcgcggtc gtgggcagg agccagaaga   18480 cgcgtcggcg gaaggtgccg gacgtacgtg aggggcgggc ccgcgcatgg agcacggcgt   18540
atcccaccat cgcggccgtcc cggtggtagg cgggccttcc tctccggttg gggagccggt   18600
ccaggctctg tcgtacgtaa tccaggatcg agatgtcctc cagccagaca agctccgctt   18660
cctcactgat ctcgtccccg tcgatcagag cactcactcc gcctcctcct cggccacagc   18720
cgctactgga cactgtgcac cgggcctgcg gccatgagca gctaaagtc ggataccgca    18780 tcagcccggg gcggggtatg ggatcctgcg cccgccggcg gtgaaacagg cctcacgcgt   18840
cccacggagc gatcggatgc caggagatgc ctccgcgcgc gcgtgagtcc agtcctgacg   18900
tcccggtaca agaaggtgaa gatgcccgcc gcgatcaggg tccccgcgga gaccgccgtc   18960
aatcgtgtgg aggatgacgt catccgggcc gcggaccgac cgcccgcgca gaaggccgac   19020
agcgggaaca ccggcgccac ggccggcacg ccgccgatcg accgcagagg aactgccgcc   19080 gacgaccga cgctcccgcc gccatccctc ccctttcccg tgccgctgac tcggtgatgc    19140
cggccacaac agggttcccc tccacggctg aggtcacagc gtagaagcgg caccgggcaa   19200
```

```
atccatctcc cagaatgctc gcccgcggca cggaggcgaa atccggccga tgccgcacag   19260
gacccgggca cacaagcgca cggaggaagt tgagcacgct cgcctccccc gtgaacatga   19320
aggccgcttc gtccctccgc atccaggag cactgtgccg cacatcgaga tcagcaacga   19380 ccacccggc atccggggct tgatgttcca gcggccggac gccgccgcgc cgctcaacca   19440
cctcgccaac gtcctgctgc gcgccccggc gtccttgagc cggggcgaac gggaactgat   19500
cgccgcctac gtctcacacc tgaacgacac cccgttctgc gccggaaccc acggagccgc   19560
ggcagcagca cagctggacg gcggacacga ggcggtgacc gccgtcttcg ccgctccgca   19620
ggacgcaccc gtctcccccc ggatgcgcgc cctgctcgcc gtcgccgccg aggtcatggc   19680
agctgcgcgt cccgtcggcg acgagacggt agcggctgcc cgcgccgcgg gtgccgagga   19740
cagcgacatc cacgacaccg tgctgatcgc cgccgccttc tgcatgtaca accgctatgt   19800
cagctgcctg gcgaccggca tcccgacgca ggacgactac taccagcagg ctgcggaccg   19860
catcgtcacc gacggctatg ccacggcgag cggacagaac ggcacccggg ccgacgaggc   19920
tctcaccggc tgacaggcgc gggcacttcc ccccctcac ccgggcacag gtgtggccgg   19980 gtgaggggg gtggtgaggg ggcctccttc ggatcgttcg gtcttctggc ctttggtgcg   20040
gggggtgagg gtggcggggt cgacggcttc ggccggtgcg ccggtggcgt agaggccctg   20100 ggggcggtg tcgcggtcgt ggggcaggag ccagaagacg cgtcggcgga aggtgccgga   20160
cgtacgtgag gggcgggccc gcgcatggag cacggcgtat cccaccatgc ggccgtcccg   20220
gtggtaggcg ggccttcctc tccggttggg gagccggtcc aggctctgtc gtacgtaatc   20280
caggatcgag atgtcctcca gccagacaag ctccgcttcc tcactgatct cgtccccgtc   20340
gatcagagca ctcactccgc ctcctcctcg gccacagcca ggagcccgat gcccgggtag   20400
tacttgcgct ggttcgacag cagcatctcc ttcggtgacg ccagtccgac ggcttcccgg   20460 atgcgggcg cgaaggcccg ggacgaggcg ggattgatgc cctcgtgccg ggaccaggcc   20520
gtgtaggcgt ggtacaggcg ggcctgttcg actctgtggt ggggctggaa ggtgcagcgt   20580
tcggtgagga agcggccggt gtggtcttcg gtttcggcgt aggcggtggt ggcgatgcgg   20640
acggtttccg gtccggtgag gtcgcggggg ctgttgaggt agtggtgggc tccggtgatg   20700
agccagttga ggatgccggg gccttcctcg gtgacgagga tgtcggcgag gttgtcgatt   20760
ttctgctggt cggagacgac gcggtcgaag gggatcaggc gcatccggcg ccagaaggcg   20820
tagccgccgg tgccgacttc ggggcggtgg ttgcccagga ccagagtttt gtgggtgggg   20880
gcgaaggaga agaagtcctg gcgcatccgg cgtgctttga tgcggtcgcc gccggtcagg   20940
agtttcaccc gggactcgtc gaaccggtca ccgggcttga cctcggaaca cacgatcacg   21000
cggcgtccgt ggagttcggc gaggtcggtg gggtgcccct cgaagggacg ggccatcagg   21060
aaaccgggcg cgcggcgtc cgcgtagtcg cccagcagct tgatcaggac gtcgagcagt   21120
acggactttc cgttcttgcc cgatccgaac aggaacggca tgacctgcgc tccgacgtca   21180
ccggtgaggg agtaaccgag caggagatgc aggaaacgga tcatctcccg gccccgcgcg   21240
tcgtccccga aggtatcggt caggaagaga tcccagcgcg gcgtcggcat ctgccggggg   21300
ccgatcgagg tcgagcgcga atggaagtcc cggtccgggt ccgcgccccg cagcttcccc   21360
gaccgcaggt ccaccacccc cgccggcgtg cacagcatgt acggatccgc gtccagcgcc   21420
cccgcactga gcaccatccc cggcgccgat ctcgcctggc tcaacaacgc gttgatcccc   21480
gacgtgctca acgcacgccg ccggtgcttg cgcagcgccg catcggaata cacccccgc   21540
```

-continued

```
ggatcggtcg ccgcgatact ctccgccatc tcaccagcga cccacagcac cgtgtcgtcc      21600
tcatcgctct gccaccgcgt gccgtcccac cggtaccacc ccagcccgt cacatgccgg       21660 tagtcctgcg cgtacaaccg cacgaacagc ttcgcgttcc cccgatccgt caacgaatcc      21720
ggtaacaacc ccaccccaa cacctgctcc gggcccgcag acgcctctgc acgacccgga       21780
acccctcccg cgggcagcga aggcccggca gaagtggacc gtgcgaggat ctgggctgcc      21840
acggcgtgag cgtcgaagcc ggacggcgga cggcctccgg gggtcatccc tctctcctca      21900
ggtacagcgg ccggcgcgca ccggccgaca tcccgctgcg gatgatccca gcggctttcc      21960
tgccctgccc cggccgggct gcggccgcgg tgtcctgaag gatcc                     22005
```

<210> SEQ ID NO 3
<211> LENGTH: 15
<212> TYPE: DNA
<213> ORGANISM: Streptomyces globisporus

<400> SEQUENCE: 3
atgggcatga cgggt                                                          15

<210> SEQ ID NO 4
<211> LENGTH: 15
<212> TYPE: DNA
<213> ORGANISM: Streptomyces globisporus

<400> SEQUENCE: 4
ctagaggatc ccggg                                                          15

<210> SEQ ID NO 5
<211> LENGTH: 15
<212> TYPE: DNA
<213> ORGANISM: Streptomyces globisporus

<400> SEQUENCE: 5
atgccgcgga ttccc                                                          15

<210> SEQ ID NO 6
<211> LENGTH: 15
<212> TYPE: DNA
<213> ORGANISM: Streptomyces globisporus

<400> SEQUENCE: 6
tcagctgtcg atgtc                                                          15

<210> SEQ ID NO 7
<211> LENGTH: 15
<212> TYPE: DNA
<213> ORGANISM: Streptomyces globisporus

<400> SEQUENCE: 7
atgaccatcg ccact                                                          15

<210> SEQ ID NO 8
<211> LENGTH: 15
<212> TYPE: DNA
<213> ORGANISM: Streptomyces globisporus

<400> SEQUENCE: 8
tcagaggccg agcac                                                          15

<210> SEQ ID NO 9
<211> LENGTH: 15

```
<212> TYPE: DNA
<213> ORGANISM: Streptomyces globisporus

<400> SEQUENCE: 9
atgagctcgc tactg                                                    15

<210> SEQ ID NO 10
<211> LENGTH: 15
<212> TYPE: DNA
<213> ORGANISM: Streptomyces globisporus

<400> SEQUENCE: 10
ctaggagccg gtcgc                                                    15

<210> SEQ ID NO 11
<211> LENGTH: 15
<212> TYPE: DNA
<213> ORGANISM: Streptomyces globisporus

<400> SEQUENCE: 11
atgagcagca gcgcc                                                    15

<210> SEQ ID NO 12
<211> LENGTH: 15
<212> TYPE: DNA
<213> ORGANISM: Streptomyces globisporus

<400> SEQUENCE: 12
tcattcgtcg gctgc                                                    15

<210> SEQ ID NO 13
<211> LENGTH: 15
<212> TYPE: DNA
<213> ORGANISM: Streptomyces globisporus

<400> SEQUENCE: 13
gtgagggctc tgccg                                                    15

<210> SEQ ID NO 14
<211> LENGTH: 15
<212> TYPE: DNA
<213> ORGANISM: Streptomyces globisporus

<400> SEQUENCE: 14
tcagacggcg gaggg                                                    15

<210> SEQ ID NO 15
<211> LENGTH: 15
<212> TYPE: DNA
<213> ORGANISM: Streptomyces globisporus

<400> SEQUENCE: 15
gtgagcgtca ccgac                                                    15

<210> SEQ ID NO 16
<211> LENGTH: 15
<212> TYPE: DNA
<213> ORGANISM: Streptomyces globisporus

<400> SEQUENCE: 16
tcaacccgcc ctgcg                                                    15

<210> SEQ ID NO 17
```

-continued

```
<211> LENGTH: 15
<212> TYPE: DNA
<213> ORGANISM: Streptomyces globisporus

<400> SEQUENCE: 17
atgaggatgc tggtg                                                    15

<210> SEQ ID NO 18
<211> LENGTH: 15
<212> TYPE: DNA
<213> ORGANISM: Streptomyces globisporus

<400> SEQUENCE: 18
gtggctgtgc tcgca                                                    15

<210> SEQ ID NO 19
<211> LENGTH: 15
<212> TYPE: DNA
<213> ORGANISM: Streptomyces globisporus

<400> SEQUENCE: 19
atgaggatgc tggtg                                                    15

<210> SEQ ID NO 20
<211> LENGTH: 15
<212> TYPE: DNA
<213> ORGANISM: Streptomyces globisporus

<400> SEQUENCE: 20
tcagccgacg gcgtc                                                    15

<210> SEQ ID NO 21
<211> LENGTH: 15
<212> TYPE: DNA
<213> ORGANISM: Streptomyces globisporus

<400> SEQUENCE: 21
gtgacagcag tcaag                                                    15

<210> SEQ ID NO 22
<211> LENGTH: 15
<212> TYPE: DNA
<213> ORGANISM: Streptomyces globisporus

<400> SEQUENCE: 22
tcatgtggcc ggttg                                                    15

<210> SEQ ID NO 23
<211> LENGTH: 15
<212> TYPE: DNA
<213> ORGANISM: Streptomyces globisporus

<400> SEQUENCE: 23
gtggagtact ggaac                                                    15

<210> SEQ ID NO 24
<211> LENGTH: 15
<212> TYPE: DNA
<213> ORGANISM: Streptomyces globisporus

<400> SEQUENCE: 24
tcaggcctga ggggc                                                    15
```

```
<210> SEQ ID NO 25
<211> LENGTH: 15
<212> TYPE: DNA
<213> ORGANISM: Streptomyces globisporus

<400> SEQUENCE: 25
gtgccccacg gtgca                                                    15

<210> SEQ ID NO 26
<211> LENGTH: 15
<212> TYPE: DNA
<213> ORGANISM: Streptomyces globisporus

<400> SEQUENCE: 26
ctacagccct ccgag                                                    15

<210> SEQ ID NO 27
<211> LENGTH: 15
<212> TYPE: DNA
<213> ORGANISM: Streptomyces globisporus

<400> SEQUENCE: 27
atgtcttcaa cccgt                                                    15

<210> SEQ ID NO 28
<211> LENGTH: 15
<212> TYPE: DNA
<213> ORGANISM: Streptomyces globisporus

<400> SEQUENCE: 28
tcagccgcgc aggaa                                                    15

<210> SEQ ID NO 29
<211> LENGTH: 15
<212> TYPE: DNA
<213> ORGANISM: Streptomyces globisporus

<400> SEQUENCE: 29
atgctggaga aatgc                                                    15

<210> SEQ ID NO 30
<211> LENGTH: 15
<212> TYPE: DNA
<213> ORGANISM: Streptomyces globisporus

<400> SEQUENCE: 30
tcagacgagc tcctt                                                    15

<210> SEQ ID NO 31
<211> LENGTH: 15
<212> TYPE: DNA
<213> ORGANISM: Streptomyces globisporus

<400> SEQUENCE: 31
atggagtacg gcccc                                                    15

<210> SEQ ID NO 32
<211> LENGTH: 15
<212> TYPE: DNA
<213> ORGANISM: Streptomyces globisporus

<400> SEQUENCE: 32
tcatgccgtg cgcac                                                    15
```

```
<210> SEQ ID NO 33
<211> LENGTH: 15
<212> TYPE: DNA
<213> ORGANISM: Streptomyces globisporus

<400> SEQUENCE: 33
atgagcggcg gcccg                                                     15

<210> SEQ ID NO 34
<211> LENGTH: 15
<212> TYPE: DNA
<213> ORGANISM: Streptomyces globisporus

<400> SEQUENCE: 34
tcacctcgcc ggacg                                                     15

<210> SEQ ID NO 35
<211> LENGTH: 15
<212> TYPE: DNA
<213> ORGANISM: Streptomyces globisporus

<400> SEQUENCE: 35
atgtcgttac gtcac                                                     15

<210> SEQ ID NO 36
<211> LENGTH: 15
<212> TYPE: DNA
<213> ORGANISM: Streptomyces globisporus

<400> SEQUENCE: 36
tcagccgaag gtcag                                                     15

<210> SEQ ID NO 37
<211> LENGTH: 15
<212> TYPE: DNA
<213> ORGANISM: Streptomyces globisporus

<400> SEQUENCE: 37
atgaaggcac ttgta                                                     15

<210> SEQ ID NO 38
<211> LENGTH: 15
<212> TYPE: DNA
<213> ORGANISM: Streptomyces globisporus

<400> SEQUENCE: 38
tcaggccgcg atctc                                                     15

<210> SEQ ID NO 39
<211> LENGTH: 15
<212> TYPE: DNA
<213> ORGANISM: Streptomyces globisporus

<400> SEQUENCE: 39
gtggacgtgt cagcg                                                     15

<210> SEQ ID NO 40
<211> LENGTH: 15
<212> TYPE: DNA
<213> ORGANISM: Streptomyces globisporus

<400> SEQUENCE: 40
tcaggaccgc gcacc                                                     15
```

```
<210> SEQ ID NO 41
<211> LENGTH: 15
<212> TYPE: DNA
<213> ORGANISM: Streptomyces globisporus

<400> SEQUENCE: 41
atgaagccga tcggg                                                    15

<210> SEQ ID NO 42
<211> LENGTH: 15
<212> TYPE: DNA
<213> ORGANISM: Streptomyces globisporus

<400> SEQUENCE: 42
tcaggacgac ttgtt                                                    15

<210> SEQ ID NO 43
<211> LENGTH: 15
<212> TYPE: DNA
<213> ORGANISM: Streptomyces globisporus

<400> SEQUENCE: 43
atgccttccc ccttc                                                    15

<210> SEQ ID NO 44
<211> LENGTH: 15
<212> TYPE: DNA
<213> ORGANISM: Streptomyces globisporus

<400> SEQUENCE: 44
tcaggtgcgc tcggc                                                    15

<210> SEQ ID NO 45
<211> LENGTH: 15
<212> TYPE: DNA
<213> ORGANISM: Streptomyces globisporus

<400> SEQUENCE: 45
gtgagagacg gccgg                                                    15

<210> SEQ ID NO 46
<211> LENGTH: 15
<212> TYPE: DNA
<213> ORGANISM: Streptomyces globisporus

<400> SEQUENCE: 46
tcacgtggtg atggc                                                    15

<210> SEQ ID NO 47
<211> LENGTH: 15
<212> TYPE: DNA
<213> ORGANISM: Streptomyces globisporus

<400> SEQUENCE: 47
atgaccgacc agtgc                                                    15

<210> SEQ ID NO 48
<211> LENGTH: 15
<212> TYPE: DNA
<213> ORGANISM: Streptomyces globisporus

<400> SEQUENCE: 48
```
tcacagcaac tcctc                                               15

<210> SEQ ID NO 49
<211> LENGTH: 15
<212> TYPE: DNA
<213> ORGANISM: Streptomyces globisporus

<400> SEQUENCE: 49
gtgagcttgt ggtct                                                15

<210> SEQ ID NO 50
<211> LENGTH: 15
<212> TYPE: DNA
<213> ORGANISM: Streptomyces globisporus

<400> SEQUENCE: 50
tcaggccggt tcggc                                                15

<210> SEQ ID NO 51
<211> LENGTH: 15
<212> TYPE: DNA
<213> ORGANISM: Streptomyces globisporus

<400> SEQUENCE: 51
gtgcgtccct tccgt                                                15

<210> SEQ ID NO 52
<211> LENGTH: 15
<212> TYPE: DNA
<213> ORGANISM: Streptomyces globisporus

<400> SEQUENCE: 52
tcagcggagc ggacg                                                15

<210> SEQ ID NO 53
<211> LENGTH: 15
<212> TYPE: DNA
<213> ORGANISM: Streptomyces globisporus

<400> SEQUENCE: 53
atgccagcac cgact                                                15

<210> SEQ ID NO 54
<211> LENGTH: 15
<212> TYPE: DNA
<213> ORGANISM: Streptomyces globisporus

<400> SEQUENCE: 54
tcagtcgttg ccgcg                                                15

<210> SEQ ID NO 55
<211> LENGTH: 15
<212> TYPE: DNA
<213> ORGANISM: Streptomyces globisporus

<400> SEQUENCE: 55
atgcgggtga tgatc                                                15

<210> SEQ ID NO 56
<211> LENGTH: 15
<212> TYPE: DNA
<213> ORGANISM: Streptomyces globisporus

<400> SEQUENCE: 56

```
tcatcggtcc gcctc                                                      15

<210> SEQ ID NO 57
<211> LENGTH: 15
<212> TYPE: DNA
<213> ORGANISM: Streptomyces globisporus

<400> SEQUENCE: 57
atgaccaagc acgcc                                                      15

<210> SEQ ID NO 58
<211> LENGTH: 15
<212> TYPE: DNA
<213> ORGANISM: Streptomyces globisporus

<400> SEQUENCE: 58
tcatacggcg gcgcc                                                      15

<210> SEQ ID NO 59
<211> LENGTH: 15
<212> TYPE: DNA
<213> ORGANISM: Streptomyces globisporus

<400> SEQUENCE: 59
gtgagcgcac aactc                                                      15

<210> SEQ ID NO 60
<211> LENGTH: 15
<212> TYPE: DNA
<213> ORGANISM: Streptomyces globisporus

<400> SEQUENCE: 60
tcacggctgt gcctg                                                      15

<210> SEQ ID NO 61
<211> LENGTH: 15
<212> TYPE: DNA
<213> ORGANISM: Streptomyces globisporus

<400> SEQUENCE: 61
atgtcttcaa cccgt                                                      15

<210> SEQ ID NO 62
<211> LENGTH: 15
<212> TYPE: DNA
<213> ORGANISM: Streptomyces globisporus

<400> SEQUENCE: 62
tcagccgcgc aggaa                                                      15

<210> SEQ ID NO 63
<211> LENGTH: 15
<212> TYPE: DNA
<213> ORGANISM: Streptomyces globisporus

<400> SEQUENCE: 63
atgacgacgt ccgac                                                      15

<210> SEQ ID NO 64
<211> LENGTH: 15
<212> TYPE: DNA
<213> ORGANISM: Streptomyces globisporus
```

```
<400> SEQUENCE: 64
tcaggaggtg aaggg                                                    15

<210> SEQ ID NO 65
<211> LENGTH: 15
<212> TYPE: DNA
<213> ORGANISM: Streptomyces globisporus

<400> SEQUENCE: 65
atggcattga ctcaa                                                    15

<210> SEQ ID NO 66
<211> LENGTH: 15
<212> TYPE: DNA
<213> ORGANISM: Streptomyces globisporus

<400> SEQUENCE: 66
tcagcgcagc tggat                                                    15

<210> SEQ ID NO 67
<211> LENGTH: 15
<212> TYPE: DNA
<213> ORGANISM: Streptomyces globisporus

<400> SEQUENCE: 67
atgacgcggc cggtg                                                    15

<210> SEQ ID NO 68
<211> LENGTH: 15
<212> TYPE: DNA
<213> ORGANISM: Streptomyces globisporus

<400> SEQUENCE: 68
tcagcgggtg agccg                                                    15

<210> SEQ ID NO 69
<211> LENGTH: 15
<212> TYPE: DNA
<213> ORGANISM: Streptomyces globisporus

<400> SEQUENCE: 69
gtgtccaccg tttcc                                                    15

<210> SEQ ID NO 70
<211> LENGTH: 15
<212> TYPE: DNA
<213> ORGANISM: Streptomyces globisporus

<400> SEQUENCE: 70
tcactgcgtt ccgga                                                    15

<210> SEQ ID NO 71
<211> LENGTH: 18
<212> TYPE: DNA
<213> ORGANISM: Streptomyces globisporus
```

<400> SEQUENCE: 71
gtgtgcccgg tgacagac                                           18

<210> SEQ ID NO 72
<211> LENGTH: 18
<212> TYPE: DNA
<213> ORGANISM: Streptomyces globisporus

<400> SEQUENCE: 72
tcagcccacg ggctggga                                           18

<210> SEQ ID NO 73
<211> LENGTH: 18
<212> TYPE: DNA
<213> ORGANISM: Streptomyces globisporus

<400> SEQUENCE: 73
gtgttgggcg atgaggac                                           18

<210> SEQ ID NO 74
<211> LENGTH: 18
<212> TYPE: DNA
<213> ORGANISM: Streptomyces globisporus

<400> SEQUENCE: 74
tcagaccgcg gacatctg                                           18

<210> SEQ ID NO 75
<211> LENGTH: 18
<212> TYPE: DNA
<213> ORGANISM: Streptomyces globisporus

<400> SEQUENCE: 75
atggccggcc tggtcatg                                           18

<210> SEQ ID NO 76
<211> LENGTH: 18
<212> TYPE: DNA
<213> ORGANISM: Streptomyces globisporus

<400> SEQUENCE: 76
tcaggacccg agggtcac                                           18

<210> SEQ ID NO 77
<211> LENGTH: 18
<212> TYPE: DNA
<213> ORGANISM: Streptomyces globisporus

<400> SEQUENCE: 77
gtggaccaga cgtctacg                                           18

<210> SEQ ID NO 78
<211> LENGTH: 18
<212> TYPE: DNA
<213> ORGANISM: Streptomyces globisporus

<400> SEQUENCE: 78
tcatgcaggt gcagcgtg                                           18

<210> SEQ ID NO 79
<211> LENGTH: 18
<212> TYPE: DNA

<210> SEQ ID NO 79
<211> LENGTH: 18
<212> TYPE: DNA
<213> ORGANISM: Streptomyces globisporus

<400> SEQUENCE: 79
atgaggccgc tcgttcgg                    18

<210> SEQ ID NO 80
<211> LENGTH: 18
<212> TYPE: DNA
<213> ORGANISM: Streptomyces globisporus

<400> SEQUENCE: 80
tcatcccggc ccggcggc                    18

<210> SEQ ID NO 81
<211> LENGTH: 18
<212> TYPE: DNA
<213> ORGANISM: Streptomyces globisporus

<400> SEQUENCE: 81
atgagaacgc ggcgacgc                    18

<210> SEQ ID NO 82
<211> LENGTH: 18
<212> TYPE: DNA
<213> ORGANISM: Streptomyces globisporus

<400> SEQUENCE: 82
tcacggccgg aggcgtac                    18

<210> SEQ ID NO 83
<211> LENGTH: 15
<212> TYPE: DNA
<213> ORGANISM: Streptomyces globisporus

<400> SEQUENCE: 83
atgtgctccc gtacc                       15

<210> SEQ ID NO 84
<211> LENGTH: 15
<212> TYPE: DNA
<213> ORGANISM: Streptomyces globisporus

<400> SEQUENCE: 84
tcagccggac tgtcg                       15

<210> SEQ ID NO 85
<211> LENGTH: 15
<212> TYPE: DNA
<213> ORGANISM: Streptomyces globisporus

<400> SEQUENCE: 85
atggcccttc acccg                       15

<210> SEQ ID NO 86
<211> LENGTH: 15
<212> TYPE: DNA
<213> ORGANISM: Streptomyces globisporus

<400> SEQUENCE: 86
tcagccggcc tgggc                       15

<210> SEQ ID NO 87
<211> LENGTH: 18
<212> TYPE: DNA
<213> ORGANISM: Streptomyces globisporus

<400> SEQUENCE: 87
atgtctacgg gctatctc                                                  18

<210> SEQ ID NO 88
<211> LENGTH: 18
<212> TYPE: DNA
<213> ORGANISM: Streptomyces globisporus

<400> SEQUENCE: 88
tcagccgccg gtggcgcc                                                  18

<210> SEQ ID NO 89
<211> LENGTH: 18
<212> TYPE: DNA
<213> ORGANISM: Streptomyces globisporus

<400> SEQUENCE: 89
atgttctccc ccgccgcc                                                  18

<210> SEQ ID NO 90
<211> LENGTH: 18
<212> TYPE: DNA
<213> ORGANISM: Streptomyces globisporus

<400> SEQUENCE: 90
tcagtacgcc tggtgggc                                                  18

<210> SEQ ID NO 91
<211> LENGTH: 18
<212> TYPE: DNA
<213> ORGANISM: Streptomyces globisporus

<400> SEQUENCE: 91
atgaattcgc tcgacgac                                                  18

<210> SEQ ID NO 92
<211> LENGTH: 18
<212> TYPE: DNA
<213> ORGANISM: Streptomyces globisporus

<400> SEQUENCE: 92
tcagctcccg gtcgccgc                                                  18

<210> SEQ ID NO 93
<211> LENGTH: 18
<212> TYPE: DNA
<213> ORGANISM: Streptomyces globisporus

<400> SEQUENCE: 93
atgaccgcga cgaatcct                                                  18

<210> SEQ ID NO 94
<211> LENGTH: 18
<212> TYPE: DNA
<213> ORGANISM: Streptomyces globisporus

<400> SEQUENCE: 94
ctaggcggcg cgtcccgc                                                  18

<210> SEQ ID NO 95
<211> LENGTH: 18
<212> TYPE: DNA
<213> ORGANISM: Streptomyces globisporus

<400> SEQUENCE: 95
atgagcacca cggccgag                                                  18

<210> SEQ ID NO 96
<211> LENGTH: 18
<212> TYPE: DNA
<213> ORGANISM: Streptomyces globisporus

<400> SEQUENCE: 96
tcagccgcgc gccgacgg                                                  18

<210> SEQ ID NO 97
<211> LENGTH: 18
<212> TYPE: DNA
<213> ORGANISM: Streptomyces globisporus

<400> SEQUENCE: 97
atgaccctgg aggcctac                                                  18

<210> SEQ ID NO 98
<211> LENGTH: 18
<212> TYPE: DNA
<213> ORGANISM: Streptomyces globisporus

<400> SEQUENCE: 98
tcatgcgggg ctcccggt                                                  18

<210> SEQ ID NO 99
<211> LENGTH: 18
<212> TYPE: DNA
<213> ORGANISM: Streptomyces globisporus

<400> SEQUENCE: 99
gtgaaaagtg actctgcc                                                  18

<210> SEQ ID NO 100
<211> LENGTH: 18
<212> TYPE: DNA
<213> ORGANISM: Streptomyces globisporus

<400> SEQUENCE: 100
tcaacggcga gttggctg                                                  18

<210> SEQ ID NO 101
<211> LENGTH: 18
<212> TYPE: DNA
<213> ORGANISM: Streptomyces globisporus

<400> SEQUENCE: 101
gtgaccacga acaccatc                                                  18

<210> SEQ ID NO 102
<211> LENGTH: 18
<212> TYPE: DNA

<213> ORGANISM: Streptomyces globisporus

<400> SEQUENCE: 102
tcacccgcga tctcgatc                                              18

<210> SEQ ID NO 103
<211> LENGTH: 1
<212> TYPE: DNA
<213> ORGANISM: Streptomyces globisporus

<400> SEQUENCE: 103 a                                                                 1

<210> SEQ ID NO 104
<211> LENGTH: 18
<212> TYPE: DNA
<213> ORGANISM: Streptomyces globisporus

<400> SEQUENCE: 104
tcacctcgcc gtactcac                                              18

<210> SEQ ID NO 105
<211> LENGTH: 15
<212> TYPE: DNA
<213> ORGANISM: Streptomyces globisporus

<400> SEQUENCE: 105
atcatcccga tcatc                                                 15

<210> SEQ ID NO 106
<211> LENGTH: 15
<212> TYPE: DNA
<213> ORGANISM: Streptomyces globisporus

<400> SEQUENCE: 106
tcatgccgcc cttcc                                                 15

<210> SEQ ID NO 107
<211> LENGTH: 15
<212> TYPE: DNA
<213> ORGANISM: Streptomyces globisporus

<400> SEQUENCE: 107
atgagccgca tagcc                                                 15

<210> SEQ ID NO 108
<211> LENGTH: 15
<212> TYPE: DNA
<213> ORGANISM: Streptomyces globisporus

<400> SEQUENCE: 108
tcacgcgcgg gcgct                                                 15

<210> SEQ ID NO 109
<211> LENGTH: 15
<212> TYPE: DNA
<213> ORGANISM: Streptomyces globisporus

<400> SEQUENCE: 109
gtgaccgtgc ccggt                                                15

<210> SEQ ID NO 110
<211> LENGTH: 15
<212> TYPE: DNA
<213> ORGANISM: Streptomyces globisporus

<400> SEQUENCE: 110
tcatacaggc accgt                                                15

<210> SEQ ID NO 111
<211> LENGTH: 15
<212> TYPE: DNA
<213> ORGANISM: Streptomyces globisporus

<400> SEQUENCE: 111
atggcggaga gtttc                                                15

<210> SEQ ID NO 112
<211> LENGTH: 15
<212> TYPE: DNA
<213> ORGANISM: Streptomyces globisporus

<400> SEQUENCE: 112
tcacttctcc ttcac                                                15

<210> SEQ ID NO 113
<211> LENGTH: 15
<212> TYPE: DNA
<213> ORGANISM: Streptomyces globisporus

<400> SEQUENCE: 113
gtgccccggg ccttt                                                15

<210> SEQ ID NO 114
<211> LENGTH: 15
<212> TYPE: DNA
<213> ORGANISM: Streptomyces globisporus

<400> SEQUENCE: 114
tcatgcgacg gcgcc                                                15

<210> SEQ ID NO 115
<211> LENGTH: 15
<212> TYPE: DNA
<213> ORGANISM: Streptomyces globisporus

<400> SEQUENCE: 115
gtggcatcgg taccg                                                15

<210> SEQ ID NO 116
<211> LENGTH: 15
<212> TYPE: DNA
<213> ORGANISM: Streptomyces globisporus

<400> SEQUENCE: 116 tcagggtat gtgag                                                 15

<210> SEQ ID NO 117
<211> LENGTH: 15
<212> TYPE: DNA

<213> ORGANISM: Streptomyces globisporus

<400> SEQUENCE: 117
atgctgccac ggacg 15

<210> SEQ ID NO 118
<211> LENGTH: 15
<212> TYPE: DNA
<213> ORGANISM: Streptomyces globisporus

<400> SEQUENCE: 118
tcagcgcgtc cggcg 15

<210> SEQ ID NO 119
<211> LENGTH: 15
<212> TYPE: DNA
<213> ORGANISM: Streptomyces globisporus

<400> SEQUENCE: 119
gtgatgaccc actgc 15

<210> SEQ ID NO 120
<211> LENGTH: 15
<212> TYPE: DNA
<213> ORGANISM: Streptomyces globisporus

<400> SEQUENCE: 120
tcaggccttc ggggc 15

<210> SEQ ID NO 121
<211> LENGTH: 15
<212> TYPE: DNA
<213> ORGANISM: Streptomyces globisporus

<400> SEQUENCE: 121
gtgacgacga gcggc 15

<210> SEQ ID NO 122
<211> LENGTH: 15
<212> TYPE: DNA
<213> ORGANISM: Streptomyces globisporus

<400> SEQUENCE: 122
tcagctcgcc gccgg 15

<210> SEQ ID NO 123
<211> LENGTH: 15
<212> TYPE: DNA
<213> ORGANISM: Streptomyces globisporus

<400> SEQUENCE: 123
atcgcggcac acgac 15

<210> SEQ ID NO 124
<211> LENGTH: 15
<212> TYPE: DNA
<213> ORGANISM: Streptomyces globisporus

<400> SEQUENCE: 124
tcagctcccc tcctg                                                          15

<210> SEQ ID NO 125
<211> LENGTH: 15
<212> TYPE: DNA
<213> ORGANISM: Streptomyces globisporus

<400> SEQUENCE: 125
gtggacgagg ccggc                                                          15

<210> SEQ ID NO 126
<211> LENGTH: 15
<212> TYPE: DNA
<213> ORGANISM: Streptomyces globisporus

<400> SEQUENCE: 126
tcacccggat gtcgt                                                          15

<210> SEQ ID NO 127
<211> LENGTH: 15
<212> TYPE: DNA
<213> ORGANISM: Streptomyces globisporus

<400> SEQUENCE: 127
gtgagtgctc tgatc                                                          15

<210> SEQ ID NO 128
<211> LENGTH: 15
<212> TYPE: DNA
<213> ORGANISM: Streptomyces globisporus

<400> SEQUENCE: 128
tcaccgcgga acgga                                                          15

<210> SEQ ID NO 129
<211> LENGTH: 15
<212> TYPE: DNA
<213> ORGANISM: Streptomyces globisporus

<400> SEQUENCE: 129
gtgccgcttc tacgc                                                          15

<210> SEQ ID NO 130
<211> LENGTH: 15
<212> TYPE: DNA
<213> ORGANISM: Streptomyces globisporus

<400> SEQUENCE: 130
ctactggaca ctgtg                                                          15

<210> SEQ ID NO 131
<211> LENGTH: 15
<212> TYPE: DNA
<213> ORGANISM: Streptomyces globisporus

<400> SEQUENCE: 131
atgccgcaca ggacc                                                          15

<210> SEQ ID NO 132
<211> LENGTH: 15
<212> TYPE: DNA

<213> ORGANISM: Streptomyces globisporus

<400> SEQUENCE: 132
tcagccggtg agagc    15

<210> SEQ ID NO 133
<211> LENGTH: 15
<212> TYPE: DNA
<213> ORGANISM: Streptomyces globisporus

<400> SEQUENCE: 133
gtgagtgctc tgatc    15

<210> SEQ ID NO 134
<211> LENGTH: 15
<212> TYPE: DNA
<213> ORGANISM: Streptomyces globisporus

<400> SEQUENCE: 134
tcaccccggc acagg    15

<210> SEQ ID NO 135
<211> LENGTH: 15
<212> TYPE: DNA
<213> ORGANISM: Streptomyces globisporus

<400> SEQUENCE: 135
atcacccccg gaggc    15

<210> SEQ ID NO 136
<211> LENGTH: 15
<212> TYPE: DNA
<213> ORGANISM: Streptomyces globisporus

<400> SEQUENCE: 136
tcactccgcc tcctc    15

<210> SEQ ID NO 137
<211> LENGTH: 23
<212> TYPE: DNA
<213> ORGANISM: Streptomyces globisporus

<400> SEQUENCE: 137
agctccatca agtcsatgrt cgg    23

<210> SEQ ID NO 138
<211> LENGTH: 26
<212> TYPE: DNA
<213> ORGANISM: Streptomyces globisporus

<400> SEQUENCE: 138
ccggtgttsa csgcgtagaa ccaggc    26

<210> SEQ ID NO 139
<211> LENGTH: 18
<212> TYPE: DNA
<213> ORGANISM: Streptomyces globisporus
<220> FEATURE:
<221> NAME/KEY: misc_feature
<222> LOCATION: (9)..(9)
<223> OTHER INFORMATION: n is a, c, g, or t

<400> SEQUENCE: 139
gacacvgcnt gytcbtcv    18

<210> SEQ ID NO 140
<211> LENGTH: 18
<212> TYPE: DNA
<213> ORGANISM: Streptomyces globisporus
<220> FEATURE:
<221> NAME/KEY: misc_feature
<222> LOCATION: (13)..(13)
<223> OTHER INFORMATION: n is a, c, g, or t

<400> SEQUENCE: 140
rtgsgcrttv gtnccrct                                                 18

<210> SEQ ID NO 141
<211> LENGTH: 26
<212> TYPE: DNA
<213> ORGANISM: Streptomyces globisporus

<400> SEQUENCE: 141
gcstcccgsg acctgggctt cgactc                                        26

<210> SEQ ID NO 142
<211> LENGTH: 26
<212> TYPE: DNA
<213> ORGANISM: Streptomyces globisporus

<400> SEQUENCE: 142
agsgasgasg agcaggcggt stcsac                                        26

<210> SEQ ID NO 143
<211> LENGTH: 26
<212> TYPE: DNA
<213> ORGANISM: Streptomyces globisporus

<400> SEQUENCE: 143
agsgasgasg agcaggcggt stcsac                                        26

<210> SEQ ID NO 144
<211> LENGTH: 24
<212> TYPE: DNA
<213> ORGANISM: Streptomyces globisporus

<400> SEQUENCE: 144
gggwrctggy rsggsccgta gttg                                          24

<210> SEQ ID NO 145
<211> LENGTH: 20
<212> TYPE: DNA
<213> ORGANISM: Streptomyces globisporus

<400> SEQUENCE: 145
aggtggaggc gctcaccgag                                               20

<210> SEQ ID NO 146
<211> LENGTH: 20
<212> TYPE: DNA
<213> ORGANISM: Streptomyces globisporus

<400> SEQUENCE: 146
gggcgtcagg ccgtaagaag                                               20

BIOSYNTHESIS OF ENEDIYNE COMPOUNDS BY MANIPULATION OF C-1027 GENE PATHWAY

CROSS-REFERENCE TO RELATED APPLICATIONS

This application is a continuation-in-part of U.S. Ser. No. 10/159,257, filed on May 31, 2002, which is a continuation-in-part of U.S. Ser. No. 09/478,188, filed on Jan. 5, 2000 now abandoned, which claims benefit under 35 U.S.C. §119 of provisional application U.S. Ser. No. 60/115,434, filed on Jan. 6, 1999, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was supported in part by a grant from the National Institutes of Health CA78747. The Government of the United States of America may have certain rights in this invention.

FIELD OF THE INVENTION

This invention relates to the field of enediyne antibiotics. In particular this invention elucidates the gene cluster controlling the biosynthesis of the C-1027 enediyne and the biosynthesis of enediyne compounds by manipulation of C-1027 gene pathway.

BACKGROUND OF THE INVENTION

The enediyne antibiotics are currently the focus of intense research activity in the fields of chemistry, biology, and medical sciences, because of their unique molecular architecture, biological activities, and modes of actions (Doyle and Borders (1995) *Enediyne antibiotics as antitumor agents*. Marcel-Dekker, New York, Thorson et al. (1999) *Bioorg. Chem.*, 27: 172–188). Since the unveiling of the structure of neocarzinostatin chromophore (Edo et al. (1985) *Tetrahedron Lett.* 26: 331–340) in 1985, the enediyne family has grown steadily. Thus far, there have been three basic groups within the enediyne antibiotic family: (a) the calicheamicin/esperamicin type, which includes the calicheamicins, the esperamicins, and namenamicin, (b) the dynemicin type, and (c) the chromoprotein type, consisting of an apoprotein and an unstable enediyne chromophore. The latter group includes neocarzinostatin, kedarcidin, C-1027 (FIG. 1), and maduropeptin, whose enediyne chromophore structures have been established, as well as several others whose enediyne chromophore structures are yet to be determined due to their instability (Thorson et al. (1999) *Bioorg. Chem.*, 27: 172–188). N1999A2, in contrast to the other chromoproteins, exists as an enediyne chromophore alone despite the fact that its structure is very similar to the other chromoprotein chromophore (Ando et al.(1998) *Tetra. Letts.*, 39: 6495–6480).

As a family, the enediyne antibiotics are the most potent, highly active antitumor agents ever discovered. Some members are 1000 times more potent than adriamycin, one of the most effective, clinically used antitumor antibiotics (Zhen et al. (1989) *J. Antibiot.* 42: 1294–1298). All members of this family contain a unit consisting of two acetylenic groups conjugated to a double bond or incipient double bond within a nine or ten-membered ring; i.e., the enediyne core as exemplified by C-1027 in FIG. 1. As the consequence of this structural feature, these compounds share a common mechanism of action: the enediyne core undergoes an electronic rearrangement to form a transient benzenoid diradical, which is positioned in the minor groove of DNA so as to damage DNA by abstracting hydrogen atoms from deoxyriboses on both strands (FIG. 1). Reaction of the resulting deoxyribose carbon-centered radicals with molecular oxygen initiates a process that results in both single-strand and double-strand DNA cleavages (Doyle and Borders (1995) *Enediyne antibiotics as antitumor agents*. Marcel-Dekker, New York; Ikemoton et al. (1995) *Proc. Natl. Acad. Sci. USA* 92:10506–10510; Myers et al. (I 997) *J. Am. Chem. Soc.* 119: 2965–2972; Stassinopoulos et al. (1996) *Science* 272: 1943–1946; Thorson et al. (1999) *Bioorg. Chem.*, 27: 172–188; Xu et al. (1997) *J. Am. Chem. Soc.* 119: 1133–1134). This novel mechanism of DNA damage has important implications for their application as potent cancer chemotherapeutic agents (Doyle and Borders (1995) supra.; Sievers et al. (1999) *Blood* 93: 3678–3684).

As an alternative to making structural analogs of microbial metabolites by chemical synthesis, manipulations of genes governing secondary metabolism offer a promising alternative allowing preparation of these compounds biosynthetically (Cane et al. (1998) *Science* 282: 63–68; Hutchinson and Fujii. (1995) *Ann. Rev. Microbiol.* 49: 201–38; Katz and Donadio (1993) *Ann. Rev. Microbiol.* 47: 875–912). The success of the latter approach depends critically on the availability of novel genetic systems and on genes encoding novel enzyme activities. The enediynes offer a distinct opportunity to study the biosynthesis of their unique molecular scaffolds and the mechanism of self-resistance to extremely cytotoxic natural products. Elucidation of these aspects provides access to rational engineering of enediyne biosynthesis for novel drug leads and makes it possible to construct enediyne overproducing strains by de-regulating the biosynthetic machinery. In addition, elucidation of an enediyne gene cluster contributes to the general field of combinatorial biosynthesis by expanding the repertoire of novel polyketide synthase (PKS) and deoxysugar biosynthesis genes as well as other genes uniquely associated with enediyne biosynthesis, leading to the making of novel enediynes via combinatorial biosynthesis.

SUMMARY OF THE INVENTION

This invention provides nucleic acid sequences and characterization of the gene cluster responsible for the biosynthesis of the enediyne C-1027 (produced by *Streptomyces globisporus*). In particular structural and functional characterization is provided for the open reading frames (ORFs) comprising this gene cluster. Thus, in one embodiment, this invention provides an isolated nucleic acid comprising a nucleic acid selected from the group consisting of a nucleic acid encoding any of C-1027 open reading frames (ORFs) –7 through 60, excluding ORF 9 (cagA); a nucleic acid encoding a polypeptide encoded by any of C-1027 open reading frames (ORFs) –7 through 60, excluding ORF 9 (cagA); and a nucleic acid amplified by polymerase chain reaction (PCR) using primer pairs that amplify any of C-1027 open reading frames (ORFs) –7 through 60, excluding ORF 9 (cagA). In certain embodiments, preferred nucleic acids comprise a nucleic acid encoding at least one, preferably at least two and more preferably at least three or more open reading frames between orf(–3) and orf54. In one embodiment, preferred nucleic acids comprise a nucleic acid encoding at least two (more preferably at least three or more)

open reading frames (ORFs) selected from the group consisting of ORF-1 through ORF 60 or sgcR3, excluding ORF 9 (cagA).

In another embodiment this invention provides an isolated nucleic acid comprising a nucleic acid that specifically hybridizes under stringent conditions to an open reading frame (ORF) of the C-1027 biosynthesis gene cluster, excluding ORF 9 (cagA), and can substitute for the ORF to which it specifically hybridizes to direct the synthesis of an enediyne. In certain embodiments this also includes nucleic acids that would stringently hybridize indicated above, but for the degeneracy of the nucleic acid code. In other words, if silent mutations could be made in the subject sequence so that it hybridizes to the indicated sequence(s) under stringent conditions, it would be included in certain embodiments. Particularly preferred nucleic acids comprises a nucleic acid that specifically hybridizes under stringent conditions to a nucleic acid selected from the group consisting of orf(−7), orf(−6), orf(−5), orf(−4), orf(−3), orf(−2) orf(−1), orf0, orf1, orf2, orf3, orf4, orf5, orf6, orf7, orf8, orf10, orf11, orf12, orf13, orf14, orf15, orf16, orf17, orf18, orf19, orf20, orf21, orf22, orf23, orf24, orf25, orf26, orf27, orf28, orf29, orf30, orf31, orf32, orf33, orf34, orf35, orf36, orf37, orf38, orf39, orf40, orf41, orf42, orf43, orf44, orf45, orf46, orf47, orf48, orf49, orf50, orf51, orf52, orf53, orf54, orf55, orf56, orf57, orf58, orf59, and orf60. Particularly preferred isolated nucleic acid comprises a nucleic acid selected from the group consisting of orf(−7), orf(−6), orf(−5), orf(−4), orf(−3), orf(−2), orf(−1), orf0, orf1, orf2, orf3, orf4, orf5, orf6, orf7, orf8, orf10, orf11, orf12, orf13, orf14, orf15, orf16, orf17, orf18, orf19, orf20, orf21, orf22, orf23, orf24, orf25, orf26, orf27, orf28, orf29, orf30, orf31, orf32, orf33, orf34, orf35, orf36, orf37, orf38, orf39, orf40, orf41, orf42, orf43, orf44, orf45, orf46, orf47, orf48, orf49, orf50, orf51, orf52, orf53, orf54, orf55, orf56, orf57, orf58, orf59, orf60, The nucleic acid may comprise a nucleic acid that is a single nucleotide polymorphism (SNP) of a nucleic acid selected from the group consisting of orf(−7), orf(−6), orf(−5), orf (−4), orf(−3), orf(−2), orf(−1), orf0, orf1, orf2, orf3, orf4, orf5, orf6, orf7, orf8, orf10, orf11, orf12, orf13, orf14, orf15, orf16, orf17, orf18, orf19, orf20, orf21, orf22, orf23, orf24, orf25, orf26, orf27, orf28, orf29, orf30, orf31, orf32, orf33, orf34, orf35, orf36, orf37, orf38, orf39, orf40, orf41, orf42, orf43, orf44, orf45, orf46, orf47, orf48, orf49, orf50, orf51, orf52, orf53, orf54, orf55, orf56, orf57, orf58, orf59, and orf60.

This invention also provides an isolated gene cluster comprising open reading frames encoding polypeptides sufficient to direct the assembly of a C-1027 enediyne or a C-1027 enediyne analogue. The gene cluster may be present in a cell, more preferably in a bacterial cell (e.g. *Actinomycetes, Actinioplainetes, Actinomadura, Micromonospora,* or *Streptomycetes*). Particular preferred bacterial cells include, but are not limited to *Streptomyces globisporus, Streptomyces lividans, Streptomyces coelicolor, Micromonospora echinospora* spp. *calichlenisis, Actinomadura verrucosopora, Micromonospora chersina, Streptomyces carzinostaticus,* and *Actinomycete* L585-6. The gene cluster may contain one or more open reading frames operatively linked to a heterologous promoter (e.g. a constitutive or an inducible promoter).

This invention also provides for a polypeptide encoded by any one or more of the nucleic acids described herein.

Also provided are host cell(s) (e.g. eukaryotic cells or bacterial cells as described herein) transformed with one or more of the expression vectors described herein. Preferred host cells are transformed with an exogenous nucleic acid comprising a gene cluster encoding polypeptides sufficient to direct the assembly of a C-1027 enediyne or a C-1027 enediyne analogue. In certain embodiments, heterologous nucleic acid may comprise only a portion of the gene cluster, but the cell will still be able to express an enediyne.

This invention also provides methods of chemically modifying a biological molecule. The methods involve contacting a biological molecule that is a substrate for a polypeptide encoded by a C-1027 biosynthesis gene cluster open reading frame, with a polypeptide encoded by a C-1027 biosynthesis gene cluster open reading frame whereby the polypeptide chemically modifies the biological molecule. In one preferred embodiment, the polypeptide is an enzyme selected from the group consisting of a hydroxylase, a homocysteine synthase, a dNDP-glucose dehydrogenase, a citrate carrier protein, a C-methyl transferase, an N-methyl transferase, an aminotransferase, a CagA apoprotein, an NDP-glucose synthase, an epimerase, an acyl transferase, a coenzyme F390 synthase, and epoxidase hydrolase, an anthranilate synthase, a glycosyl transferase, a monooxygenase, a type II condensation protein, an aminomutase, a type II adenylation protein, an O-methyl transferase, a P-450 hydroxylase, an oxidoreductase, and a proline oxidase. In a preferred embodiment the method involves contacting the biological molecule with at least two (preferably at least three or more) different polypeptides encoded by C-1027 biosynthesis gene cluster open reading frames. The contacting may be in a host cell (e.g. a eukaryotic cell or a bacterial cell) or the contacting can be ex vivo. The biological molecule can be a endogenous metabolite produced by said host cell or an exogenous supplied metabolite. In preferred embodiments, the host cell is a bacterial cell or eukaryotic cell (e.g., a mammalian cell, a yeast cell, a plant cell, a fungal cell, an insect cell, etc.). In certain preferred embodiments, the host cell synthesizes sugars and glycosylates the biological molecule. In other preferred embodiments, the host cell synthesizes deoxysugars. The method can further involve contacting the biological molecule with a polyketide synthase or a non-ribosomal polypeptide synthetase. The contacting can be in a cell (e.g., a bacterial cell) or ex vivo. In one preferred embodiment the method comprises contacting the biological molecule with at substantially all of the polypeptides encoded by C-1027 biosynthesis gene cluster open reading frames and said method produces an enediyne or enediyne analogue. In another preferred embodiment, the biological molecule is a fatty acid and the biological molecule is contacted with a C-1027 orf polypeptide selected from the group consisting of an epoxide hydrase, a monooxygenase, an iron-sulfer flavoprotein, a p-450 hydroxylase, an oxidoreductase, and a proline oxidase. In certain embodiments, the biological molecule is a fatty acid and said biological molecule is contacted with a plurality of C-1027 orf polypeptides comprising an epoxide hydrase, a monooxygenase, an iron-sulfer flavoprotein, a p-450 hydroxylase, an oxidoreductase, and a proline oxidase. In one especially preferred embodiment, the biological molecule is contacted with polypeptides encoded by ORF17, ORF20, ORF21, ORF29, ORF30, ORF32, ORF35, and ORF38. In another especially preferred embodiment, the biological molecule is contacted with polypeptides encoded by ORF 15, ORF 16, ORF 28, ORF3, ORF 14, and ORF 13, and, in certain embodiments, ORF 4 and ORF 3 as well.

In certain embodiments, the method may comprise contacting a sugar with one or more C-1027 open reading frame polypeptides selected from the group consisting of a dNDP-glucose synthase, a dNDP glucose dehydratase, an epimerase, an aminotransferase, a C-methyltransferase, an N-methyltransferase, and a glycosyl transferase. A particularly preferred variant of this method comprises contacting a dNDP-glucose with a plurality of C-1027 open reading frame polypeptides comprising a dNDP-glucose synthase, a dNDP glucose dehydratase, an epimerase, an aminotransferase, a C-methyltransferase, an N-methyltransferase, and a glycosyl transferase.

In certain other embodiments, the method comprises contacting an amino acid with one or one or more C-1027 open reading frame polypeptides selected from the group consisting of a hydroxylase, an aminomutase, a type II NRPS condensation enzyme, a type II NRPS adenylation enzyme, and a type II peptidyl carrier protein. These methods may involve contacting an amino acid with a plurality of C-1027 open reading frame polypeptides comprising a hydroxylase, a halogenase, an aminomutase, a type II NRPS condensation enzyme, a type II NRPS adenylation enzyme, and a type II peptidyl carrier protein. In particularly preferred embodiments, the amino acid is a tyrosine.

This invention also provides a method of synthesizing a chromaprotein type enediyne core, said method comprising contacting a fatty acid with one or more C-1027 orf polypeptides selected from the group consisting of an epoxide hydrase, a monooxygenase, an iron-sulfer flavoprotein, a p-450 hydroxylase, an oxidoreductase, and a proline oxidase. In preferred embodiments, the fatty acid may be contacted with a plurality of C-1027 orf polypeptides comprising an epoxide hydrase, a monooxygenase, an iron-sulfer flavoprotein, a p-450 hydroxylase, an oxidoreductase, and a proline oxidase. In particularly preferred embodiments, the fatty acid is contacted with polypeptides encoded by ORF 17, ORF20, ORF21, ORF29, ORF30, ORF32, ORF35, and ORF38.

In still yet another embodiment, this invention provides a method of synthesizing a deoxysugar. This method involves contacting a sugar with one or more C-1027 open reading frame polypeptides selected from the group consisting of a dNDP-glucose synthase, a dNDP glucose dehydratase, an epimerase, an aminotransferase, a C-methyltransferase, an N-methyltransferase, and a glycosyl transferase. In preferred embodiments, this method involves contacting a dNDP-glucose with a plurality of C-1027 open reading frame polypeptides comprising a dNDP-glucose synthase, a dNDP glucose dehydratase, an epimerase, an aminotransferase, a C-methyltransferase, an N-methyltransferase, and a glycosyl transferase. In particularly preferred embodiments, the dNDP-glucose is contacted with polypeptides encoded by orf17, orf20, orf21, orf29, orf30, orf32, orf35, and orf38.

This invention also provides methods of synthesizing a beta amino acid by contacting an amino acid with one or more C-1027 open reading frame polypeptides selected from the group consisting of a hydroxylase, an aminomutase, a type II NRPS condensation enzyme, a type II NRPS adenylation enzyme, and a type II peptidyl carrier protein. The method preferably comprises contacting an amino acid with a plurality of C-1027 open reading frame polypeptides comprising a hydroxylase, a halogenase, an aminomutase, a type II NRPS condensation enzyme, a type II NRPS adenylation enzyme, and a type II peptidyl carrier protein. Particularly preferred embodiments comprise contacting the amino acid (e.g. tyrosine) with polypeptides encoded by ORF 4, ORF11, ORF24, ORF23, ORF25, and ORF26.

Also provided are methods of synthesizing an enediyne or an enediyne analogue. These methods involve culturing a cell (e.g. a eukaryotic cell or a bacterium) comprising a recombinantly modified C-1027 gene cluster under conditions whereby said cell expresses said enediyne or enediyne analogue; and recovering the enediyne or enediyne analogue. In preferred embodiments, the gene cluster is present in a bacterium (e.g., *Actinomycetes, Actinoplanetes, Actinomadura, Micromonospora,* or *Streptomycetes*). Particularly preferred bacteria include, but are not limited to *Streptomyces globisporus, Streptomyces lividans, Streptomyces coelicolor, Micromonospora echinospora* spp. *calichenisis, Actinomadura verrucosopora, Micromonospora chersina, Streptomyces carzinostaticus,* and *Actinomycete* L585-6. In another preferred embodiment, the gene cluster is present in a eukaryotic cell (e.g. a mammalian cell, a yeast cell, a plant cell, a fungal cell, an insect cell, etc.). In certain preferred embodiments, the host cell synthesizes sugars and glycosylates the enediyne or enediyne analogue. In other preferred embodiments, the host cell synthesizes deoxysugars. In preferred embodiments, the host cell is a bacterial cell or eukaryotic cell (e.g., a mammalian cell, a yeast cell, a plant cell, a fungal cell, an insect cell, etc.). In certain preferred embodiments, the host cell synthesizes sugars and glycosylates the biological molecule. In other preferred embodiments, the host cell synthesizes deoxysugars. The method can further involve contacting the biological molecule with a polyketide synthase or a non-ribosomal polypeptide synthetase. The contacting can be in a cell (e.g., a bacterial cell) or ex vivo. In one preferred embodiment the method comprises contacting the biological molecule with at substantially all of the polypeptides encoded by C-1027 biosynthesis gene cluster open reading frames and said method produces an enediyne or enediyne analogue. In another preferred embodiment, the biological molecule is a fatty acid and the biological molecule is contacted with a C-1027 orf polyeptide selected from the group consisting of an epoxide hydrase, a monooxygenase, an iron-sulfer flavoprotein, a p-450 hydroxylase, an oxidoreductase, and a proline oxidase. In certain embodiments, the biological molecule is a fatty acid and said biological molecule is contacted with a plurality of C-1027 orf polypeptides comprising an epoxide hydrase, a monooxygenase, an iron-sulfer flavoprotein, a p-450 hydroxylase, an oxidoreductase, and a proline oxidase. In one especially preferred embodiment, the biological molecule is contacted with polypeptides encoded by ORF 17, ORF20, ORF21, ORF29, ORF30, ORF32, ORF35, and ORF38. In another especially preferred embodiment, the biological molecule is contacted with polypeptides encoded by ORF 15, ORF 16, ORF 28, ORF3, ORF 14, and ORF 13, and, in certain embodiments, ORF 4 and ORF 3 as well.

This invention also provides a method of making a cell (e.g., a bacterial or eukaryotic cell) resistant to an enediyne or an enediyne metabolite. This method involves expressing in the cell one or more isolated C-1027 open reading frame nucleic acids that encode a protein selected from the group consisting of a CagA apoprotein, a SgcB transmembrane efflux protein, a transmembrane transport protein, a Na+/H+ transporter, an ABC transport, a glycerol phosphate tranporter, and a UvrA-like protein. In preferred embodiments, the isolated C-1027 open reading frame nucleic acids are selected from the group consisting of orf 9, orf2, orf 27, orf 0, orf 1 c-terminus, off 2, and orf 1 N-terminus. Certain embodiments exclude cagA (orf 9).

In one embodiment, this invention specifically excludes one or more of open reading frames −7 through 42. In particular, in one embodiment this invention excludes cagA (orf9), and/or sgcA (orf1), and/or sgcB (orf2).

One embodiment of the present invention provides C-1027 enediyne or a C-1027 enediyne analogue produced by an isolated gene cluster comprising open reading frames encoding polypeptides sufficient to direct the assembly of a C-1027 enediyne or a C-1027 enediyne analogue. The gene cluster may be present in a cell, more preferably in a bacterial cell (e.g. *Actinomycetes, Actinoplanetes, Actinomadura, Micromonospora*, or *Streptomycetes*). Particularly preferred bacterial cells include, but are not limited to an *Streptomyces globisporus, Streptomyces lividans, Streptomyces coelicolor, Micromonospora echinospora* spp. *calichenisis, Actinomadura verrucosopora, Micromonospora chersina, Streptomyces carzinostaticus*, and *Actinomycete* L585-6. The gene cluster may contain one or more open reading frames operatively linked to a heterologous promoter (e.g. a constitutive or an inducible promoter).

Also provided are C-1027 enediyne or a C-1027 enediyne analogue produced by host cell(s) (e.g. eukaryotic cells or bacterial cells as described herein) transformed with one or more of the expression vectors described herein. Preferred host cells are transformed with an exogenous nucleic acid comprising a gene cluster encoding polypeptides sufficient to direct the assembly of a C-1027 enediyne or a C-1027 enediyne analogue. In certain embodiments, heterologous nucleic acid may comprise only a portion of the gene cluster, but the cell will still be able to express an enediyne.

C-1027 enediyne or a C-1027 enediyne analogue are produced by the methods of chemically modifying a biological molecule. These methods involve contacting a biological molecule that is a substrate for a polypeptide encoded by a C-1027 biosynthesis gene cluster open reading frame with a polypeptide encoded by a C-1027 biosynthesis gene cluster open reading frame, whereby the polypeptide chemically modifies the biological molecule. In one preferred embodiment, the polypeptide is an enzyme selected from the group consisting of a hydroxylase, a homocysteine synthase, a dNDP-glucose dehydrogenase, a citrate carrier protein, a C-methyl transferase, an N-methyl transferase, an aminotransferase, a CagA apoprotein, an NDP-glucose synthase, an epimerase, an acyl transferase, a coenzyme F390 synthase, and epoxidase hydrolase, an anthranilate synthase, a glycosyl transferase, a monooxygenase, a type II condensation protein, an aminomutase, a type II adenylation protein, an O-methyl transferase, a P-450 hydroxylase, an oxidoreductase, and a proline oxidase. In another preferred embodiment, the method involves contacting the biological molecule with at least two (preferably at least three or more) different polypeptides encoded by C-1027 biosynthesis gene cluster open reading frames. The contacting may be in a host cell (e.g. a eukaryotic cell or a bacterial cell) or the contacting can be ex vivo. The biological molecule can be an endogenous metabolite produced by said host cell or an exogenous supplied metabolite. In preferred embodiments, the host cell is a bacterial cell or eukaryotic cell (e.g., a mammalian cell, a yeast cell, a plant cell, a fungal cell, an insect cell, etc.). In certain preferred embodiments, the host cell synthesizes sugars and glycosylates the biological molecule. In other preferred embodiments, the host cell synthesizes deoxysugars. The method can further involve contacting the biological molecule with a polyketide synthase or a non-ribosomal polypeptide synthetase. The contacting can be in a cell (e.g., a bacterial cell) or ex vivo. In one preferred embodiment the method comprises contacting the biological molecule with substantially all of the polypeptides encoded by C-1027 biosynthesis gene cluster open reading frames and said method produces an enediyne or enediyne analogue. In another preferred embodiment, the biological molecule is a fatty acid and the biological molecule is contacted with a C-1027 orf polypeptide selected from the group consisting of an epoxide hydrase, a monooxygenase, an iron-sulfer flavoprotein, a p-450 hydroxylase, an oxidoreductase, and a proline oxidase. In certain embodiments, the biological molecule is a fatty acid and said biological molecule is contacted with a plurality of C-1027 orf polypeptides comprising an epoxide hydrase, a monooxygenase, an iron-sulfer flavoprotein, a p-450 hydroxylase, an oxidoreductase, and a proline oxidase. In one especially preferred embodiment, the biological molecule is contacted with polypeptides encoded by ORF 17, ORF20, ORF21, ORF29, ORF30, ORF32, ORF35, and ORF38. In another especially preferred embodiment, the biological molecule is contacted with polypeptides encoded by ORF 15, ORF 16, ORF 28, ORF3, ORF 14, and ORF 13, and, in certain embodiments, ORF 4 and ORF 3 as well.

In certain embodiments, an enediyne core is produced by a method, wherein the method comprises contacting a sugar with one or more C-1027 open reading frame polypeptides selected from the group consisting of a dNDP-glucose synthase, a dNDP glucose dehydratase, an epimerase, an aminotransferase, a C-methyltransferase, an N-methyltransferase, and a glycosyl transferase. A particularly preferred variant of this method comprises contacting a dNDP-glucose with a plurality of C-1027 open reading frame polypeptides comprising a dNDP-glucose synthase, a dNDP glucose dehydratase, an epimerase, an aminotransferase, a C-methyltransferase, an N-methyltransferase, and a glycosyl transferase.

In certain other embodiments, an enediyne core may be produced by a method, wherein the method comprises contacting an amino acid with one or one or more C-1027 open reading frame polypeptides selected from the group consisting of a hydroxylase, an aminomutase, a type II NRPS condensation enzyme, a type II NRPS adenylation enzyme, and a type II peptidyl carrier protein. These methods may involve contacting an amino acid with a plurality of C-1027 open reading frame polypeptides comprising a hydroxylase, a halogenase, an aminomutase, a type II NRPS condensation enzyme, a type II NRPS adenylation enzyme, and a type II peptidyl carrier protein. In particularly preferred embodiments, the amino acid is a tyrosine.

In another embodiment of the present invention, an enediyne core is produced by a method of synthesizing a chromaprotein type enediyne core, said method comprising contacting a fatty acid with one or more C-1027 orf polypeptides selected from the group consisting of an epoxide hydrase, a monooxygenase, an iron-sulfer flavoprotein, a p-450 hydroxylase, an oxidoreductase, and a proline oxidase. In preferred embodiments, the fatty acid may be contacted with a plurality of C-1027 orf polypeptides comprising an epoxide hydrase, a monooxygenase, an iron-sulfer flavoprotein, a p-450 hydroxylase, an oxidoreductase, and a proline oxidase. In particularly preferred embodiments, the fatty acid is contacted with polypeptides encoded by ORF17, ORF20, ORF21, ORF29, ORF30, ORF32, ORF35, and ORF38.

In still yet another embodiment, an enediyne core is produced by a method including a method of synthesizing a deoxysugar. This method involves contacting a sugar with one or more C-1027 open reading frame polypeptides selected from the group consisting of a dNDP-glucose synthase, a dNDP glucose dehydratase, an epimerase, an aminotransferase, a C-methyltransferase, an N-methyltransferase, and a glycosyl transferase. In preferred embodiments, this method involves contacting a dNDP-glucose with a plurality of C-1027 open reading frame polypeptides comprising a dNDP-glucose synthase, a dNDP glucose dehydratase, an epimerase, an aminotransferase, a C-methyltransferase, an N-methyltransferase, and a glycosyl transferase. In particularly preferred embodiments, the dNDP-glucose is contacted with polypeptides encoded by orf17, orf20, orf21, orf29, orf30, orf32, orf35, and orf38.

This invention also provides producing the enediyne core by a method, wherein the method includes synthesizing a beta amino acid by contacting an amino acid with one or one or more C-1027 open reading frame polypeptides selected from the group consisting of a hydroxylase, an aminomutase, a type II NRPS condensation enzyme, a type II NRPS adenylation enzyme, and a type II peptidyl carrier protein. The method preferably comprises contacting an amino acid with a plurality of C-1027 open reading frame polypeptides comprising a hydroxylase, a halogenase, an aminomutase, a type II NRPS condensation enzyme, a type II NRPS adenylation enzyme, and a type II peptidyl carrier protein. Particularly preferred embodiments comprise contacting the amino acid (e.g. tyrosine) with polypeptides encoded by ORF 4, ORF11, ORF24, ORF23, ORF25, and ORF26.

Also provided are methods of synthesizing an enediyne or an enediyne analogue. These methods involve culturing a cell (e.g. a eukaryotic cell or a bacterium) comprising a recombinantly modified C-1027 gene cluster under conditions whereby said cell expresses said enediyne or enediyne analogue; and recovering the enediyne or enediyne analogue. In preferred embodiments, the gene cluster is present in a bacterium (e.g., *Actinomycetes*, *Actinoplanetes*, *Actinomadura*, *Micromonospora*, or *Streptomycetes*). Particularly preferred bacteria include, but are not limited to *Streptomyces globisporus*, *Streptomyces lividans*, *Streptomyces coelicolor*, *Micromonospora echinospora* spp. *calichenisis*, *Actinomadura verrucosopora*, *Micromonospora chersina*, *Streptomyces carzinostaticus*, and *Actinomycete* L585-6. In another preferred embodiment, the gene cluster is present in a eukaryotic cell (e.g. a mammalian cell, a yeast cell, a plant cell, a fungal cell, an insect cell, etc.). The host cell can be one that synthesizes sugars and glycosylates the enediyne or enediyne analogue. The host can be one that synthesizes deoxysugars.

The contacting may be in a host cell (e.g. a eukaryotic cell or a bacterial cell) or the contacting can be ex vivo. The biological molecule can be a endogenous metabolite produced by said host cell or an exogenous supplied metabolite. In preferred embodiments, the host cell is a bacterial cell or eukaryotic cell (e.g., a mammalian cell, a yeast cell, a plant cell, a fungal cell, an insect cell, etc.). In certain preferred embodiments, the host cell synthesizes sugars and glycosylates the biological molecule. In other preferred embodiments, the host cell synthesizes deoxysugars. The method can further involve contacting the biological molecule with a polyketide synthase or a non-ribosomal polypeptide synthetase. The contacting can be in a cell (e.g., a bacterial cell) or ex vivo. In one preferred embodiment the method comprises contacting the biological molecule with at substantially all of the polypeptides encoded by C-1027 biosynthesis gene cluster open reading frames and said method produces an enediyne or enediyne analogue. In another preferred embodiment, the biological molecule is a fatty acid and the biological molecule is contacted with a C-1027 orf polyeptide selected from the group consisting of an epoxide hydrase, a monooxygenase, an iron-sulfer flavoprotein, a p-450 hydroxylase, an oxidoreductase, and a proline oxidase. In certain embodiments, the biological molecule is a fatty acid and said biological molecule is contacted with a plurality of C-1027 orf polypeptides comprising an epoxide hydrase, a monooxygenase, an iron-sulfer flavoprotein, a p-450 hydroxylase, an oxidoreductase, and a proline oxidase. In one especially preferred embodiment, the biological molecule is contacted with polypeptides encoded by ORF17, ORF20, ORF21, ORF29, ORF30, ORF32, ORF35, and ORF38. In another especially preferred embodiment, the biological molecule is contacted with polypeptides encoded by ORF 15, ORF 16, ORF 28, ORF3, ORF 14, and ORF 13, and, in certain embodiments, ORF 4 and ORF 3 as well.

In another embodiment of the present invention, a compound is provided having a formula:

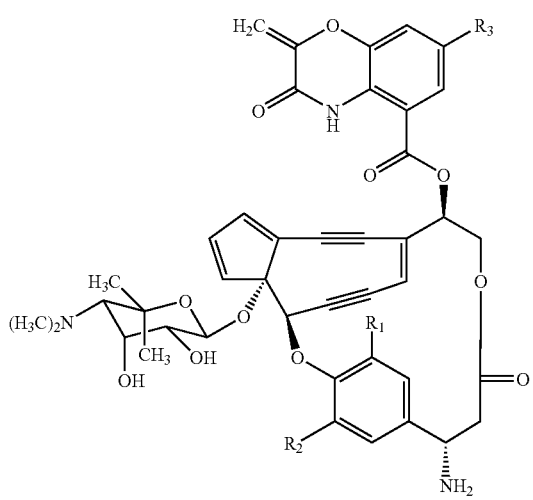

wherein $R_1$ is H or OH; $R_2$ is Cl or H; $R_3$ is $OCH_3$ or H; with the proviso that $R_1$ is not OH when $R_2$ is Cl and $R_3$ is $OCH_3$.

Another embodiment of the present invention, a compound is provided having a formula:

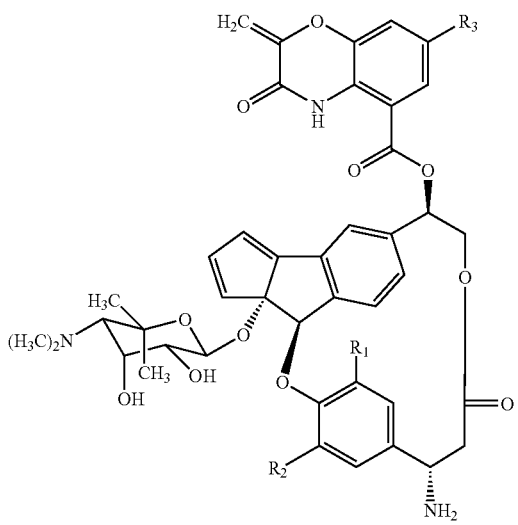

wherein $R_1$ is H or OH; $R_2$ is Cl or H; $R_3$ is $OCH_3$ or H; with the proviso that $R_1$ is not OH when $R_2$ is Cl and $R_3$ is $OCH_3$.

In one embodiment of the present invention, the enediyne or enediyne analogue produced by the C-1027 gene cluster is a C-1027 deshydroxy compound, a C-1027 deschloro compound or a C-1027 desmethoxy compound.

One embodiment of the present invention comprises a pharmaceutical composition comprising a therapeutically effective amount of the enediyne compound dissolved or suspended in a pharmaceutically acceptable carrier, wherein said compound is a biosynthesized enediyne compound.

In one embodiment, the biosynthesized enediyne compound is conjugated to a polymer or a monoclonal antibody.

One embodiment of the present invention includes an enediyne analogue produced by a transformed host cell comprising a modified C-1027 biosynthesis gene cluster sufficient to direct the assembly of a C-1027 enediyne analogue.

Another embodiment of the present invention comprises an enediyne analogue produced by a transformed host cell comprising a C-1027 biosynthesis gene cluster sufficient to direct the assembly of a C-1027 enediyne analogue, wherein the gene cluster is no longer effective in producing naturally-occurring C-1027.

DEFINITIONS

The terms "C-1027 open reading frame", and "C-1027 ORF" refer to an open reading frame in the C-1027 biosynthesis gene cluster as isolated from *Streptomyces globisporus*. The term also embraces the same open reading frames as present in other enediyne-synthesizing organisms (e.g. other strains and/or species of *Streptomyces, Actinomyces*, and the like). The term encompasses allelic variants and single nucleotide polymorphisms (SNPs). In certain instances the C-1027 ORF is used synonymously with the polypeptide encoded by the C-1027 ORF and may include conservative substitutions in that polypeptide. The particular usage will be clear from context.

The terms "isolated," "purified" or "biologically pure" refer to material which is substantially or essentially free from components which normally accompany it as found in its native state. With respect to nucleic acids and/or polypeptides the term can refer to nucleic acids or polypeptides that are no longer flanked by the sequences typically flanking them in nature.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49:1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111 :2321, O-methylphophoroamidite linkages (see Eckstein, *Oligonucleotides and Analogues: A Practical Approach,* Oxford University Press), and peptide nucleic acid backbones and linkages (see Egholm (1992) *J. Am. Chem. Soc.* 114:1895; Meier et al. (1992) *Chem. Int. Ed.* *Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

A "coding sequence" or a sequence which "encodes" a particular polypeptide (e.g. a PKS, an NRPS, etc.), is a nucleic acid sequence which is ultimately transcribed and/or translated into that polypeptide in vitro and/or in vivo when placed under the control of appropriate regulatory sequences. In certain embodiments, the boundaries of the coding sequence are determined by a start codon at the 5' (amino) terminus and a translation stop codon at the 3'(carboxy) terminus. A coding sequence can include, but is not limited to, cDNA from procaryotic or eucaryotic mRNA, genomic DNA sequences from procaryotic or eucaryotic DNA, and even synthetic DNA sequences. In preferred embodiments, a transcription termination sequence will usually be located 3' to the coding sequence.

Expression "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Recombination" refers to the reassortment of sections of DNA or RNA sequences between two DNA or RNA molecules. "Homologous recombination" occurs between two DNA molecules which hybridize by virtue of homologous or complementary nucleotide sequences present in each DNA molecule.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes part I chapter 2 Overview of principles of hybridization and the strategy of nucleic acid probe assays*, Elsevier, New York Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) *Molecular Cloning—A Laboratory Manual* (2nd ed.) Vol. 1–3, Cold Spring Harbor Laboratory, Cold Spring Harbor Press, NY, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. In general, a signal to noise ratio of 2×(or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Expression vectors are defined herein as nucleic acid sequences that direct the transcription of cloned copies of genes/cDNAs and/or the translation of their mRNAs in an appropriate host. Such vectors can be used to express genes or cDNAs in a variety of hosts such as bacteria, bluegreen algae, plant cells, insect cells and animal cells. Expression vectors include, but are not limited to, cloning vectors, modified cloning vectors, and specifically designed plasmids or viruses. Specifically designed vectors allow the shuttling of DNA between hosts, such as bacteria-yeast or bacteria-animal cells. An appropriately constructed expression vector preferably contains: an origin of replication for autonomous replication in a host cell, a selectable marker, optionally one or more restriction enzyme sites, and optionally one or more constitutive or inducible promoters. In preferred embodiments, an expression vector is a replicable DNA construct in which a DNA sequence encoding one or more PKS and/or NRPS domains and/or modules is operably linked to suitable control sequences capable of effecting the expression of the products of these synthase and/or synthetases in a suitable host. Control sequences include a transcriptional promoter, an optional operator sequence to control transcription and sequences which control the termination of transcription and translation, and so forth.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (1), Leucine (L), Methionine (M), Valine (V); and 6) Phenylalanine (F), Tyrosine (Y), Tryptophan (W).

The "group consisting of orf(−7) through orf(60)" refers to the group consisting of orf(−7), orf(−6), orf(−5), orf(−4), orf(−3), orf(−2), orf(−1), orf0, orf1, orf2, orf3, orf4, orf5, orf6, orf7, orf8, orf10, orf11, orf12, orf13, orf14, orf15, orf16, orf17, orf18, orf19, orf20, orf21, orf22, orf23, orf24, orf25, orf26, orf27, orf28, orf29, orf30, orf31, orf32, orf33, orf34, orf35, orf36, orf37, orf38, orf39, orf40, orf41, orf42, orf43, orf44, orf45, orf46, orf47, orf48, orf49, orf50, orf51, orf52, orf53, orf54, orf55, orf56, orf57, orf58, orf59, and orf60 as identified in Tables II and III. In certain embodiments ORF 9 (cagA) is excluded.

A "biological molecule that is a substrate for a polypeptide encoded by a enediyne (e.g., C-1027) biosynthesis gene" refers to a molecule that is chemically modified by one or more polypeptides encoded by open reading frame(s) of the C-1027 biosynthesis gene cluster. The "substrate" may be a native molecule that typically participates in the biosynthesis of an enediyne, or can be any other molecule that can be similarly acted upon by the polypeptide.

A "polymorphism" is a variation in the DNA sequence of some members of a species. A polymorphism is thus said to be "allelic," in that, due to the existence of the polymorphism, some members of a species may have the unmutated sequence (i.e. the original "allele") whereas other members may have a mutated sequence (i.e. the variant or mutant "allele"). In the simplest case, only one mutated sequence may exist, and the polymorphism is said to be diallelic. In the case of diallelic diploid organisms, three genotypes are possible. They can be homozygous for one allele, homozygous for the other allele or heterozygous. In the case of diallelic haploid organisms, they can have one allele or the other, thus only two genotypes are possible. The occurrence of alternative mutations can give rise to trialleleic, etc. polymorphisms. An allele may be referred to by the nucleotide(s) that comprise the mutation.

"Single nucleotide polymorphism" or "SNPs are defined by their characteristic attributes. A central attribute of such a polymorphism is that it contains a polymorphic site, "X," most preferably occupied by a single nucleotide, which is the site of the polymorphism's variation (Goelet and Knapp U.S. patent application Ser. No. 08/145,145). Methods of identifying SNPs are well known to those of skill in the art (see, e.g., U.S. Pat. No. 5,952,174).

Abbreviations used herein include LB, Luria-Bertani; NGDH, dNDP-glucose 4,6-dehydratase; nt, nucleotide; ORF, open reading frame; PCR, polymerase chain reaction; PEG, polyethyleneglycol; PKS, polyketide synthase; RBS, ribosomal binding site; Apr, apramycin; R, resistant; Th, thiostrepton; WT, wild-type; and TS, temperature sensitive.

BRIEF DESCRIPTION OF THE DRAWINGS

FIG. 5A shows a restriction map of the 75-kb sgc gene cluster from S. globisporus as represented by three cosmid clones. FIG. 5B illustrates the genetic organization of the sgcA, sgcB, and cagA genes, showing that they are clustered in the sgc gene cluster. Probe 1, the 0.55-kb dNDP-glucose 4,6-dehydratase gene fragment from pBS1002. Probe 2, the 0.73-kb cagA fragment from pBS1003. A, ApaI; B, BamHI; E, EcoRI; K, KpnI, S, SacII; Sp, SphI. FIG. 5C shows the genetic organization of the C-1027 biosynthesis gene cluster.

FIG. 6 shows the DNA and deduced amino acid sequences of the 3.0-kb BamHI fragment from pBS1007, showing the sgcA and sgcB genes. Possible RBSs are boxed. The presumed translational start and stop sites are in boldface. Restriction enzyme sites of interest are underlined. The amino acids, according to which the degenerated PCR primer were designed for amplifying the dNDP-glucose 4,6-dehydratase gene from S. globisporus, are underlined.

FIG. 7 shows the amino acid sequence alignment of SgcA with three other dNDP-glucose 4,6-dehydratases. Gdh, TDP-glucose 4,6-dehydratase of S. erythraea (AAA68211); MtmE, TDP-glucose 4,6-dehydratase in the mithramycin pathway of S. argillaceus (CAA71847); TylA2, TDP-glucose 4,6-dehydratase in the tylosin pathway of S. fradiae (S49054). Given in parentheses are protein accession numbers. The αβα fold with the NAD$^+$-binding motif of GxGxxG is boxed.

FIG. 8A shows construction of sgcA disruption mutant and restriction maps of the wild-type S. globisporus C-1027 and S. globisporus SB1001 mutant strains showing predicted fragment sizes upon BamHI digestion. FIGS. 8B and 8C show a Southern analysis of S. globisporus C-1027 (lane 1) and S. globisporus SB1001 (lanes 2, 3, and 4, three individual isolates) genomic DNA, digested with BamHI, using (FIG. 8B) pOJ260 vector or (FIG. 8C) the 0.75-kb SacII/KpnI fragment of sgcA from pBS1012 as a probe, respectively. B, BamHI; K, KpnI; S, SacII.

FIGS. 9A, 9B, 9C, and 9D illustrate the determination of C-1027 production in various S. globisporus strains by assaying their antibacterial activity against M. luteus. FIG. 9A:1, S. globisporusC-1027; 2,3, and 4, S. globisporus SB1001 (three individual isolates); 5, S. globisporus AF67; 6, S. globisporus AF40. FIG. 9B: 1, S. globisporus C-1027; 2, S. globisporus SB1001 (pWHM3); 3 and 4, S. globisporus SB1001 (pBS1 15) (two individual isolates). Both S. globisporus SB1001 (pWHM3) and S. globisporus SB1001 (pBS1015) were grown in the presence of 5 µg/mL thiostrepton. FIG. 9C: I, S. globisporusC-1027; 2, S. globisporus SB1001 (pBS1015); 3. S. globisporus SB1001; 4. S. globisporus SB1001 (pWHM3); 5. S. globisporus AF40; 6. S. globisporus AF44. All S. globisporus strains were grown in the absence of thiostrepton. FIG. 9D: 1. S. globisporus (pKC1139); 2. S. globisporus (pBS1018).

FIG. 12 shows that the upstream boundary has been determined to be between orf(−3) and sgcB1, and the downstream boundary has been determined to be between sgcR3 and orf54.

FIG. 13A shows a comparison between the SgcE PKS catalyzing the nine-membered enediyne core in C-1027 biosynthesis and the CalD8 PKS catalyzing the ten-membered enediyne core in calicheamicin biosynthesis. FIG. 13B shows a proposal of the C-1027 core biosynthesis by the SgcE PKS and other accessory proteins.

(FIG. 14) Bdeoxy amino sugar, (FIG. 14C) β-amino acid, and (FIG. 14D) benzoxazolinate.

FIG. 17 illustrates a demonstration of the production of novel C-1027 analogs by engineering the C-1027 biosynthetic pathway in S globisporus. Mutant strain generation, C-1027 and its novel analog isolation and HPCL conditions are described herein. The new peaks, detected from the mutant strains, exhibited a different retention time than C-1027 and its aromatized product as observed from the wild type strain are examples of novel C-1027 analogs. The structures of deshydroxy-C-1027 (3) and its aromatized product (9) have been confirmed by electrospray ionization-mass spectrometry analysis.

FIG. 22 shows a clear inhibition zone as exhibited by the desmethoxy-C-1027 compound isolated from *S. globisporus* sgcD4 (22A) and sgcD3 (22B) mutant strains using *M. luteus* as a testing organism.

DETAILED DESCRIPTION

This invention provides a complete gene cluster regulating the biosynthesis of C-1027, the most potent member of the enediyne antitumor antibiotic family. C-1027 is produced by *Streptomyces globisporus* C-1027 and consists of an apoprotein (encoded by the cagA gene) and a nonpeptidic chromophore. The C-1027 chromophore could be viewed as being derived biosynthetically from a benzoxazolinate, a deoxyamino hexose, a β-amino acid, and an enediyne core. Adopting a strategy to clone the C-1027 biosynthesis gene cluster by mapping a putative dNDP-glucose 4,6-dehydratase (NGDH) gene to cagA resulted in the localization 75 kb contiguous DNA from *S. globisporus* encoding a complete C-1027 gene cluster.

Initial sequencing of the cloned gene cluster revealed two genes, sgcA and sgcB, that encode an NGDH enzyme and a transmembrane efflux protein, respectively, and confirmed that the cagA gene resides approximately 14 kb upstream of the sgcA,B locus. The involvement of the cloned gene cluster in C-1027 biosynthesis was demonstrated by disrupting the sgcA gene to generate C-1027-nonproducing mutants and by complementing the sgcA mutants in vivo to restore C-1027 production.

Figure 10:
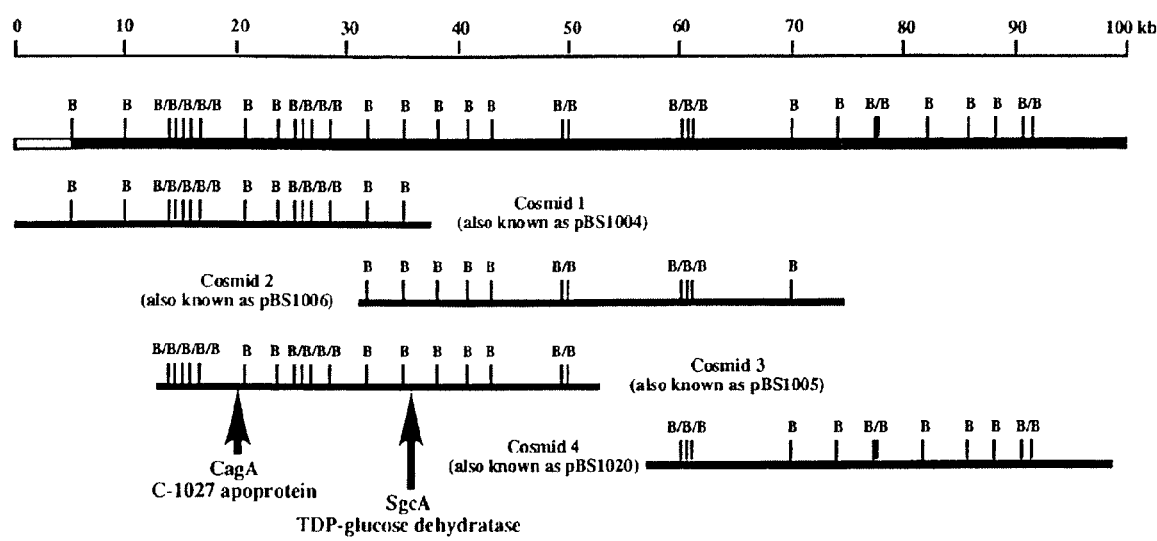
FIG. 10 shows a restriction map of the 100-kb DNA region from S. globisporus as represented by four overlapping cosmid clones (B, BamHI).
Figure 11:
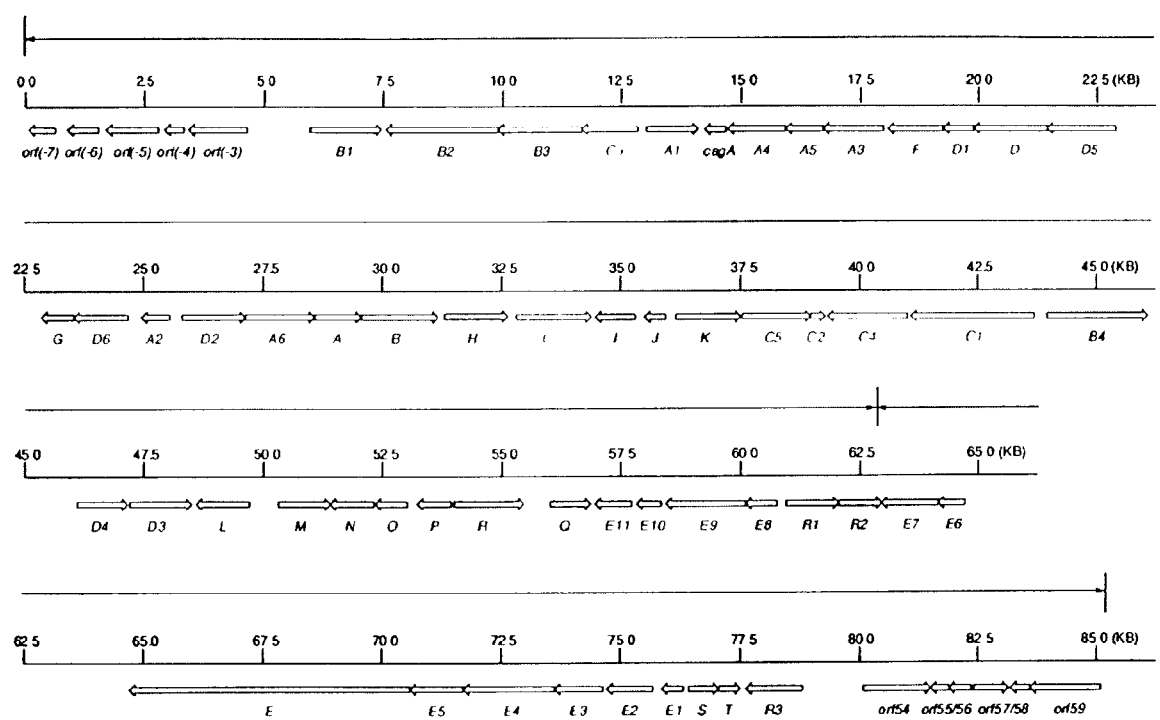
FIG. 11 illustrates the genetic organization of the C-1027 biosynthesis gene cluster form S. globisporus.

Subsequent DNA sequence analysis provided the complete enediyne C-1027 gene cluster sequence (SEQ ID NOs: 1 and 2) revealing open reading frames (orf) from orf(−7) to sgcR2 and sgcE7 (partial) (FIG. 10 and FIG. 11). All of the open reading frames (orfs) have been given gene names as shown in Tables II and III. Open reading frame 33 is now assigned to two genes (sgcO and sgcP) as illustrated in Table III.

The C-1027 gene biosynthesis gene cluster is extended to 85,168 bp by the addition of cosmid 4 as illustrated in FIG. 10 which encodes sgcE7, sgcR3, and orf54 to orf59 (FIG. 11 and Sequence Listing). Putative functions for these genes have been assigned according to sequence homology with proteins with confirmed or predicted functions in the database and are summarized in Tables II and III.

Figure 12:
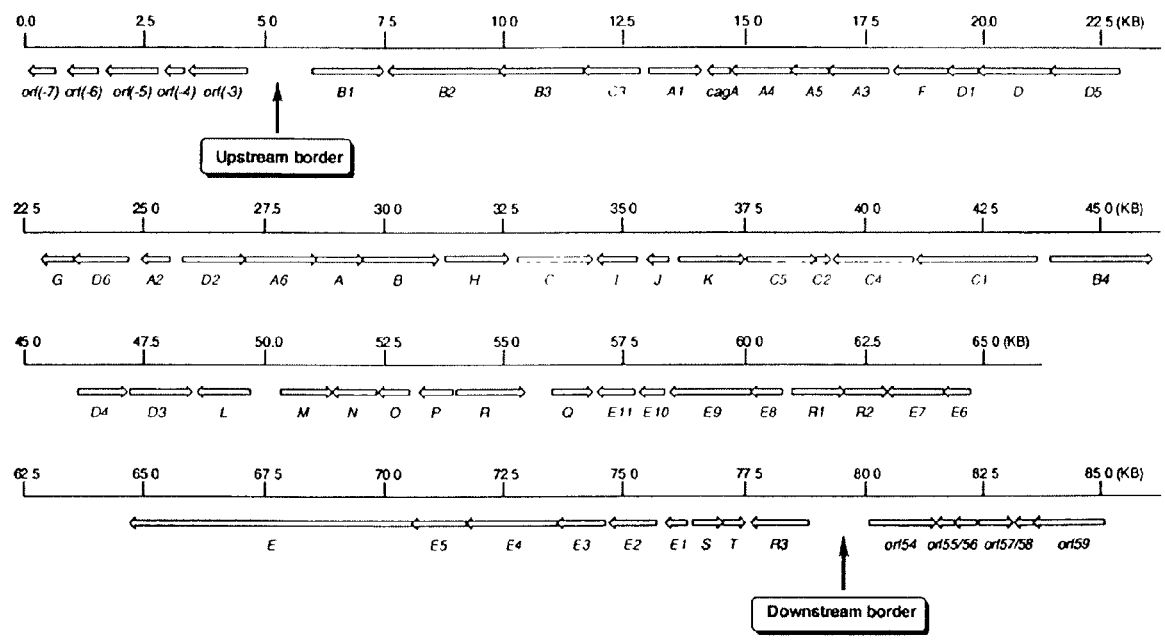
FIG. 12 illustrates the organization of the C-1027 biosynthesis gene cluster and determination of its upstream and downstream boundaries.

The boundary of the C-1027 biosynthesis gene cluster has been established by insertional gene disruption to generate *S. globisporus* mutants, followed by fermentation of these mutants to examine their ability for C-1027 production. As summarized in FIG. 12, the upstream and downstream boundaries of the C-1027 biosynthesis gene cluster have been assigned to be between orf(−3) and sgcB1 and sgcR3 and orf54, respectively (FIG. 12).

To determine the upstream boundary, orf(−5), orf(−3), sgcB1, sgcB2, sgcC3, sgcA3, and sgcA5 were each disrupted to generate the corresponding *S. globisporus* mutant strains, respectively. These mutant strains were cultured under standard conditions for C-1027 production with the *S. globisporus* wild-type strain as a positive control. C-1027 production was analyzed by HPLC. As summarized in FIG. 4, disrupting orf(−5), orf(−3). sgcB1, or sgcB2, respectively, had no effect on C-1027 production and the corresponding *S. globisporus* mutant strains produced C-1027 as the *S. globisporus* wild-type strain.

In contrast, disrupting sgcC3, sgcA3, or sgcA5 yielded *S. globisporus* mutant strains whose ability to produce C-1027 was completely abolished. Therefore, genes upstream of sgcB2 are not essential for C-1027 production and hence are not a part of the C-1027 biosynthesis gene cluster, while sgcC3, sgcA3, and sgcA5 are essential for C-1027 production and hence, must be within the C-1027 gene cluster. These results defined the upstream boundary of the C-1027 biosynthesis gene cluster to be between orf(−3) and sgcB1. sgcB1 and sgcB2 are preferably included as part of the C-1027 gene cluster, although their gene disruption mutants can produce C-1027 normally. Since sgcB1 and sgcB2 encode putative C-1027 resistance proteins, inactivation of them may have little effect on C-1027 production because of multiple C-1027 resistance mechanisms within the C-1027 gene cluster.

To determine the downstream boundary, sgcE7, sgcE, sgcE2, sgcR3, and orf54 were each disrupted to generate the corresponding *S. globisporus* mutant strains respectively. These mutant strains were similarly cultured under the standard conditions for C-1027 production with the *S. globisporus* wild type strain as positive control. C-1027 production was analyzed by HPLC.

As summarized in Table 1, disrupting sgcE7, sgcE, sgcE2, or sgcR3 abolished C-1027 production completely, while disrupting orf54 had no effect on C-1027 production. Therefore, genes upstream of sgcR3 were essential for C-1027 production and hence are within the C-1027 biosynthesis gene cluster, while genes downstream of orf54 are not essential for C-1027 production and hence are not a part of the C-1027 gene cluster. These results therefore defined the downstream boundary of the C-1027 biosynthesis gene cluster to be between sgcR3 and orf54.

Three types of polyketide synthases (PKSs) are known for polyketide biosynthesis in bacteria: type I and type II systems, both of which use acyl carrier protein (ACP) to activate substrates as described herein channel the growing intermediates for aliphatic and aromatic polyketides, respectively, and the type III system that has no apparent amino acid sequence similarity to the former and acts directly on acyl CoAs, largely for monocyclic aromatic polyketides. The enediyne cores bear no structural resemblance to any of the polyketides studied to date, failing to predict what type of PKS may be responsible for their biosynthesis. In fact, a controversy remained as to whether the enediyne cores are assembled via a de novo polyketide biosynthesis, or by degradation from a fatty acid precursor, although feeding experiments with 13C-labeled precursors for neocarzinostatin, dynemicin, and esperamicin unambiguously established that the enediyne cores were all derived from minimally eight head-to-tail acetate units.

TABLE I

The production of C-1027 by *S. globisporus* wild-type and mutant strains as determined by HPLC analysis. The mutant strains were isolated by insertional gene disruption of the targeted genes. *S. globisporus* wild-type and mutant strains were grown under standard conditions for C-1027 production. Holo-C-1027 chromoprotein complex was isolated from the fermentation broth by $(NH_4)_2SO_4$ precipitation. The C-1027 chromophore was extracted from the holo-chromoprotein complex with ethyl acetate. HPLC analysis was carried out on a Prodigy ODS-2 column (5μ, 150 × 4.6 mm, Phenomenex, Torrance, CA), eluted isocratically with 20 mM potassium phosphate (pH 6.86)/CH3CN (50:50, v/v) at a flow rate of 1.0 ml/min and UV detection at 350 nm.

| Strain | C-1027 (% yield) |
|---|---|
| Wild-type | 100 |
| orf(−5) mutant | 100 |
| orf(−3) mutant | 100 |

TABLE I-continued

The production of C-1027 by *S. globisporus* wild-type and mutant strains as determined by HPLC analysis. The mutant strains were isolated by insertional gene disruption of the targeted genes. *S. globisporus* wild-type and mutant strains were grown under standard conditions for C-1027 production. Holo-C-1027 chromoprotein complex was isolated from the fermentation broth by (NH4)2SO4 precipitation. The C-1027 chromophore was extracted from the holo-chromoprotein complex with ethyl acetate. HPLC analysis was carried out on a Prodigy ODS-2 column (5μ, 150 × 4.6 mm, Phenomenex, Torrance, CA), eluted isocratically with 20 mM potassium phosphate (pH 6.86)/CH3CN (50:50, v/v) at a flow rate of 1.0 ml/min and UV detection at 350 nm.

| Strain | C-1027 (% yield) |
|---|---|
| sgcB1 mutant | 100 |
| sgcB2 mutant | 100 |
| sgcC3 mutant | 0 |
| sgcA5 mutant | 0 |
| sgcA3 mutant | 0 |
| sgcE7 mutant | 0 |
| sgcE mutant | 0 |
| sgcE2 mutant | 0 |
| sgcR3 mutant | 0 |
| orf54 mutant | 100 |

Figure 13A:
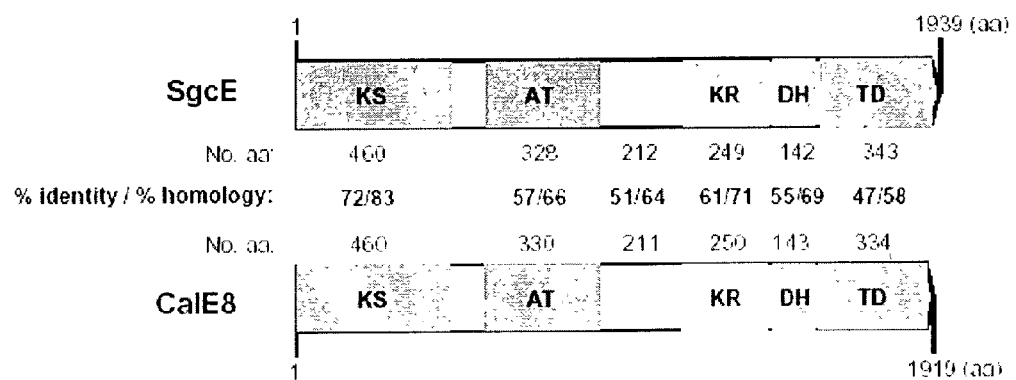
FIGS. 13A and 13B illustrate enediyne core structure and biosynthesis.
Figure 13B:
Figure 14A:
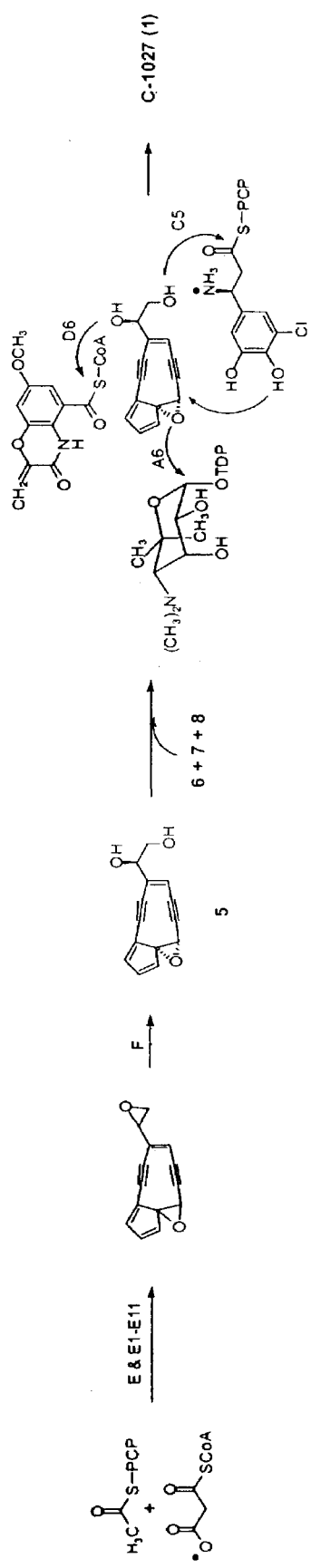
FIGS. 14A–14D illustrate biosynthetic pathways for (FIG. 14A) enediyne core and a convergent assembly strategy for the C-1027 chromophore.
Figure 15:
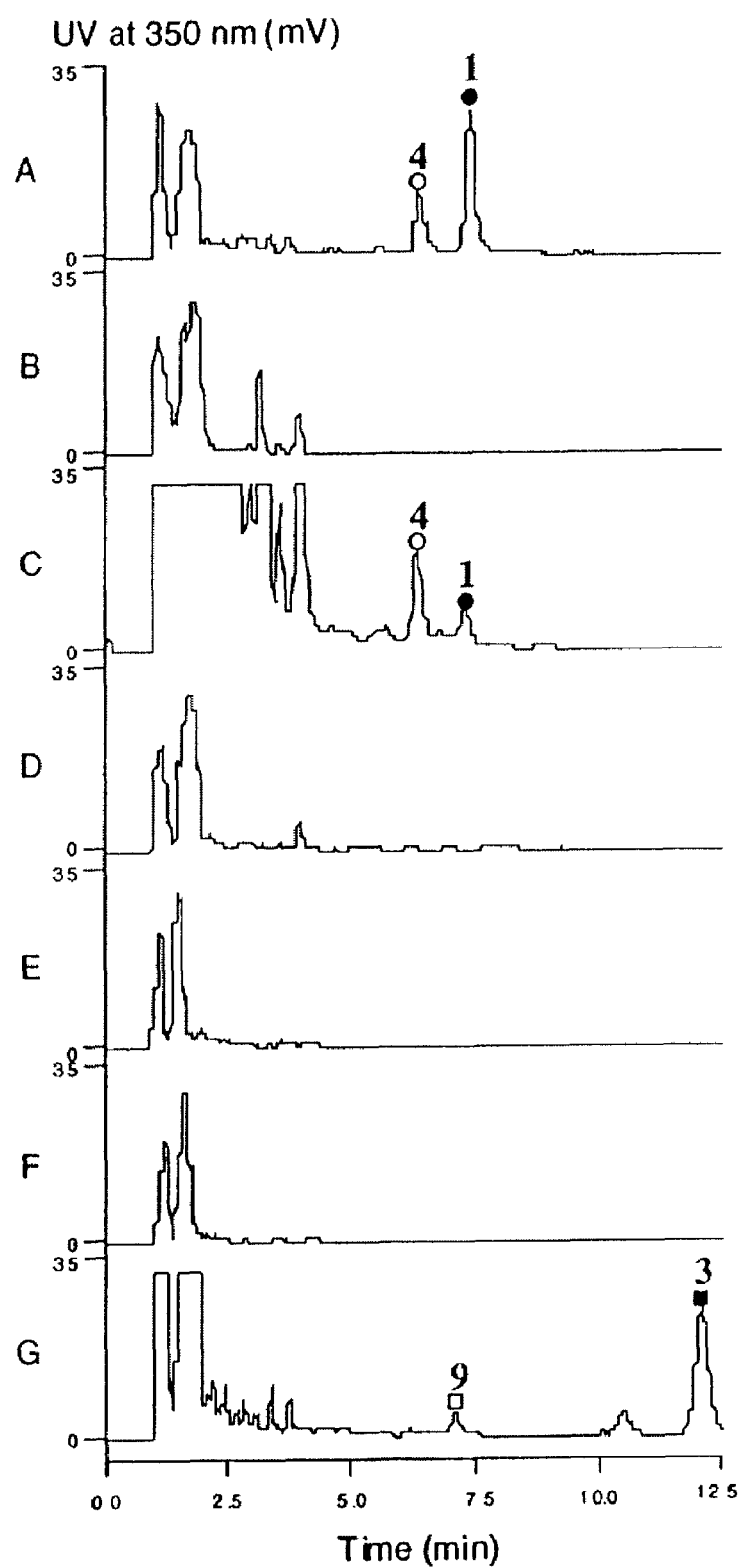
FIGS. 15 panels A–G show HPLC analysis of the C-1027 chromophores isolated from S. globisporus strains: (Panel A) wild-type, (Panel B) sgcE replacement mutant SB1005, (Panel C) SB 1005 complemented by pBS1019 that overexpresses sgcE, (Panel D) sgcA disruption mutant SB1001, (Panel E) sgcC1 disruption mutant SB 1003, (Panel F) sgcD6 disruption mutant SB1004, (G) sgcC disruption mutant SB1006. Structures for 1, 3, 4, and 9 are shown in FIG. 18.

Strikingly, of the genes identified within the C-1027 cluster, there is only one, sgcE, that encodes a PKS. SgcE contains six domains—the ketoacyl synthase (KS), acyltransferase (AT), ketoreductase (KR), and dehydratase (DH) ACPs, and a domain at the COOH-terminus (TD) that, unique only to enediyne PKSs, shows no sequence homology to any other proteins (FIG. 13). SgcE can be envisaged catalyzing the assembly of a nascent linear polyunsaturated intermediate from acetyl and malonyl CoAs in an iterative process, which, upon action of other enzyme activities, is subsequently desaturated to furnish the two yne groups and cyclized to afford the enediyne core (FIG. 14A). An enzyme that catalyzes the formation of an acetylenic bond from a C—C double bond has been reported from the plant *Crepis alpine* and characterized as acetylenase that is a non-heme diiron protein. While no such homolog was found within the C-1027 cluster, close comparison of the C-1027 gene cluster with that for neocarzinostatin, another nine-membered enediyne antibiotic revealed a group of orfs (sgcE1 to sgcE11), in addition to sgcE, that are highly conserved. SgcE6, SgcE7, and SgcE9 resemble various oxidoreductases, SgcE1, SgcE2, SgcE3, SgcE4, SgcE5, SgcE8, or SgcE11 show no sequence homology, or homology only to proteins of unknown functions, and sgcE10 is highly homologous to a family of thioesterases. These enzymes, together with the SgcF epoxide hydrolase, serve as candidates for processing the nascent linear polyunsaturated intermediate into an enediyne intermediate such as 5 (FIGS. 13B and 14A). To experimentally test this hypothesis, the sgcE domain was replaced with the erythromycin resistance gene, ermE. The Resultant *S. globisporus* SB1005 mutant strain completely lost its ability to produce 1 (FIG. 15, panel B), and this phenotype can be complemented by introduction of pBS1019, in which the expression of sgcE is under the control of the constitutive ermE* promoter, into SB1005, restoring 1 production to the level comparable to the wild-type organism (FIG. 15, panel C). These findings unambiguously established that C-1027 enediyne core biosynthesis proceeds via a polyketide pathway.

TABLE II

Summary of the C-1027 gene cluster open reading frames (-7 to 26), primers for ORF amplification, and proposed functions

| ORF# gene name | Relative position Size | Primers | Function | Seq ID No. |
|---|---|---|---|---|
| orf(-7) | 658—11 | Fwd: ATG GGC ATG ACG GGT | very weak homology | 3 |
| orf(-7) | 648 bp | Rev: CTA GAG GAT CCC GGG | to putative hydroxylase | 4 |
| orf(-6) | 1478—930 | Fwd: ATG CCG CGG ATT CCC | Viral infectivity | 5 |
| orf(-6) | 549 bp | Rev: TCA GCT GTC GAT GTC | potentiator protein | 6 |
| orf(-5) | 2713—1649 | Fwd: ATG ACC ATC GCC ACT | N-truncated | 7 |
| orf(-5) | 1065 bp | Rev: TCA GAG GCC GAG CAC | Methionine synthase (likely psuedogene) | 8 |
| orf(-4) | 3238—2851 | Fwd: ATG AGC TCG CTA CTG | Viral | 9 |
| orf(-4) | 387 bp | Rev: CTA GGA GCC GGT CGC | transcription factor | 10 |
| orf(-3) | 4971—3442 | Fwd: ATG AGC AGC AGC GCC | Viral Homolog | 11 |
| orf(-3) | 1530 bp | Rev: TCA TTC GTC GGC TGC | possibly primase | 12 |
| orf(-2) | 5982—7478 | Fwd: GTG AGG GCT CTG CCG | Glycerol-Phosphate | 13 |
| sgcB1 | 3027 hp | Rev: TCA GAC GGC GGA GGG | ABC Transporter (SnoX drug resistance) | 14 |
| orf(-1) | 9900—7573 | Fwd: GTG AGC GTC ACC GAC | UvrA-like drug | 15 |
| sgcB2 | 2328 bp | Rev: TCA ACC CGC CCT GCG | resistance pump | 16 |

TABLE II-continued

Summary of the C-1027 gene cluster open reading frames (−7 to 26), primers for ORF amplification, and proposed functions

| ORF# gene name | Relative position Size | Primers | Function | Seq ID No. |
|---|---|---|---|---|
| orf0 sgcB3 | 11349–9982 1368 bp | Fwd: ATG AGG ATG CTG GTG Rev: GTG GCT GTG CTC GCA | Na$^+$/H$^+$ efflux pump | 17 18 |
| orf1 sgcA | 28590–29588 999 bp | Fwd: ATG AGG ATG CTG GTG Rev: TCA GCC GAC GGC GTC | dNTP-glucose dehydratase | 19 20 |
| orf2 sgcB | 29632–31197 1566 hp | Fwd: GTG ACA GCA GTC AAG Rev: TCA TGT GGC CGG TTG | Transmembrane efflux protein | 21 22 |
| orf3 sgcH | 31280–32590 1311 bp | Fwd: GTG GAG TAC TGG AAC Rev: TCA GGC CTG AGG GGC | Coenzyme F390 synthase phenylacetyl-CoA ligase | 23 24 |
| orf4 sgcC | 32809–34392 1584 hp | Fwd: GTG CCC CAC GGT GCA Rev: CTA CAG CCC TCC GAG | phenol hydroxylase chlorophenol-4-monoxygenase | 25 26 |
| orf5 sgcK | 35274–34458 | Fwd: ATG TCT TCA ACC CGT Rev: TCA GCC GCG CAG GAA | citrate transport protein | 27 28 |
| orf6 sgcA3 | 17924–16653 1272 bp | Fwd: ATG CTG GAG AAA TGC Rev: TCA GAC GAG CTC CTT | C-methyl transferase hydroxylase | 29 30 |
| orf7 sgcA5 | 16653–15919 735 bp | Fwd: ATG GAG TAC GGC CCC Rev: TCA TGC CGT GCG CAC | N-methyltransferase | 31 32 |
| orf8 sgcA4 | 15922–14690 1233 bp | Fwd: ATG AGC GGC GGC CCG Rev: TCA CCT CGC CGG ACG | Aminotransferase | 33 34 |
| orf9 cagA | 14643–14212 432 bp | Fwd: ATG TCG TTA CGT CAC Rev: TCA GCC GAA GGT CAG | CagA | 35 36 |
| orf10 sgcA1 | 13012–14079 1068 bp | Fwd: ATG AAG GCA CTT GTA Rev: TCA GGC CGC GAT CTC | dNTP-glucose synthase | 37 38 |
| orf11 sgcC3 | 12835–11351 1485 bp | Fwd: GTG GAC GTG TCA GCG Rev: TCA GGA CCG CGC ACC | Hydroxylase, Halogenase | 39 40 |
| orf12 sgcA2 | 25564–24986 579 bp | Fwd: ATG AAG CCG ATC GGG Rev: TCAGGA CGA CTT GTT | dNTP-4-keto-6-deoxyglucose 3,5-epimerase | 41 42 |
| orf13 sgcD6 | 24702–23566 1137 bp | Fwd: ATG CCT TCC CCC TTC Rev: TCA GGT GCG CTC GGC | 3-O-acyltransferase | 43 44 |
| orf14 sgcD5 | 22878–21424 1455 bp | Fwd: GTG AGA GAC GGC CGG Rev: TCA CGT GGT GAT GGC | Coenzyme F-390 Synthase Phenylacetyl CoA Ligase | 45 46 |
| orf15 sgcD | 21407–19926 1482 bp | Fwd: ATG ACC GAC CAG TGC Rev: TCA CAG CAA CTC CTC | Anthranilate Synthase I | 47 48 |
| orf16 sgcD1 | 19929–19267 663 bp | Fwd: GTG AGC TTG TGG TCT Rev: TCA GGC CGG TTC GGC | Anthranilate Synthase II | 49 50 |
| orf17 sgcF | 19191–18031 1161 bp | Fwd: GTG CGT CCC TTC CGT Rev: TCA GCG GAG CGG ACG | epoxide hydrolase | 51 52 |
| orf18 sgcJ | 35938–35516 423 bp | Fwd: ATG CCA GCA CCG ACT Rev: TCA GTC GTT GCC GCG | Unknown | 53 54 |
| orf19 sgcA6 | 27214–28593 1380 bp | Fwd: ATG CGG GTG ATG ATC Rev: TCA TCG GTC CGC CTC | glycosyl transferase | 55 56 |
| orf20 sgcD2 | 25815–27170 1356 bp | Fwd: ATG ACC AAG CAC GCC Rev: TCA TAC GGC GGC GCC | squalene monooxygenase | 57 58 |

TABLE II-continued

Summary of the C-1027 gene cluster open reading frames (−7 to 26), primers for ORF amplification, and proposed functions

| ORF# gene name | Relative position Size | Primers | Function | Seq ID No. |
|---|---|---|---|---|
| orf21 sgcG | 23546–22875 672 bp | Fwd: GTG AGC GCA CAA CTC Rev: TCA CGG CTG TGC CTG | hypothetical Fe-S flavoprotein | 59 60 |
| orf22 sgcI | 35274–34458 816 bp | Fwd: ATG TCT TCA ACC CGT Rev: TCA GCC GCG CAG GAA | haloacetate dehalogenase hydrolase | 61 62 |
| orf23 sgcC5 | 37559–38938 1380 bp | Fwd: ATG ACG ACG TCC GAC Rev: TCA GGA GGT GAA GGG | peptide synthetase | 63 64 |
| orf24 sgcC4 | 40986–39367 1620 bp | Fwd: ATG GCA TTG ACT CAA Rev: TCA GCG CAG CTG GAT | Histidine Ammonia lyase | 65 66 |
| orf25 sgcC1 | 42611–41052 1560 bp | Fwd: ATG ACG CGG CCG GTG Rev: TCA GCG GGT GAG CCG | Type II adenylation protein | 67 68 |
| orf26 sgcC2 | 38983–39264 282 bp | Fwd: GTG TCC ACC GTT TCC Rev: TCA CTG CGT TCC GGA | Type II peptidyl carrier protein | 69 70 |

TABLE III

C-1027 gene cluster open reading frames (27 to 60), primers for ORF amplification, and proposed functions

| ORF | Relative Position Size (bp) | Primers | Function | SEQ ID NO. |
|---|---|---|---|---|
| orf27 sgcB4 | 43945–46023 | Fwd: GTG TGC CCG GTG ACA GAC Rev: TCA GCC CAC GGG CTG GGA | Antibiotic Transporter | 71 72 |
| orf28 sgcD4 | 46167–47171 | Fwd: GTG TTG GGC GAT GAG GAC Rev: TCA GAC CGC GGA CAT CTG | O-methyltransferase | 73 74 |
| orf29 sgcD3 | 47227–48485 | Fwd: ATG GCC GGC CTG GTC ATG Rev: TCA GGA CCC GAG GGT CAC | p450 hydroxylase | 75 76 |
| orf30 sgcL | 48610–49714 | Fwd: GTG GAC CAG ACG TCT ACG Rev: TCA TGC AGG TGC AGC GTG | Oxidoreductase | 77 78 |
| orf31 sgcM | 50350–51390 | Fwd: ATG AGG CCG CTC GTT CGG Rev: TCA TCC CGG CCC GGC GGC | Unknown Protein | 79 80 |
| orf32 sgcN | 51420–52341 | Fwd: ATG AGA ACG CGG CGA CGC Rev: TCA CGG CCG GAG GCG TAC | Oxidoreductase | 81 82 |
| orf33 sgcO | 52366–53013 | Fwd: ATG TGC TCC CGT ACC Rev: TCA GCC GGA CTG TCG | Unknown protein | 83 84 |
| orf33 sgcP | 53246–53926 | Fwd: ATG GCC CTT CAC CCG Rev: TCA GCC GGC CTG GGC | Type II ACP/PCP | 85 86 |
| orf34 sgcR | 54230–55379 | Fwd: ATG TCT ACG GGC TAT CTC Rev: TCA GCC GCC GGT GGC GCC | Unknown Protein | 87 88 |
| orf35 sgcQ | 56027–56881 | Fwd: ATG TTC TCC CCC GCC GCC Rev: TCA GTA CGC CTG GTG GGC | Oxidase/ Dehydrogenase | 89 90 |
| orf36 sgcE11 | 56928–57730 | Fwd: ATG AAT TCG CTC GAC GAC Rev: TCA GCT CCC GGT CGC CGC | Unknown Protein | 91 92 |
| orf37 sgcE10 | 57834–58304 | Fwd: ATG ACC GCG ACG AAT CCT Rev: CTA GGC GGC GCG TCC CGC | Regulatory | 93 94 |
| orf38 sgcE9 | 58440–60091 | Fwd: ATG AGC ACC ACG GCC GAG Rev: TCA GCC GCG CGC CGA CGG | Oxidoreductase | 95 96 |

TABLE III-continued

C-1027 gene cluster open reading frames (27 to 60), primers for ORF amplification, and proposed functions

| ORF | Relative Position Size (bp) | Primers | Function | SEQ ID NO. |
|---|---|---|---|---|
| orf39 sgcE8 | 60092–60622 | Fwd: ATG ACC CTG GAG GCC TAC<br>Rev: TCA TGC GGG GCT CCC GGT | Regulatory | 97<br>98 |
| orf40 sgcR1 | 60940–62020 | Fwd: GTG AAA AGT GAC TCT GCC<br>Rev: TCA ACG GCG AGT TGG CTG | Regulatory | 99<br>100 |
| orf41 sgcR2 | 62045–62899 855 bp | Fwd: GTG ACC ACG AAC ACC ATC<br>Rev: TCA CCC GCG ATC TCG ATC | Regulatory | 101<br>102 |
| orf42 sgcE7 | 64136–62787 1350 bp | Fwd: (partial ORF)<br>Rev: TCA CCT CGC CGT ACT CAC | p450 hydroxylase | 103<br>104 |
| orf45 sgcE6 | 64681–64133 549 bp | Fwd: ATC ATC CCG ATC ATC<br>Rev: TCA TGC CGC CCT TCC | Oxidoreductase | 105<br>106 |
| orf46 sgcE | 70581–64762 5820 bp | Fwd: ATG AGC CGC ATA GCC<br>Rev: TCA CGC GCG GGC GCT | Type I polyketide synthase | 107<br>108 |
| orf47 sgcE5 | 71708–70578 1131 bp | Fwd: GTG ACC GTG CCC GGT<br>Rev: TCA TAC AGG CAC CGT | Unknown | 109<br>110 |
| orf48o sgcE4 | 73633–71705 1929 bp | Fwd: ATG GCG GAG AGT TTC<br>Rev: TCA CTT CTC CTT CAC | Unknown | 111<br>112 |
| orf49 sgcE3 | 74616–73630 987 bp | Fwd: GTG CCC CGG GCC TTT<br>Rev: TCA TGC GAC GGC GCC | Unknown | 113<br>114 |
| orf50 sgcE2 | 75693–74712 982 bp | Fwd: GTG GCA TCG GTA CCG<br>Rev: TCA GGG GTA TGT GAG | Unknown | 115<br>116 |
| orf51 sgcE1 | 76321–75878 444 bp | Fwd: ATG CTG CCA CGG ACG<br>Rev: TCA GCG CGT CCG GCG | Unknown | 117<br>118 |
| orf52 sgcS | 76426–77031 606 bp | Fwd: GTG ATG ACC CAC TGC<br>Rev: TCA GGC CTT CGG GGC | Unknown | 119<br>120 |
| orf53 sgcT | 77036–77497 462 bp | Fwd: GTG ACG ACG AGC GGC<br>Rev: TCA GCT CGC CGC CGG | Unknown | 121<br>122 |
| orf54 sgcR3 | 78774–77587 1188 bp | Fwd: ATC GCG GCA CAC GAC<br>Rev: TCA GCT CCC CTC CTG | Regulatory protein | 123<br>124 |
| orf55 sgc54 | 80065–81489 1425 bp | Fwd: GTG GAC GAG GCC GGC<br>Rev: TCA CCC GGA TGT CGT | Orf(-3) homolog | 125<br>126 |
| orf56 sgc55 | 81860–81447 414 bp | Fwd: GTG AGT GCT CTG ATC<br>Rev: TCA CCG CGG AAC GGA | orf(-4) homolog | 127<br>128 |
| orf57 sgc56 | 82356–81886 471 bp | Fwd: GTG CCG CTT CTA CGC<br>Rev: CTA CTG GAC ACT GTG | Unknown | 129<br>130 |
| orf58 sgc57 | 82413–83096 684 bp | Fwd: ATG CCG CAC AGG ACC<br>Rev: TCA GCC GGT GAG AGC | Unknown | 131<br>132 |
| orf59 sgc58 | 83518–83120 399 bp | Fwd: GTG AGT GCT CTG ATC<br>Rev: TCA CCC CGG CAC AGG | Orf(-4) homolog | 133<br>134 |
| orf60 sgc59 | 85050–83515 1536 bp | Fwd: ATC ACC CCC GGA GGC<br>Rev: TCA CTC CGC CTC CTC | Orf(-3) homolog | 135<br>136 |

Figure 14B:
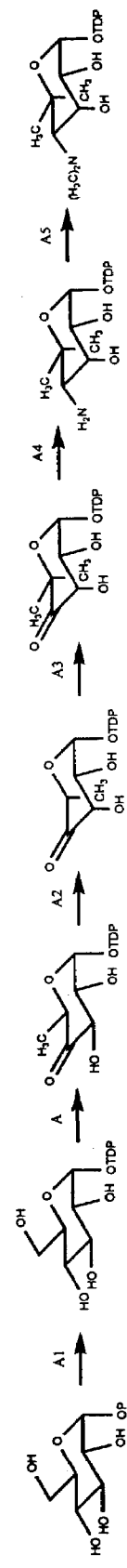

The availability of the gene cluster has set the stage to investigate the molecular basis of C-1027 biosynthesis and to engineer novel enediyne compounds by manipulating C-1027 biosynthesis genes. Thus, the seven deoxy aminosugar biosynthesis genes encode a TDP-glucose synthetase (SgcA I), a TDP-glucose 4,6dehydratase (SgcA), a TDP-4-keto-6-deoxyglucose epimerase (SgcA2), a C-methyl transferase (SgcA3), and amino transferase (SgcA4), an N-methyl transferase (SgcA5), and a glycosyl transferase (SgcA6). Together they are in an exact agreement with the enzyme functions that would be required for the biosynthesis of 6 from glucose-1-phosphate (FIG. 14B) and the attachment of 6 to 5 (FIG. 14A).

Figure 14C:
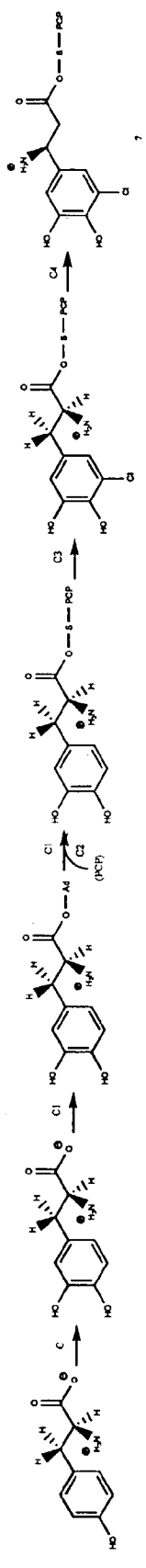

This hypothesis was validated experimentally by inactivating sgcA, and the resultant S. globisporus SB1001 mutant strain completely lost its ability to produce 1 (FIG. 15, panel D). The six β-amino acid biosynthesis genes encode a phenol hydroxylase (SgcC), a nonribosomal peptide synthetase halogenase (SgcC3), and aminomutase (SgcC4), and an NRPS condensation enzyme (SgcC5). These enzyme functions agree well with the proposed biosynthetic pathway for 7 from tyrosine (FIG. 14C), which is apparently activated as aminoacyl-S-PCP for its attachment to 5 by SgcC5 (FIG. 14A). Although the precise timing of each reaction in the pathways remains unknown, i.e., the substrate for any of these reactions could be a free amino acid or aminoacyl-S-PCT, sequence analysis of SgcC1 suggests that it activates an a-amino acid. Indeed inactivation of sgcC1 resulted in the isolation of the S. globisporus SB 1003 mutant strain that completely lost its ability to produce 1 (FIG. 15, panel E).

Figure 14D:
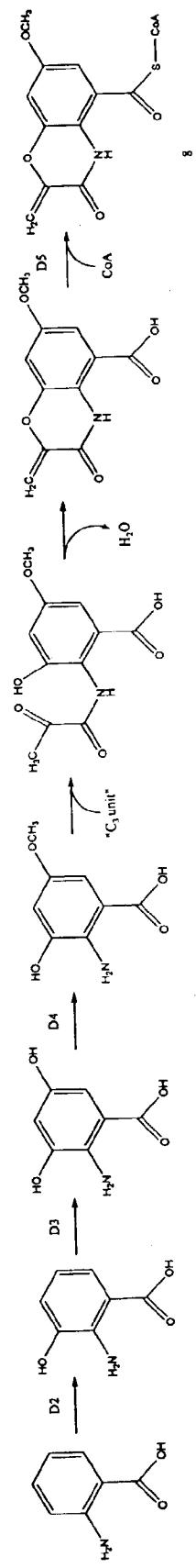

The seven benzoxazolinate biosynthesis genes encode the anthranilate synthase I and II subunits (SgcD and SGCD1), a monoxygenase (SgcD2), a p-450 hydroxylase (SgcD3), and O-methyltransferase (SgcD4), a coenzyme A (CoA) ligase (SgcD5), and an acyltransferase (SgcD6). These enzyme functions support the hypothesis that the biosynthesis of 8 starts from anthranilate, a commonly available intermediate from the shikimate pathway (FIG. 14D). The co-localization of SgcD and SgcD1 along with the rest of the C-1027 production genes assures the availability of anthranilate for secondary metabolite biosynthesis. Although it remains unclear what the origin of the C3 unit is and how it is fused to the anthranilate intermediate to form the morpholinone moiety of 8, the latter is apparently activated as acyl-S-CoA for its attachment to 5 by SgcD6 (FIG. 14A). sgcD6 was inactivated to test this hypothesis, and the resultant S. globisporus SB1004 mutant strain completely lost its ability to produce 1 (FIG. 15, panel F). The fact that the biosynthetic building blocks are activated as aminoacy-S-ACP, acyl-S-CoA, and nucleotide diphosphosugar, and attached to the enediyne core by an NRPS condensation enzyme, an acyltransferase, and a glycosyl transferase, respectively, highlights natures efficiency and versatility in synthesizing complex molecules.

Figure 16:
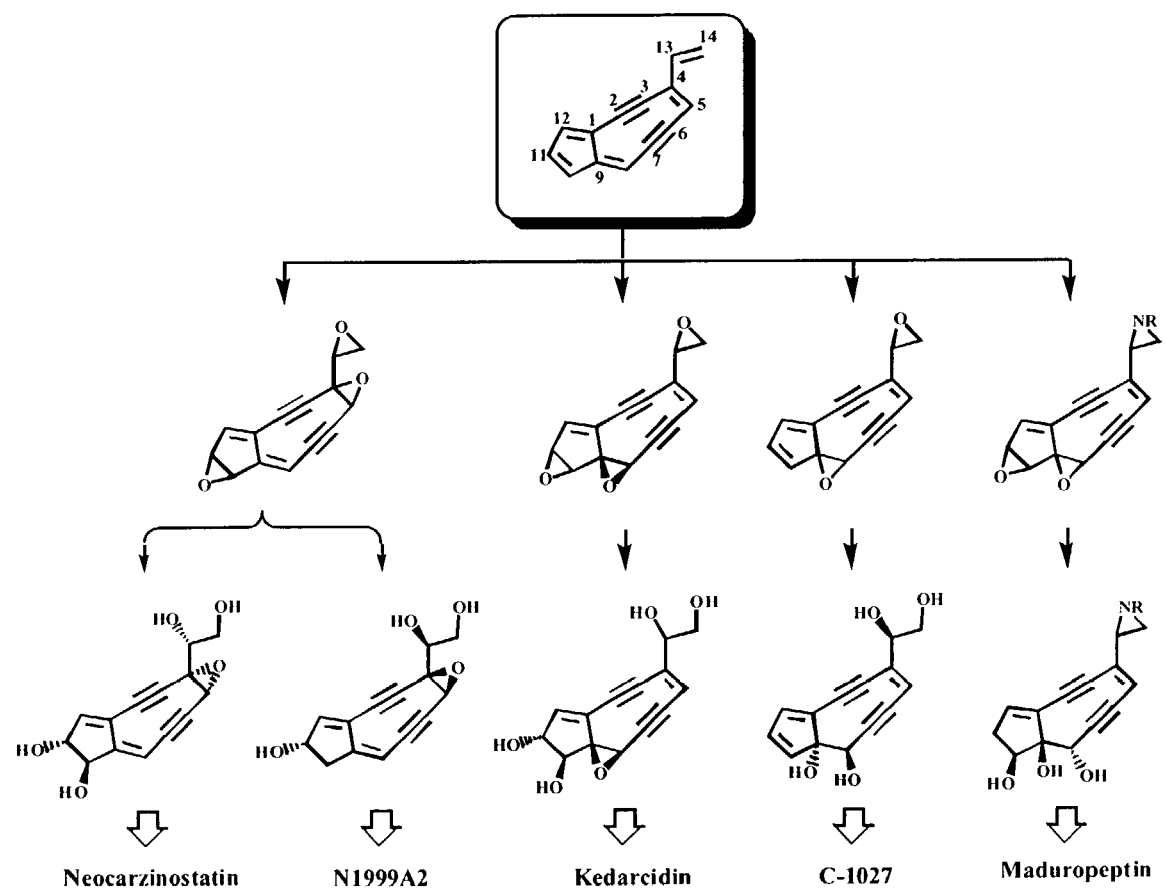
FIG. 16 illustrates C-1027 biosynthesis in S. globisporus as a model for the biosynthesis of the chromoprotein family of enediyne antibiotics. Variation of the C-1027 enediyne core biosynthetic pathway leads to all members of this family known to date.

The data presented herein unambiguously establish a convergent pathway for C-1027 biosynthesis, the enediyne core of which proceeds via a polyketide pathway (FIG. 14). Given the similar enediyne core structure, C-1027 biosynthesis can be viewed as a model for the biosynthesis of the chromoprotein family of all enediyne antibiotics known to date. Variation of the C-1027 enediyne core polyketide biosynthetic pathway can lead to the other members of this family (FIG. 16).

The C-1027 open reading frames encode polypeptides exhibiting a wide variety of enzymatic activities (e.g., epoxide hydrase, monooxygenase, oxidoreductase, P-450 hydroxylase, etc.). The isolated C-1027 gene cluster can be used to synthesize C-1027 enediyne antibiotics and/or analogues thereof. The C-1027 gene cluster can also be modified and/or augmented to increase C-1027 and/or C-1027 analogue production.

Several genes were inactivated within the C-1027 gene cluster (sgcN, sgcD4, sgcC3, and sgcC) to demonstrate the production of novel enediyne metabolites by manipulating genes governing the C-1027 biosynthesis. A shown in FIG. 17, several novel enediynes have already been produced by S. globisporus mutant strains, demonstrating the feasibility of the production of novel enediyne compounds by rational engineering of C-1027 biosynthesis. For example, inactivation of sgcC resulted in the isolation of the S. globisporus SB1006 mutant strain. The latter strain produces a chromoprotein that is biologically active as judged by bioassay against M luteus, but is distinct from 1 upon HPLC analysis (FIG. 15m, panel A vs 15, panel G and FIG. 17). The new compounds were isolated and subjected to ESI-MS analysis: 3 exhibited a (M+H)$^+$ ion at m/z=830 consistent with the molecular formula of $C_{43},H_{42},N_3O_{12}Cl$, and 9 showed a (M+H)$^+$ ion at m/z=830, consistent with the molecular formula of $C_{43}H_{44}N_3O_{12}Cl$. By comparison with 1, the new compounds were deduced to be deshydroxy-C-1027 (3) and its aromatized product (9), as would be predicted according to FIG. 14C. Intriguingly, 3 is at lest 5-fold more stable than 1 at 25° C. in respect to undergoing the Bergman cyclization, a property that could be potentially explored in developing C-1027 into a clinically useful drug.

Alternatively, various components of the C-1027 gene cluster can be used to synthesize and/or chemically modify a wide variety of metabolites. Thus, for example, ORF 6 (C-methyltransferase) can be used to methylate a carbon, while ORF 12, an epimerase, can be used to change the conformation of a sugar. The ORFs can be combined in their native configuration or in modified configurations to synthesize a wide variety of biomolecules/metabolites. Thus, for example, various combinations of C-1027 open reading frames can be used to synthesize an enediyne core, to synthesize a deoxy sugar, to synthesize a β-amino acid, to make a benzoxazolinate, etc (see, e.g., FIGS. 2, 3, and 4).

The native C-1027 gene cluster ORFs can be re-ordered, modified, and combined with other biosynthetic units (e.g. polyketide synthases (PKSs) or catalytic domains thereof and/or non-ribosomal polypeptide synthetases (NRPSs) or catalytic domains thereof) to produce a wide variety of molecules. Large chemical libraries can be produced and then screened for a desired activity.

The C-1027 gene cluster also includes a number of drug resistance genes (see, e.g., Table IV) that confer resistance to C-1027 and/or metabolites involved in C-1027 biosynthesis thereby permitting the cell to complete the enediyne biosynthesis. These resistance genes can be used to confer enediyne resistance on a cell lacking such resistance or to augment the enediyne resistance of a cell that does tolerate enediynes. Such cells can be used to produce high levels of enediynes and/or enediyne metabolites, and/or enediyne analogues.

TABLE IV

C-1027 cluster drug resistance genes.

| ORF | Protein | Mechanism |
|---|---|---|
| orf9: | CagA apoprotein | Drug sequestering |
| orf2: | SgcB transmembrane efflux protein | Drug exporting |
| orf27 | Transmembrane transport protein | Drug exporting |
| orf0 | Na$^+$/H$^+$ transporter | Drug exporting |
| orf(-1) | ABC transport (C-terminus) | Drug exporting |
| orf(-2) | Glycerol phosphate transporter | Drug exporting |
| orf(-1) | UvrA-like protein (N-terminus) | DNA repairing |

I. Isolation, Preparation, and Expression of C-1027 Nucleic Acids.

The C-1027 gene cluster nucleic acids can be isolated, optionally modified, and inserted into a host cell to create and/or modify a metabolic (biosynthetic) pathway and thereby enable that host cell to synthesize and/or modify various metabolites. Alternatively the C-1027 gene cluster nucleic acids can be expressed in the host cell and the encoded C-1027 polypeptide(s) recovered for use as chemical reagents, e.g. in the ex vivo synthesis and/or chemical modification of various metabolites. Either application typically entails insertion of one or more nucleic acids encoding one or more isolated and/or modified C-1027 enediyne open reading frames in a suitable host cell. The nucleic acid(s) are typically in an expression vector, a construct containing control elements suitable to direct expression of the C-1027 polypeptides. The expressed C-1027 polypeptides in the host cell then act as components of a metabolic/biosynthetic pathway (in which case the synthetic product of the pathway is typically recovered) or the C-1027 polypeptides themselves are recovered. Using the sequence information provided herein, cloning and expression of C-1027 nucleic acids can be accomplished using routine and well known methods.

A) C-1027 Nucleic Acids.

The nucleic acids comprising the C-1027 gene cluster are identified in Tables II and III and are listed in the sequence listing provided herein. In particular, Tables II and III identify genes and functions of open reading frames (ORFs) in the C-1027 enediyne biosynthesis gene cluster and identify primers suitable for the amplification/isolation of any one or more of the C-1027 open reading frames. Of course, using the sequence information provided herein, other primers suitable for amplification/isolation of one or more C-1027 open reading frames can be determined according to standard methods well known to those of skill in the art (e.g. using Vector NTI Suite™, InforMax, Gaithersberg, Md., USA).

Typically, such amplifications will utilize the DNA or RNA of an organism containing the requisite genes (e.g. *Streptomyces globisporus*) as a template. Typical amplification conditions include the following PCR temperature program: initial denaturing at 94° C. for 5 min, 24–36 cycles of 45 sec at 94° C., 1 min at 60° C., 2 min at 72° C., followed by additional 7 min at 72° C. One of skill will appreciate that optimization of such a protocol, e.g. to improve yield, etc. is routine (see, e.g., U.S. Pat. No. 4,683,202; Innis (1990) *PCR Protocols A Guide to Methods and Applications* Academic Press Inc. San Diego, Calif., etc). In addition, primer may be designed to introduce restriction sites and so facilitate cloning of the amplified sequence into a vector.

In one embodiment, this invention provides nucleic acids for the recombinant expression of an enediyne (e.g. a C-1027 enediyne or an analogue thereof). Such nucleic acids include isolated gene cluster(s) comprising open reading frames encoding polypeptides sufficient to direct the assembly of the enediyne. In other embodiments of this invention, the C-1027 open reading frames may be unchanged, but the control elements (e.g. promoters, enhancers, etc.) may be modified. In still other embodiments, the nucleic acids may encode selected components (e.g. one or more C-1027 or modified C-1027 open reading frames) and/or may optionally contain other heterologous biosynthetic elements including, but not limited to polyketide synthase (PKS) and/or non-ribosomal polypeptide synthetase (NRPS) modules or enzymatic domains.

Such variations may be introduced by design, for example to modify a known molecule in a specific way, e.g. by replacing a single substituent of the enediyne with another, thereby creating a derivative enediyne molecule of predicted structure. Alternatively, variations can be made randomly, for example, by making a library of molecular variants of a known enediyne by systematically or haphazardly replacing one or more open reading frames in the biosynthetic pathway. Production of alternative/modified enediyne, and hybrid enediyne PKSs and/or NRPSs and hybrid systems is described below.

Using the information provided herein, other approaches to cloning the desired sequences will be apparent to those of skill in the art. For example, the enediyne, and/or optionally PKS and/or NRPS modules or enzymatic domains of interest can be obtained from an organism that expresses such, using recombinant methods, such as by screening cDNA or genomic libraries, derived from cells expressing the gene, or by deriving the gene from a vector known to include the same. The gene can then be isolated and combined with other desired biosynthetic elements using standard techniques. If the gene in question is already present in a suitable expression vector, it can be combined in situ, with, e.g., other PKS subunits, as desired. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence can be assembled from overlapping oligonucleotides prepared by standard methods and assembled into a complete coding sequence (see, e.g., Edge (1981) *Nature* 292:756; Nambair et al. (1984) *Science* 223: 1299; Jay et al. (1984) *J. Biol. Chem.* 259:6311). In addition, it is noted that custom gene synthesis is commercially available (see, e.g. Operon Technologies, Alameda, Calif.).

Examples of such techniques and instructions sufficient to direct persons of skill through many cloning exercises are found in Berger and Kimmel (1989) *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY; Ausubel (19 1994) *Current Protocols in Molecular Biology*, Current Protocols, a joint venture between Greene Publishing Associates, Inc. and John Wiley & Sons, Inc., U.S. Pat. No. 5,017,478; and European Patent No. 0,246,864.

B) Expression of C-1027 Open Reading Frames.

The choice of expression vector depends on the sequence(s) that are to be expressed. Any transducible cloning vector can be used as a cloning vector for the nucleic acid constructs of this invention. However, where large clusters are to be expressed, phagemids, cosmids, Pls, YACs, BACs, PACs, HACs, or similar cloning vectors are used for cloning the nucleotide sequences into the host cell. Phagemids, cosmids, and BACs, for example, are advantageous vectors due to the ability to insert and stably propagate therein larger fragments of DNA than in M13 phage and lambda phage, respectively. Phagemids which will find use in this method generally include hybrids between plasmids and filamentous phage cloning vehicles. Cosmids which will find use in this method generally include lambda phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., supra). The utility of employing such vectors having different marker genes may be exploited to facilitate a determination of successful transduction.

In preferred embodiments of this invention, vectors are used to introduce C-1027 biosynthesis genes or gene clusters into host (e.g. *Streptomyces*) cells. Numerous vectors for use in particular host cells are well known to those of skill in the art. For example described in Malpartida and Hopwook, (1984) *Nature*, 309:462–464; Kao et al., (1994), *Science*, 265: 509–512; and Hopwood et al., (1987) *Methods Enzymol.*, 153:116–166 all describe vectors for use in various *Streptomyces* hosts.

In one preferred embodiment, *Streptomyces* vectors are used that include sequences that allow their introduction and maintenance in *E. coli*. Such *Streptomyces/E. coli* shuttle vectors have been described (see, for example, Vara et al., (1989) *J. Bacteriol.*, 171:5872–5881; Guilfoile & Hutchinson (1991) *Proc. Natl. Acad. Sci. USA*, 88: 8553–8557.)

The wild-type and/or modified C-1027 enediyne open reading frame(s) of this invention can be inserted into one or more expression vectors using methods known to those of skill in the art. Expression vectors will include control sequences operably linked to the desired open reading frame. Suitable expression systems for use with the present invention include systems that function in eucaryotic and/or prokaryotic host cells. However, as explained above, prokaryotic systems are preferred, and in particular, systems compatible with *Streptomyces* spp. are of particular interest. Control elements for use in such systems include promoters, optionally containing operator sequences, and ribosome binding sites. Particularly useful promoters include control sequences derived from enediyne, and/or PKS, and/or NRPS gene clusters. Other promoters (e.g. ermE* as illustrated in Example 1) are also suitable. Other bacterial promoters, such as those derived from sugar metabolizing enzymes, such as galactose, lactose (lac) and maltose, will also find use in the present constructs. Additional examples include promoter sequences derived from biosynthetic enzymes such as tryptophan (trp), the beta-lactamase (b/a) promoter system, bacteriophage lambda PL, and T5. In addition, synthetic promoters, such as the tac promoter (U.S. Pat. No. 4,551,433), which do not occur in nature also function in bacterial host cells. In *Streptomyces*, numerous promoters have been described including constitutive promoters, such as ErmE and TcmG (Shen and Hutchinson, (1994) *J. Biol. Chem.* 269: 30726–30733), as well as controllable promoters such as actI and actIII (Pleper et al., (1995) *Nature, vol.* 378: 263–266; Pieper et al., (1995) *J. Am. Chem. Soc.*, 117: 11373–11374; and Wiesmann et al., (1995) *Chem. & Biol.* 2: 583–589).

Other regulatory sequences may also be desirable which allow for regulation of expression of the enediyne open reading frame(s) relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The various enediyne cluster open reading frames, and/or PKS, and/or NRPS clusters or subunits of interest can be cloned into one or more recombinant vectors as individual cassettes, with separate control elements, or under the control of a single promoter. The various open reading frames can include flanking restriction sites to allow for the easy deletion and insertion of other open reading frames so that hybrid synthetic pathways can be generated. The design of such unique restriction sites is known to those of skill in the art and can be accomplished using the techniques described above, such as site-directed mutagenesis and PCR.

Methods of cloning and expressing large nucleic acids such as gene clusters, including PKS- or NRPS-encoding gene clusters, in cells including *Streptomyces* are well known to those of skill in the art (see, e.g., Stutzman-Engwall and Hutchinson (1989) *Proc. Natl. Acad. Sci. USA*, 86: 3135–3139; Motamedi and Hutchinson (1987) *Proc. Natl. Acad. Sci. USA*, 84: 4445–4449; Grim et al. (1994) *Gene*, 151: 1–10; Kao et al. (I 994) *Science*, 265: 509–512; and Hopwood et al. (1987) *Meth. Enzymol.*, 153: 116–166). In some examples, nucleic acid sequences of well over 100 kb have been introduced into cells, including prokaryotic cells, using vector-based methods (see, for example, Osoegawa et al., (1998) *Genomics*, 52: 1–8; Woon et al., (1998) *Genomics*, 50: 306–316; Huang et al., (1996) *Nucl. Acids Res.*, 24: 4202–4209). In addition, the cloning and expression of C-1027 enediyne is illustrated in Example 1.

C) Host Cells.

The vectors described above can be used to express various protein components of the enediyne, and/or enediyne shunt metabolites, and/or other modified metabolites for subsequent isolation and/or to provide a biological synthesis of one or more desired biomolecules (e.g. C-1027 and/or a C-1027 analogue, etc.). Where one or more proteins of the enediyne biosynthetic gene cluster are expressed (e.g. overexpressed) for subsequent isolation and/or characterization, the proteins are expressed in any prokaryotic or eukaryotic cell suitable for protein expression. In one preferred embodiment, the proteins are expressed in *E. coli*.

Host cells for the recombinant production of the subject enediynes, enediyne metabolites, shunt metabolites, etc. can be derived from any organism with the capability of harboring a recombinant enediyne gene cluster and/or subset thereof. Thus, the host cells of the present invention can be derived from either prokaryotic or eucaryotic organisms. Preferred host cells are those of species or strains (e.g. bacterial strains) that naturally express enediynes. Such host cells include, but are not limited to *Actinomycetes, Actinoplanetes*, and *Streptomycetes, Actinomadura, Micromonospra*, and the like. Particularly preferred host cells include, but are not limited to *Streptomyces globisporus, Streptomyces lividans, Streptomyces coelicolor, Micromonospora echinospora* spp. *calichenisis, Actinomadura verrucosopora, Micromonospora chersina, Streptomyces carzinostaticus*, and *Actinomycete* L585-6. Other suitable host cells include, but are not limited to *S. verticillis S. ambofaciens, S. avermitilis, S. azureus, S. cinnamonensis, S. coelicolor, S. curacoi, S. erythraeus, S. fradiae, S. galilaeus, S. glaucescens, S. hygroscopicus, S. lividans, S. parvulus, S. peucetius, S. rimosus, S. roseofulvus, S. thermotolerans*, and *S. violaceoruber* (see, e.g., Hopwood and Sherman (1990) *Ann. Rev. Genet.* 24: 37–66; O'Hagan (1991) *The Polyketide Metabolites*, Ellis Horwood Limited, etc.).

In certain embodiments, a eukaryotic host cell is preferred (e.g. where certain glycosylation patterns are desired). Suitable eukaryotic host cells are well known to those of skill in the art. Such eukaryotic cells include, but are not limited to yeast cells, insect cells, plant cells, fungal cells, and various mammalian cells (e.g. COS, CHO HeLa cells lines and various myeloma cell lines).

D) Recovery of the Expression Product.

Recovery of the expression product (e.g., enediyne, enediyne analogue, enediyne biosynthetic pathway polypeptide, etc.) is accomplished according to standard methods well known to those of skill in the art. Thus, for example, where enediyne biosynthetic gene cluster proteins are to be expressed and isolated the proteins can be expressed with a convenient tag to facilitate isolation (e.g. a $His_6$ tag). Other standard protein purification techniques are suitable and well known to those of skill in the art (see, e.g., (Quadri et al. (1998) *Biochemistry* 37: 1585–1595; Nakano et al. (1992) *Mol. Gen. Genet.* 232: 313–321, etc.).

Similarly where components (e.g. enediyne biosynthetic cluster orfs) are used to synthesize and/or modify various biomolecules (e.g. enediynes, enediyne analogues, shunt metabolites, etc.) the desired product and/or shunt metabolite(s) are isolated according to standard methods well know to those of skill in the art (see, e.g., Carreras and Khosla (1998) *Biochemistry* 37: 2084–2088, Deutscher (1990) *Methods in Enzymology Volume* 182: *Guide to Protein Purification*, M. Deutscher, ed. etc.).

II. Use of C-1027 Open Reading Frames in Directed Biosynthesis.

Elements (e.g. open reading frames) of the C-1027 biosynthetic gene cluster and/or variants thereof can be used in a wide variety of "directed" biosynthetic processes (i.e. where the process is designed to modify and/or synthesize one or more particular preselected metabolite(s)). Essentially the entire C-1027 gene cluster can be used to synthesize a C-1027 enediyne and/or a C-1027 enediyne analogue. Individual C-1027 cluster open reading frames can be used to perform chemically modifications on particular substrates and/or to synthesize various metabolites. Thus, for example, ORF 6 (C-methyltransferase) can be used to methylate a carbon, while ORF 7 (N-methyltransferase) can be used to methylate a nitrogen. ORF 12 and epimerase can be used to change the conformation of a sugar, and ORF 8 (an amino transferase) can be used to aminate a suitable substrate. Similarly, combinations of C-1027 open reading frames can be used to direct the synthesis of various metabolites (e.g. β-amino acids, deoxysugars, benzoxazolinates, and the like). These examples are merely illustrative. One of skill in the art, utilizing the information provided here, can perform literally countless chemical modifications and/or syntheses using either "native" enediyne biosynthesis metabolites as the substrate molecule, or other molecules capable of acting as substrates for the particular enzymes in question. Other substrates can be identified by routine screening. Methods of screening enzymes for specific activity against particular substrates are well known to those of skill in the art.

The biosyntheses can be performed in vivo, e.g. by providing a host cell comprising the desired C-1027 gene cluster open reading frames and/or in vivo, e.g., by providing the polypeptides encoded by the C-1027 gene cluster ORFs and the appropriate substrates and/or cofactors.

A) Synthesis of Enediynes and Enediyne Analogues.

In one embodiment, this invention provides for the synthesis of C-1027 enediynes and/or C-1027 analogues or derivatives. In a preferred embodiment, this is accomplished by providing a cell comprising a C-1027 gene cluster and culturing the cell under conditions whereby the desired enediyne or enediyne analogue is synthesized. The cell can be a cell that does not normally synthesize an enediyne and the entire gene cluster can be transfected into the cell. Alternatively, a cell that typically synthesizes enediynes can be utilized and all or part of the C-1027 gene cluster can be introduced into the cell.

Enediyne derivatives/analogues can be produced by varying the order of, or kind of, gene cluster subunits present in the cell, and/or by changing the host cell (e.g. to a eukaryotic cell that glycosylates the biosynthetic product), and/or by providing altered metabolites (e.g. adding exogenous aglycones to a host that carries a gene cassette of the deoxysugar biosynthesis and glycosylation genes for the production of glycosylated metabolites), etc.

In certain embodiments, the host cell need not be transfected with an entire C-1027 gene cluster. Rather, various components of a C-1027 gene cluster can be altered within a cell already harboring a C-1027 cluster. By varying or adding various biosynthetic open reading frames, C-1027 enediyne variants can be produced.

The use of standard techniques of molecular biology (gene disruption, gene replacement, gene supplement) can be used to modulate and/or otherwise alter enediyne and/or other metabolite (e.g. shunt metabolite) production in an organism that naturally synthesizes an enediyne (e.g. *S. globisporus*) or an organism that is modified to synthesize an enediyne.

In addition, or alternatively, control sequences that alter the expression of various open reading frames can be introduced that alter the amount and/or timing of enediyne production. Thus, for example, by placing particular C-1027 open reading frames under control of a constitutive promoter (ermE*) C-1027 production was increased by as much as 4-fold (see, e.g. Table V and Example 1).

TABLE V

Alteration of C-1027 production by engineering the C-1027 biosynthesis gene cluster.

| Strain | Yield (%) |
|---|---|
| WT | 100 |
| WT/pKC1139 | 100 |
| WT/ermE*/ORF 2 | >150 |
| WT/ORF 9 | >100 |
| WT/ermE*/ORF 9 | <10 |
| WT/ORF 10, 11 | >100 |
| WT/ermE*/ORF 10, 11 | >100 |
| WT/ORF 9, 10, 11 | >400 |

ORF 2: transmembrane efflux protein; ORF 9: CagA apoprotein; ORF 10: TDP-glucose synthase; ORF 11; Hydroxylase/halogenase Where enediyne analogues are synthesized, it will often prove desirable to assay them for biological activity. Such assays are well know to those of skill in the art. One such assay is illustrated in Example 1. Briefly, this example depicts an assay of antibacterial activity against *M. luteus* as described by Hu et al. (1988) *J. Antibiot.* 41: 1575–1579). Other suitable assays for enediyne activity will be known to those of skill in the art.

B) Use of C-1027 Open Reading Frames to Synthesize an Enediyne Core.

Figure 4:
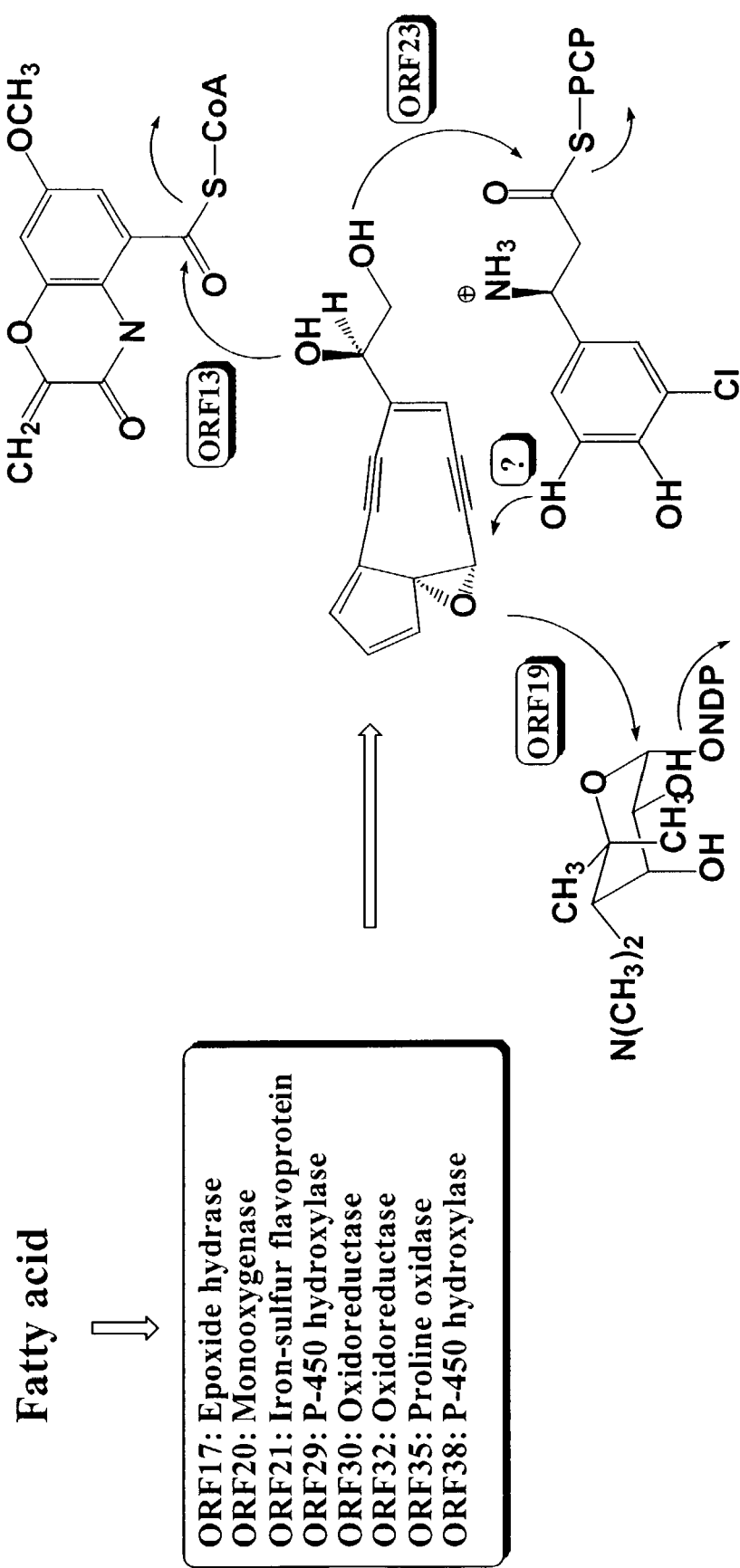
FIG. 4 illustrates the synthesis of the enediyne core and final assembly of the C-1027 enediyne.

The C-1027 open reading frames described herein, or variants thereof, can be used to synthesize an enediyene core, e.g., from a fatty acid precursor. One such synthetic pathway is illustrated in FIG. 4. This reaction scheme utilizes ORF 17 (epoxide hydrase), ORF 20 (monooxygenase), ORF 21 (iron-sulfur flavoprotein), ORF 29 (P-450 hydroxylase, ORF 30 (oxidoreductase), ORF 32 (oxidoreductase), ORF 35 (proline oxidase), and ORF 38 (P-450 hydroxylase) to synthesize anenediyne core.

This synthetic pathway is not considered limiting but merely illustrative. Using this as a model, one of ordinary skill in the art can design numerous other synthetic schemes to produce enediyne cores and/or core variants.

C) Use of C-1027 Open Reading Frames to Synthesize Deoxy Sugars.

The biosynthesis of various deoxy sugars (e.g., deoxyhexoses) typically share a common key intermediate—4-keto-6-deoxyglucose nucleoside diphosphate or its analogs, whose formation from glucose nucleoside diphosphate is catalyzed by the NGDH enzyme, an $NAD^+$-dependent oxidoreductase (Liu and Thorson (1994) *Ann. Rev. Microbiol.* 48: 223–256; Piepersberg (1997) pp. 81–163. In *Biotechnology of antibiotics,* 2nd ed. W. R. Strohl (ed). Marcel Dekker, New York.). Similarly, the C-1027 gene cluster includes an NAGDH enzyme which can be exploited to synthesize a variety of deoxy sugars.

Figure 1:
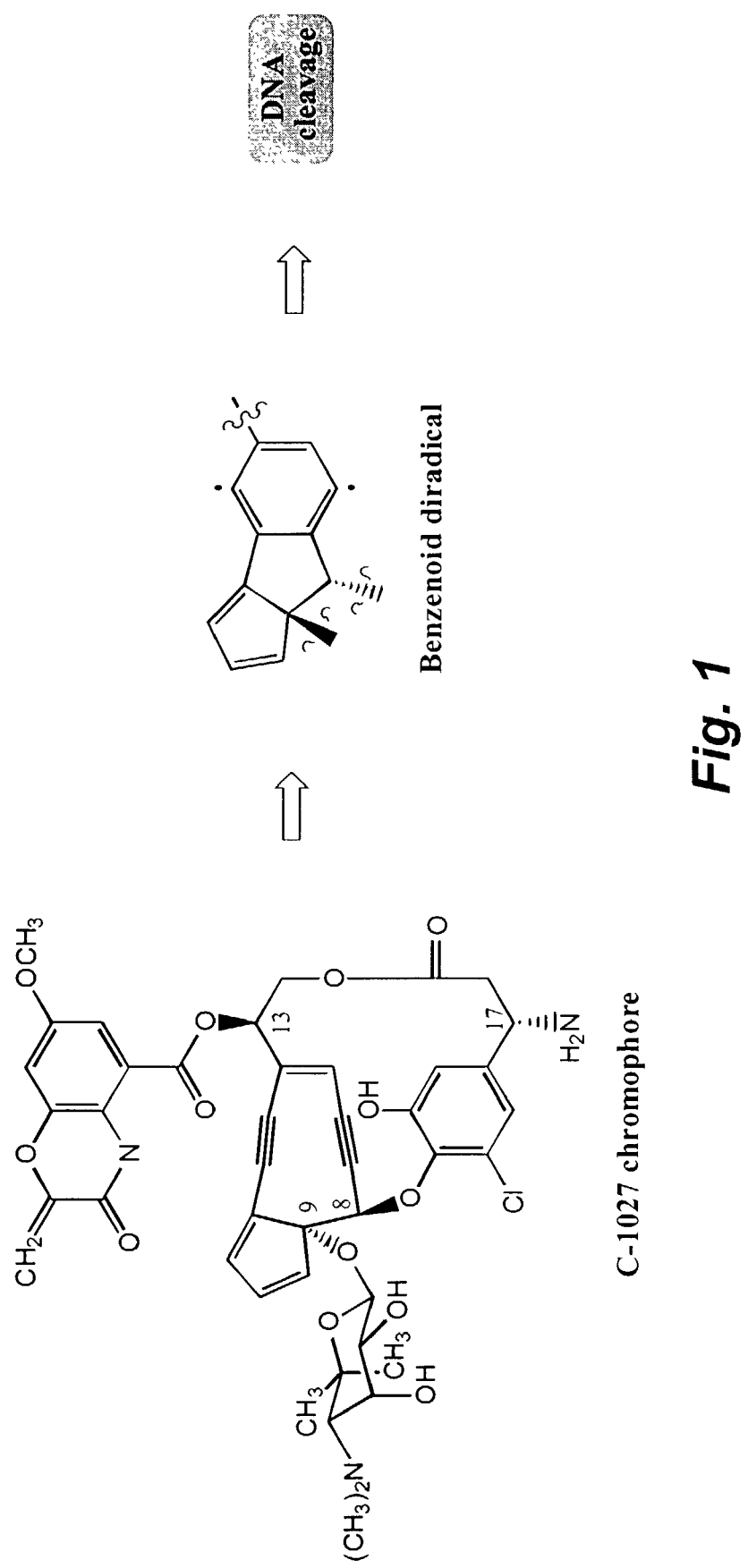
FIG. 1 illustrates the structures of C-1027 chromophore and the benzenoid diradical intermediate proposed to initiate DNA cleavage.
Figure 2:
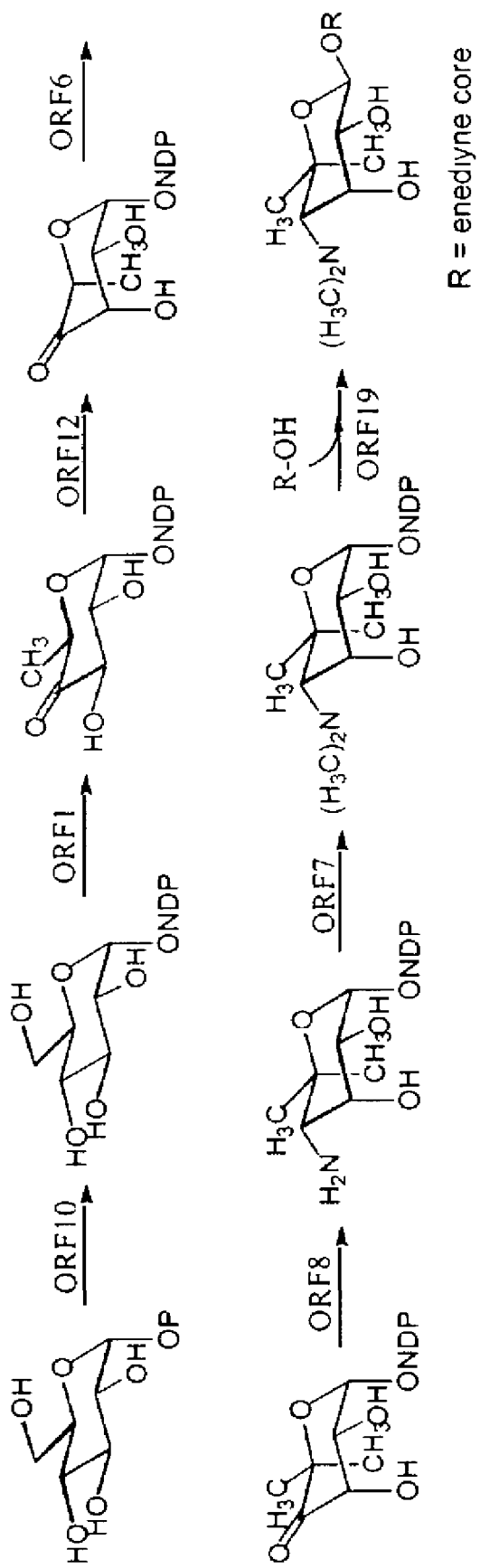
FIG. 2 illustrates a scheme using C-1027 open reading frame polypeptides for the synthesis of deoxysugars.

One illustrative synthetic pathway is shown in FIG. 2. This biosynthetic scheme utilizes ORF 10 (dNDP-glucose synthase), ORF 1 (dNDP-glucose dehydratase), ORF 12 (epimerase), ORF 8 (aminotransferase), ORF 6 (C-methyltransferase), ORF 7 (N-methyltransferase) and ORF 19 (glycosyl transferase).

This synthetic pathway is not considered limiting but merely illustrative. Using this as a model, one of ordinary skill in the art can design numerous other synthetic schemes to produce various deoxy sugars.

D) Use of C-1027 Open Reading Frames to Synthesize β-Amino Acids.

Figure 3A:
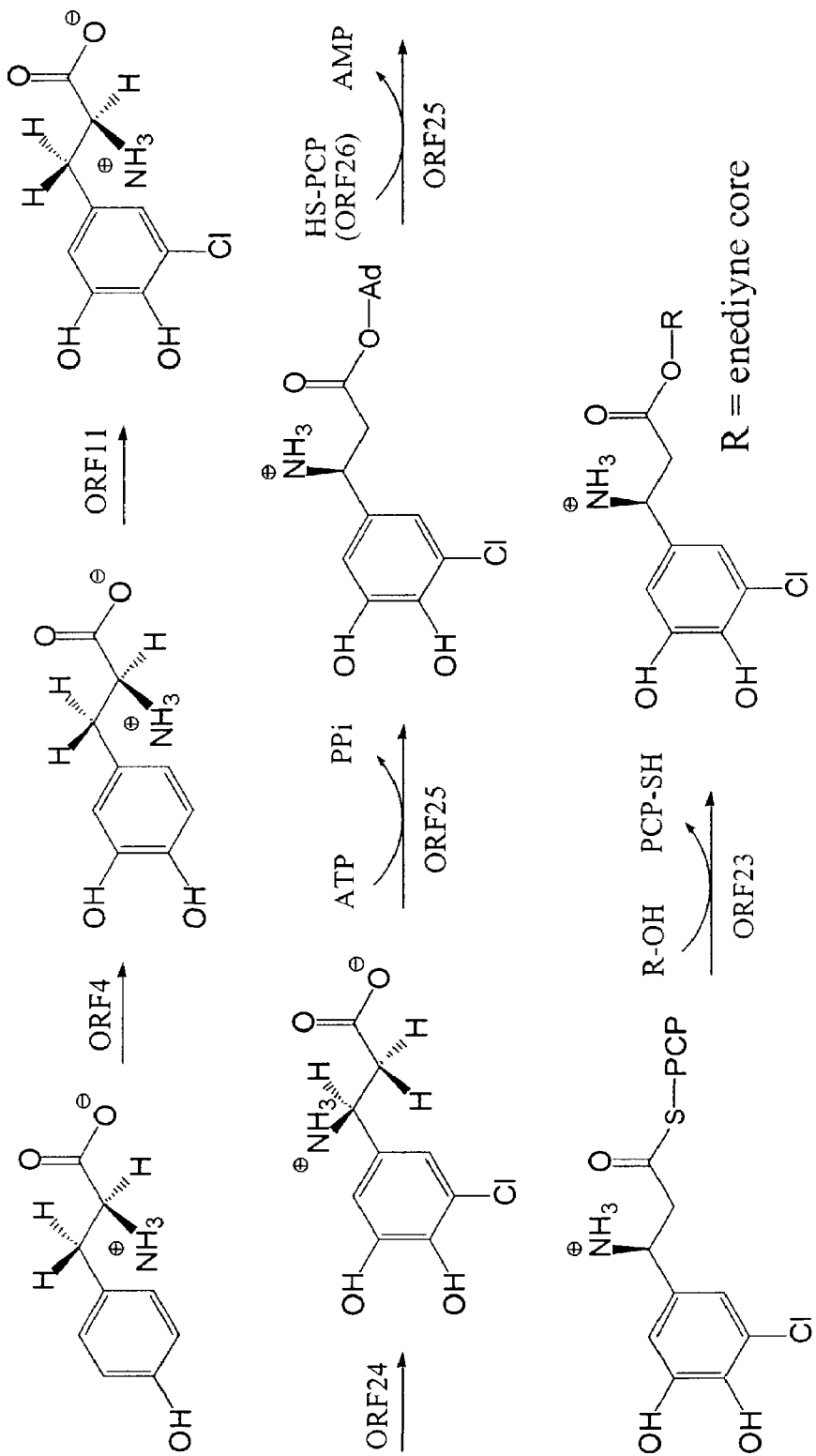
FIG. 3A illustrates a scheme using C-1027 open reading frame polypeptides for the synthesis of a β-amino acid.

In still another embodiment, C-1027 biosynthetic polypeptides can be used in the biosynthesis of β-amino acids. One illustrative synthetic pathway is shown in FIG. 3A. This biosynthetic scheme utilizes ORF 4 (hydroxylase), ORF 11 (hydroxylase/halogenase), ORF 24 (aminomutase), ORF 23 (type II NRPS condensation enzyme), ORF 25 (type II NRPS adenylation enzyme), and ORF 26 (type II peptidyl carrier protein).

Again, this synthetic pathway is not considered limiting but merely illustrative. Using this as a model, one of ordinary skill in the art can design numerous other synthetic schemes to produce other beta amino acids.

E) Use of C-1027 Open Reading Frames to Synthesize Benzoxazolinates.

Figure 3B:
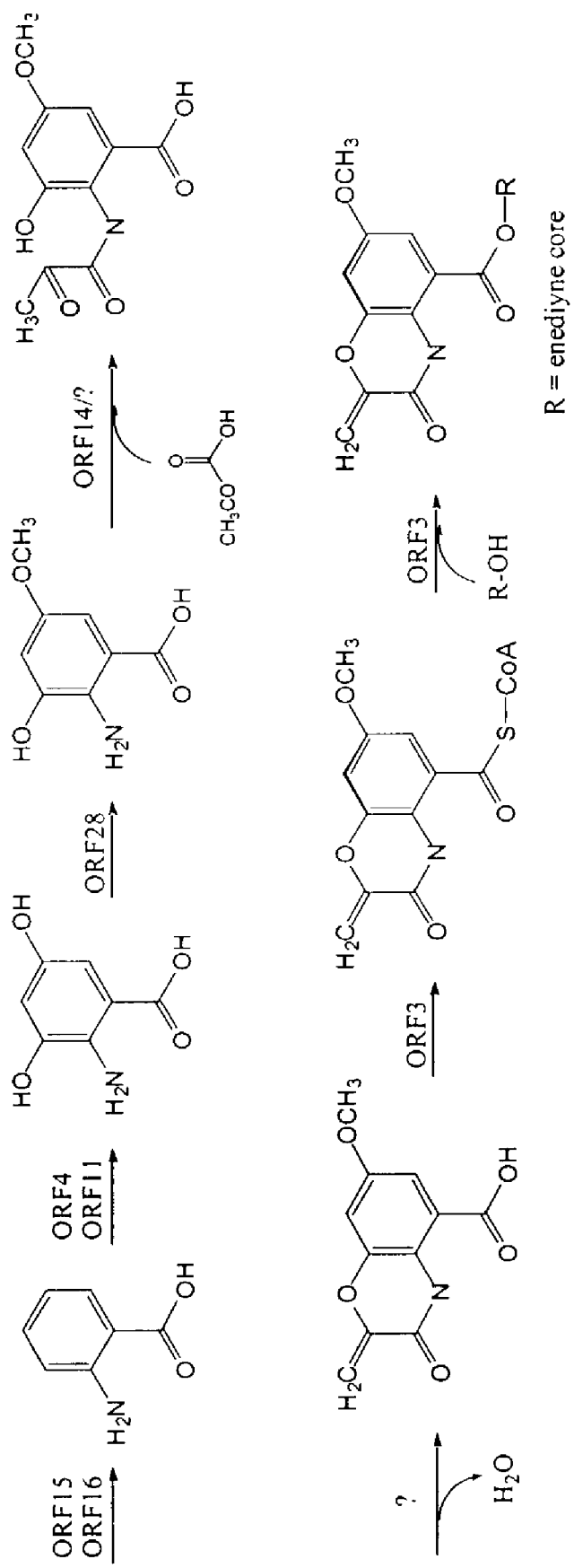
FIG. 3B illustrates a scheme using C-1027 open reading frame polypeptides for the synthesis of a benzoxazolinate.

The C-1027 open reading frames can also be used to synthesize a benzoxazolinate. One illustrative synthetic pathway is shown in FIG. 3B. This biosynthetic scheme utilizes ORF 15 (anthranilate synthase I), ORF 16 (anthranilate synthase II), ORF 4 (phenol hydroxylase/chlorophenol-4-monooxygenase), ORF 11 (Hydroxylase/Halogenase), ORF 28 (O-methyltransferase), ORF 3 (coenzyme F390 synthetase), ORF 14 (coenzyme F390 synthetase), and ORF 13 (O-acyltransferase). Again, this synthetic pathway is not considered limiting but merely illustrative. Using this as a model, one of ordinary skill in the art can design numerous other synthetic schemes to produce other benzoxazolinates.

III. Generation of Chemical Diversity.

In addition to the directed modification and/or biosynthesis of various metabolites as described above, the C-1027 biosynthetic gene cluster open reading frames can be utilized, by themselves or in combination with other biosynthetic subunits (e.g. NRPS and/or PKS modules and/or enzymatic domains of other PKS and/or NRPS systems), to produce a wide variety of compounds including, but not limited to, various enediyne or enediyne derivatives, various polyketides, polypeptides, polyketide/polypeptide hybrids, various thiazoles, various sugars, various methylated polypeptides/polyketides, and the like.

As with the directed production of various metabolites described above, such compounds can be produced, in vivo or in vitro, by catalytic biosynthesis, e.g., using large, enediyne cluster units and/or modular PKSs, NRPSs, and hybrid PKS/NRPS systems. In a preferred embodiment large combinatorial libraries of cells harboring various megasynthetases can be produced by the random or directed modification of particular pathways and then selected for the production of a molecule or molecules of interest. It will be appreciated that, in certain embodiments, such libraries of megasynthetases/modified pathways, can be used to generate large, complex combinatorial libraries of compounds which themselves can be screened for a desired activity.

Such combinatorial libraries can be created by the deliberate modification/variation of selected biosynthetic pathways and/or by random/haphazard modification of such pathways.

A) Directed Engineering of Novel Synthetic Pathways.

In numerous embodiments of this invention, novel polyketides, polypeptides, and combinations thereof are created by modifying the enediyne gene cluster ORFs and/or known PKSs, and/or NRPSs so as to introduce variations into metabolites synthesized by the enzymes. Such variations may be introduced by design, for example to modify a known molecule in a specific way, e.g. by replacing a single monomeric unit within a polymer with another, thereby creating a derivative molecule of predicted structure. Such variations can also be made by adding one or more modules or enzymatic domains to a known PKS or NRPS or enediyne cluster, or by removing one or more module from a known PKS or NRPS.

Using any of these methods, it is possible to introduce PKS domains, NRPS domains, and entediyne domains into a megasynthetase. Mutations can be made to the native enediyne, and/or NRPS, and/or PKS subunit sequences and such mutants can be used in place of the native sequence, so long as the mutants are able to function with other subunits (domains) in the synthetic pathway. Such mutations can be made to the native sequences using conventional techniques such as by preparing synthetic oligonucleotides including the mutations and inserting the mutated sequence into the gene encoding a NRPS and/or PKS subunit using restriction endonuclease digestion. (see, e.g., Kunkel, (1985) *Proc. Natl. Acad. Sci. USA* 82: 448; Geisselsoder et al. (1987) *BioTechniques* 5: 786). Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located (Zoller and Smith (1983) *Meth. Enzymol.* 100: 468). Primer extension is effected using DNA polymerase. The product cloned and clones containing the mutated DNA, which are derived by segregation of the primer extended strand, are selected. Selection can be accomplished using the mutant primer as a hybridization probe. The technique is also applicable for generating multiple point mutations (see, e.g., Dalbie-McFarland et al. (1982) *Proc. Natl. Acad. Sci USA* 79:6409). PCR mutagenesis will also find use for effecting the desired mutations.

B) Random Modification of Enediyne Pathways.

In another embodiment, variations can be made randomly, for example by making a library of molecular variants (e.g. of a known enediyne) by randomly mutating one or more elements of the subject gene cluster or by randomly replacing one or more open reading frames in a gene cluster with one or more of alternative open reading frames.

The various open reading frames can be combined into a single multi-modular enzyme, thereby dramatically increasing the number of possible combinations obtained using these methods. These combinations can be made using standard recombinant or nucleic acid amplification methods, for example by shuffling nucleic acid sequences encoding various modules or enzymatic domains to create novel arrangements of the sequences, analogous to DNA shuffling methods described in Crameri et al. (1998) Nature 391: 288–291, and in U.S. Pat. Nos. 5,605,793 and 5,837,458. In addition, novel combinations can be made in vitro, for example by combinatorial synthetic methods. Novel molecules or molecule libraries can be screened for any specific activity using standard methods.

Random mutagenesis of the nucleotide sequences obtained as described above can be accomplished by several different techniques known in the art, such as by altering sequences within restriction endonuclease sites, inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, and hydroxylamine, agents which damage or remove bases thereby preventing normal base-pairing such as hydrazine or formic acid, analogues of nucleotide precursors such as nitrosoguanidine, 5-bromouracil, and 2-aminopurine, or acridine intercalating agents such as proflavine, acriflavine, quinacrine, and the like. Generally, plasmid DNA or DNA fragments are treated with chemicals, transformed into E. coli and propagated as a pool or library of mutant plasmids.

Large populations of random enzyme variants can be constructed in vivo using "recombination-enhanced mutagenesis." This method employs two or more pools of, for example, $10^6$ mutants each of the wild-type encoding nucleotide sequence that are generated using any convenient mutagenesis technique, described more fully above, and then inserted into cloning vectors.

C) Incorporation and/or Modification of Non-C-1027 Cluster Elements.

In either the directed or random approaches, nucleic acids encoding novel combinations of gene cluster ORFs are introduced into a cell. In one embodiment, nucleic acids encoding one or more enediyne synthetic cluster ORFS and/or PKS and/or NRPS domains are introduced into a cell so as to replace one or more domains of an endogenous gene cluster within a cell. Endogenous gene replacement can be accomplished using standard methods, such as homologous recombination. Nucleic acids encoding an entire enediyne, enediyne ORF, PKS, NRPS, or combination thereof can also be introduced into a cell so as to enable the cell to produce the novel enzyme, and, consequently, synthesize the novel polymer. In a preferred embodiment, such nucleic acids are introduced into the cell optionally along with a number of additional genes, together called a 'gene cluster,' that influence the expression of the genes, survival of the expressing cells, etc. In a particularly preferred embodiment, such cells do not have any other enediyne and/or PKS- and/or NRPS-encoding genes or gene clusters, thereby allowing the straightforward isolation of the molecule(s) synthesized by the genes introduced into the cell.

Furthermore, the recombinant vector(s) can include genes from a single enediyne and/or PKS and/or NRPS gene cluster, or may comprise hybrid replacement PKS gene clusters, or with, e.g., a gene for one cluster replaced by the corresponding gene from another gene cluster. For example, it has been found that ACPs are readily interchangeable among different synthases without an effect on product structure. Furthermore, a given KR can recognize and reduce polyketide chains of different chain lengths. Accordingly, these genes are freely interchangeable in the constructs described herein. Thus, the replacement clusters of the present invention can be derived from any combination of PKS and/or NRPS gene sets that ultimately function to produce an identifiable polyketide.

Examples of hybrid replacement clusters include, but are not limited to, clusters with genes derived from two or more of the act gene cluster, the whiE gene cluster, frenolicin (fren), granaticin (gra), tetracenomycin (tcm), 6-methylsalicylic acid (6-msas), oxytetracycline (otc), tetracycline (tet), erythromycin (ery), griseusin (gris), nanaomycin, medermycin, daunorubicin, tylosin, carbomycin, spiramycin, avermectin, monensin, nonactin, curamycin, rifamycin and candicidin synthase gene clusters, among others. (For a discussion of various PKSs, see, e.g., Hopwood and Sherman (1990) Ann. Rev. Genet. 24: 37–66; O'Hagan (1991) The Polyketide Metabolites, Ellis Horwood Limited.)

A number of hybrid gene clusters have been constructed, having components derived from the act, fren, tcm, gris and gra gene clusters (see, e.g., U.S. Pat. No. 5,712,146). Other hybrid gene clusters, as described above, can easily be produced and screened using the disclosure herein, for the production of identifiable polyketides, polypeptides or polyketide/polypeptide hybrids.

Host cells (e.g. Streptomyces) can be transformed with one or more vectors, collectively encoding a functional PKS/NRPS set, or a cocktail comprising a random assortment of enediyne ORFs and/or PKS and/or NRPS genes, modules, active sites, or portions thereof. The vector(s) can include native or hybrid combinations of enediyne ORFs, and/or PKS and/or NRPS subunits or cocktail components, or mutants thereof. As explained above, the gene cluster need not correspond to the complete native gene cluster but need only encode the necessary enediyne ORFs and/or PKS and/or NRPS components to catalyze the production of the desired product(s).

IV. Variation of Starter and/or Extender Units, and/or Host Cells.

In addition to varying the nucleic acids comprising the subject gene cluster, variations in the products produced by the gene cluster(s) can be obtained by varying the the host cell, the starter units and/or the extender units. Thus, for example different fatty acids can be utilized in the enediyne synthetic pathway resulting in different enediyne variants. Similarly, different intermediate metabolites can be provided (e.g. endogenously produced by the host cell, or produced by an introduced herterologous construct, and/or supplied from an exogenous source (e.g. the culture media)). Similarly, varying the host cell can vary the resulting product(s). For example, a gene cassette carrying the enediyne biosynthesis genes can be introduced into a deoxysugar-synthesizing host for the production of glycosylated enediyne metabolites.

V. Use of C-1027 Resistance Genes.

The antibiotic C-1027 and metabolites present in C-1027 biosynthesis are highly potent cytotoxins. Accordingly the biosynthesis of C-1027 is facilitated by the presence of one or more antibiotic (e.g. enediyne) resistance genes. Without being bound to a particular theory, it is believed that CagA and SgcB function cooperatively to provide resistance. It is also believed that the C-1027 chromophore is first sequestered by binding to the preaproprotein CagA (ORF 9) to form a complex, which is then transported out of the cell by the efflux pump SgcB (ORF 2) and processed by removing the leader peptide to yield the chromoprotein. Other genes that appear to mediate resistance in the C-1027 biosynthesis gene cluster include a transmembrane transport protein (ORF 27), a $Na^+/H^+$ transporter (ORF 0), an ABC transporter (ORF −1, C-terminus), a glycerol phosphate transporter (ORF −2), and a UvrA-like protein (ORF −1, N-terminus) (see, e.g., Table III).

These ORFs and/or the polypeptides encoded by these ORFs can be utilized alone, or in combination with one or more other C-1027 ORFs to confer resistance to enediyne or enediyne metabolites on a cell. This is useful in a wide variety of contexts. For example, to increase production of enediynes. For example, it is believed that C-1027 resistance could be a limiting factor at the onset of C-1027 production. Provision of an extra copy of the plasmid-born sgcB, and overexpression of sgcB under the control of the constitutive ermE* promoter resulted in increase of C-1027 production (see example 1).

In a therapeutic context, it is sometimes desirable to confer resistance on certain vulnerable cells. Thus, for example, where an enediyne is used as a chemotherapeutic, transfection of vulnerable, but healthy cells (e.g. liver cells remote from the tumor site, stem cells, etc.) with vector(s) expressing the resistance gene(s) permits administration of the enediyne at a higher dosage with fewer adverse effects to the organism. Such approaches have been taken using the multi-drug resistance gene (MDR1) expressing p-glycoprotein.

In another embodiment vectors are provided containing one or more resistance genes of this invention under control of a constitutive and/or inducible promoter thereby providing a "ready-made" expression system suitable for the expression of an enediyne or enediyne metabolite at high concentration.

It is also noted that the resistance genes are expected to confer resistance to compounds other than enediynes. The resistance genes are expected to confer resistance to essentially any cytotoxic compound that can act as a substrate for the resistance gene(s) of this invention.

VI. Kits.

In still another embodiment, this invention provides kits for practice of the methods described herein. In one preferred embodiment, the kits comprise one or more containers containing nucleic acids encoding one or more of the C-1027 biosynthesis gene cluster open reading frames. Certain kits may comprise vectors encoding the sgc gene cluster orfs and/or cells containing such vectors. The kits may optionally include any reagents and/or apparatus to facilitate practice of the methods described herein. Such reagents include, but are not limited to buffers, labels, labeled antibodies, bioreactors, cells, etc.

In addition, the kits may include instructional materials containing directions (i.e., protocols) for the practice of the methods of this invention. Preferred instructional materials provide protocols utilizing the kit contents for creating or modifying C-1027 gene cluster and/or for synthesizing or modifying a molecule using one or more sgc gene cluster ORFs. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Genes for production of the enediyne antitumor antibiotic C-1027 in *Streptomyces globisporus* are clustered with the cagA gene that encodes the C-1027 apoprotein.

Biosynthesis of C-1027 in *Streptomyces globisporus* C-1027 was studied as a model for the enediyne family of antitumor antibiotics (Thorson et al. (1999) *Bioorg. Chem.,* 27: 172–188). C-1027 consists of a non-peptidic chromophore and an apoprotein, CagA [also called C-1027AG (Otani et al. (1991) *Agri. Biol. Chem.* 55: 407–417)]. The C-1027 chromophore is extremely unstable in the protein-free state, the structure of which was initially deduced from an inactive but more stable degradation product (Minami et al. (1993) *Tetrahedron Lett.* 34: 2633–2636) and subsequently confirmed by spectroscopic analysis of the natural product (Yoshida et al. (1993) *Tetrahedron Lett.* 34: 2637–2640) (FIG. 1). While the absolute stereochemistry of the deoxysugar moiety was established by total synthesis (Iida et al. (1993) *Tetrahedron Lett.* 34: 4079–4082), the 8S, 9S, 13S and 17R configuration of the C-1027 chromophore were based only on computer modeling (Okuno et al. (1994) *J. Med. Chem.* 37: 2266–2273). Although no biosynthetic study has been carried out specifically on C-1027, the polyketide origin of the enediyne cores has been implicated by feeding experiments with $^{13}C$-labeled acetate for the neocarzinostatin chromophore A (Hensens et al. (1989) *J. Am. Chem. Soc.* 111: 3295–3299), dynemicin (Tokiwa et al. (1992) *J. Am. Chem. Soc.* 114: 4107–4110), and esperamicin (Lam et al. (1993) *J. Am. Chem. Soc.* 115: 12340–12345), and deoxysugar biosynthesis has been well characterized in actinomycetes (Liu and Thorson (1994) *Ann. Rev. Microbiol.* 48: 223–256; Piepersberg (1997) pp. 81–163. In *Biotechnology of antibiotics,* 2nd ed. W. R. Strohl (ed). Marcel Dekker, New York). Given the structural similarity of C-1027 to the other enediyne cores and to deoxysugars found in other secondary metabolites, cloning of either a PKS or a deoxysugar biosynthesis gene was the first step of identifying the C-1027 gene cluster from *S. globisporus.*

Furthermore, the CagA apoprotein of C-1027 has been isolated, its amino acid sequence has been determined, and the corresponding cagA gene has been cloned and sequenced (Otani et al. (1991) *Agri. Biol. Chem.* 55: 407–417; Sakata et al. (1992) *Biosci. Biotech. Biochem.* 56: 1592–1595). Since genes encoding secondary metabolite production in actinomycetes have invariably been found to be clustered in one region of the microbial chromosome (Hopwood (1997) *Chem. Rev.* 97: 2465–2497), it is further reasoned that mapping the cagA gene with either a putative PKS gene, a deoxysugar biosynthesis gene, or both to the same region of the *S. globisporus* chromosome should be viewed as strong evidence supporting the proposition that the cloned genes constitute the C-1027 biosynthesis gene cluster.

The cloning and sequencing of two genes, sgcA (*Streptomyces globisporus* C-1027) and sgcB, that encode a dNDP-glucose 4,6-dehydratase (NGDH) and a transmembrane efflux protein, respectively, was done. The sgcA,B locus is indeed clustered with the cagA gene, leading to the localization of a 75-kb gene cluster from *S. globisporus*. The involvement of the cloned gene cluster in C-1027 biosynthesis was demonstrated by disrupting the sgcA gene to generate C-1027-nonproducing mutants and by complementing the sgcA mutants in vivo to restore C-1027 production. These results, together with similar effort in the Thorson laboratory on the calicheamicin gene cluster (Thorson et al. (1999) *Bioorg. Chem.,* 27: 172–188), represent the first cloning of a gene cluster for enediyne antitumor antibiotic biosynthesis.

Materials and Methods.

Bacterial Strains and Plasmids.

*Escherichia coli* DH5α was used as a general host for routine subcloning (Sambrook et al. (1989) *Molecular cloning, a laboratory manual.* Cold Spring Harbor Laboratory, Cold Spring Harbor, NY). *E. coli* XL 1-Blue MR (Stratagene, La Jolla, Calif.) was used as the transduction host for cosmid library construction. *E. coli* S17-1 was used as the donor host for *E. coli-S. globisporus* conjugation (Mazodier et al. (1989) *J. Bacteriol.* 171: 3583–3585). *Micrococcus luteus* ATCC9431 was used as the testing organism to assay the antibacterial activity of C-1027 (Hu et al. (1988) *J. Antibiot.* 41: 1575–1579). The pGEM-3zf, -5zf, and -7zf and pGEM-T vectors were from Promega (Madison, Wis.). *S. globisporus* strains and other plasmids in this study are listed in Table VI.

TABLE VI

Strains and plasmids.

| Strain or plasmid | Relevant Characteristics |
|---|---|
| *S. globisporus* | |
| C-1027 | Wild-type (Hu et al. (1988) J. Antibiot. 41: 1575–1579) |
| AF40 | Mutant resulted from acriflavine treatment of *S. globisporus* C-1027, C-1027-nonproducing (Mao et al. (1997) Chinese J. Biotechnol. 13: 195–199) |
| AF44 | Mutant resulted from acriflavine treatment of *S. globisporus* C-1027, C-1027-nonproducing (Mao et al., supra) |
| AF67 | Mutant resulted from acriflavine treatment of *S. globisporus* C-1027, C-1027-nonproducing (Mao et al., supra) |
| SB1001 | sgcA-disrupted mutant resulted from integration of pBS1012 into *S. globisporus* C-1027 Apr$^R$, C-1027-nonproducing |
| SB1002 | sgcA-disrupted mutant resulted from integration of pBS1013 into *S. globisporus* C-1027 Apr$^R$, C-1027-nonproducing |
| Plasmids: | |
| pOJ446 | *E. coli*-Streptomyces shuttle cosmid, Apr$^R$ (Bierman et al. (1992) Gene, 116: 43– |
| pOJ260 | *E. coli* vector, non-replicating in Streptomyces, Apr$^R$ (Bierman et al. supra) |
| pKC1139 | *E. coli*-Streptomyces shuttle vector, rep$^{TS}$, Apr$^R$ (Bierman et al. supra) |
| pWHM3 | *E. coli*-Streptomyces shuttle vector, Th$^R$ (Vara et al. (1989) J. Bacteriol. 171: 5872–5881) |
| pWHM79 | ermE* promoter in pGEM-3zf (Shen and Hutchinson (1996) Proc. Natl. Acad. Sci. USA 93: 6600–6604) |
| pBS1001 | 0.75-kb PCR product amplified from *S. globisporus* with type I PKS primers in pGEM-T |
| pBS1002 | 0.55-kb PCR product amplified from *S. globisporus* with NGDH gene primers in pGEM-T |
| pBS1003 | 0.73-kb PCR product amplified from pBS1005 with cagA primers in pGEM-T |
| pBS1004 | pOJ446 *S globisporus* genomic library cosmid |
| pBS1005 | pOJ446 *S globisporus* genomic library cosmid |
| pBS1006 | pOJ446 *S globisporus* genomic library cosmid |
| pBS1007 | 3.0-kb BamHI fragment from pBS1005 in pGEM-3zf, sgcA, sgcB |
| pBS1008 | 4.0-kb BamHI fragment from pBS1005 in pGEM-3zf, cagA |
| pBS1009 | 1.0-kb KpnI truncated fragment of sgcA from pBS1007 in pGEM-3zf |
| pBS1010 | 0.75-kb SacII/SphI internal fragment of sgcA from pBS1009 in pGEM-5zf |
| pBS1011 | 0.75-kb SacI/SphI internal fragment of sgcA from pBS1010 in pGEM-3zf |
| pBS1012 | 0.75-kb EcoRI/HindIII internal fragment of sgcA from pBS1010 in pOJ260 |
| pBS1013 | 0.75-kb EcoRI/HindIII internal fragment of sgcA from pBS1010 in pKC1139 |
| pBS1014 | 2.0-kb EcoRI/SphI fragment from pBS1007 in the SmaI/SphI sites of pWHM79, ermE*, sgcA |
| pBS1015 | 2.5-kb EcoRI/HindIII fragment from pBS1014 in pWHM3, ermE*, sgcA |
| pBS1016 | Self-ligation of the 5.2-kb KpnI fragment from pBS1007 |
| pBS1017 | 0.45-kb EcoRI/SacI fragment from pWHM79 in EcoRI/SacI sites of pBS1016, ermE*, sgcB |
| pBS1018 | 2.5-kb EcoRI/HindIII fragment from pBS1017 in pKC1139, ermE*, sgcB |

Biochemicals and Chemicals.

Ampicillin, apramycin, nalidixic acid, and thiostrepton were from Sigma (St. Louis, Mo.). Unless specified otherwise, restriction enzymes and other molecular biology reagents were from standard commercial sources.

Media and Culture Conditions.

*E. coli* strains carrying plasmids were grown in Luria-Bertani (LB) medium and were selected with appropriate antibiotics. *S. globisporus* strains were grown on ISP-4 (Difco Laboratories, Detroit, Mich.) or R2YE at 28° C. for sporulation and in TSB (Hopwood et al. (1985) *Genetic manipulation of Streptomyces: a laboratory manual.* John Innes Foundation, Norwich, UK) supplemented with 5 mM $MgCl_2$ and 0.5% glycine at 28° C., 250 rpm for isolation of genomic DNA. For transformation, *S. globisporus* strains were grown in YEME (Hopwood et al., supra.) for preparation of protoplasts and on R2YE for protoplast regeneration. For conjugation, both the *E. coli* S17-1 donors and the *S. globisporus* recipients (upon germination in TSB) were prepared in LB, and donors/recipients were grown on either ISP-4 medium with 0.05% yeast extract and 0.1% tryptone or AS-1 medium (Baltz (1980) *Dev. Ind. Microbiol.* 21: 43–54; Bierman et al. (1992) *Gene* 116: 43–69) at 30° C. for isolation of exconjugants.

For C-1027 production, *S. globisporus* strains were grown either on R2YE or ISP-4 agar medium at 28° C. or in liquid medium by a two-stage fermentation. For liquid culture, the seed inoculum was prepared by inoculating 50 mL medium (consisting of 2% glycerol, 2% dextrin, 1% fish meal, 0.5% peptone, 0.2% $(NH_4)_2SO_4$, and 0.2% $CaCO_3$, pH 7.0) with an aliquot of spore suspension, incubating at 28° C., 250 rpm for two days. To a fresh 50 mL of the same medium was then added the seed culture (5%), and incubation continued at 28° C., 250 rpm for three to six days (Hu et al. (1988) *J. Antibiot.* 41: 1575–1579). The fermentation supernatants were harvested by centrifugation (Eppendorf 5415C, 4° C., 10 min, 14,000 rpm) on day 3, 4 and 5, and assayed for their antibacterial activity against *M. luteus* (Hu et al. (1988) *J. Antibiot.,* 41: 1575–1579).

DNA Isolation and Manipulation.

Plasmid preparation and DNA extraction were carried out by using commercial kits (Qiagen, Santa Clarita, Calif.). Total *S. globisporus* DNA was isolated according to literature protocols (Hopwood et al. (1985) *Genetic manipulation of Streptomyces: a laboratory manual*. John Innes Foundation, Norwich, UK; Rao et al. (1987) *Methods Enzymol*. 153: 166–198). Restriction endonuclease digestion and ligation followed standard methods (Sambrook et al. (1989) *Molecular cloning, a laboratory manual*. Cold Spring Harbor Laboratory, Cold Spring Harbor, N.Y.). For Southern analysis, digoxigenin labeling of DNA probes, hybridization, and detection were performed according to the protocols provided by the manufacturer (Boehringer Mannheim Biochemicals, Indianapolis, Ind.).

DNA Sequencing.

Automated DNA sequencing was carried out on an ABI Prism 377 DNA Sequencer using the ABI Prism dye terminator cycle sequencing ready reaction kit and AmpliTaq DNA polymerase FS (Perkin-Elmer/ABI, Foster City, Calif.). Sequencing service was provided by either the DBS Automated DNA Sequencing Facility, UC Davis, or Davis Sequencing Inc. (Davis, Calif.). Data were analyzed by ABI Prism Sequencing 2.1.1 software and the Genetics Computer Group program (Madison, Wis.).

Polymerase Chain Reaction (PCR).

Primers were synthesized at the Protein Structure Laboratory, UC Davis. PCR was carried out on a Gene Amp PCR System 2400 (Perkin-Elmer/ABI) with Taq polymerase and buffer from Promega. A typical PCR mixture consisted of 5 ng of *S. globisporus* genomic or plasmid DNA as template, 25 pmoles of each primers, 25 μM dNTP, 5% DMSO, 2 units of Taq polymerase, 1×buffer, with or without 20% glycerol in a final volume of 50 μL. The PCR temperature program was as follows: initial denaturing at 94° C. for 5 min, 24–36 cycles of 45 sec at 94° C., 1 min at 60° C., 2 min at 72° C., followed by additional 7 min at 72° C.

For type II PKS, the following two pairs of degenerate primers were used—5'-AGC TCC ATC AAG TCS ATG RTC GG-3' (forward, SEQ ID NO: 137), 5'-CC GGT GTT SAC SGC GTA GAA CCA GGC G-3' (reverse, SEQ ID NO: 138) and 5'-GAC ACV GCN TGY TCB TCV-3' (forward, SEQ ID NO: 139), 5'-RTG SGC RTT VGT NCC RCT-3' (SEQ ID NO: 140) (B, C+G+T; N, A+C+G+T; R, A+G; S, C+G; V, A+C+G; Y, C+T) (reverse) (Seow et al. (1997) *J. Bacteriol.*, 179: 7360–7368). No product was amplified under all conditions tested. For type I PKS, the following pair of degenerate primers were used—5'-GCS TCC CGS GAC CTG GGC TTC GAC TC-3' (forward, SEQ ID NO: 141), 5'-AG SGA SGA SGA GCA GGC GGT STC SAC-3' (S, G+C) (reverse, SEQ ID NO: 142) (Kakavas et al. (1997) *J. Bacteriol.*, 179: 7515–7522). A distinctive product with the predicted size of 0.75 kb was amplified in the presence of 20% glycerol and cloned into pGEM-T according to the protocol provided by the manufacturer (Promega) to yield pBS1001.

For NGDH, the following pair of degenerate primers were used—5'-CS GGS GSS GCS GGS TTC ATC GG-3' (forward, SEQ ID NO: 143)/5'-GG GWR CTG GYR SGG SCC GTA GTT G-3' (R, A+G; S, C+G; W, A+T; Y, C+T) (reverse, SEQ ID NO: 144) (Decker, et al. (1996) *FEMS Lett.*, 141: 195–201). A distinctive product with the predicted size of 0.55 kb was amplified and cloned into pGEM-T to yield pBS1002.

For cagA, the following pair of primers, flanking its coding region, were used—5'-AG GTG GAG GCG CTC ACC GAG-3' (forward, SEQ ID NO: 145)/5'-G GGC GTC AGG CCG TAA GAA G-3' (reverse, SEQ ID NO: 146) (Sakata et al. (1992) *Biosci. Biotechnol. Biochem.*, 56: 159201595). A distinctive product with the predicted size of 0.73 kb was amplified from pBS1005 and cloned into pGEM-T to yield pBS1003.

Genomic Library Construction and Screening.

*S. globisporus* genomic DNA was partially digested with MboI to yield a smear around 60 kb, as monitored by electrophoresis on a 0.3% agarose gel. This sample was dephosphorylated upon treatment with shrimp alkaline phosphatase and ligated into the *E. coli-Streptomyces* shuttle vector pOJ446 (Bierman et al. (1992) *Gene* 116: 43–69) that was prepared by digestion with HpaI, shrimp alkaline phosphatase treatment, and additional digestion with BamHI. The resulting ligation mixture was packaged with the Gigapack II XL two-component packaging extract (Stratagene). The package mixture was transduced into *E. coli* XL 1-Blue MR. The transduced cells were spread onto LB plates containing apramycin (100 μg/mL) and incubated at 37° C. overnight. The titer of the primary library was approximately 6,000 colony-forming units per μg of DNA. Restriction enzyme analysis of twelve randomly selected cosmids confirmed that the average size of inserts was about 35 to 45 kb (Rao et al. (1987) *Meth. Enzymol.*, 153: 166–198).

Figure 5A:
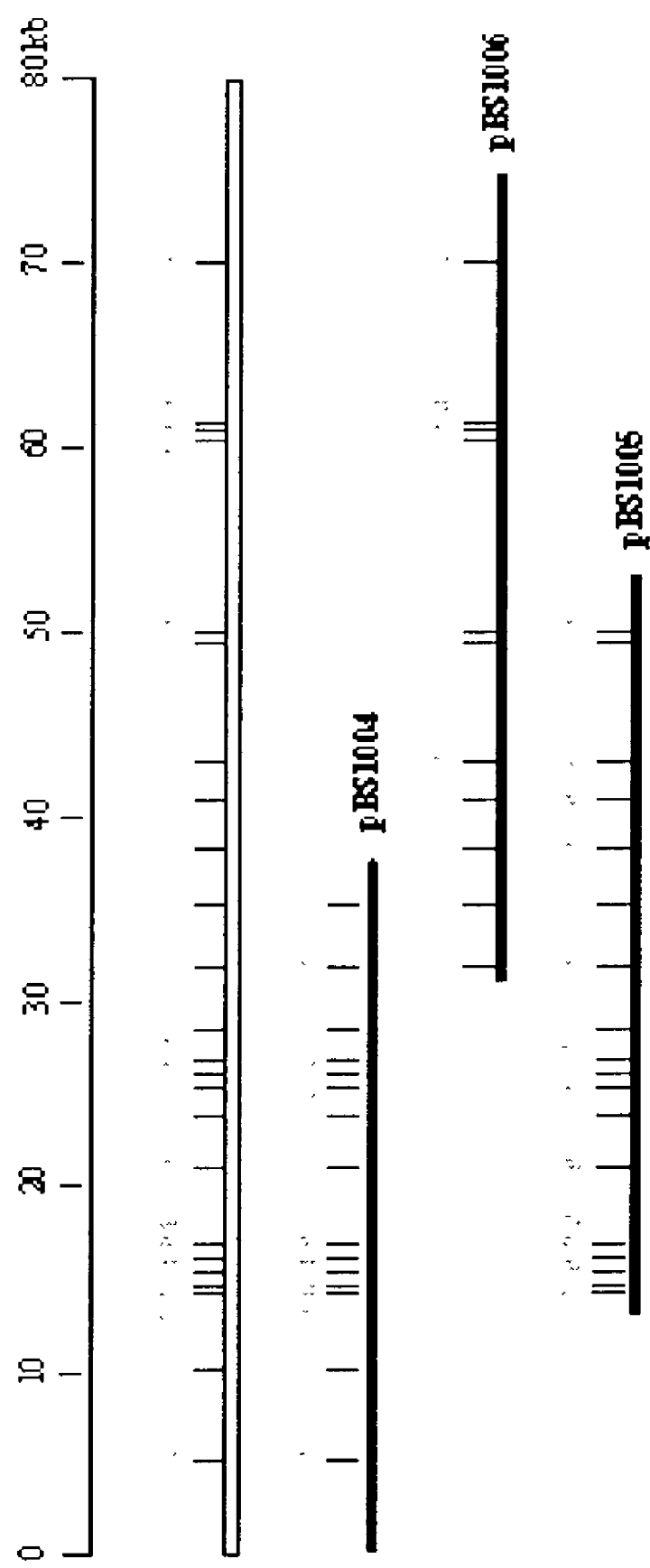
FIGS. 5A, 5B, and 5C illustrate the organization of the C-1027 enediyne biosynthetic gene cluster.
Figure 5B:
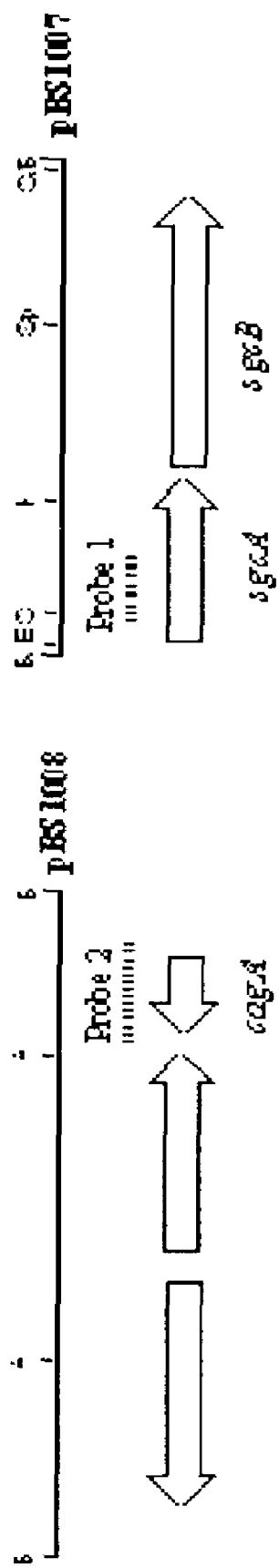

To screen the genomic library, colonies from five LB plates containing apramycin (100 μg/mL, with approximately 2,000 colonies per plate) were transferred to nylon transfer membranes (Micro Separations, Inc., Westborough, Mass.) and screened by colony hybridization with the PCR-amplified 0.55-kb NGDH fragment from pBS1002 as a probe. The positive cosmid clones were re-screened by PCR with primers for NGDH and confirmed by Southern hybridization (Sambrook et al., supra.). Further restriction enzyme mapping and chromosomal walking of these overlapping cosmids led to the genetic localization of the 75-kb sgc gene cluster, as represented by pBS1004, pBS1005, and pBS1006 (FIG. 5A). A 3.0-kb BamHI fragment from pBS1005 that hybridized to the NGDH probe was cloned into the same sites of pGEM-3zf to yield pBS1007. Similarly, a 4.0-kb BamHI fragment from pBS1005 that hybridizes to the PCR-amplified 0.73-kb cagA probe from pBS1003 was cloned into the same sites of pGEM-3zf to yield pBS1008 (FIG. 5B).

Generation of sgcA Mutants by Insert-directed Homologous Recombination in *S. globisporus*.

A 1.0-kb KpnI fragment from pBS1007, containing the C-terminal truncated sgcA, was subcloned into pGEM-3zf to yield pBS1009. An internal fragment of sgcA was moved sequentially as a 0.75-kb SacII/SphI fragment from pBS1009 into the same sites of pGEM-5zf to yield pBS1010 and as a 0.75-kb SacI/SphI fragment from pBS1010 into the same sites of pGEM-3zf to yield pBS1011. The latter plasmid was digested with EcoRI and HindIII, and the resulting 0.75-kb EcoRI/HindIII fragment was cloned into the same sites of pOJ260 and pKC1139 (Bierman et al. (1992) Gene, 116: 43–69 to yield pBS1012 and pBS1013, respectively.

Introduction of pBS1012 and pBS1013 into *S. globisporus* was carried out by either polyethyleneglycol (PEG)-mediated protoplast transformation (Hopwood et al. (1985) *Genetic manipulation of Streptomyces: a laboratory manual*. John Innes Foundation, Norwich, UK) or *E. coli-S. globisporus* conjugation (Bierman et al. (1992) Gene 116: 43–69; Matsushima and Baltz (1996) *Microbiology* 142: 261–267; Matsushima et al. (1994) *Gene* 146: 39–45), methods for both were developed recently in the Inventor's laboratory. In brief, for transformation, pBS1012 and pBS1013 were propagated in *E. coli* ET12567 (MacNeil et al. (1992) *Gene* 111: 61–68), and the resulting double strand plasmid DNA was denatured by alkaline treatment (Ho and Chater (1997) *J. Bacteriol.* 179: 122–127). The latter DNA (5 µL) and 200 µL of 25% PEG 1000 in P buffer (Hopwood et al. supra) were sequentially added to 50 µL of *S. globisporus* protoplasts ($10^9$) in P buffer. The resulting suspension was mixed immediately and spread on R2YE plates. After incubation at 28° C. for 16 to 20 hrs, the plates were overlaid with soft R2YE (0.7% agar) containing apramycin (100 µg/mL, final concentration); incubation continued until colonies appeared (in 5 to 7 days). For conjugation, *E. coli* S17-1 (pBS1012) or *E. coli* S17-1 (pBS1013) was grown to an $OD_{600}$ of 0.3 to from a 20-mL culture were pelleted by centrifugation, washed in LB, and resuspended in 2 mL of LB as the *E. coli* donors. *S. globisporus* spores ($10^3$ to $10^9$) were washed, resuspended in TSB, and incubated at 50° C. for 10 min to activate germination. After additional incubation at 37° C. for 2 to 5 hrs, the spores were pelleted and resuspended in LB as the *S. globisporus* recipients. The donors (100 µL) and recipients (100 µL) were mixed and spread equally onto two modified ISP-4 or AS-I plates supplemented freshly with 10 mM $MgCl_2$ (see Media and culture conditions). The plates were incubated at 28° C. for 16 to 22 hrs. After removal of most of the *E. coli* S 17-1 donors by washing the surface with sterile water, the plates were overlaid with 3 mL of soft LB (0.7% agar) containing nalidixic acid (50 µg/mL, final concentration) and apramycin (100 µg/mL, final concentration) and incubated at 28° C. until exconjugants appeared (in approximately 5 days).

Unlike pBS1012, which is a *Streptomyces* non-replicating plasmid, pBS1013 bears a temperature-sensitive *Streptomyces* replication origin (Bierman et al. (1992) *Gene* 116: 43–69; Muth et al. (1989) *Mol. Gen. Genet.* 219: 341–348) that is unable to replicate at temperatures above 34° C. (Table IV), while the *S. globisporus* wild-type strain grows normally up to 37° C. Thus, spores of *S. globisporus* (pBS1013), from either the transformants or the exconjugants, were spread onto R2YE plates containing apramycin (100 µg/mL). The plates were incubated directly at 37° C., and mutants, resulting from single crossover homologous recombination between pBS1013 and the *S. globisporus* chromosome, were readily obtained in 7 to 10 days. Alternatively, the plates were first incubated at 28° C. for 2 days until pinpoint-size colonies became visible and then shifted to 37° C. to continue incubation. Mutants resulting from single crossover homologous recombination grew out of the original pinpoint-size colonies as easily distinguishable sectors in 7 to 10 days.

Construction of the sgcA and sgcB Expression Plasmids.

pBS1007 was digested with EcoRI, and made blunt-ended by treatment with the Klenow fragment of DNA polymerase I. Upon additional digestion with SphI, the resulting 2.0-kb blunt-ended SphI fragment containing the intact sgcA gene was cloned into the SmaI/SphI sites of pWHM79 (Shen et al. (1996) *Proc. Natl. Acad. Sci., USA,* 93: 6600–6604) to yield pBS1014. The latter was digested with EcoRI and HindIII, and the resulting 2.5-kb EcoRI/HindIII fragment was cloned into the same sites of pWHM3 (Vara et al. (1989) *J. Bacteriol.* 171: 5872–5881) to yield pBS1015, in which the expression of sgcA is under the control of the ermE* promoter (Bibb et al. (1994) *Mol. Microbiol.* 14: 533–545).

Alternatively, pBS1007 was digested with KpnI, removing most of the sgcA gene, and the 5.2-kb KpnI fragment was recovered and self-ligated to yield pBS1016. The ermE* promoter was subcloned from pWHM79 (Shen et al. (1996) *Proc. Natl. Acad. Sci., USA,* 93: 6600–6604) as a 0.45-kb EcoRI/SacI fragment and cloned into the same sites of pBS1016 to yield pBS1017. The latter was digested with EcoRI and HindIII, and the resulting 2.5-kb EcoRI/HindIII fragment was cloned into the same sites of pKC1139 to yield pBS1018, in which the expression of sgcB is under the control of the ermE* promoter.

Determination of C-1027 Production.

The production of C-1027 was detected by assaying its antibacterial activity against *M. luteus* (Hu et al. (1988) *J. Antibiot.* 41: 1575–1579). From liquid culture, fermentation supernant (180 µL) was added to stainless steel cylinders placed on LB plates pre-seeded with overnight *M. luteus* culture (0.01 % vol/vol). From solid culture, a small square block (0.5×0.5×0.5 $cm^3$) of agar from either R2YE or ISP-4 medium was directly placed on *M. luteus*-seeded LB plates. The plates were incubated at 37° C. for 24 hrs, and C-1027 production was estimated by measuring the size of inhibition zones.

Nucleotide Sequence Accession Number.

The nucleotide sequence reported here has been deposited in the GenBank database with the accession number AF201913.

Results.

No Polyketide Synthase Gene was Amplified by PCR from *S. globisporus*.

On the assumption that the C-1027 enediyne core is of polyketide origin, the PCR approach was adopted to screen *S. globisporus* for any putative PKS genes, although it is far from certain a priori if the biosynthesis of the enediyne core invokes a PKS and, if so, whether the enediyne PKS will exhibit a type I or type II structural organization. PCR methods for cloning either type I or type II PKS genes have been developed, and these methods have proven to be very effective in cloning PKS genes from various polyketide-producing actinomycetes (Kakavas et al. (1997) *J. Bacteriol.* 179: 7515–7522; Seow et al. (1997) *J. Bacteriol.* 179: 7360–7368). While no distinctive product was amplified under all conditions examined with both pairs of primers designed for type II PKS, a single product with the expected size of 0.75 kb was readily amplified by PCR from *S. globisporus* with primers designed for type I PKS, which was subsequently cloned (pBS1001). Intriguingly, sequence analysis of six randomly selected pBS1001 clones yielded an identical product—indicative of a specific PCR amplification—the deduced amino acid sequence of which, however, showed no homology to known PKSs (data not shown), excluding the possibility of using PKS as a probe to identify the sgc biosynthesis gene cluster.

Cloning of a Putative NGDH Gene by PCR from *S. globisporus*.

The biosynthesis of various deoxyhexoses share a common key intermediate—4-keto-6-deoxyglucose nucleoside diphosphate or its analogs—whose formation from glucose nucleoside diphosphate is catalyzed by the NGDH enzyme, an $NAD^+$-dependent oxidoreductase (Liu and Thorson (1994) *Ann. Rev. Microbiol.* 48: 223–256; Piepersberg (I 997) pp. 81–163. In *Biotechnology of antibiotics,* 2nd ed. W. R. Strohl (ed). Marcel Dekker, New York). The PCR method was adopted to clone the putative NGDH gene from *S. globisporus* with primers designed according to the homologous regions of various NGDH enzymes from actinomycetes (Decker et al. (1996) *FEMS Lett.* 141: 195–201), resulting in the amplification of a single product with the expected size of 0.55 kb (pBS1002). Sequence analysis of pBS1002 confirmed its identity as a part of a putative NGDH gene.

To clone the complete NGDH gene, an *S. globisporus* genomic library, constructed in the *E. coli-Streptomyces* shuttle vector pOJ446 (Bierman et al. (1992) *Gene* 116: 43–69; Rao et al. (1987) *Methods Enzymol.* 153: 166–198), was analyzed by Southern hybridization with the PCR-amplified 0.55-kb fragment from pBS1002 as a probe. Of the 10,000 colonies screened, 36 positive colonies were identified, 9 of which were confined by PCR to harbor the DGDH gene. Restriction enzyme mapping showed that all of them contained a single 3.0-kb BamHI fragment hybridizing to the NGDH probe. Additional chromosomal walking from this locus eventually led to the localization of the 75-kb sgc gene cluster, covered by 18 overlapping cosmids as represented by pBS1004, pBS1005, and pBS1006 (FIG. 5A). The 3.0-kb BamHI fragment was subcloned (pBS1007) (FIG. 5B), and its nucleotide (nt) sequence was determined.

Analysis of the DNA Sequences of the sgcA and sgcB Genes.

Two complete open reading frames (ORFs) (sgcA and sgcB) were identified within the 3.0-kb BamHI fragment of pBS1007, the 3,035-nt sequence of which is shown in FIG. 6. The sgcA gene most likely begins with an ATG at nt 101, preceded by a probable ribosome biding site (RBS), GGAGG, and ends with a TGA stop codon at nt 1099. SgcA should therefore encode a 332-amino acid protein with a molecular weight of 36,341 and an isoelectric point of 6.01. A Gapped-BLAST search showed that the deduced sgcA gene product is highly homologous to various putative and known NGDH enzymes from antibiotic-producing actinomycetes, including Gdh from the erythromycin biosynthesis gene cluster in *Saccharopolyspora erythraea* (64% identity and 70% similarity) (Linton et al. (1995) *Gene* 153: 33–40), MtmE from the mithramycin biosynthesis gene cluster in *Streptomyces argillaceus* (64% identity and 68% similarity) (Lombo et al. (1997) *J. Bacteriol.* 179: 3354–3357), and TylA2 from the tylosin biosynthesis gene cluster in *Streptomyces fradiae* (62% identity and 68% similarity) (Merson-Davies and Cundliffe (1994) *Mol. Microbiol.* 13: 349–355) (FIG. 7). A conserved sequence of 14 amino acid residues close to the N-termini can be easily identified in these proteins, which has been described as a βαβ fold with an NAD$^+$-binding motif, GxGxxG, (FIG. 7, boxed), consistent with their biochemical role in deoxyhexose biosynthesis (Liu and Thorson (1994) *Ann. Rev. Microbiol.* 48: 223–256; Piepersberg (1997) pp. 81–163. In *Biotechnology of antibiotics*, 2nd ed. W. R. Strohl (ed). Marcel Dekker, New York). The function of Gdh and MtmE as TDP-glucose 4,6-dehydratases, requiring NAD$^+$ as a cofactor, has been confirmed by an enzyme assay following expression of the gdh (Linton et al. (1995) *Gene* 153: 33–40) and mtmE gene (Lombo et al. (1997) *J. Bacteriol.* 179: 3354–3357) in *E. coli*, respectively, and by purification of the Gdh protein from *Sacc. erythraea* (Vara et al. (1989) *J. Bacteriol.* 171: 5872–5881). From these data, it is reasonable to suggest that sgcA encodes the NGDH enzyme required for the biosynthesis of the 4,6-dideoxy-4-dimethylamino-5-methylrhamnose moiety of the C-1027 chromophore.

Transcribed in the same direction as sgcA, the sgcB gene is located 43 nt downstream of sgcA. It should begin with a GTG at nt 1143, preceded by a probable RBS, AGGAG, and end with a TGA at nt 2708 (FIG. 6). Correspondingly, sgcB should therefore encode a 521-amino acid protein with a molecular weight of 52,952 and an isoelectric point of 4.64. Database comparison of the deduced sgcB product revealed that SgcB is closely related to a family of membrane efflux pumps, such as LfrA from *Mycobacterium smegmatis* (43% identity and 50% similarity, protein accession number AAC43550) (Takiff et al. (1996) *Proc. Natl. Acad. Sci. USA* 93: 362–366), OrfA from *Streptomyces cinnamomeus* (42% identity and 47% similarity, protein accession number AAB71209) (Sommer et al. (1997) *Appl. Environ. Microbiol.* 63: 3553–3560), and RifP from the rifamycin biosynthesis gene cluster in *Amycolatopsis mediterranei* (35% identity and 44% similarity, protein accession number AAC01725) Augus et al. (1998) *Chem. Biol.* 5: 69–79). These proteins are membrane-localized transporters involved in the transport of antibiotics (conferring resistance), sugars, and other substances. While direct evidence is lacking for RifP conferring rifamycin resistance in *A. mediterranei* by transporting it out of the cells (August et al. (1998) *Chem. Biol.*, 5: 68–79), it has been proven that LfrA employs the transmembrane proton gradient in an antiporter mode to drive the efflux of intracellular antibiotics, resulting in fluoroquinolone resistance in *M. smegmatis* (Takiff et al. (1996) *Proc. Natl. Acad. Sci. USA* 93: 362–366). On the basis of the high degree of amino acid sequence conservation, an equivalent role could be proposed for SgcB, conferring resistance by exporting C-1027 from *S. globisporus*.

The cagA Gene is Clustered with the sgcA and sgcB Locus.

Figure 5C:
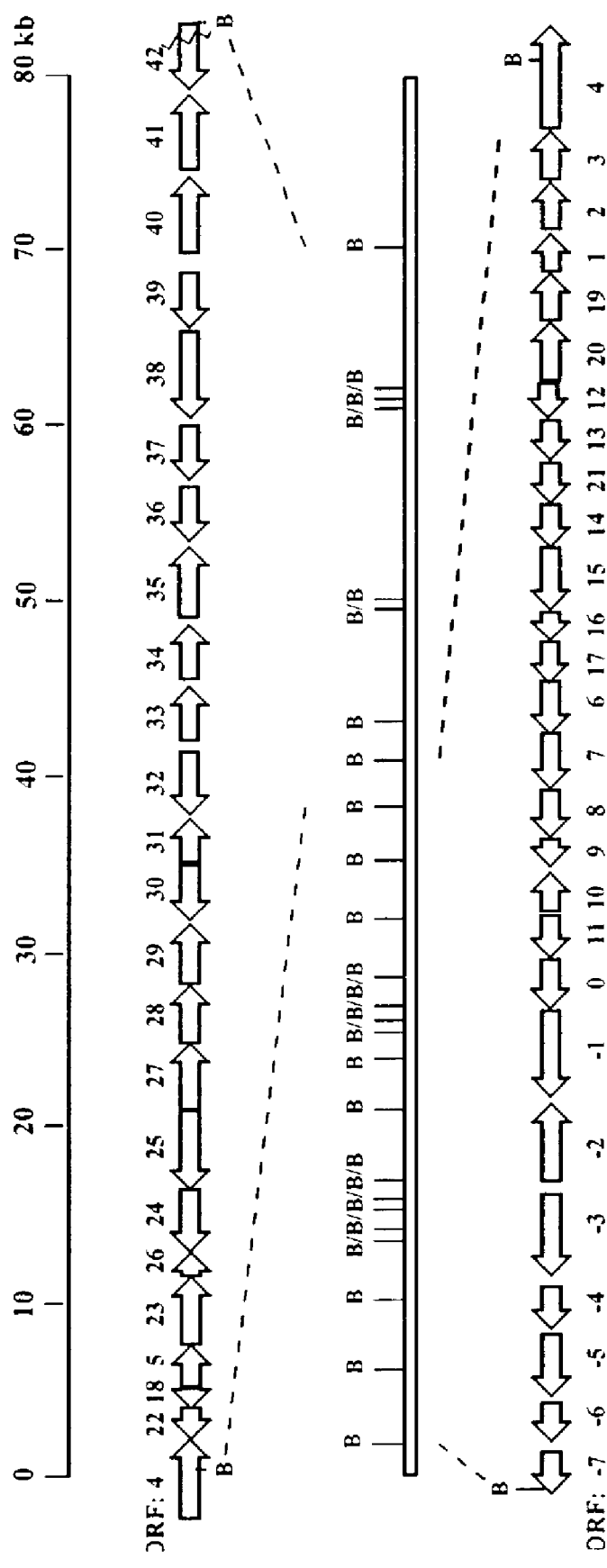

To determine if cagA is clustered with the sgcA and sgcB locus, PCR primers were designed according to the flanking regions of cagA (Sakata et al. (1992) *Biosci. Biotech. Biochem.* 56: 1592–1595). A single product with the predicted size of 0.73 kb was indeed amplified from several of the overlapping cosmids (which cover the 75-kb sgc cluster), including pBS1004 and pBS1005, the identity of which as cagA was confirmed by sequencing. Restriction enzyme mapping and Southern hybridization analysis localized cagA to a single 4.0-kb BamHI fragment that is approximately 14 kb upstream of the sgcA,B locus (FIG. 5B). The 4.0-kb BamHI fragment was subcloned (pBS1008), and its nt sequence was determined, revealing the cagA gene along with two additional ORFs (data not shown) (FIG. 5). As reported earlier, cagA encodes a 142-amino acid protein that is processed by cleavage of a 32-amino acid lead peptide to yield the mature CagA apoprotein (Sakata et al. (1992) *Biosci. Biotech. Biochem.* 56: 1592–1595).

Disruption of the sgcA Gene in *S. globisporus*.

Figure 8A:
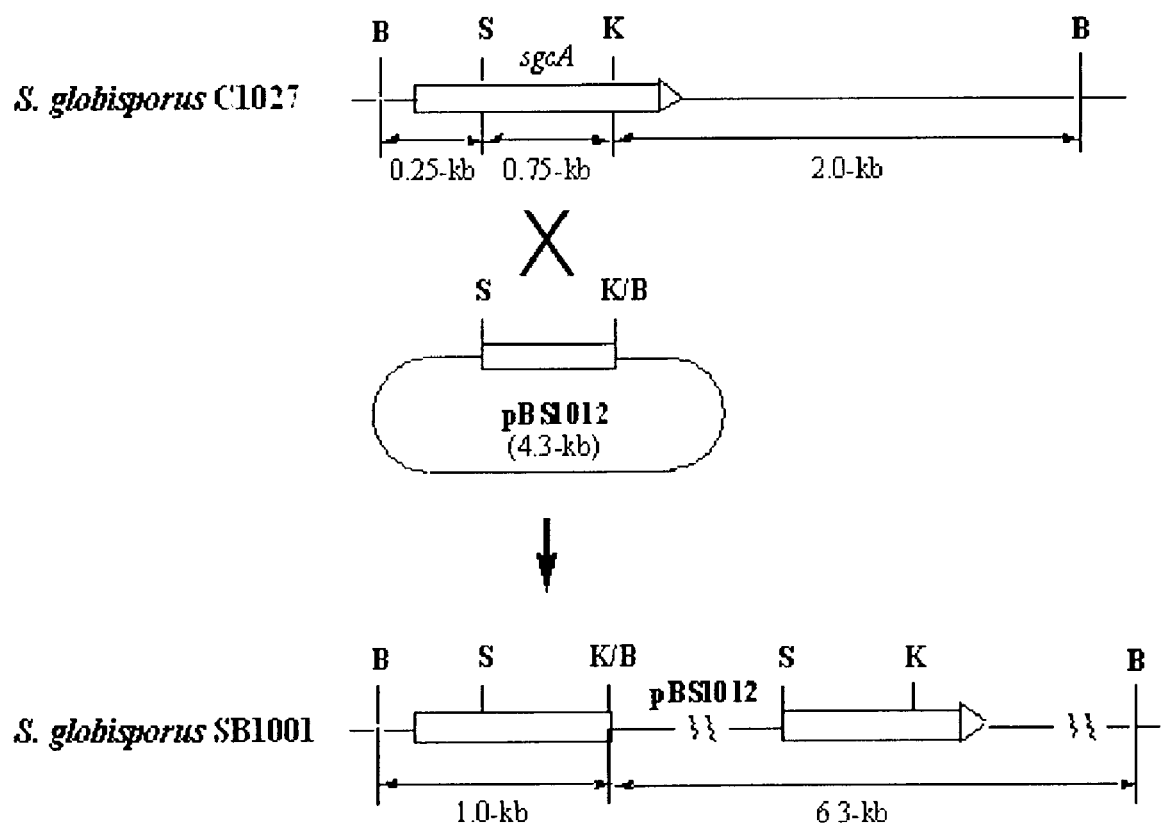
FIGS. 8A and 8B show disruption of sgcA by single crossover homologous recombination.

To examine if the cloned sgc cluster encodes C-1027 biosynthesis, sgcA was insertionally disrupted by a single crossover homologous recombination event to generate C-1027-nonproducing mutant strains (FIG. 8A). Two plasmids were used—pBS1012 (a pOJ260 derivative) and pBS1013 (a pKC1139 derivative), each of which contain a 0.75-kb internal fragment from sgcA (Table IV). After introduction of pBS1012 into *S. globisporus* either by PEG-mediated protoplast transformation or *E. coli-S. globisporus* conjugation, transformants or exconjugants that were resistant to apramycin were isolated in all cases. Since pBS1012 is derived from the Streptomyces non-replicating plasmid of pOJ260, these isolates must have resulted from integration of pBS1012 into the *S. globisporus* chromosome by homologous recombination. Plasmid pBS1013 was similarly introduced into *S. globisporus*. However, since pBS1013 is derived from pKC1139 that carries the temperature-sensitive *Streptomyces* replication origin from pSG5 and can replicate normally at 28° C. (Muth et al. (1989) *Mol. Gen. Genet.* 219: 341–348), these isolates were subjected to incubation at the non-permissive temperature of 37° C. to eliminate free plasmids from the host cells. As expected, normal growth stopped except for the recombinants that continue to grow at 37° C., indicative of integration of pBS1013 into *S. globisporus* by homologous recombination. The apramycin-resistant S. globisporus SB 1001 and S. globisporus SB 1002 strains were chosen as representatives of mutant strains with disrupted sgcA gene resulted from integration of pBS1012 and pBS1013, respectively.

Figure 8B:
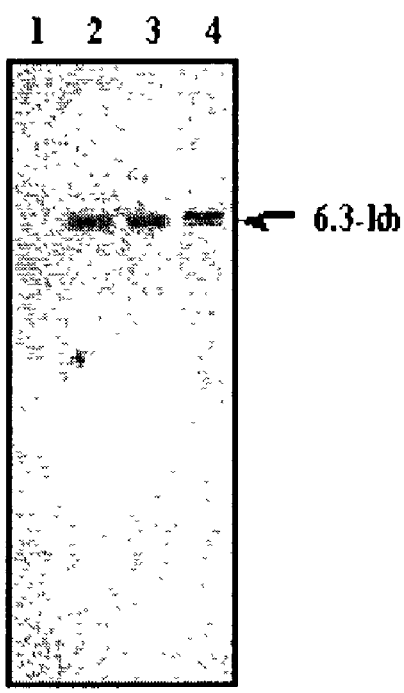
Figure 8C:
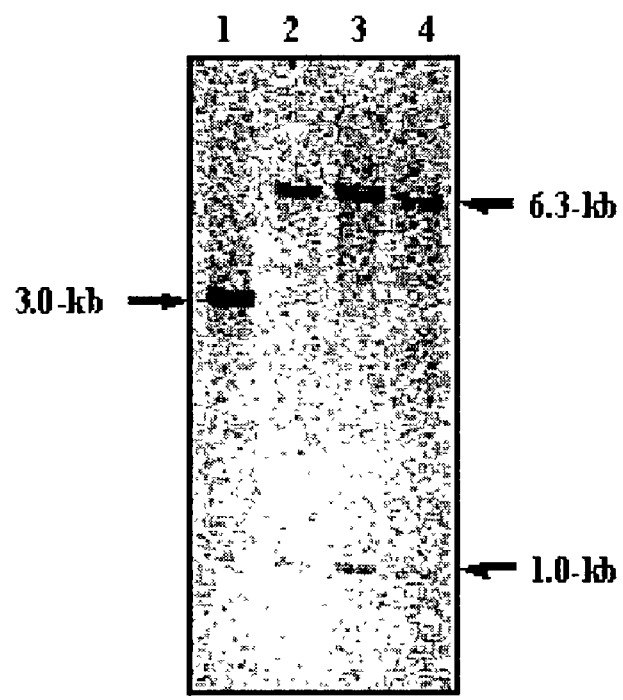

To confirm that targeted sgcA disruption has occurred by a single crossover homologous recombination event, Southern analysis of the DNA from the mutant strains was performed as exemplified for S. globisporus SB1001 with either pOJ260 or the 0.75-kb SacII/KpnI internal fragment of sgcA from pBS1010 as a probe. As shown in FIG. 8B, a distinctive band of the predicted size of 6.3 kb was detected with the pOJ260 vector as a probe in all mutant strains (lanes 2, 3, and 4); this band was absent from the wild-type strain (lane 1). Complementarily, when using the 0.75-kb SacII/KpnI internal fragment of sgcA as a probe (FIG. 8C), the 3.0-kb band in the wild-type strain (lane 1) was split into two fragments with the size of 6.3 kb and 1.0 kb in the mutant strains (lanes 2, 3, and 4), as would be expected for disruption of sgcA by a single crossover homologous recombination event.

S. globisporus SB1001 and S. globisporus SB1002 are C-1027-nonproducing Mutants.

No apparent difference in growth characteristics and morphologies between the wild-type S. globisporus and mutant S. globisporus SB1001 and S. globisporus SB1002 strains was observed. While C-1027 production in the wild-type S. globisporus strain could be detected on day 3, peaked on day 5, and continued for a few more days, as judged by assaying the antibacterial activity of the culture supernant against M. luteus (Hu et al. (1988) J. Antibiot 41: 1575–1579), C-1027 production is completely abolished in the sgcA mutant strains S. globisporus SB1001 and S. globisporus SB1002 (FIG. 9A). The latter phenotype was identical to that of the AF40, AF44, and AF67 mutants, C-1027-nonproducing S. globisporus strains that have been characterized previously (FIGS. 9A and 9C) (Mao, et al. (1997) Chinese J. Biotechnol. 13: 195–199).

In vivo Complementation of S. globisporus SB1001.

The ability of the wild-type sgcA gene to complement the disrupted sgcA gene was tested in the S. globisporus SB1001 strain. The construction of pBS1015, in which the expression of sgcA is under the control of the constitutive ermE* promoter, was described in Materials and Methods. Both the pBS1015 construct and the pWHM3 vector as a control were introduced by transformation into the S. globisporus SB1001 mutant strains. Culture supernants from each transformant were bioassayed against M. luteus for C-1027 production. pBS1015 restored C-1027 production to S. globisporus SB1001 to the wild-type level; no C-1027 production was detected in the control in which pWHM3 was introduced into S. globisporus BS1001 (FIGS. 9B and 9C). A significant reduction of C-1027 production was observed when S. globisporus SB1001(pBS1015) was cultured under identical conditions but without thiostrepton (FIG. 9B vs. 6C), indicative that pBS1015 may be unstable in S. globisporus SB1001 in the absence of antibiotic selection pressure.

Expression of sgcB in S. globisporus.

The effect of sgcB on C-1027 production was tested in the wild-type S. globisporus strain. The construction of pBS1018, in which the expression of sgcB is under the control of the constitutive ermE* promoter, was described in Materials and Methods. pBS1018 and the pKC1139 vector as a control were each introduced by conjugation into S. globisporus. Culture supernatants from each exconjugant were harvested on days 3, 4, and 5, and assayed for C-1027 production by determining the antibacterial activity against M. luteus. While no apparent difference for C-1027 production was observed between the S. globisporus and S. globisporus (pKC1139) strains, a significant increase in C-1027 production (150125%) was evident in the early stage of S. globisporus (pBS1018) fermentation (FIG. 9D, day 3). However, such effect on C-1027 production leveled off as the fermentation proceeded and became insignificant when the culture reached the late stationary phase of fermentation (FIG. 9D, day 4 and 5).

Discussion.

The inability to clone the putative enediyne PKS gene by PCR, with degenerate primers designed according to the highly conserved amino acid sequences of either type I or type II PKSs, or by DNA hybridization, with homologous type I or type II PKS as probes (data not shown), was unexpected, since feeding experiments by incorporation of [1-$^{13}$C]- and [1,2-$^{13}$C] acetate into the enediyne cores of esperamicin (Lam et al. (1993) J. Am. Chem. Soc. 115: 12340–12345), dynemicin (Tokiwa et al. (1992) J. Am. Chem. Soc. 114: 4107–4110), and neocarzinostatin (Hensens et al. (1989) J. Am. Chem. Soc. 111: 3295–3299) supported their polyketide origin. Although the enediyne cores are structurally distinct from either the reduced or aromatic polyketides, the biosynthesis of which is well characterized by type I or type II PKS, respectively, it could be imagined that an enediyne PKS catalyzes the biosynthesis of a polyunsaturated linear heptaketide intermediate that is subsequently cyclized into the enediyne core structure (Hu et al. (1994) Mol. Microbiol. 14: 163–172; Spaink et al. (1991) Nature 354: 125–130; Thorson et al. (1999) Bioorg. Chem., 27: 172–188). Alternatively, Hensens and co-workers proposed a fatty acid origin for the enediyne core that was also consistent with the isotope labeling results. These authors suggested oleate as a precursor that is shortened by loss of carbons from both ends and is desaturated via the oleate-crepenynate pathway to furnish the enediyne core (Hensens et al. (1989) J. Am. Chem. Soc. 111: 3295–3299). The latter pathway resembles polyacetylene biosynthesis in higher plants and fungi and requires an acetylene forming enzyme—a plant gene encoding such an enzyme was identified recently (Lee et al. (1998) Science 280: 915–918). The DNA sequence analysis of approximately 60 kb of the sgc gene cluster, fails to reveal any gene that resembles PKS.

Although little is known about the resistance mechanism for the enediyne antibiotics in general, the apoproteins of the chromoprotein type of enediynes could be viewed as resistance elements that confer self-resistance to the producing organisms by drug sequestration (Thorson et al. (1999) Bioorg. Chem., 27: 172–188). Such a resistance mechanism is in fact well established in antibiotic-producing actinomycetes, for example, BlmA, the bleomycin-binding protein from Streptomyces verticillus (Shen et al. (1999) Bioorg. Chem. 27: 155–171). Given the fact that antibiotic production genes have invariably been found to be clustered in one region of the microbial chromosome, consisting of structural, resistance, and regulatory genes, the Inventors adopted a strategy to clone the sgc gene cluster by mapping a putative C-1027 structural gene to the previously cloned cagA gene, considered as a resistance gene that encodes the C-1027 apoprotein.

NGDH was chosen as the putative C-1027 structural gene on the basis of the 4,6-dideoxy-4-dimethylamino-5-methyl-rhamnose moiety of the C-1027 chromophore. It has been well established that all deoxyhexoses could be derived from the common intermediate of 4-keto-6-deoxyglucose nucleoside diphosphate, the biosynthesis of which from glucose nucleoside diphosphate is catalyzed by an NGDH enzyme. NGDH gene was cloned from *S. globisporus* by PCR and used it as a probe to screen an *S. globisporus* genomic library, resulting in the isolation of the 75-kb sgc gene cluster. DNA sequence analysis of a 3.0-kb BamHI fragment of the sgc cluster confirmed the presence of the NGDH protein, encoded by sgcA, along with sgcB that encodes a transmembrane efflux protein (FIG. 6). The cagA gene indeed resides approximately 14 kb upstream of sgcA (FIG. 5); DNA sequence analysis of a 4.0-kb BamHI fragment confirmed the identity of cagA along with two additional ORFs (data not shown). These results underline once again the effectiveness of cloning natural product biosynthesis gene clusters by exploiting the clustering phenomenon between resistance and structural genes.

The involvement of the cloned gene cluster in C-1027 biosynthesis was demonstrated by disrupting the sgcA gene to generate *S. globisporus* mutants, the ability of which to produce C-1027 was completely abolished (FIG. 9A), and by complementing the sgcA mutants in vivo upon expression of SgcA in trans to restore C-1027 production (FIGS. 9B and 6C). These data unambiguously establish that sgcA is essential for C-1027 production, and thus support the conclusion that the cloned gene cluster encodes C-1027 biosynthesis. It should be pointed out that, although the sgcA mutants *S. globisporus* SB 1001 and *S. globisporus* SB 1002 were characterized as C-1027-nonproducing on the basis of the antibacterial assay alone (FIG. 9A), this phenotype was identical to that of the controls of the AF40, AF44, and AF67 mutants (FIGS. 9A and 9C). The latter strains were isolated previously upon randomly mutagenizing the wild-type *S. globisporus* strain with acriflavine and confirmed to be C-1027-nonproducing by both the antibacterial bioassay and an antitumor spermatogonial assay (Mao, et al. (1997) *Chinese J. Biotechnol.* 13: 195–199), providing strong support to the current study. Gene disruption and complementation in *S. globisporus* were made possible by the recently developed genetic system that allowed us to introduce plasmid DNA into *S. globisporus* via either PEG-mediated protoplast transformation (Hopwood et al. (1985) *Genetic manipulation of Streptomyces: a laboratory manual.* John Innes Foundation, Norwich, UK) or *E. coli-S. globisporus* conjugation (Bierman et al. (1992) *Gene* 116: 43–69; Matsushima and Baltz (1996) *Microbiology* 142: 261–267; Matsushima et al. (1994) *Gene* 146: 39–45) for analyzing the sgc biosynthesis gene cluster in vivo. Given the difficulties encountered with calicheamicin biosynthesis in *Micromonospora echinospora*, into which all attempts to introduce plasmid DNA have failed (Thorson et al. (1999) *Bioorg. Chem.*, 27: 172–188), the latter results underscore the importance of selecting C-1027 as a model system for enediyne biosynthesis so that many of the genetic tools developed in Streptomyces species can now be directly applied to the study of enediyne biosynthesis.

Finally, the function of sgcB was probed by examining C-1027 production, following expression of the gene in the wild-type *S. globisporus* strain. Database comparison of the deduced amino acid sequence clearly suggested SgcB as a transmembrane efflux protein, conferring resistance by exporting C-1027 out of the cell. Hence, in addition to CagA, SgcB could be viewed as the second resistance element identified for C-1027 biosynthesis. Multiple resistance genes have been identified in numerous antibiotic biosynthesis gene clusters (Hopwood (1997) *Chem. Rev.* 97: 2465–2497). It could be imagined that CagA and SgcB function cooperatively to provide resistance—the C-1027 chromophore is first sequestered by binding to the preproprotein CagA to form a complex, which is then transported out of the cell by the efflux pump SgcB and processed by removing the leader peptide to yield the chromoprotein, although there is no experimental data to substantiate this speculation. Since it is known that yields for antibiotic production could be profoundly altered by the introduction of extra copies of regulatory, resistance, or structural genes into wild-type organisms (Hutchinson (1994) *Bio/Technology* 12: 375–380), we tested the effect of overexpressing sgcB in *S. globisporus* on C-1027 production. While no apparent adverse effect on C-1027 production was observed upon introduction of the pKC1139 vector into *S. globisporus* (data not shown), a significant increase in C-1027 production (150±25%) was observed in the early stage of *S. globisporus* (pBS1017) fermentation (FIG. 9D, day 3), supporting the predicted function for SgcB in C-1027 biosynthesis. C-1027 resistance could be a limiting factor at the onset of C-1027 production, which is circumvented by the extra copy of the plasmid-born sgcB, and overexpression of sgcB under the control of the constitutive ermE* promoter results in increase of C-1027 production. However, as the *S. globisporus* (pBS1017) fermentation proceeds to its stationary phase, C-1027 resistance is no longer a limiting factor for overall C-1027 production, and the effect of the extra copy of SgcB on C-1027 production consequently became insignificant (FIG. 9D, day 5).

In conclusion, genetic analysis of enediyne biosynthesis has heretofore met with little success in spite of considerable effort (Thorson et al. (1999) *Bioorg. Chem.*, 27: 172–188). The localization of the sgc gene cluster and characterization of the sgcA and sgcB genes have now provided an excellent basis for genetic and biochemical investigations and/or modification of C-1027 biosynthesis, and gene disruption and overexpression in *S. globisporus* clearly demonstrated the potential to construct enediyne-overproducing strains and to produce novel enediynes that may have enhanced potency as novel anticancer drugs using combinatorial biosynthesis and targeted mutagenesis. The results from C-1027 biosynthesis should facilitate the cloning and characterization of biosynthesis gene clusters of other enediyne antibiotics in Streptomyces as well as in other actinomycetes, and could have a great impact on the overall field of combinatorial biosynthesis.

Example 2

Biosynthesis of Enediyne Antitumor Antibiotic C-1027 by a Polyketide Synthase and Engineered Biosynthesis of a C-1027 Analog C-1027 is an extremely potent antitumor agent with a unique molecular architecture and mode of action. Cloning and characterization of the 85-kb C-1027 biosynthesis gene cluster from *Streptomyces globisporus* revealed (1) an iterative type I polyketide synthase (PKS) that is distinct from any bacterial PKSs known to date, (2) a general polyketide pathway for the biosynthesis of both the nine- and ten-membered enediyne antibiotics, and (3) a convergent biosynthetic strategy for the C-1027 chromophore from four building blocks. Manipulation of genes governing C-1027 biosynthesis allowed us to produce a new enediyne compound in a predicted manner.

Figure 18:
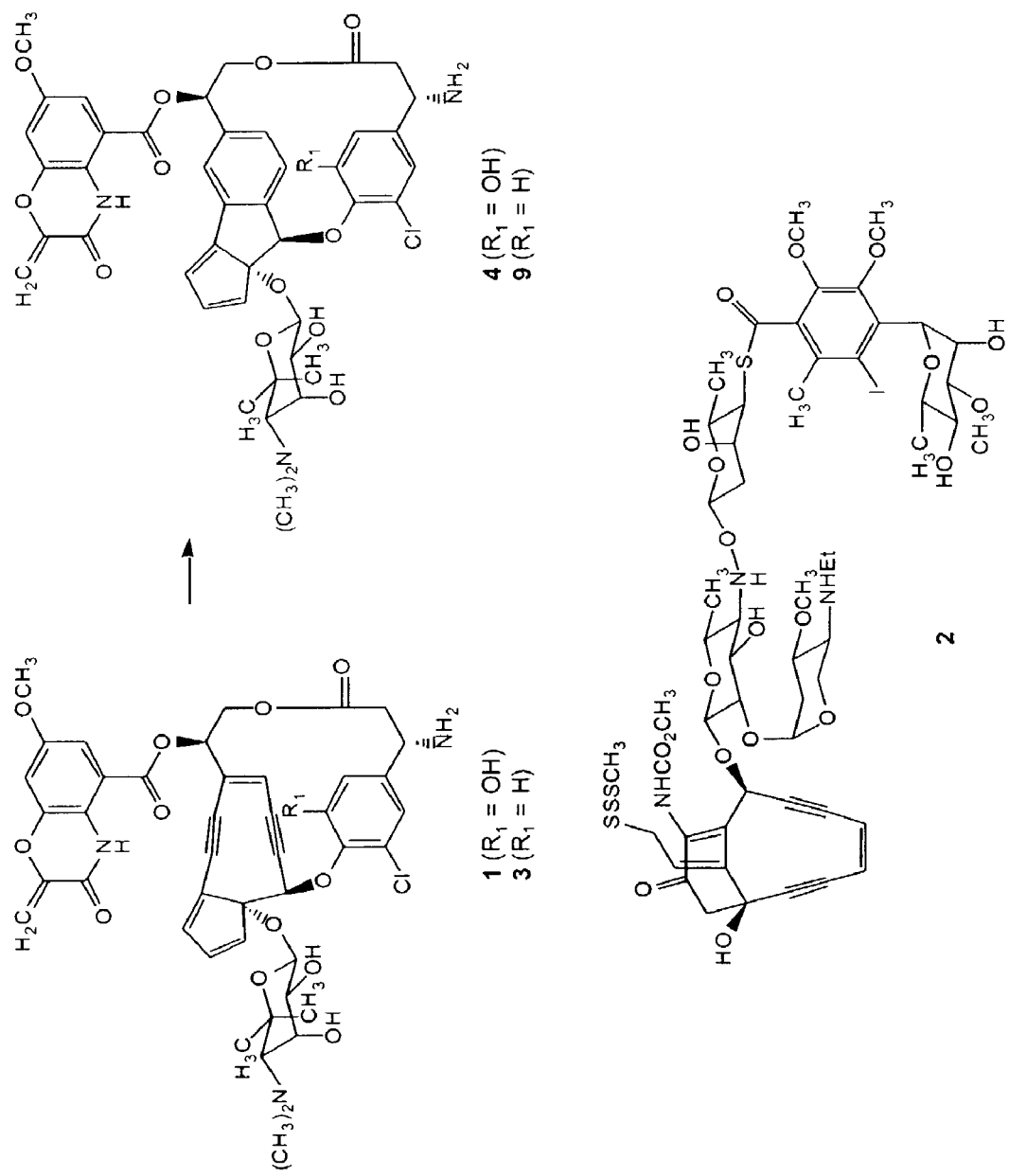
FIG. 18 shows the structures of the C-1027 (1) and deshydroxy-C-1027 (3) chromophores and their aromatized products (4 and 9), and calicheamicin (2).

C-1027 is a chromoprotein antibiotic produced by *Streptomyces globisporus* and composed of an apoprotein and the C-1027 chromophore (1) (Otani (1988) *J. Antibiot.* 41:1580). It belongs to the enediyne family of antibiotics, structurally characterized by a unit consisting of two acetylenic groups conjugated to a double bond or incipient double bond within a nine- or ten-membered ring, i.e., the enediyne core, as exemplified by 1 or calicheamicin $\lambda^1_1$ (2), respectively (FIG. 18). The enediyne antibiotics are extremely potent antitumor agents with a unique molecular architecture and mode of action (Nicolaou (1991) *Angew. Chem. Int. Ed. Engl.* 30: 1387; Xi and Goldberg (1999) Pp. 553–592 In: *Comprehensive Natural Products Chemistry*, Vol. 7, D. Barton, K. Nakanish, O. Meth-Cohn, Eds. (Elesvier, New York; Brukner (2000) *Curr. Opinion Oncologic, Endocrine & Met. Invest. Drugs* 2: 344). Although the natural enediynes have seen limited use as clinical drugs mainly because of significant toxicity, various polymer-based delivery systems or enediyne-antibody conjugates have shown clinical promise and success in anticancer chemotherapy. For example, the poly(styrene-co-maleic acid)-conjugated neocarzinostatin has been used clinically against hepatoma in Japan since 1994 (Maeda and Konno (1997) Pp 227–267 In: *Neocarzinostatin: the Past, Present, and Future of an Anticancer Drug*, H. maeda, K. Edo, N. Ishida, Eds. (Speinger-Verlag, New York). A CD33 monoclononal antibody (MAb)-calicheamicin conjugate was approved in U.S. in 2000 for acute myeloid leukemia patients (Sievers et al., (1999) *Blood* 93: 3678). Several MAb-C-1027 conjugates are under evaluation as promising anticancer drugs (Brukner (2000) *Curr. Opinion Oncologic, Endocrine & Met. Invest. Drugs* 2: 344). These successes have demonstrated that the enediynes can be developed into powerful drugs when their extremely potent cytotoxicity is harnessed and delivered directly onto the targeted tumor cells. A challenge is the synthesis of enediynes and their analogs for further mechanistic and clinical studies.

Complementary to making microbial metabolites and their structural analogs by chemical synthesis, genetic manipulations of genes governing secondary metabolism offer a promising alternative to preparing these structurally complex natural products biosynthetically (Cane et al. (1998) *Science* 282: 63; Du and Shen (2001) *Curr. Opinion Drug Discov. Develop.* 4: 215; Staunton and Wilkinson (1998) *Top. Curr. Chem.* 195: 49; Shen (2000) *Top. Curr. Chem.* 209: 1). The success of the latter approach depends on the cloning and genetic and biochemical characterization of the biosynthetic pathways of the metabolites. Given the structural complexity and remarkable biological activity, the enediynes offer a distinct opportunity to decipher the genetic and biochemical basis for the biosynthesis of an unprecedented molecular scaffold and to explore ways to make novel antitumor agents by manipulating genes governing enediyne biosynthesis.

Cloning, sequencing, and characterization of the complete C-1027 biosynthesis gene cluster from *S. globisporus*, revealing an iterative type I polyketide synthase (PKS) with unprecedented domain organization and a convergent biosynthetic strategy for 1 from four biosynthetic building blocks was completed. These results, in conjunction with the similar findings for 2, have established a new paradigm both in PKS structure and mechanism for the formation of both nine- and ten-membered enediyne antibiotics.

The sgcAB genes that encode a TDP-glucose 4,6-dehydratase and transmembrane efflux protein, respectively, were cloned and characterized, which demonstrated that sgcAB was essential for C-1027 production in *S. globisporus* (see, e.g. U.S. Ser. No. 09/478,188 and Liu and Shen (2000) Antimicrobiol. Agents Chemother. 44: 382). Since antibiotic production genes commonly occur as a cluster in actinomycetes, the inventors conducted chromosomal walking from the sgcAB locus to identify the C-1027 biosynthesis gene cluster. An 85-kb contiguous DNA from *S. globisporus* was sequenced and analyzed, revealing 67 open reading frames (orfs).

The C-1027 gene cluster was previously mapped to three overlapping cosmids, pBS1004, pBS1005, and pBS1006 (U.S. Ser. No. 09/478,188; Liu and Shen (2000) *Antimicrobiol. Agents Chemother.* 44: 382). Chromosomal walking from pBS1006 led to the isolation of an additional cosmid pBS1020, and together they covered 110-kb contiguous *S. globisporus* DNA, 85-kb of which was sequenced. orfs were identified by using the CODONPREFERENCE method in the GCG software. The overall GC content of the sequenced region is 70.1 %. Functional assignments were made by comparison of the deduced gene products with proteins of known functions in the database and summarized in the GenBank under accession number AY048670 (see also, FIG. 12).

To determine the boundaries of the C-1027 gene cluster, orfs at both ends of the sequenced region were subjected to inactivation by gene disruptions—inactivation of genes within the C-1027 gene cluster, as exemplified by sgcA, sgcC, sgcC1, sgcD6, and sgcE, abolished C-1027 production (FIG. 15), while that of genes outside the C-1027 gene cluster, such as orf(−5), orf(−3), and orf54, had no effect on C-1027 production, leading to the assignment of the cluster boundaries at sgcB1 and sgcR3, respectively.

Inactivation by gene disruption of orf(−5), orf(−3), sgcC, sgcC1, sgcD6, and orf54 was carried out as reported herein for sgcA. Essentially, a 0.5–1 kb fragment internal to the target gene was cloned into pOJ260, and the resulting construct was introduced into *S. globisporus* by conjugation. Recombinant strain was isolated by selection for apramycin resistance and confirmed by Southern analysis.

C-1027 production was monitored by bioassay against *Micrococcus luteus* (Liu and Shen (2000) *Antimicrobiol. Agents Chemother.* 44: 382) and high performance liquid chromatography (HPLC) analysis of 1 (15), which undergoes facile Bergman cyclization to yield the aromatized product (4) (FIGS. 18 and 15A) (Minami et al. (1993) *Tetrahedron Lett.* 34: 2633; Yoshida et al. (1993) *Tetrahedron Lett.* 34: 2637). The identities of 1 and 4 were confirmed by electrospray ionization-mass spectrometry (ESI-MS) analyses: 1 showed $(M+H)^+$ and $(M+Na)^+$ ions at m/z=844 and 866, consistent with the molecular formula of $C_{43}H_{42}N_3O_{13}Cl$, and 4 showed a $(M+H)^+$ ion at m/z=846, consistent with the molecular formula of $C_{43}H_{44}N_3O_{13}Cl$. Consistent with the structure of 1, those identified within the C-1027 cluster include thirteen genes, sgcE to sgcE11 and sgcF, encoding the enediyne core (5) biosynthesis, seven genes, sgcA to sgcA6, encoding deoxy aminosugar (6) biosynthesis, six genes, sgcC to sgcC5, encoding β-amino acid (7) biosynthesis, and seven genes, sgcD to sgcD6, encoding benzoxazolinate (8) biosynthesis (FIG. 12).

Three types of PKSs are known for polyketide biosynthesis in bacteria: type I and type II systems, both of which use acyl carrier protein (ACP) to activate substrates and channel the growing intermediates, for aliphatic (Staunton and Wilkinson (1998) *Top. Curr. Chem.* 195: 49) and aromatic polyketides (Shen (2000) *Top. Curr. Chem.* 209: 1), respectively, and the type III system that has no apparent amino acid sequence similarity to the former and acts directly on acyl CoAs, largely for monocyclic aromatic polyketides (Funa et al. (1999) *Nature* 400: 897). The enediyne cores bear no structural resemblance to any of the polyketides studied to date, failing to predict what type of PKS may be responsible for their biosynthesis. In fact, a controversy remains as to whether the enediyne cores are assembled via de novo polyketide biosynthesis or degradation from a fatty acid precursor, although feeding experiments with $^{13}$C-labeled precursors for neocarzinostatin (Hensens et al. (1989) *J. Am. Chem. Soc.* 111: 3295), dynemicin (Tokiwa et al.(1992) *J. Am. Chem. Soc.* 114: 4107), and esperamicin (Lam et al. (1993) *J. Am. Chem. Soc.* 115: 12340) unambiguously established that the enediyne cores were all derived from minimally eight head-to-tail acetate units. Strikingly, of the genes identified within the C-1027 cluster, there is only one, sgcE, that encodes a PKS. SgcE contains five domains—the ketoacyl synthase (KS), acyltransferase (AT), ketoreductase (KR), and dehydratase (DH) domains that are characteristic of known PKSs and a domain at the COOH-terminus (TD) that, unique only to enediyne PKSs, shows no sequence homology to any other proteins, as well as a region between AT and KR that might contain a putative ACP domain (FIG. 13A). SgcE could be envisaged to catalyze the assembly of a nascent linear polyunsaturated intermediate from acetyl and malonyl CoAs in an iterative process, which, upon action of other enzyme activities, is subsequently desaturated to furnish the two yne groups and cyclized to afford the enediyne core. An enzyme that catalyzes the formation of an acetylenic bond from a C—C double bond has been reported from the plant *Crepis alpina* and characterized as acetylenase that is a non-heme diiron protein (Lee et al. (1998) *Science* 280: 915). While no such homolog was found within the C-1027 cluster, close comparison of the C-1027 gene cluster with that for neocarzinostatin, another nine-membered enediyne antibiotic (the neocarzintostatin cluster was cloned, sequenced, and characterized from *Streptomyces carzinostaticus* ATCC 15944), revealed a group of orfs (sgcE1 to sgcE11), in addition to sgcE, that are highly conserved. SgcE6, SgcE7, and SgcE9 resemble various oxidoreductases, SgcE1, SgcE2, SgcE3, SgcE4, SgcE5, SgcE8, or SgcE11 show no sequence homology or homology only to proteins of unknown functions, and SgcE10 is highly homologous to a family of thioesterases. These enzymes, together with the SgcF epoxide hydrolase, serve as candidates for processing the nascent linear polyunsaturated intermediate into an enediyne intermediate such as 5 (FIG. 12).

To experimentally test this hypothesis, sgcE was inactivated by replacing it with a mutant copy in which the KS domain is replaced with the erythromycin resistance gene, ermE. sgcE was mutated by replacing the 371-bp BamHI fragment that harbors the KS domain with the ermE resistance gene, and cloned into pOJ260 to yield pBS1019. The latter was introduced into *S. globisporus* by conjugation (Liu and Shen (2000) *Antimicrobiol. Agents Chemother.* 44: 382) and selected first for both erythromycin and apramycin resistance and then for the loss of apramycin resistance to isolate the *S. globisporus* SB 1005 mutant strain whose genotype was confirmed by Southern analysis. To complement the sgcE mutation in SB1005, a 450-bp ErmE* fragment and a 6.2-kb sgcE fragment were cloned into pKC1139 to yield pBS1005, which was introduced into SB1005 by conjugation as described (Id.).

The resultant *S. globisporus* SB 1005 mutant strain completely loses its ability to produce 1 (FIG. 15, panel B), and this phenotype can be complemented by introduction of pBS1019, in which the expression of sgcE is under the control of the constitutive ermE* promoter, into SB1005, restoring 1 production to a level comparable to the wild-type organism (FIG. 15, panel C). These findings unambiguously established that C-1027 enediyne core biosynthesis proceeds via a polyketide pathway.

Remarkably, the SgcE enediyne PKS exhibits head-to-tail sequence homology (56% identity and 67% similarity) with an identical domain organization to the CalE8 enediyene PKS that catalyzes the biosynthesis of the ten-membered enediyne core of 2 in *Micromonospora echinospora* (FIG. 13A). These results suggest that the nine- and ten-membered enediyne cores share a common polyketide pathway. Very recently, type I PKSs acting iteratively to synthesize polyunsaturated polyketides from acetyl and malonyl CoAs have been reported, such as the LNKS and LDKS enzymes that catalyze lovastatin biosynthesis in fungus *Aspergillus terreus* (Kennedy et al (1999) *Science* 284: 1368) and the putative PKS enzymes that catalyze polyunsaturated fatty acid biosynthesis in the marine bacterium *Shewanella* and marine protist *Schizochytrium* (Metz et al. (2001) *Science* 293: 290). However, the enediyne PKSs as a family are apparently distinct in both structure and mechanism from any bacterial PKSs known to date.

The availability of the gene cluster has now set the stage to investigate the molecular basis for C-1027 biosynthesis and to engineer novel enediyne compounds by manipulating C-1027 biosynthesis genes. Thus, the seven deoxy aminosugar biosynthesis genes encode a TDP-glucose synthetase (SgcA1), a TDP-glucose 4,6-dehydratase (SgcA), a TDP-4-keto-6-deoxyglucose epimerase (SgcA2), a C-methyl transferase (SgcA3), an amino transferase (SgcA4), an N-methyl transferase (SgcA5), and a glycosyl transferase (SgcA6). Together, they are in an exact agreement with the enzyme functions that would be required for the biosynthesis of 6 from glucose-1-phosphate (FIG. 14B) and the attachment of 6 to 5 (FIG. 14A). This hypothesis was validated experimentally by inactivating sgcA (12), and the resultant *S. globisporus* SB1001 mutant strain completely loses its ability to produce 1 (FIG. 15, panel D). The six β-amino acid biosynthesis genes encode a phenol hydroxylase (SgcC), a nonribosomal peptide synthetase (NRPS) adenylation enzyme (SgcC 1), an NRPS peptidyl carrier protein (PCP) (SgcC2), a halogenase (SgcC3), an aminomutase (SgcC4), and an NRPS condensation enzyme (SgcC5). These enzyme functions agree well with the proposed biosynthetic pathway for 7 from tyrosine (FIG. 14C), which is apparently activated as aminoacyl-S-PCP for its attachment to 5 by SgcC5 (FIG. 14A). Although the precise timing of each reaction in the proposed pathway remains unknown, i.e., the substrate for any of these reactions could be a free amino acid or aminoacyl-S-PCP, sequence analysis of SgcC1 suggests that it activates an α-amino acid (Stachelhaus et al. (1999) *Chem. Biol.* 6: 493; Challis et al. (2000) *Chem. Biol.* 7: 211). The latter prediction is consistent with the recent finding that covalent tethering of an amino acid as aminoacyl-S-PCP for modification is a general strategy to sequester, and thus divert, a fraction of the amino acid into secondary metabolism (29). Indeed, inactivation of sgcC1 resulted in the isolation of the *S. globisporus* SB1003 mutant strain (14) that completely loses its ability to produce 1 (FIG. 15, panel E). The seven benzoxazolinate biosynthesis genes encode the anthranilate synthase I and II subunits (SgcD and SgcD1), a monoxygenases (SgcD2), a P-450 hydroxylase (SgcD3), an O-methyl transferase (SgcD4), a coenzyme A (CoA) ligase (SgcD5), and an acyltransferase (SgcD6). These enzyme functions support the hypothesis that the biosynthesis of 8 starts from anthranilate, a commonly available intermediate from the shikimate pathway (FIG. 14D). The co-localization of SgcD and SgcD1 along with the rest of the C-1027 production genes assures the availability of anthranilate for secondary metabolite biosynthesis. Although it remains unclear what the origin of the $C_3$ unit is and how it is fused to the anthranilate intermediate to form the morpholinone moiety of 8, the latter is apparently activated as acyl-S-CoA for its attachement to 5 by SgcD6 (FIG. 14A). sgcD6 was inactivated to experimentally support this hypothesis (14), and the resultant *S. globisportus* SB1004 mutant strain completely loses its ability to produce I (FIG. 15, panel F). The fact that the biosynthetic building blocks are activated as aminoacy-S-ACP, acyl-S-CoA, and nucleotide diphosphosugar, and attached to the enediyne core by an NRPS condensation enzyme, an acyltransferase, and a glycosyl transferase, respectively, highlights once again nature's efficiency and versatility in synthesizing complex molecules.

Finally, we inactivated the sgcC hydroxylase gene to demonstrate the production of novel enediyne metabolites by manipulating genes governing C-1027 biosynthesis (as described above). The resulting *S. globisporus* SB 1006 mutant strain still produces a chromoprotein that is biologically active as judged by bioassay against *M. luteus* but is distinct from 1 upon HPLC analysis (FIG. 15, panel G). The new compounds were isolated as described above and subjected to ESI-MS analysis: 3 exhibited a $(M+H)^+$ ion at m/z=828, consistent with the molecular formula of $C_{43}H_{42}N_3O_{12}Cl$, and 9 showed a $(M+H)^+$ ion at m/z=830, consistent with the molecular formula of $C_{43}H_{44}N_3O_{12}Cl$. By comparison with 1, the new compounds were deduced to be deshydroxy-C-1027 (3) and its aromatized product (9), as would be predicted according to FIG. 14C. Intriguingly, 3 is at least 5-fold more stable than 1 at 25° C. in respect to undergoing the Bergman cyclization, a property that could be potentially explored in developing C-1027 into a clinically useful drug. Applying methods of combinatorial biosynthesis to the enediyne system may produce novel polyketides.

Deshydroxy C-1027 and other biologically active enediyne analogues were produced as decribed below.

Deshydroxy-C-1027:

Mutant construction: A 0.91 -kb internal fragment of the sgcC gene was cloned into the suicide vector pOJ260. The resultant recombinant plasmid of pOJ260 derivative was introduced into the wild-type *S. globisporus* strain via conjugation. The target sgcC gene was disrupted by integration of the recombinant plasmid into the chromosomal copy of sgcC via a single crossover homologous recombination event, resulting in the isolation of the *S. globisporus* sgcC mutant strain.

Bioassay: The *S. globisporus* sgcC mutant strain was cultured under the identical conditions as the wild-type strain. Following the same isolation procedure of C-1027 from the *S. globisporus* wild-type strain, deshydroxy-C-1027 was isolated from the *S. globisporus* sgcC mutant strain. Using the *M. luteus* as a testing organism, deshydroxyl-C-1027 is active against *M. luteus* as evidnced by the clear inhibition zone on the bioassay plate as evidenced in FIG. 20 and structure as evidenced in FIG. 19.

Figures 23A, 23B:
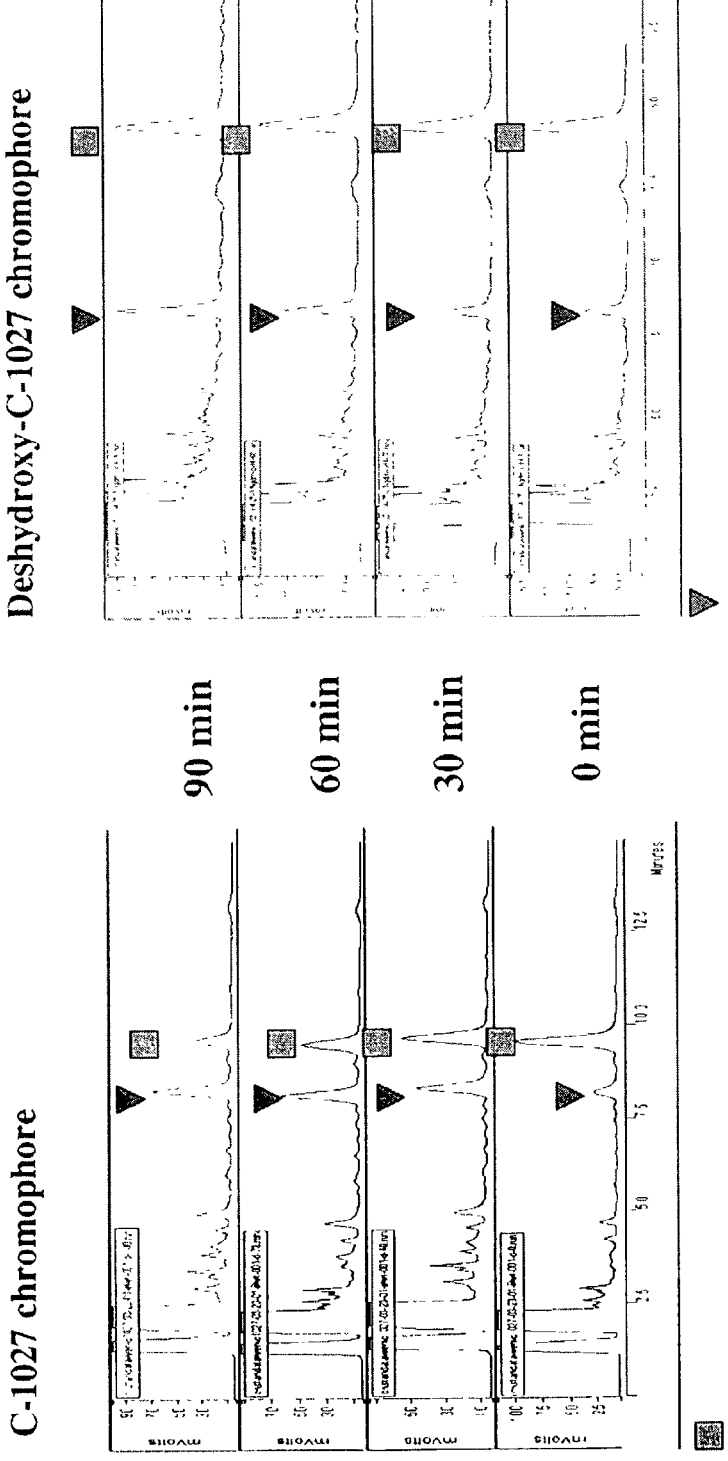
FIG. 23 shows a comparison of degradation rate of enediyne compounds, depicting C-1027 chromophore (23A) and Deshydroxy-C-1027 chromophore (23B).

The comparison of degration rate of enediyne compounds is shown in FIG. 23–FIG. 23A shows the degradation rate of C-1027 chromophore at 25° C. and FIG. 23B shows the rate of degradation for deshydroxy-C-1027 chromophore compound.

Deschloro-C-1027:

Mutant construction: A 1.0-kb internal fragment of the sgcC3 gene was cloned into the temperature-sensitive vector pKC1139. The resultant recombinant plasmid of pKC1139 derivative was introduced into the wild-type *S. globisporus* strain via conjugation. The target sgcC3 gene was disrupted by integration of the recombinant plasmid into the chromosomal copy of sgcC3 via a single crossover homologous recombination event after shifting the incubation temperature to 37° C., resulting in the isolation of the *S. globisporus* sgcC3 mutant strain.

Figure 19:
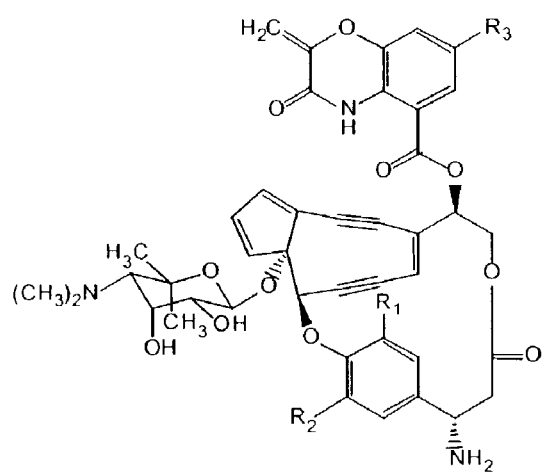
FIG. 19 shows the structure of C-1027 chromophore, and isolated enediyne analogues, Deshydroxy-C-1027, Deschoro-C-1027 and Desmethoxy-C-1027.
Figure 20:
FIG. 20 shows a clear inhibition zone as exhibited by the deshydroxy-C-1027 compound isolated from S. globisporus sgcC mutant strains using M. luteus as a testing organism.
Figure 21:
FIG. 21 shows a clear inhibition zone as exhibited by the deschloro-C-1027 compound isolated from *S. globisporus* sgcC3 mutant strains using *M. luteus* as a testing organism.

Bioassay: The *S. globisporus* sgcC3 mutant strain was cultured under the identical conditions as the wild-type strain. Following the same isolation procedure of C-1027 from the *S. globisporus* wild-type strain, deschloro-C-1027 as shown in FIG. 19 was isolated from the *S. globisporus* sgcC3 mutant strain. Using the *M. luteus* as a testing organism, deschloro-C-1027 is active against *M. luteus* as evidenced by the clear inhibition zone on the bioassay plate, as shown in FIG. 21.

Desmethoxy-C-1027

Mutant construction: Two desmethoxy-C-1027-producing *S. globisporus* recombinant strains were constructed—an *S. globisporus* sgcD4 mutant strain and an *S. globisporus* sgcD3 mutant strain.

To construct the sgcD4 mutant, a 0.8-kb internal fragment of the sgcD4 gene was cloned into the temperature-sensitive vector pKC1139. The resultant recombinant plasmid of pKC1139 derivative was introduced into the wild-type *S. globisporus* strain via conjugation. The target sgcD4 gene was disrupted by integration of the recombinant plasmid into the chromosomal copy of sgcD4 via a single crossover homologous recombination event after shifting the incubation temperature to 37° C., resulting in the isolation of the *S. globisporus* sgcD4 mutant strain.

To construct the sgcD3 mutant, a 1.0-kb internal fragment of sgcD3 gene was cloned into the suicide vector pOJ260. The resultant recombinant plasmid of pOJ260 derivative was introduced into the wild-type *S. globisporus* strain via conjugation. The target sgcD3 gene was disrupted by integration of the recombinant plasmid into the chromosomal copy of sgcD3 via a single crossover homologous recombination event, resulting in the isolation of the *S. globisporus* sgcD3 mutant strain.

Bioassay: Both the *S. globisporus* sgcD4 and D3 mutant strains were cultured under the identical conditions as the wild-type strain. Following the same isolation procedure of C-1027 from the *S. globisporus* wild-type strain, desmethoxy-C-1027 as shown in FIG. 19 was isolated from both *S. globisporus* sgcD4 and sgcD3 mutant strains. Using the *M. luteus* as a testing organism, desmethoxy-C-1027 is active against *M. luteus* as evidnced by the clear inhibition zone on the bioassay plate, as shown in FIG. 22.

Where clinical application of the enediyne analogues is undertaken, it may be necessary to prepare the complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions of the present invention include an effective amount of the analogue, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also may be incorporated into the compositions.

In one embodiment of the present invention, enediyne analogs may be delivered to target tissues in the form of polymer or monoclonal antibody conjugates. As described above, various polymer-based and antibody conjugate delivery systems are known and are currently being utilized in chemotherapeutic strategies involving the naturally-occurring C-1027 enediyne. In the present invention, enediyne analogs may, for example, be chemically-modified to form poly(styrene-co-maleic acid)-conjugated enediyne analogs useful as therapeutics, particularly chemotherapeutics. (See, e.g., *Neocarzinostatin: the Past, Present, and Future of an Anticancer Drug*, H. maeda, K. Edo, N. Ishida, Eds. (Springer-Verlag, New York (Maeda and Konno (1997) pp. 227–267)). In addition, enediynes according to the present invention may be conjugated with monoclonal antibodies to form monoclononal antibody (MAb)-enediyne analog conjugates. The CD33 monoclononal antibody is illustrative of a useful Mab for this approach and may effectuate the targeting of an enediyne analog to cancerous tissues in various contexts, including in patients afflicted with acute myeloid leukemia. (See, e.g., Sievers et al., (1999) *Blood* 93: 3678.) As previously noted, several MAb-C-1027 conjugates are under evaluation as promising anticancer drugs. (Brukner (2000) *Curr. Opinion Oncologic, Endocrine & Met. Invest. Drags* 2: 344).

Solutions of therapeutic compositions may be prepared in water suitably mixed with a surfactant (e.g., hydroxypropylcellulose). Dispersions also may be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components of the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for treatment of skin cancers, to prevent chemotherapy-induced alopecia or other dermal hyperproliferative disorder. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic composition is determined based on the intended goal. The term "unit dose" or "dosage" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance. For the instant application, it is envisioned that the amount of therapeutic composition comprising a unit dose will range from about 5–30 mg of the enediyne analogue.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

[chemical structure]

wherein $R_1$ is H or OH; $R_2$ is Cl or H; $R_3$ is OCH$_3$ or H; with the proviso that $R_1$ is not OH when $R_2$ is Cl and $R_3$ is OCH$_3$.

2. A compound according to claim 1, wherein $R_1$ is H, $R_2$ is Cl, and $R_3$ is OCH$_3$.

3. A compound according to claim 1, wherein $R_1$ is OH, $R_2$ is H, and $R_3$ is OCH$_3$.

4. A compound according to claim 1, wherein $R_1$ is OH, $R_2$ is Cl, and $R_3$ is H.

5. A compound according to claim 1, wherein said compound is conjugated to a polymer or a monoclonal antibody.

6. A pharmaceutical composition comprising a therapeutically effective amount of the enediyne compound according to claim 1 dissolved or suspended in a pharmaceutically acceptable carrier.

7. A pharmaceutical composition of claim 6, wherein $R_1$ is H, $R_2$ is Cl, and $R_3$ is OCH$_3$.

8. A pharmaceutical composition of claim 6, wherein $R_1$ is OH, $R_2$ is H, and $R_3$ is OCH$_3$.

9. A pharmaceutical composition of claim 6, wherein $R_1$ is OH, $R_2$ is Cl, and $R_3$ is H.

10. A compound having the formula:

[chemical structure]

wherein $R_1$ is H or OH; $R_2$ is Cl or H; $R_3$ is OCH$_3$ or H; with the proviso that $R_1$ is not OH when $R_2$ is Cl and $R_3$ is OCH$_3$.

11. A compound according to claim 10, wherein $R_1$ is H, $R_2$ is Cl, and $R_3$ is OCH$_3$.

12. A compound according to claim 10, wherein $R_1$ is OH, $R_2$ is H, and $R_3$ is OCH$_3$.

13. A compound according to claim 10, wherein $R_1$ is OH, $R_2$ is Cl, and $R_3$ is H.

* * * * *